US012543694B2

(12) United States Patent
Ben Khaled et al.

(10) Patent No.: US 12,543,694 B2
(45) Date of Patent: Feb. 10, 2026

(54) METHOD FOR REDUCING NORNICOTINE IN TOBACCO

(71) Applicant: BRITISH AMERICAN TOBACCO (INVESTMENTS) LIMITED, London (GB)

(72) Inventors: Sara Ben Khaled, London (GB); Francisco Anastacio De Abreu E Lima, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 1230 days.

(21) Appl. No.: 17/250,552

(22) PCT Filed: Aug. 1, 2019

(86) PCT No.: PCT/GB2019/052165
§ 371 (c)(1),
(2) Date: Feb. 2, 2021

(87) PCT Pub. No.: WO2020/025963
PCT Pub. Date: Feb. 6, 2020

(65) Prior Publication Data

US 2021/0368855 A1 Dec. 2, 2021

(30) Foreign Application Priority Data

Aug. 2, 2018 (GB) ..................................... 1812603

(51) Int. Cl.
*A01H 5/12* (2018.01)
*A01H 1/00* (2006.01)
*A01H 6/82* (2018.01)

(52) U.S. Cl.
CPC ............ *A01H 6/823* (2018.05); *A01H 1/101* (2021.01); *A01H 5/12* (2013.01)

(58) Field of Classification Search
None
See application file for complete search history.

(56) References Cited

U.S. PATENT DOCUMENTS

| | | | |
|---|---|---|---|
| 2012/0117933 A1 | | 5/2012 | Dewey et al. |
| 2014/0059714 A1 | * | 2/2014 | Matarasso et al. |
| 2014/0123987 A1 | | 5/2014 | Xu et al. |
| 2015/0173319 A1 | | 6/2015 | Frederick et al. |
| 2015/0315603 A1 | | 11/2015 | Bovet et al. |
| 2017/0303582 A1 | | 10/2017 | Lu et al. |
| 2018/0119163 A1 | | 5/2018 | Kudithipudi et al. |

FOREIGN PATENT DOCUMENTS

| | | |
|---|---|---|
| CN | 102276710 A | 12/2011 |
| EP | 1033405 | 9/2000 |
| WO | 03097790 A2 | 11/2003 |
| WO | 2015169927 A1 | 11/2015 |
| WO | 2015197727 A2 | 12/2015 |
| WO | 2016210303 A1 | 12/2016 |
| WO | 2018067985 A1 | 4/2018 |

OTHER PUBLICATIONS

Thompson, S., "Phenotype Analysis of Tobacco Lines Expressing a Deregulated *Arabidopsis* Ca-ATPase (ACA2)", Thesis, Texas A&M University, Dec. 2010, 65 pages.*

Database Uniprot, "Manganese tolerance protein 2", EBI accession No. G5CCK8, 4 pages, Dec. 14, 2011.

Database Uniprotkb, "Metal tolerance protein 9-like", Accession No. A0A1S4DAN3, 6 pages, Apr. 12, 2017.

International Searching Authority in connection with PCT/GB2019/052165 filed Aug. 1, 2019, "The International Search Report and the Written Opinion of the International Searching Authority, or the Declaration", 18 pages, mailed Jan. 24, 2020.

Caldwell et al., "Intragastric Nitrosation of Nicotine Is Not a Significant Contributor to Nitrosamine Exposure", Annual New York Academy of Sciences, vol. 686, pp. 213-227, May 28, 1993.

Futai et al., "Handbook of ATPases: Biochemistry, Cell Biology, Pathophysiology", pp. 1-24, published Jun. 24, 2004.

Kadiiska et al., "On the Mechanism of the Enzyme-inducing Action of Some Heavy Metal Salts", Arch Toxicol, vol. 56, pp. 167-169, 1985.

Saitoh et al., "The Alkaloid Contents of Sixty *Nicotiana* Species", Phytochemistry, vol. 24, No. 3, pp. 477-480, 1985.

Bush et al., "Formation of Tobacco-Specific Nitrosamines in Air-Cured Tobacco", Recent Advances in Tobacco Science, vol. 27, pp. 1-26, 2001.

Gavilano et al., "Genetic Engineering of *Nicotiana tabacum* for Reduced Nornicotine Content", J. Agric. Food Chem., vol. 54, pp. 9071-9078, 2006.

Hildreth et al., "Tobacco nicotine uptake permease (NUP1) affects alkaloid metabolism", PNAS, vol. 108, No. 44, pp. 18179-18184, Nov. 1, 2011.

Kato et al., "Tobacco Nicotine Uptake Permease Regulates the Expression of a Key Transcription Factor Gene in the Nicotine Biosynthesis Pathway1[C][W]", Plant Physiology, vol. 166, pp. 2195-2204, Dec. 2014.

Lewis et al., "RNA interference (RNAi)-induced suppression of nicotine demethylase activity reduces levels of a key carcinogen in cured tobacco leaves", Plant Biotechnology Journal, vol. 6, pp. 346-354, 2008.

Mei et al., "In planta regulation of the *Arabidopsis* Ca2+/H+ antiporter CAX1", Journal of Experimental Botany, vol. 58, No. 12, pp. 3419-3427, 2007.

(Continued)

*Primary Examiner* — Phuong T Bui
(74) *Attorney, Agent, or Firm* — McKee, Voorhees & Sease, PLC

(57) ABSTRACT

The present invention relates to a method of reducing the content of at least one tobacco specific nitrosamine (TSNA) or a precursor of a TSNA in tobacco comprising expressing a deregulated cation efflux protein in a tobacco plant, or plant part thereof, or plant cell.

3 Claims, 58 Drawing Sheets

Specification includes a Sequence Listing.

(56) References Cited

OTHER PUBLICATIONS

Morita et al., "Vacuolar transport of nicotine is mediated by a multidrug and toxic compound extrusion (MATE) transporter in *Nicotiana tabacum*", PNAS, vol. 106, No. 7, pp. 2447-2452, Feb. 17, 2009.
Otani et al., "Characterization of Vacuolar Transport of the Endogenous Alkaloid Berberine in Coptis japonica1", Plant Physiology, vol. 138, pp. 1939-1946, Aug. 2005.
Siminszky et al., "Conversion of nicotine to nornicotine in *Nicotiana tabacum* is mediated by CYP82E4, a cytochrome P450 monooxygenase", PNAS, vol. 102, No. 41, pp. 14919-14924, Oct. 11, 2005.
Shitan et al., "Identification of a nicotine transporter in leaf vacuoles of *Nicotiana tabacum*", Plant Signaling & Behavior, vol. 4, Issue 6, pp. 530-532, Jun. 2009.
Shoji et al., "Multidrug and Toxic Compound Extrusion-Type Transporters Implicated in Vacuolar Sequestration of Nicotine in Tobacco Roots1[C][W]", Plant Physiology, vol. 149, pp. 708-718, Feb. 2009.
Xu et al., "Biochemical and molecular characterizations of nicotine demethylase in tobacco", Physiologia Plantarum, vol. 129, pp. 307-319, 2007.
Jiang et al., "Research progress on cation diffusion facilitator (CDF) family proteins," Journal of Natural Science of Heilongjiang University, Aug. 2014, vol. 31, No. 4, pp. 517-528.
Lopez-Redondo et al., "Structural basis for the alternating access mechanism of the cation diffusion facilitator Yiip," PNAS, Mar. 20, 2018, vol. 115, No. 12, pp. 3042-3047.
Nechifor, M., "Magnesium and Zinc Involvement in Tobacco Addiction," Journal of Addiction Research and Therapy, 2012, vol. S2, pp. 1-5.

* cited by examiner

TMD: Transmembrane domain; RD: Regulatory domain; CED: Cation efflux domain; Circles: metal

FIG. 5

SEQ ID No. 1

ATTATTTTTTCCTATATAAACATTAATCATACGACTACAACCAGAGGAATTAATCGTTCAAATATAACT
AACTACTCCTCTAAACATGGAGATAAGTCGCAGCAATGTTAGTGGTGGTGGCGGCAGCGGCGGCGC
TCTGGACGACAGTTTTAGCAGTTTTAGGACGGAACTGCTGTCTCCGGCTGCTCAGGCGGTGGTGGAT
CAGTCGTCTTCGTCGGCGTCATGGAGACTTAACATTAGCGAATTCCGTCTTCCCGAACGAAGCCGCTC
CTCCTCCGATCATCACTCCTTTAGTGTCCGTCGTCTACTTCCCACTCCCAGTATGTGTATATATATATAT
ATATATATATATATTCCTCACTTCACTTGTCTTTACAATGTATTAAACCTTTCTACTTCCTTTGAACTTCT
TCGGATTTGTTAATTAATGTTAAGAGATTTGAGGGAAGCCTTGGCTTACTGGTAAAGTGATGGCATG
TGACTTCCCAGTCACATGTTTAAGCCGTGTTAAAGTTGTTGGCATGTGACCTCCTGGTCACAGGTTTA
AGCCGTGGAAATAGACTTTCGTAGAAATACAGGTAAAGAAATGCAGGTAAGGTTGCGTACTTGTGA
TCTGGCCCTTTCTCGAATCTCGCACATAAATGAAGCTTAGTGCCTTTTTTTAAGGTTAATAGTTTTTTA
GTCAGAATAGTACCAAAATTAGACTAGAAGATTCATAGTTCTAATATTGGTAAACCAAAATTTACGAC
TTATATATATTTACATAAATGGGCGAGGAATCTTTATTCTTATCATGCCATAGTCCATGGAACGTACT
GAGCCTTTAATTTCTATTTGCTATTGCTGGGAAATGAATCAGATGGCCAATTTTCTTATGTATACATAT
TCTCACTGGTATGGGATCGAATCGGCGACAGAACTCCAAGTTAGAGGATTCTTTTTCATTAAGTCATT
ACTTATTTTAAGTTCAAGTAACAGCACTGGAAGTTCAACTAAGAGTTGATAAACATGATCAGTGAAA
CTCACAATTGTTTGTCCTAAATTTTGGATCTTTACTTGGAAAGTGTAGATGTTAGTATATGCTTATGCT
ATACTGGCCAGCAGTGCTCGTAACAGTATCTATGAGTACTAATAGGCTTATGCTATATTACTGTATTT
ATAATGCTAATCAGCTAATGAGATATGATAACTCATATATGACAACTACAGTAGGAAATTCAGATAA
CCATATTCATTTTTTCAGTAGTCTCAGTTTTGAGTTTTGCTTTTCCCTTGCCTGAGTTTACCTAATGGAA
TCATTTGAAATTCATCCGTAGGGAAACAAGGTAAAATTGCTGAATACTACAAAAAACAAGAAAGGCT
GCTTGAAGGGTTCAATGAGATGGACACCATTAATGAATCTGGTTGTTTACCTGGAAGTCTAACTGAG
GTGTGTTTCTGGAATCTGGATACTGTTTTCAATTGATGATAAGTATGTGAATTTTTGTATCGACCGATC
ATGTTTGTTCAGGATGAAATGAAGCAGCTTGCAAGAAGTGAAAGGATGGCTATTCATTTATCAAACA
TGGCTAATGTGGTTCTTTTCATTGCAAAAATCTACGCTTCTATTGAGAGCAGATCTTTGGCTGTAATC
GCGTCAACGTTGGACTCCCTCTTAGACCTCTTATCAGGGTTTATACTGTGGTTCACTTCTCATGCCATG
AAAAATCCAAACCAGTATCACTATCCTATTGGAAAAAAGAGGATGCAGCCATTGGTGAGTCTTCAAA
TATATGTGACATCCCTTAAAAGAATTATCTCTGGCATTTGTTCTGTTTCGTGTCTGCGATAAAATGACC
TTAATGTTCAATTCATGGATCATATTTTACCTTGTTTCTGTAGAACCCTTTTTACTCATTAGATGCAATT
TGTTCAGGGTATTATTGTTTTTGCATCTGTAATGGCGACACTAGGATTACAAATATTGTTCGAGTCAG
CTAAAGAACTCATAACTAAGGTATGTGAATTGCTTCACTTCAACTATCCTGAGAATTTTCAGAGCAGC
AGGTTCTTATGGTTAGTAGAGTTTTGAGTTTCTAAAATCTTTTACATCAAGACAAAAAAAAACATGCA
ATTTATAGGAAACAAGAAGACGAAAAACGGGTTGAGTTACTACTGAAATGAAGTTGTAGCCAAACC
AGTTAGGCCAAAGATGTTTACATAAGATAAATTAGGCTACTGTATACTACCTAATAAAAAGGGACTG
GTTTTGATATTTCTACTGATGTTGCATAGCTAAGTGAAGATTAACTCGCATAGTGCTACTTCAATTGTA
GGATATAGACTTGTAACTTACTGCAATTTCACTAACAATTGCATTACCCTTGACATCTTAATCTACGTT
TGTTGTTTCGGTGGTTCTATGCTTACGATCAGTCTCGCCCTGAGATGGACCATGAGAAGGAAAAATG
GACGATTGGTATTATGGTCTCTGTCACTATGGTCAAGTTTCTGCTTATGGTCTACTGTCGAAGGTTCA
AAAACGAAATCGTAAGAGCCTATGCTCAAGATCATTTCTTTGATGTCATCACCAACTCAGTTGGATTA
GTGACTGCTGTCTTAGCAGTCCGATTCTACTGGTGGATTGATCCTACGGGAGCTATAATTGTGAGTTC
ACAATCACAACTCAAATATTTCAATTAGTAAGCTTGTAAATATATACTCCAACCTTGTTTCACACTGCT
GGTGATGTTAAGAGTCTAATACATCTTGCATATTCAGATAGCTATGTACACAATTAGCACGTGGGCG

FIG. 5 (Continued)

AAGACAGTGGCAGAAAATGTCTGGTCACTCATTGGAAGAACAGCTCCACCAGATTTTCTTACGAAAT
TAACCTATCTTATATGGAATCATCACGAAGAGATCAAGCACATTGATACTGTTCGAGCATATACTTTT
GGTGCTCATTATTTTGTAGAGGTTGATATAGTGTTGCCAGAGGACATGCTGTTGAACAAGGCACATA
ATATTGGTGAGACACTGCAAGAAAAATTGGAGCAACTCCCTGAAGTTGAGCGAGCTTTTGTTCATAT
AGACTTCGAGTTCACTCACAGGCCAGAACACAAAACTATGGTATAATGACACCAGAATTTAAACTCT
ATGTGTTCAACCTTAAAGATTTTTAGCGTTGAATCAATCATATTTTTAAAGTTATGGGTTCATTTCTAC
TATTTGTTGCAATTTTAATAATTTTTACGCATAAATTTGTATTTCGCGTCGAAAGTACTAGGTTCACAT
GAATCCGGTATCAAAGGGCTAGATCCGCCCCCTGACTACACATCATTTACGGTGTTTCTTTTTGTAAC
TCAAAATAATTTTAATGGTGCTTCTTAGAGTTGAATCTGTGAATTAGTCGCACCTTTAAGGCTTATGA
GATGGG

FIG. 6

SEQ ID No. 2

ATGGAGATAAGTCGCAGCAATGTTAGTGGTGGTGGCGGCAGCGGCGGCGCTCTGGACGACAGTTTTAGC
AGTTTTAGGACGGAACTGCTGTCTCCGGCTGCTCAGGCGGTGGTGGATCAGTCGTCTTCGTCGGCGTCAT
GGAGACTTAACATTAGCGAATTCCGTCTTCCCGAACGAAGCCGCTCCTCCTCCGATCATCACTCCTTTAGT
GTCCGTCGTCTACTTCCCACTCCCAGGAAACAAGGTAAAATTGCTGAATACTACAAAAAACAAGAAAGGC
TGCTTGAAGGGTTCAATGAGATGGACACCATTAATGAATCTGGTTGTTTACCTGGAAGTCTAACTGAGGA
TGAAATGAAGCAGCTTGCAAGAAGTGAAAGGATGGCTATTCATTTATCAAACATGGCTAATGTGGTTCTT
TTCATTGCAAAAATCTACGCTTCTATTGAGAGCAGATCTTTGGCTGTAATCGCGTCAACGTTGGACTCCCT
CTTAGACCTCTTATCAGGGTTTATACTGTGGTTCACTTCTCATGCCATGAAAAATCCAAACCAGTATCACTA
TCCTATTGGAAAAAAGAGGATGCAGCCATTGGGTATTATTGTTTTTGCATCTGTAATGGCGACACTAGGA
TTACAAATATTGTTCGAGTCAGCTAAAGAACTCATAACTAAGTCTCGCCCTGAGATGGACCATGAGAAGG
AAAAATGGACGATTGGTATTATGGTCTCTGTCACTATGGTCAAGTTTCTGCTTATGGTCTACTGTCGAAGG
TTCAAAAACGAAATCGTAAGAGCCTATGCTCAAGATCATTTCTTTGATGTCATCACCAACTCAGTTGGATT
AGTGACTGCTGTCTTAGCAGTCCGATTCTACTGGTGGATTGATCCTACGGGAGCTATAATTATAGCTATGT
ACACAATTAGCACGTGGGCGAAGACAGTGGCAGAAAATGTCTGGTCACTCATTGGAAGAACAGCTCCAC
CAGATTTTCTTACGAAATTAACCTATCTTATATGGAATCATCACGAAGAGATCAAGCACATTGATACTGTT
CGAGCATATACTTTTGGTGCTCATTATTTTGTAGAGGTTGATATAGTGTTGCCAGAGGACATGCTGTTGAA
CAAGGCACATAATATTGGTGAGACACTGCAAGAAAAATTGGAGCAACTCCCTGAAGTTGAGCGAGCTTTT
GTTCATATAGACTTCGAGTTCACTCACAGGCCAGAACACAAAACTATGGTATAA

FIG. 7

SEQ ID No. 3

MEISRSNVSGGGGSGGALDDSFSSFRTELLSPAAQAVVDQSSSSASWRLNISEFRLPERSRSSSDHHSFSVRRLL
PTPRKQGKIAEYYKKQERLLEGFNEMDTINESGCLPGSLTEDEMKQLARSERMAIHLSNMANVVLFIAKIYASIE
SRSLAVIASTLDSLLDLLSGFILWFTSHAMKNPNQYHYPIGKKRMQPLGIIVFASVMATLGLQILFESAKELITKS
RPEMDHEKEKWTIGIMVSVTMVKFLLMVYCRRFKNEIVRAYAQDHFFDVITNSVGLVTAVLAVRFYWWIDPT
GAIIIAMYTISTWAKTVAENVWSLIGRTAPPDFLTKLTYLIWNHHEEIKHIDTVRAYTFGAHYFVEVDIVLPEDM
LLNKAHNIGETLQEKLEQLPEVERAFVHIDFEFTHRPEHKTMV

FIG. 8

SEQ ID No. 4

ATAAACATTAATCATACGACTATAACCAGAGGAATTAATTGTTCAAATATTAGAAACTACTCCTCTAAAC
ATGGAGATGAGTCGGAGTGACGTTAGTGGTGGCGGCGGCAGCGGCGGCGCTTTGGACGACAGTTTTAGCA
GTTTTAGGACGGAACTACTGTCTCCGGCTGCTCAGGCGGTGGTGGATCAGTCGTCTTCTTCGGCGTCATG
GAGACTTAACATTAGCGAATTCCGTCTTCCCGAACGAAGCCGCTCCTCCTCCGATCATCACACCTTTAGT
GTCCGTCGCCTACTTCCCACTCCCAGTATGTATGTGTATATATATATATATTATATTCCTCTCTTCACTT
GTCTTTACAATGTATTAAACCTTTCTACTCTTTGAACTTCTTCGGCTTTGTTAATTAGTGTTGAGAGTTT
TGAAAGGTAGCCTGACGTAACTGGTAAAGTTGTCGCCATGTGACCTCCTGGTCACAGGTTAGAAATAGTC
TCTTGCGTAAATGCAGGGTATGACTGCGTACAATATTTATATGAAATAAATATGAAGTACAAGAACCCAG
ACTCTCTCAAAACACCACGCATAGCTGGAACTTAGTGCACTAGCCACGCTTTTTAATGTTAAGAGTTTTC
TACTCAGAATAGTACCAAAATTAGACTAGAAGATTCATAGTTCTAATATTGGCAAACCAAAATTTACGAC
TTATATATATTTACATAAATGGGCGATGAATCTTTATTCTTATCATGCCATAGTCCATGGAACATACTAA
GCCTTTAATTTCTACTCCCTCCGTTTCAATTCATGTGAACTCATTTGATCGGGCACGGAATTTAAGAAAA
GAGAGAAAACTTTTGAACTTCTGGTGTAAATGAGGCACATATATTTTATGTGGCTATAAATTATTGCATA
AAGATAAATTGTTTCCAAATAGGGAAATGACTCATTCTTTTTGGTATGTACTAAAAAGGAAATAGGGAAA
CGGAGGGAGTATTTGCTATTGCTGGGAAATGAATCAGATGGCCAATTTTCTTATGTATATATACATATTC
TCACTGGCATGGGATCAAATCGGCGACAGAACTCCAAGTTAGAGGACTCTTTTTCATGAAGTCATTACTT
AATTTAAGTTCAAGTAACAGCAGTGGAAGTTCAACTAAGAGTTGATAAACATGATCAGTGAAACTCACAA
TTGTTCGTCCAAATTTCGGATATTCACTTGGAAGGTGTAGATGTTAGTATATGCTTATGCTATATTGGCC
AGCAGTACTCGTAGCAGTATCTATGAGTACTAAAATGCTTATGCTATATTACTGTATTTGTAATGTTAAT
GAGATATGATTACTCATATATATGACAACTACAGGGGGAGATTCAGATAACCAAGTTCATTTCAGTCTGT
AATTCAGTCTCAGTTTTGAGTTTTGCTTTTCTCTTGGGTGAGTTTACCTGATGAAATTATTTTAAATTCA
TCCGTAGGAAAACAAGGTAAAATTGCTGAATACTACAAAAAACAAGAAAGGCTGCTTGAAGGGTTCAATG
AGATGGACACCATTAATGAATCTGGCTGTTTACCTGGAAGTCTAACTGAGGTTGGTTTCTGAAATCTGGA
TACTATTTGCAATTGACGAATAAGTATGTGAATTTTTGTATCGACCGACCATGTTTTTTCAGGATGAAAT
GAAGCAGCTAGCAAGGAGTGAAAGGATGGCTATTCATTTATCAAACATGGCTAATGTGGTTCTTTTCATT
GCAAAAATCTACGCTTCTATTGAGAGCAGATCTTTGGCTGTAATCGCGTCAACGTTGGACTCCCTCTTAG
ACCTCTTATCAGGGTTTATACTGTGGTTCACTTCTCATGCCATGAAAAATCCAAACCAGTATCACTATCC
TATTGGAAAAAAGAGGATGCAGCCAGTGGTGAGTCTTCAAATATATGTAACATCCTGAAATTATTATCTC
TGGCTTTTGTTCTGTCTTCGTTTATTTGCAAAAATGACCTTAATGTTCAATACATAGATCACATTTTACA
TTTGACCTTCACATTTTTTCCTTTGCTGTTGCTGATACATTGTCTCTTTCCTTCTTGTGCCGAGGGTCTA
CCGAAAACAGCCTCTCTACTCCTCCGGAGTAGGGGTAAGGTCTGCGTACACACTACCCTCCCCAGACTCA
ACTTGTGGGATCTCATTGGGTTGTTGTTGTCTGTAGAACTGTTTTATAGATCACATTTTACCTTGTTTCC
GTTGAACCGTTTTTACTCATTAGTTGCATTTTCTTCAGGGTATTATTGTTTTTGCATCTGTGATGGCGAC
ACTAGGATTACAAATGTTGTTCGAGTCTGCTAAGGAACTCATAACTAAGGTATGTGAATTGGTTCACCTC
AACTATCCTGAGAATTTTCAGAGCAGCAGGTTCTTATGGCTGTATTAGTAGAGTTTTGAGTTTCTATAAT
CTTTAACATCAAGATGAAAAACCATGCAATTTATAGGAAACAAGAAGACGAAAAAGGGGTTGAGTTACTA
CTGAAATGAAGTTGCAGTCAAAACAGTTAAGCCAAAGATGTTTACATAAGATAAATTAGGCTACTGTATA
CTACTAATAAAAGTGACTGGTTTTGATATTTCTATTGATGTTGCATAGCTTAATAAAGATTATCTCGCAT
AGTGCTACTTCTATTGTAGGATATAGACTTGTAAGTTATTGCATTTTCACTAACAATTGCATTACGCTTG
ACATCTTAACCTATGTTTGTTGTTTCGATGGTTCTATGCTTACGATCAGTCTCGCCCTGAGATGGATCAT
GAGAAGGAAAAATGGACAATTGGGATTATGGTCTCTGTCACTATGGTCAAGTTTCTGCTTATGATCTACT
GTCGAAGGTTCAAAAACGAAATCGTAAGAGCCTATGCTCAAGATCATTTCTTTGATGTCATCACTAACTC
AGTTGGATTAGTGACGGCTGTCTTAGCAGTACGATTCTACTGGTGGATTGATCCTACAGGAGCTATAATT
GTGAGTTCACAATCACAACTCAAAAACTTACACAATTAGCAATCACACTTCTGGTAATGTCAATAGTCTA
ATATATTTTGCATATCCAGATAGCTGTGTACACAATTAGCACGTGGGCGAAGACAGTGGCTGAAAATGTC
TGGTCGCTCATTGGAAGAACAGCTCCACCAGATTTTCTTACGAAATTAACCTATCTTATATGGAATCATC
ACGAAGAGATCAAGCACATTGATACTGTTAGAGCATATACTTTTGGTGCGCATTACTTTGTGGAGGTTGA
TATAGTGTTGCCAGAGGACATGCTGTTGAATCAGGCACATAATATTGGTGAGACACTGCAAGAAAAATTG

FIG. 8 (Continued)

GAGCAACTCCCTGAAGTTGAGCGAGCTTTTGTTCATATAGACTTTGAGTTCACTCACAGGCCAGAACACA
AAACCATGGTATAATGACATAGTGGTTGCAACAAGTACGCACATAGGCGGATCCAAGCTTTAAACTCTAT
ACGTACAACCTTTAAGATTTTTAGCGTTGAACTGATCATATTTTTAAAGTTATGGCTTCATATCTACTAC
TATTTGTTGCAATTTTAATAAATTTTTTTACATAAATTTGTATTCTACATCGAAAGTACTGGGTTCAGAT
AAACTTGGTGACCAAAGGGCTGGATCCGCCCCTGACTACACATTATTTACA

FIG. 9

SEQ ID No. 5

ATGGAGATGAGTCGGAGTGACGTTAGTGGTGGCGGCGGCAGCGGCGGCGCTTTGGACGACAGTTTTAGCA
GTTTTAGGACGGAACTACTGTCTCCGGCTGCTCAGGCGGTGGTGGATCAGTCGTCTTCTTCGGCGTCATG
GAGACTTAACATTAGCGAATTCCGTCTTCCCGAACGAAGCCGCTCCTCCTCCGATCATCACACCTTTAGT
GTCCGTCGCCTACTTCCCACTCCCAGAAAACAAGGTAAAATTGCTGAATACTACAAAAAACAAGAAAGGC
TGCTTGAAGGGTTCAATGAGATGGACACCATTAATGAATCTGGCTGTTTACCTGGAAGTCTAACTGAGGA
TGAAATGAAGCAGCTAGCAAGGAGTGAAAGGATGGCTATTCATTTATCAAACATGGCTAATGTGGTTCTT
TTCATTGCAAAAATCTACGCTTCTATTGAGAGCAGATCTTTGGCTGTAATCGCGTCAACGTTGGACTCCC
TCTTAGACCTCTTATCAGGGTTTATACTGTGGTTCACTTCTCATGCCATGAAAAATCCAAACCAGTATCA
CTATCCTATTGGAAAAAAGAGGATGCAGCCAGTGGGTATTATTGTTTTTGCATCTGTGATGGCGACACTA
GGATTACAAATGTTGTTCGAGTCTGCTAAGGAACTCATAACTAAGTCTCGCCCTGAGATGGATCATGAGA
AGGAAAAATGGACAATTGGGATTATGGTCTCTGTCACTATGGTCAAGTTTCTGCTTATGATCTACTGTCG
AAGGTTCAAAAACGAAATCGTAAGAGCCTATGCTCAAGATCATTTCTTTGATGTCATCACTAACTCAGTT
GGATTAGTGACGGCTGTCTTAGCAGTACGATTCTACTGGTGGATTGATCCTACAGGAGCTATAATTATAG
CTGTGTACACAATTAGCACGTGGGCGAAGACAGTGGCTGAAAATGTCTGGTCGCTCATTGGAAGAACAGC
TCCACCAGATTTTCTTACGAAATTAACCTATCTTATATGGAATCATCACGAAGAGATCAAGCACATTGAT
ACTGTTAGAGCATATACTTTTGGTGCGCATTACTTTGTGGAGGTTGATATAGTGTTGCCAGAGGACATGC
TGTTGAATCAGGCACATAATATTGGTGAGACACTGCAAGAAAAATTGGAGCAACTCCCTGAAGTTGAGCG
AGCTTTTGTTCATATAGACTTTGAGTTCACTCACAGGCCAGAACACAAAACCATGGTATAA

FIG. 10

SEQ ID No. 6

MEMSRSDVSGGGGSGGALDDSFSSFRTELLSPAAQAVVDQSSSSASWRLNISEFRLPERSRSSSDHHTFS
VRRLLPTPRKQGKIAEYYKKQERLLEGFNEMDTINESGCLPGSLTEDEMKQLARSERMAIHLSNMANVVL
FIAKIYASIESRSLAVIASTLDSLLDLLSGFILWFTSHAMKNPNQYHYPIGKKRMQPVGIIVFASVMATL
GLQMLFESAKELITKSRPEMDHEKEKWTIGIMVSVTMVKFLLMIYCRRFKNEIVRAYAQDHFFDVITNSV
GLVTAVLAVRFYWWIDPTGAIIIAVYTISTWAKTVAENVWSLIGRTAPPDFLTKLTYLIWNHHEEIKHID
TVRAYTFGAHYFVEVDIVLPEDMLLNQAHNIGETLQEKLEQLPEVERAFVHIDFEFTHRPEHKTMV

FIG. 11

SEQ ID No. 7

ACAGTTTGAGCCTATTTTTCCTCTCATTATATCTATGTGTTATCTTTCCTCAAAAGTATCTTTAACTAAA
CCTATCTTTAGAAGAGTCCTTTTGCGTCTCCCTACTTCGACTTACTAGTATACAACTATAGATAAATATC
AAAACACAAGTACATTGTCATTCGTACAAATATTTAGTAACAATTTTCATGGAAATCGTTGGCGGTAACG
GTGGTGATCATGGCGGCGCCACTCATCAGCCGTTGCCGTTGTCGTTATCTTCCTCTTCGCCGTCGGCGTC
GTGGAGGCTGAATATAGGGGAGTTTCGTGTCCCTGAAAATGGCACTGCTGATCATCGTCAATCTTTCAGT
TTACGTCGACTCTTACGTCGCCCTTCTAGTAATTTTCCTTCCTTTTATCTTTTATATTTCTTCTATGATA
TTGTTTGCTAGCTTTATTGCACTTGTCGAAAAAAAAAAAACTACTTGGAAATCATTGCATTTTAATGGTA
TTTGAATCCATTCAACCATCTCCTAGCAAATTACTCCCACCGTTTTATTTTATGTGAATTTGTTTGACTG

FIG. 11 (Continued)

AAAACAAAATTTAAGAAAGGAATTACTACTTTGGAACTTGTAGTATTAAACATTTCACCACCTTAATTTG
TATGTAAAATAAAAATAATTAATGTTAAATTATTTCTAAATATAGAAAGATCGTCTTTTTTTGAAAGCAA
GATTAAAAAATAATTGTGTGTTTTAAGTACAACTCACTTCAACCAATTGTTTTAAGTTCTAACTTTGGTT
TGGATATCCTTTTTTTTCTTTTGTCTTCAAGAACTACTTAACTAAGAAAATAGTTTTTATAAATTTTCTA
TTACCTATCTTAGTTTTCAGCCTGTCAACATCCATTATTTGTAAGGATTTTATCTTTTATCTTACAAATC
ATTTTCATATATATCTCTATATATAGAAAAACAAGGCAAAGTAGCTGAATATTACGAGAAGCAAGAAAGG
TTGGTTGAAGGGTTCAATGAGATGGACACTGTTCATGAATCTGGCTTTTTACCTGGAACTCTAACCGAGG
TTCGTCTCTTTTCCTCAATAATAAACTGATAATGAAAGAATTTATACGTCACTTAAAAATTCACACAAGA
TATGATATATAGGCCGGTGCATAAAGTATTCTGTATCCACGCAGGGTCTTGGAAGTATCACCGCACCACC
TCAAGAAGTGTGATGTAGACAGCCGACCTAATGCAAATATTAGTGGTTGCTTTTACGGCTCGAACCCGTG
ACCTGTAGGTCACACGACAACTTTATTATTTTTTTAGTCATGAGTCTCATGACCTATATGTCACTTAAAA
ATATATTACTGTTAAATATTTATAATAAGAAAAATTAATAACCTGGAAAATAAGTCAAACAGCCTCGTAG
GATATATATATTAATAGTGTAATTTTTTTTTTATAGTCAATATTTGGCCTCAGTATCACAGCTTGGGGAT
ATGATGTCGGGGCATGTGTCCCCTAACTTTTCTAAGTTTAATTTCCTACTCTTAGGAAATGTCAAATTTT
TGGAAATTTTGCTTTAGTGAAAATTCTTCTTCTCCTTCTTTCCTTGTAAAAGTGTCCTACTCTTCAGAAG
TTTTGTGTTTTTGGCATAAGTTTACTTGTGGGAGGTCAACTTTACTATTTTTCAAGTTCGTTACTTCACT
TATTTATAGATGGTTAGTTTAAGTTATCTTTCAAGTGACATATAGTAGTAGAAAATTTTTAGATTGTTAAT
GCATAAAAGGTTAAAAGTTAAACTCAAAAAAAGAGCATAACTTATAAACAACAATTACTTTTTTTTAAAC
CTTTTGTTAGGTCACTTAACAGATAATTACAAGTCACGGTCTATAATATATAAGTGAGACTAGTAATCTT
AACAAATTCTGATAACTTGCTACAACAGGTCAAAATAGTCTAACTAATAAAGTAGGATTAATCTCACTTT
TATTCTCTACAACTCAATATTTGTCAGGATGAAATGAAGCAGCTTGCTAAGAGTGAGAGGATGGCAATTC
ATGTATCAAACATAGCAAATGTGGTTCTTTTCATTGCAAAAATCTATGCTTCTATTGCAAGTAGATCTTT
GGCTGTGATTGCATCAACTTTGGACTCACTCTTAGACTTATTGTCTGGATTTATTCTGTGGTTCACTGTA
TATGCAATGAAAAATCCAAACCAATACCACTATCCAATTGGTAAAAAGAGAATGCAGCCTGTGGTGAGTC
TTCAAAAATAACGTTGTGACATTTTGATATTTGTTACATTCATTCTATACTTTGTGTCAGTCTGATATGA
GTTTTATAGCCAAATAAAATATTTATATGTAATATTTATAGGGTATTATTGTTTTTGCATCGGTGATGGC
AACCCTTGGATTACAAATACTATTTGAGTCTGGTAAAGAACTCATACATAAGGTACGTGACTCGGTTCTC
TAAAGTCTTTTTTTAGAAAAAAAAAGGAATTTCTAAATTTAACTTTTCAAAATAATACAAAATGATGAAA
ACTGTTCTCCTATATCATGATCTTTCTCTTGGACTTCAAGACGCAGTTGTTTATGCTACATTATTTGGCT
ATTAGATGAAGTATTGACCAATATCTTTATGCACGTTAGTTGACTTTTATGTACTCATAGTATAAAAAAG
ATATTTATACAATTTGGTCTTATATAACGTGATATATGTAACTTTGATGATAAGCATTACTCCATTTGTT
TAATTAATATGACGGTATTTCACTAAATATGGAGTTCAAGAAACAAAAAAAAAGGAGACTTCTGCAACTT
GTGTTCATACATGCCATGAAATTTTGTGGCTATAAAATCATGTCATTAAGGATAAAATGCAAGATGAGGA
GTAATTGGTAAATATTTAGTACTATCACAGATTAAACTACACTAATGTCAGTTTATTGTTTCTTCTTGTT
CAATGCTTATCATATCAGTCTCGTCCTAATACGGATCCTGAGAAGGAAAAATGGATGATTGGGATCATGG
TCTCTGTCACTGTTGTTAAGTTTCTGCTTATGGTTTATTGTCGAAGATTCAAGAATGAAATTGTAAGAGC
CTATGCTCAAGACCATTTATTTGATGTCATTACCAACTCTGTTGGATTAGTGACTGCAGTTTTAGCAATT
CGATTCTGCTGGTGGATTGATCCTACGGGAGCTATATTGGTGAGTTCACAATCATCACTTATACTTCTTT
TGCTTTTATCTACTTATTTAATAGGCATCTCGATGCATAACGTATTTCCCGTTCATACATGATTCGGGAA
AAGCCGCACCTAAAAGGTATGATATAGATATCCTACCCTAATGCAAGCATTAATGATTGCTTTCACGGTT
CGAACCATATAGTGGTGTTCGCATCAACTTGCGCAGCACCTCAACTATTTCACTTAGTACATGTAATCTC
TCACTAAAAAATTTACCGGACACCTTGTTACTCCCCAAGGCTTTGGCGTGTGGGAATAACTTGTATTTTT
TGTCTCTACTAGAAAAGGAATCCTAATTTCAACCTTTATATCAATTTTATTGATCACTAAGTCATACTCT
TGGGTGCACGTGCACACACATACGACACTACATCTGTCTCAATTTACTAAGTACTATTTCCTTTTTGTTT
TCTTTTGTCCTGAAAGATTGATATCTTTATAGCTTTAGAAACTCCAAACATTTATTTATATTTTTATATC
AAGATTGACACCTTTATGTATATATGGTATTTCTGACTTATTAAGCATATTAAACTTCTATGTCAGAGAT
CTCTTTTATTTTTTAAACTTCATGTCTAGTCAAAGGATGCTAAACCAATTGTGGTGGACGACTATCACTA
AATGATTGAGCAAATAAAATGAGTAGAAATTTTCAAAGACATCCCTCCAAATTTTCCATTATTATTAAGG
ATAACATTATGTATTTGCAGATAGCACTATACACAATTGGTACGTGGGCAAAGACAGTAATCGAAAATAT
GCGATCACTCATCGGAAGAACAGCTCCACCAGAATTTCTGGCGAAATTAACATATCTTATATGGAATCAT
CACAAAGAAATCAAGCACATTGATACTGTGAGAGCATACACATTTGGTACAAATTACTTTGTGGAAGTTG

FIG. 11 (Continued)

ATATAGTTTTGCCAGAGGACATGCTTCTAAGCCAAGCACATAATATTGGTGAAACATTGCAAGAAAAATT
AGAGCAGCTTCCTGATGTTGAGAGAGCTTTTGTGCATGTTGATTTCGAGTTCACTCATAGACCAGAGCAC
AAGACTATGGTCTAATGACATAAATAAACTAGGTAATTAATAATTAAAAATTAGTTTGAGCTTGAACTTT
GTTGTTGGGCACTGTTTCCTTGCACCTGGAGTAGTAACTTACCAAAAAAAAAAGTTCTTTAATGTGGAGA
ACCCAACCATGTTGAAACTTGTTGAATTTGCATTCTCAAAATTTATGTAACCTAATGTTTATTTTTAACT
CAAGATGCCTCATGAGTCATGAACGACAAGTATATACCTACGT

FIG. 12

SEQ ID No. 8

ATGGAAATCGTTGGCGGTAACGGTGGTGATCATGGCGGCGCCACTCATCAGCCGTTGCCGTTGTCGTTAT
CTTCCTCTTCGCCGTCGGCGTCGTGGAGGCTGAATATAGGGGAGTTTCGTGTCCCTGAAAATGGCACTGC
TGATCATCGTCAATCTTTCAGTTTACGTCGACTCTTACGTCGCCCTTCTAAAAAACAAGGCAAAGTAGCT
GAATATTACGAGAAGCAAGAAAGGTTGGTTGAAGGGTTCAATGAGATGGACACTGTTCATGAATCTGGCT
TTTTACCTGGAACTCTAACCGAGGATGAAATGAAGCAGCTTGCTAAGAGTGAGAGGATGGCAATTCATGT
ATCAAACATAGCAAATGTGGTTCTTTTCATTGCAAAAATCTATGCTTCTATTGCAAGTAGATCTTTGGCT
GTGATTGCATCAACTTTGGACTCACTCTTAGACTTATTGTCTGGATTTATTCTGTGGTTCACTGTATATG
CAATGAAAAATCCAAACCAATACCACTATCCAATTGGTAAAAAGAGAATGCAGCCTGTGGGTATTATTGT
TTTTGCATCGGTGATGGCAACCCTTGGATTACAAATACTATTTGAGTCTGGTAAAGAACTCATACATAAG
TCTCGTCCTAATACGGATCCTGAGAAGGAAAAATGGATGATTGGGATCATGGTCTCTGTCACTGTTGTTA
AGTTTCTGCTTATGGTTTATTGTCGAAGATTCAAGAATGAAATTGTAAGAGCCTATGCTCAAGACCATTT
ATTTGATGTCATTACCAACTCTGTTGGATTAGTGACTGCAGTTTTAGCAATTCGATTCTGCTGGTGGATT
GATCCTACGGGAGCTATATTGATAGCACTATACACAATTGGTACGTGGGCAAAGACAGTAATCGAAAATA
TGCGATCACTCATCGGAAGAACAGCTCCACCAGAATTTCTGGCGAAATTAACATATCTTATATGGAATCA
TCACAAAGAAATCAAGCACATTGATACTGTGAGAGCATACACATTTGGTACAAATTACTTTGTGGAAGTT
GATATAGTTTTGCCAGAGGACATGCTTCTAAGCCAAGCACATAATATTGGTGAAACATTGCAAGAAAAAT
TAGAGCAGCTTCCTGATGTTGAGAGAGCTTTTGTGCATGTTGATTTCGAGTTCACTCATAGACCAGAGCA
CAAGACTATGGTCTAA

FIG. 13

SEQ ID No. 9

MEIVGGNGGDHGGATHQPLPLSLSSSSPSASWRLNIGEFRVPENGTADHRQSFSLRRLLRRPSKKQGKVA
EYYEKQERLVEGFNEMDTVHESGFLPGTLTEDEMKQLAKSERMAIHVSNIANVVLFIAKIYASIASRSLA
VIASTLDSLLDLLSGFILWFTVYAMKNPNQYHYPIGKKRMQPVGIIVFASVMATLGLQILFESGKELIHK
SRPNTDPEKEKWMIGIMVSVTVVKFLLMVYCRRFKNEIVRAYAQDHLFDVITNSVGLVTAVLAIRFCWWI
DPTGAILIALYTIGTWAKTVIENMRSLIGRTAPPEFLAKLTYLIWNHHKEIKHIDTVRAYTFGTNYFVEV
DIVLPEDMLLSQAHNIGETLQEKLEQLPDVERAFVHVDFEFTHRPEHKTMV

FIG. 14

SEQ ID No. 10

TATAGAAGAGTCCTTTTGCTTCTCCCTACTTGCAAATGATAAATATCAAAACACAAGTACATTTTCACTC
GTACAAATACTAGTAACAATTTTCATGGAGATCGTTGGCAGCAACGGCGGTGATCATGGCGGCGCCACCC
ATCAGCCGGTGCCGTTATCTTCCTCTTCACCGTCGGCGTCGTGGAGGCTGAATATAGGGGAGTTTCGTGT
CCCTGAATATGGCACTGGTGATCATCGTCAATCTTTCAGTTTACGTCGACTCTTGCGTCGCCCTTCTAGT
AATTTTCCTTCAATTTATCTTTTTTTTTGTCCTTTTATGATATTGTTTTCCATTTTTTGCACTTGTCGAA
GTAAAAACTACTTGAATAAATGGTTGAATTAAGACAAATATTGATTAATCTGAAGGTATTAAATCATTGC
ATTTTAATTGTCATTGAATTCATTTAACTATCTCCTAGAAAACTACTCTCTCGATTTTATTTTATGTGAA

FIG. 14 (Continued)

TCTATTTGATAAAAGATGAAAACTTAAGAAAGAACGGCTTTGAAACTTATGAGTTACATTTCAACATATT
TGTGCAGTAAAATTAAAAAAAAATTAAAGTAATATTATTTTTTAAATATAAAAAAGATCATGTCATTCTT
TTTAAAACAAGATTAAAAAGTAAATTGCTCTTTTAAGTACAACTCAATTCTACCAATGGTTTTAAGTTCT
AACTTTGGTTTGGATATCCTTTTAATTTCTTCTTCTTTTGTCTTCAAGAACTACTCAACTAAAGAAATTG
GTTTTAGTCTTTTTAAACAAAGAGGTATGACATTTTTTTCGATAGCTTAAAACGGAAAGTATGACATATA
AATTGGAATATATATATATGAATTAAGTACTATTATAAATTAAATCATATTTTTAAGGATTTTGTCTTTTAT
GTTACACGACTTGATGAGATCATTTTAATATCTCTATATATAGAAAAACAAGGCAAAGTAGCTGAATATT
ACGAGAAGCAAGAAAGGTTGCTTGAAGGGTTCAATGAGATGGACACTGTTCATGAATCTGGCTTTTTACC
CGGAAGTCTAACCGAGGTTTGTCTCTTTTCCTCACACTATTAAGTTACTTAAAAAAATTATTACCATTATT
TATTTATAATAAATAAAATTAGTAACCTGAAATATAAGACAAACAATATCTTATACGATATGTATACTAA
TAGTGTAAGTTTTCTTGTTACGTCAATATTTCACAGATAGGTGACATGATGTCGGGGCCGGTGTTCCCNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNN
NNNNNNNNNNNNNATTTTCCGGTGAAGGGATGCCAATTGAGTCCCCTTGCCAATGAGTGGCTCCGCCACTG
CTTTCGGCATAAGTTTACTTGTGGGAGGTCTACTTTCCTACTTTTCAAGTTCCTTACTTCAC
TTAGGAAATTTTTCAAGGAATTTAGGGTGTTCAAACTTGAAAGAAATGAAAAAATCTCCAATAAATTAAA
GAGTGTTCAATATATATATATATATATATATATAAAGATTAATATTTTACCTATATAATCAGTGTAATTT
TTTGATGAAGGGTGATCAATTAACCATCATTGATTGTTACTTAAATTTTATTGTATCGTATCGTTAAATC
CGTCGTTACGTAACGACGAAAAGTACTACTTTGTGTAACGACCAATTTGGTGTGGTCTCATCGTTACCTT
GTCTTTTCTCTCATTTCGCCCTTCATTATAATTAAATTATTTTATTTTATCTTTTACCCTGCTTCTTTAT
ATAGTAATAATTTTATTCCGTGTCATAATTTTTCTTTATGATATTGCAAATGTATTCTTCATATTGCTGG
TACTTGATATCATGAAACGACGACAAACGATACAATCTATTCAAACATTGTATTTATCAAACAATACAGT
ACAATATAATACAATACAATATATATACACTGATATCGCAAAAAAAATTATTTGCTATAATTAGTAACTT
GAAAAGTGGAACAGACAACCTAATAAAACATGTTTGCTGTCTACACTTGATATTTGACAGGATGAAATGA
AGCAGCTTGCTAAGAGTGAAAGGATGGCAATTCATGTATCAAACATAGCAAATTTGATTCTTTTCATTGC
AAAAATCTATGCTTCTATTGCAAGCAGATCTTTGGCTGTGATTGCATCAACTTTGGACTCTCTCTTAGAC
TTATTGTCTGGATTTATTCTGTGGTTCACTGTTTATGCTATGAAAAAACCAAACCAATACCACTATCCAA
TTGGTAAAAAGAGAATGCAGCCTGTGGTGAGTTTCAAATATAATGCCACATTTTGATATTTATTACATGC
ATTTTATACTTTGTGTCAGTGTGCAGTGTGATTTTAAGATTTATACTTGTAAGTAGGGGTGGCAGACGGT
CGGGCCGGGTCGGGTATGAGCGAGCCAAAACGGATAATTTAAAAAAATGGACAAATTATCCGCCCCGACC
CGTATTTGAAATGGATAAAAACGGGTTTATCCGGCGTATATGGATATCCATATTATCCCTGGCTTCTTAA
ATATGATCAGTACATATGAGAGAATTCTTTGTCTTCCAAACTTTGAGGAACTCCAATTTGAAGCTTTACA
ATGTATAAGCTAAACATATTAGTTATCCATTTGGTTAACCATTTTCTGAGTGGATAATATGGTTCTTTAT
CCATATTCGACCCATTTTTAAATGGTTCATTATCCAACCCATGTTTTAATGGATAATATGGATGGATAAC
TGTTTTTTTAAACCATTTTGCCACCTTTTCTGGTAAGTAAACTGGCCTTTATACACAATTAAAAGAAGCA
AAACATCTACCCTCCTCTTCATACTTAAAGATTGACAAAAGATTGGAGTTAACTTATATACATTAATTTT
TATATTATTTTTGCTGTAATAGGTTGTGTACCATCCCTTATAGGTTATCATATCATGTTACCGGTATCAA
AAGTTACTTTTTTTGTCAATTAACTTCATAATTAATGTACTAATTATTTACATTGTCCGTTAGAGCAGTT
AAGTATACTATTTGTGTATTTTGTCCTATTATTTTATATTTGAAGTTATCAAATTAGGGTTACTATAGAT
AGTTACCTGTAATTATATGCCATTATTATAATTTGACAGTGTAAAAAATTTCTAACCGCTCGGTGTACAC
AAGCTAAGCTCTAAATGAAAAGGTAGCCAAAACTAACATTTTAATTATCATATCAAAATCCTTTATTTCC
TTGTTTCTTCTTAATTAAAGACTACCAACAACAACAACAGCAACAACCCAGTGTAATTCCACAAGTGGGG
TCTGGGGAGGGTAATATGTACGCAGACCTTACCTCTACCCCGAGGGACAGAGAGGCTGTTTCCAGGAGAC
CCTCGCATTCTTTAACATTTTATCATATCATATTTACAGGGTATTATTGTCTTCGCATCTGTGATGGCAA

FIG. 14 (Continued)

CTCTTGGATTACAAATACTATTTGAGTCTGGTAAGGAACTCATATATAAGGTATGTGACTCAGTTTTCTG
AAGGATTCTATACTAGGAATAGATTTAAACTTATAGTTTTAAACCTATCAAGGCATTTCTGTAATCTATA
AAAAACTTCTTTAAGGTTAAAATGAAAATTTAAGGCTAAATTATTTTCAACTTTGGATATGTGTCATTAT
TTTTTGGACAGACGAATAAATAATGAGTGTCACATAAAATCAAATAAATTGAGTAATTGGTAACCTGGTA
AACATGATAATTGACTTACTATCACAAGTTAAACTACAGTTATATCATAAAAAAATATTTTGTCAGTGTA
TTTATCTTAAATTTATGCATAGTTAAACCTCTCTATAACAATCTCGTTTATTTCGAATATTTTTGGATGT
TATAGCGAAATGTTGTTATAGAGAATATATATTATAACATAATTTAAAAATTGGTTCCGAAAAAGTTTGG
CTTTTATAGTGAGGTGTTGTTATATAGGGATACTGTTATAGAGAGGTCCGACCGTAAAAGTAATTGAATT
TCACTAGTAAAATGCTTAATGCTCCACTCTTTAACACCAGATTTATTGTTTCTTCTGGTTTAATGCTTAT
GATCATCAGTCTCGTCCTAATACGGATTCTGAGAAGGAAAAATGGATGATTGGGATCATGGTCTCTGTCA
CTGTGGTAAAATTTCTGCTGATGTTGTATTGTCGAAGATTCAAGAATGAAATTGTAAGAGCCTATGCTCA
AGACCATTTCTTTGATGTCATTACCAACTCTGTTGGATTAGTGACTGCAGTTTTAGCAATTCGATTCTGC
TGGTGGATTGATCCCATGGGAGCTATATTGGTGAGTTCACAATCATCACTTATACTTCTTTTGTTTTTAT
CTCTACTTTTCTAGATGGCAGTCCGGTGCATAAAGTATTGTAAGTCCACGCAAGATCCGAATGAGAGTCG
CACCCAAAGAGTATGACGTAGACATCTTACCCTAATGCAAGGATTAGTGGTTGCTTCCACGGCTCGAACC
TGTAACCTTTAGGTCACATGGAGAGAACTTGCACATATATAGTGATGTTTGCATCAACTGGCGCACAACT
CAACTATTTCACTTAGTACATGTTATCTCTCACTAAAAAATTTACCGGACACCTTGTTACTCACCAAGGC
TTAGGCGTGTGGAATAACTCGTATTTTTTGTCTCTACTAGTAATGGAATCCTAATTTCAACCTTTATACC
AATTTTATTGACCACTAGGTCATACTCGTGGATGCATCGTGCACACACATACGACACTACATCTGTCTCA
ATTTACTAGGCACTATTTCCTTTTTTTTCTTTTGTCCTACAAGATTGACATCTTTATAGCTTTAGAAACT
CCAAACATTTATTTATATTTTTATATCAAGATTGACACCTTTATGTACGTATATATGGTATTACTGACTT
ATATATTAAGCATATTTAACTTCTGTGTCAGTTATCTCTTTTATTTCTTAAACTTCATGTCTAGTCGTGC
TAAACCAATTGTGGTGGACGACTATCACTAAATGAATGAGCAAATAAAATGAGTAGAAAATTTCAAAGAT
ATCCCTCCAAATTTTCCATTATTATTAACGATAACATTATGTATTTGCAGATAGCACTATACACAATTGG
CACATGGGCAAAGACAGTAATCGAAAACATGCGATCACTCATCGGAAGAACAGCTCCACCAGAATTTCTG
GCGAAATTGACATATCTTATATGGAATCATCACAAAGAGATAAAGCACATTGACACAGTGAGAGCATACA
CATTTGGTGCAAATTACTTTGTGGAAGTTGATATAGTTTTGCCAGAGGACATGCTTCTAAGCCAAGCACA
TAATATTGGTGAAACATTGCAAGAAAAATTAGAGCAGCTTCCTGATGTTGAGAGAGCTTTTGTGCATGTT
GATTTCGAGTTCACTCATAGACCAGAGCACAAGACTATGGTCTAATGACATAAATAAACTAGGTAATTAA
TAATTAATAATTAGTTTGAGCTTTAACTTTATTCTTTGGACACTGTTTCCTTGCACCTAAAGTAGTAACT
TACCAAAAAAAAAGTTCTTTAATGTGGAGAACCCAACAATGTTGAAACTTGTTGAATTTGCATTCTCAAA
ATTTATGTAACCTAATGTTTATTTTTAACTCAAGATGCCTAATGATTCATGAACAC

FIG. 15

SEQ ID No. 11

ATGGAGATCGTTGGCAGCAACGGCGGTGATCATGGCGGCGCCACCCATCAGCCGGTGCCGTTATCTTCCT
CTTCACCGTCGGCGTCGTGGAGGCTGAATATAGGGGAGTTTCGTGTCCCTGAATATGGCACTGGTGATCA
TCGTCAATCTTTCAGTTTACGTCGACTCTTGCGTCGCCCTTCTAAAAAACAAGGCAAAGTAGCTGAATAT
TACGAGAAGCAAGAAAGGTTGCTTGAAGGGTTCAATGAGATGGACACTGTTCATGAATCTGGCTTTTTAC
CCGGAAGTCTAACCGAGGATGAAATGAAGCAGCTTGCTAAGAGTGAAAGGATGGCAATTCATGTATCAAA
CATAGCAAATTTGATTCTTTTCATTGCAAAAATCTATGCTTCTATTGCAAGCAGATCTTTGGCTGTGATT
GCATCAACTTTGGACTCTCTCTTAGACTTATTGTCTGGATTTATTCTGTGGTTCACTGTTTATGCTATGA
AAAAACCAAACCAATACCACTATCCAATTGGTAAAAAGAGAATGCAGCCTGTGGGTATTATTGTCTTCGC
ATCTGTGATGGCAACTCTTGGATTACAAATACTATTTGAGTCTGGTAAGGAACTCATATATAAGTCTCGT
CCTAATACGGATTCTGAGAAGGAAAAATGGATGATTGGGATCATGGTCTCTGTCACTGTGGTAAAATTTC
TGCTGATGTTGTATTGTCGAAGATTCAAGAATGAAATTGTAAGAGCCTATGCTCAAGACCATTTCTTTGA
TGTCATTACCAACTCTGTTGGATTAGTGACTGCAGTTTTAGCAATTCGATTCTGCTGGTGGATTGATCCC
ATGGGAGCTATATTGATAGCACTATACACAATTGGCACATGGGCAAAGACAGTAATCGAAAACATGCGAT
CACTCATCGGAAGAACAGCTCCACCAGAATTTCTGGCGAAATTGACATATCTTATATGGAATCATCACAA
AGAGATAAAGCACATTGACACAGTGAGAGCATACACATTTGGTGCAAATTACTTTGTGGAAGTTGATATA

FIG. 15 (Continued)

GTTTTGCCAGAGGACATGCTTCTAAGCCAAGCACATAATATTGGTGAAACATTGCAAGAAAAATTAGAGC
AGCTTCCTGATGTTGAGAGAGCTTTTGTGCATGTTGATTTCGAGTTCACTCATAGACCAGAGCACAAGAC
TATGGTCTAA

FIG. 16

SEQ ID No. 12

MEIVGSNGGDHGGATHQPVPLSSSSPSASWRLNIGEFRVPEYGTGDHRQSFSLRRLLRRPSKKQGKVAEY
YEKQERLLEGFNEMDTVHESGFLPGSLTEDEMKQLAKSERMAIHVSNIANLILFIAKIYASIASRSLAVI
ASTLDSLLDLLSGFILWFTVYAMKKPNQYHYPIGKKRMQPVGIIVFASVMATLGLQILFESGKELIYKSR
PNTDSEKEKWMIGIMVSVTVVKFLLMLYCRRFKNEIVRAYAQDHFFDVITNSVGLVTAVLAIRFCWWIDP
MGAILIALYTIGTWAKTVIENMRSLIGRTAPPEFLAKLTYLIWNHHKEIKHIDTVRAYTFGANYFVEVDI
VLPEDMLLSQAHNIGETLQEKLEQLPDVERAFVHVDFEFTHRPEHKTMV

FIG. 17

SEQ ID No. 13

AAGTACTAACGTAAGCGAGTGTGCGTGGTTTCTTGATTGGACGGACGGTGGGTGAGTGGTACGGATCCTT
TGCATTCCCATTGTCCATATTCATGCCGTATTCCTAATTCCTAATAATAACTATTCCAGTATAAACAGTA
TTCAAAGTTCCAACGAAGTTCATAATTAACCAGCAGCTACTCATCTAAACATGGAAATCAGTCGCAGTAA
TGATAGTGTCACACTGGACGACAGTTTTAGGACGGAGTTGCTGTCTCCCGCTGCTCAGGCGGTGGTTGAT
CATTCCATGACTTTGGGGCCGACGTGGAAGCTCAACACAACTGACTTCCATCTTCCCCAACGCCGCTCCT
CTGATCATCAATCTTTCAGTTTCCTCCGTCTCCTACGAGTTTTCAGTAATTCCTCAGCTCATGCCATTAG
CATTTACTTTTCAAGTACTCCTGTTTATTTTACATGACATGTTGGAGTTTTTTTTTTTTTTTAAAAAAAGG
AAAACTTTTTGCATATATTATTCTAGTGCCTATATTCCATGTTAATCTATTATTTTTTGGGGAGTCAAAT
AATATTTTTTTTAACCACATTTTTTACAAATACTTTTTAAATATTTTGGAAAATTAACTATGGTAATTTA
TAGTAGTAGTTTTGATGTAATTTCTAAATATGTAAATTTAATTTCAAAAAGATTTAAAATTTTATGTGCA
AATTCATACTAAATATTAATTATTTTGATCCTAACTATTTTCTCCGGTCCACTTTAAGTGATTTTTTTGG
CCTTTTTTGTGGTCTACAATATCTGATTGTTTCATATATTAAGAATGAATTAACTTCTTCTTTCCAAAGT
TGTCTTTGGAGTAAAGAATCTAGGAGTAGTTTGTTATATTTCTAATGAACAAATTAAGGTTAAAATGATT
AATTTTATTGTTAATTAATTCTAAAAGGTGAATTTTTTAATATGTGTGAAAAGAGTAAAAAAAAATACTT
AAAGTGAACCGGAGGAAGTACTATTAAGAACTTGCCATTAATTGAAAATTTAAAGCTAAAGAGTTACCGT
ATACAAAGATGTATCCTTTTAGACCATCTCCGACTCTAACATCAAATTTCACACCAAATTTACTCCAACC
ATTACACCATTTTTTACACTAAAAAGAATATTTCTTCTCTCTCTTCTATATTATATTATTATCTTCTATT
TAAATTTTATTTTTTATTTCCTTCAAACAAATTCTATCTTTTTTTTTTCCATATTCATCATATATAATTC
ACATTCACCACTTATATAATTTTTTTTCCATATTCACCATATATAATTCTATCTTTAGCAACATTAGATA
TCTTACATTTGCATTTTTTATTTTTAAATAATGGTTATGTTTCTTTTTATACAATTATAATAATAATAAA
ATTAACTTATAATTTTATATAAATATAATATATACAAAAATTAAAATATCAAAAAAATAGGGTATAAAAT
TAAAATTATAAATATCTTAATATAAAAATTAATTATATACACAATATATGATAAATTAAAAGTTCAAAAA
AATAAAAAAAATAAAAAAGATGAATAAAATAATAATAAATCAAATTTGGTGTTGATGAATAGTGTCGCAC
CACACTATTTACGCACTATAATGGTGCAAGATTTGGTGTTCCATTGGAGCAAAAAAAAAAAATACCAAATT
TAAATTTTGTGCAAAAAATAGTGCACCTTTGAAGATACCCTTACACTTAAATGTTTGTTATTTTTCTTTA
GGATATCTGAAGCCTTTGAAACTCGATCAGTTTCCCTTTGACCCCTTTAATTTGTAACCTTAGAGTATTCT
AGTGTTATTATTATAATATCTAACAACTCTTTCTGATCATGACTATTACCTAACTTATTGATTGTTAATA
CTATCGTCTTTCAAGTGGTTCATTAGCATTACCAAAACAAAAAAAATGGTTCTTTAGTTTCTGAATATAG
AATATTGGAGTTTGATATTTTCTGGGAGTTGAAGGCTGAAGGGTGAAATTACAATCTTGTTTCTAATAGT
ACTTTACTTAAAGTTTCAATTCTTGTCTGTAGCAGAATATTATTTTGTTAATTTTCCTTCTTCCACTCTA
GCAATTTTAATTGGTTTAAGAGGGGAAATGGTCAAATATTAGCGCCTTATTATTTATTTACATCTTCCAA
CTAATGGAAGAGGAAAACGGGTAGATGGTTTTATTCAAATCCTTTACTATCTTTAATTATGTGGGACAAG
CACAGAGTTACGATTTTGAATCACTGAAAAGAGAATTGCTTGGCAAAGAAGAATTTTGAAAAGTTGTATC

FIG. 17 (Continued)

TAAAAATTTAGTAAATACAAAATCATAAAAATTTAAATACTCCGAGTCTCCAAGAACAGTTGTGCGGGAT
GCACAGGATCATGTAACATATTCTGAAGCTTGTATTGCTGATTTTTCATACTAAGGTGTCGTTTGGTAGA
GATATTAAAATAAAAATAAAAATAATGCAAGCATTAGCTTAATTTGTGCATTACTAATCCCTGGTTTGGT
ACATTTTTTCAACATATGTGTATTAGTTATACCTCCGATTTGGTATTATCCAATGTATAACTAAAACATA
ACAAACTATGGTATTAACAATGCAAGAGTTTTTAATACTTGTATAAACATGGTTAAAGACATAACTGCCC
CTCAAATCCCTCAAAACCTATTCCAAATATTTTTCGCCATATTTTTGTGGAGGGTATATTTGTAAACAAT
CAATTTTTTAAGAAATTATGCAATGCCTTAATATACCAAACTAAACAGTGGATAAGAAATAATCTCAATA
TAATTAATGATAGTATAACTAGTCTCAACATTATTAATACCATCGTTACTGATACACCTTATTCAACATT
ATTTTTAAACCTCCTACCAAGCGACCCCTAAGAATGTTTTATTTGAAGTAACTTCAAATCATATACTTGA
CCTCATTCTTGTAAAAAAAATTTGTTTGTTGAGAAGGTAAACTTGTTAAAGAAATTAGTCACATTTCTTC
CCTTTTGCATATAAAACTACGGATATCAAAGAGTTTTTGGTGTTTTATTTTGTTCAAGGTTATTAGTCCT
GTTTGATTTTGCTCTACAACTCTACAGTTTTCTTTCATATTTACTCTCTTAAAATTTAAGAAGGCGCCGG
TAATTTAACTACCAGGTTGAGGACTACCTAGCAGCCCGCGGATGGATAGGGTGGGGGAAGCGCGAAGGGG
ATGGATGTCTGAGCGGTTGAAAGAGTCAGTCTTGAAAATCAAAGTATTTATAGAATACCGGGGGTTCAAA
TCCCTCTCCATCCGCGAGATCATAAGTTGGTCTCTTGAGTTATATATAGATAAGAAGATATTGGGTCGAC
TGGACTGATATGATAGATGGAATGGTAGACTGAAGTTGTTACTTATTTTCAGTTAAGGAACAAAAATTCA
CTTGATACTCTGTAAGGGTGATATGCAAAGCAGGCAACAAAATCCATCTTTGTTGGACCAAAATATGCTC
TTAATTACTTGTAAATGTTCCCTGACCAAATGCTTTGATTGCTGAAGCTAATAGTTTAAAAACTTATCTT
TCTTGGACTGAAATAGGCTCTCTTATTTGGAATGGACATATTCAAGAATATAAGTTATCATACCCTTAGG
AATGATATACTAAGTAGGTGATTTCAGATAATCAGATTCATTGTTTCAGATAATTAAACTTTCCATTTCC
GTCTTCACTTTCTTGATCACTTGATGGAATCGTGTTAATCATGTATAGGGAATCAGAGAAAAGTTGCTGA
ATACTACAAAAAACAAGAAAGGCTGCTTGAAGGATTCAATGAGATGGACACAATTAATGAATGTGGTTAC
TTACCTGGAAATCTAACTGAGGTTGGTCTATGAGATTGGCAGATTCTTATCAGTTTAATCATCACAATTT
TTTAGTCGTCAAAATAACTTTCTTTTCTTTGTTGCACTGTCAACCAATATATACAATCACCTTTAGTGAA
ATTCGTGTGTTTGTGGATCAACTTGTGTTTATCTTCTATTGTTGTTCATAAAGCTATAATTTGCAATTTC
AAATCTCAGATGTTGTTTTTCAGGATGAATTGAAGCAACATGCTAAGAGCGAAAGGATGGCTATTCTTGT
GTCAAACATAGCAAATATGGCTCTTTTCATTGCTAAAATCTATGCTTCTATTGACAGCAGATCACTGGCT
GTAATTGCGTCTACCTTAGACTCCCTATTAGACCTCTTAGCTGGATTTATTCTGTGGTTCACTTCTCATG
CAATGAAAACGCCAAACCAATACTGTTATCCAATTGGAAAGAAGAGAATGCAGCCAGTGGTGAGTCTTCT
ACTGTTTTAATTTCTTCCAACGAACACCCTTGTTTCAGGGTATTTCTCCGAAATTAAAGTAAAAAGAAGA
AAAAAAACATATCCCTTCAGCTCCCAAGAAAGAAAAAGAAAAGATGTCTTCGCCAATTTCTGTTTATTGT
TTGAACTGATCTGCTGCAATATTTTCAGGGTATAGTTGTTTTTGCATCCGTAATGGCGACCCTGGGATTA
CAAATATTGTTCGAGTCTGGTAAAGAACTCATAACTAAGGTATGTAACTTGGTTCTCTTCAAGTGTGTTG
TGAGATGGATGTGTCATGTGTGAGCTGGTACAAGGTTGAATTTCCAAATACATGTATTTTGTAAAATTAA
TGTCGAATTGATAAAGAACTTCCCCAGAAAGTGCATTTTGGCAGCAAAATATAAAATATCTTAGAAGGTT
CTGATACCATGTTAAGCAAAATAAATTTTGGACCTAATTCAACACAACAGTTCACTCATGAGATGAGGAT
TTTTCGAGGTCATATAAAGCGATTAGAGCTCAACCTGTGTGGGATGCTAAAAATATTCATAATTCTTCTT
CCCCTAAAAGTCAGTAGCCTGGAGTTCTCTCTAGGTTTTTGTACTTCTACAATTGATTTTAAATTATTTA
CAGAGTTGAAATGGTAGTACTTTGTCCCAAGTAATTCATTCTTCACATTGATGGACATTTATATTGTTGA
AAACTAGCACTAGCTTTTATGTTAAATGAGATAGATTTTATGTACGATGTGAGTGCTTTAGGAAAAGTAG
TTGATCTTAAGGATCAAAAGGAAAGACCAAAATTAGAAGCTGAATTGCTGCTAAAAGGAATTTGCAGTAG
CATGTACAAGTTAGGCCCTCTAATCTATGTATAATGGTAAACTAGCTGTTTGTGCTCTAATTGAAATCGA
CTAGTCTTGATACGAGGATGCAACATAGATTAATAAGGACTATTCCTACACAATACATTTTGTATTGAAG
GACTGAACTCTAATTTGCCGGAATTTCATTTTGTAATATGCCTGACACTTAACCTCAATTTGTTTTTCTG
GTTCCATGCTTAATGATTTGTTTTTCTGGTTCTATGCTTAATGATTAGTCTCGTCCTGATATGGACCCTG
AGAAGGAAAAATGGATGATCGGAATTATGGTTTCTGTCACTGTGGTCAAGTTTATGCTTCTGATCTACTG
CCGAAGATTCAAAAATGAAATTGTAAGGGCCTATGCTCAAGACCATTTCTTTGATGTCATTACCAACTCA
ATCGGGTTAGCGGCAGCAGTCTTAGCCATCCATTTCTATTGGTGGATTGATCCTACTGGAGCTATAATTG
TGAGTTTAGAATTACAACACACGAACTCTTTAATCTATATACCTTGTCTGTTATCGCAATTGAGATATTT
TTGCATTCCTATGGACAACTGATCATCCTTTGTTATGTGTTTCAGATAGCACTTTACACAATGAGCACAT
GGGCAAAGACAGTGATGGAAAATGTGTGGTCACTTATTGGAAGAACAGCTCCACCCGAATTTCTAGCAAA

FIG. 17 (Continued)

GTTAACATATCTTATATGGAATCACCATGAAAGGATCAAACACATTGATACTGTTAGAGCATATAATTTT
GGCATACAATATTTTGTGGAGGTTGATATAGTGCTGCCGGAGGACATGTTCCTGAACCAGGCACATAATA
TTGGTGAAACGCTGCAGGAAAAATTGGAGCAACTTGTTGAAGTTGAGCGTGCTTTCGTCCATGTAGATTT
TGACATAACTCATAGGCTGGAACATAAGTCTATGATCAAATGACGTCAAATTGACATATAATTTTTAGAA
TGACGGCCGCTTAATTCCTGTTTAATTATACCATTGTATTTCCTATTTGTTACTCTCTATATTGGATCAG
ATGAGCTTTATCATCCGTCCCAGCTGAGAGCTTTATCGTCCTTTGGTGTGTCCCTCACCTCTCTCTTTTG
AGGCCTGTTTCCTCTACTGTCACTTCTTT

FIG. 18

SEQ ID No. 14

ATGGAAATCAGTCGCAGTAATGATAGTGTCACACTGGACGACAGTTTTAGGACGGAGTTGCTGTCTCCCG
CTGCTCAGGCGGTGGTTGATCATTCCATGACTTTGGGGCCGACGTGGAAGCTCAACACAACTGACTTCCA
TCTTCCCCAACGCCGCTCCTCTGATCATCAATCTTTCAGTTTCCTCCGTCTCCTACGAGTTTTCAGGAAT
CAGAGAAAAGTTGCTGAATACTACAAAAAACAAGAAAGGCTGCTTGAAGGATTCAATGAGATGGACACAA
TTAATGAATGTGGTTACTTACCTGGAAATCTAACTGAGGATGAATTGAAGCAACATGCTAAGAGCGAAAG
GATGGCTATTCTTGTGTCAAACATAGCAAATATGGCTCTTTTCATTGCTAAAATCTATGCTTCTATTGAC
AGCAGATCACTGGCTGTAATTGCGTCTACCTTAGACTCCCTATTAGACCTCTTAGCTGGATTTATTCTGT
GGTTCACTTCTCATGCAATGAAAACGCCAAACCAATACTGTTATCCAATTGGAAAGAAGAGAATGCAGCC
AGTGGGTATAGTTGTTTTTGCATCCGTAATGGCGACCCTGGGATTACAAATATTGTTCGAGTCTGGTAAA
GAACTCATAACTAAGTCTCGTCCTGATATGGACCCTGAGAAGGAAAAATGGATGATCGGAATTATGGTTT
CTGTCACTGTGGTCAAGTTTATGCTTCTGATCTACTGCCGAAGATTCAAAAATGAAATTGTAAGGGCCTA
TGCTCAAGACCATTTCTTTGATGTCATTACCAACTCAATCGGGTTAGCGGCAGCAGTCTTAGCCATCCAT
TTCTATTGGTGGATTGATCCTACTGGAGCTATAATTATAGCACTTTACACAATGAGCACATGGGCAAAGA
CAGTGATGGAAAATGTGTGGTCACTTATTGGAAGAACAGCTCCACCCGAATTTCTAGCAAAGTTAACATA
TCTTATATGGAATCACCATGAAAGGATCAAACACATTGATACTGTTAGAGCATATAATTTTGGCATACAA
TATTTTGTGGAGGTTGATATAGTGCTGCCGGAGGACATGTTCCTGAACCAGGCACATAATATTGGTGAAA
CGCTGCAGGAAAAATTGGAGCAACTTGTTGAAGTTGAGCGTGCTTTCGTCCATGTAGATTTTGACATAAC
TCATAGGCTGGAACATAAGTCTATGATCAAATGA

FIG. 19

SEQ ID No. 15

MEISRSNDSVTLDDSFRTELLSPAAQAVVDHSMTLGPTWKLNTTDFHLPQRRSSDHQSFSFLRLLRVFRN
QRKVAEYYKKQERLLEGFNEMDTINECGYLPGNLTEDELKQHAKSERMAILVSNIANMALFIAKIYASID
SRSLAVIASTLDSLLDLLAGFILWFTSHAMKTPNQYCYPIGKKRMQPVGIVVFASVMATLGLQILFESGK
ELITKSRPDMDPEKEKWMIGIMVSVTVVKFMLLIYCRRFKNEIVRAYAQDHFFDVITNSIGLAAAVLAIH
FYWWIDPTGAIIIALYTMSTWAKTVMENVWSLIGRTAPPEFLAKLTYLIWNHHERIKHIDTVRAYNFGIQ
YFVEVDIVLPEDMFLNQAHNIGETLQEKLEQLVEVERAFVHVDFDITHRLEHKSMIK

FIG. 20

SEQ ID No. 16

TGCATTCCCATTGTCCATATTCACGCCGTATTCCTAATAACTATTCTAGTATAAACAGTATTCAAAGTTC
CAACGAAGTTCATAATTAACCAGCAGCTACTCATCTAAACATGGAAATCAGTCGCAGTAATGAGAGTGTC
ACACTGGACGACAGTTTTAGGACGGAGTTGCTGTCTCCCGCTGCTCAGGCGGTGGTTGATCACTCCATGT
CTCTGGGGGCCGACATGGAAGCTCAACACAACTGACTTCCATCTTCCCCAACTCCGCTCCTCTGATCATCA
ATCTTTCAGTTTCCTCCGTCTCCTACGAGCTTTCAGTAATTCCTCAGCTCATGCCATTAGCCTAATTTTC
TTTTCAACTACTCCTGTAATCACATGTTGGATTTAAAAATAAAAAAAAAATAAAAAATCTTTTTTGCATA

FIG. 20 (Continued)

TATTATACTAGTGCCTATGTTCCATGTTAATCTATTATTATTTGGGGTGTCACATAATATTTTCTTTAAC
CACATTTTTTACAAATGTTTTCTAAATACTTATTTTGGAATATTAATTATGGTAATTTATACAGTAGTAG
TTTTTATGTAATTTCTAAATATGTAAATTTAAAATTACTAGTTAATTTGATCCTAACTACAATTAAGTAC
TTGCCATTATTTGAAAATTTAAAGCTAAAGAGTTACCGTATACAAAGATGTATCCTTTTACATTTATTTT
AGTGTTTGTTATTTTTGTTTACTATGTCTGAAGCCTTTGAAACTCGTTCGGTTTCCCTTTGACCTTTTAG
TTTGTAACCTTAGAGTATTCTAGTGTTATTATTATAATATCTAACTACTATTTCTGATCATAAGTCATGA
CTATTACCTAACTTATTGATAGTTAATACTATCGCCTTTCAAGTGGTTCATTAGCATTACCAAAAAAAGT
AGTTCTTTAGTTTCTGAATATAGAATATCGGAGTTGGATATTTTCGGCGAGTTGAAGCCTGAAAAGTGAA
ATTACAATCTTGTTTCTAATAGTACTTTACTTCAAGTTTCAATTCTTGTCTGTAGCATTGTAGTGGAGCA
GAATATCCTAATGTGCTCAGGAGATCTTATTAACAAAGTTTTGAATCGATTAGATATGATGGGCACTTCA
AAGGGATCAAACTTGCTAAATAAACTGGCAACTTTATAATTCAAACACCGATATGTAAAAGCTCATGGGC
CATGTCGCGACTTCATTTTGTCCTAAAAGTTCAAAGTTCCTGGTCAGATTTTTCTTTTATTATTTTGTTA
ATTTTCCTTCTTCCGCTCTAGCAATTTTAATTGGTTTAAGAGGGGAAATGGTCAAATATTAGCGCCTTAT
TGTTTATTTACATCTTCCAATTAATGGAAGAGAAAAACGGGTAGATGGTTGTATATCCAAATCCTTTACT
TTCTTTAATTATGTGGGACAAGCACAGAGTTACGATTTTGAATCATTGAAAAGAGAATTGCTTGGCAAAG
AAGAATTTTGAAAAGTTGAATCTAAAACATTTAGTAAATAGAAAATCTCAAAAATTTAAATACTCCGAGT
CTCCAAGAACAATTGTGTGGGATGCAATTGTGAAGCTTGTATTACTGATTTTTCATACTAAGGGTCGTTT
GGTAGGGGATATTAAAAAAAATAATGCAGGCATTAACTTTGTGCATTACTAATTGGAAAAATGACAATGT
ATAGGCGATGTAAAAATAATAGACGAAAAAATGTATAAAATTTGTATATTTTTTTGTATATATATACATT
TTGTATTTTGTATATATATACATTTTGTATGTTATATACAAAAATTATGCAAATTTTATACACTTCCGGC
TACCAGATGTAAATAGTTTCTAGCGCGGGCTAAAAGTGATAATACCCCTTACTAATCCCTTGTTTGGTAC
ATTTTTTGTATTAGTTATACATCCCATTTAGCATTATATTATGTATAACTAAAACATAGCAAACTATGGT
ATTAGCAATGCAAAAGTTTTTAATACTTGTATAAACATGGTTAAAGACATAACTACCCCTCAAATCCCTC
AAAACCTATTCCAAATATTTTTCACCATATTTTTCTAGAGGGTATATTTGTAAACAATCAATTTTTTAAG
AAATTATGCAATGCTTTAATATACCAAACTAAACAGTGGATAAGAAATAATCTCAGTATAATGCCGGCAT
AACTAATCCAGCACTACTGATGCACCTTATTCAACACTATTTTTATACCTCCTACCAAGCGACCCCTAAG
ATTGTTTTATTTGAAGTAACTTCAATGTTTTATTTGAAGTAACTTCAAATCATATACTTGATCTCATTCT
TGTAAAAGTGTTTTTTTTTTTGGTTGAGAAGGTAAACTTATAAAAGAAATTAGTCACATTTGCTTCCCTT
TGGCATATAAAACTACGGTGTTCCAGATATTAAAGAGTTTTGGGTGTTCTATTTAGTCCGCGGTTATTAG
TCCTGTTTGATTTTTCTCTACAGCTCTAGATTTTTCTTTCATATTTACTCTCTTAAAAGTTAAGAAGGCG
CCGATAATTTAACTACCAGGTTGAGGACCACCTGTCAGCGCGCGGATGGATAGGGTGGATGTCTGAGTGG
TTGAAAGAGTCGGTCTTGATAACCGAAGTATTTATAGAATACCGGGGGTTCGAATCCCTCTCCATCCGCG
AGAACATAAGTTCTCTCTTGAGTTATCTATAGATAAGAAGTTATTGGGCCGACTCGACTGATATGATAGA
TGGAATGGTAGACTGAAGTTGTTACTTATTTTCAGCTAAGGAACAAAAGTTCACTTGATAATCTGTAAGG
GTGATCTGCAAAGCAGGCAACAAAATCCATCTTTGTTGGACCAAAATTTGCTCTTATTTACTTGTAAATG
TTCCCTTACCAAATGCTTTGATTGCTGAAGCTAATAGTTCAAAAACTTATCTTTCTTGGACTGAAATTGG
CTCTCTTATTTGGAATGGACATAATTCAAGAGTAATGTGTTATAAGCTAATATAAGCTATCATACCCTTA
AGAATAATGCTTAAAGTAGGTGGTTTCAGATAACCAAATTCATTGTTTTAGGCAATTAAAGTTTTCACTT
TGTTTTTTAATCTAACCTGACTGCTTCATGGAATCTCTGTAATCATATATAGGGAATCAGAAAAAAGTTG
CTGAATACTACAAAAAGCAAGAAAGGCTGCTTGAAGGATTCAATGAGATGGACACAATTAATGAATGTGG
TTATTTACCTGGAAATCTAACTGAGGTTGGTCTTTTCCTCACTTGCCACAACTAATGAATGTGGTTATTT
CTGTTCTTTGTTGCACTATTTCCACCTTCAACCGAAACAATCACCTTTAGTGTTCAGAAATTCATGTGTC
TCTGGATCAGATAAGACTACTTGTGTTTATGTTCTTTTTCTTCTTGGAGAAGGTGATTTCTTGATCAATC
TCTGCCTCTTCAATAACTACAATGTTTTTCCATGTTAACCCGAGTGTATATTAGGACTTTCAGTCAGATT
CTTAGGTTTCTTGAATCTTGATCTCTGTTAATATTCGTAATAAGAATCAACAAATAATGTTGTTTTTCCT
GTCTACCAATGATTATTAATGCCAGGATGAAATGAAGCAACATGCTAAGAGCGAACGAATGGCTATTCAT
GCGTCAAACATAGCAAATATGGTTCTTTTCATTGCTAAAGTCTACGCTTCTATTGACAGCAGATCGCTGG
CTGTAATTTCATCGACCTTAGACTCGCTATTAGACCTCTTATCTGGATTTATTCTGTGGTTCACTTCTCA
TGCAATGAAAACGCCAAACCAGTACCGCTATCCAATTGGAAAGAAGAGAATGCAGCCAGTGGTGAGTCTT
CTACTGTTTTTTCTTCCAAGGAACACCCTTGTTTCAGGGTATTTCTCCGAAATTAGAGTAAAAAGAAGAA
AAAACATATTCCTTTAGCTCCCTAGAAAGAATAAGAAAAGATGTCTGATCACCAATTTATGTTTATATAT

FIG. 20 (Continued)

CTGGATAATACCTTTGTGCCTTCTGACAGTTTCCTCAAGAATTAACAGCTTAAAGGGTAGCACGTAAACC
AGAATATCTTGCTTGTGTGCAATATTTTTTACATTAATATGGTTTATTGTTTGAAATGATCTGCTGCAAT
ATTTTCAGGGTATAGTTGTTTTTGCATCCGTAATGGCGACCCTAGGATTACAAATATTGTTCGAGTCTGG
TAAAGAACTCATAACTAAGGTATGTAACTTGGTTCTCTTCAGCTGTGTCATGAGATGGATGTGTCATGTG
TGAGCTGGTACAAGGTTGAGTATTGTGACTTCTAAAAATAATGTCAAATTGATGAAGAACGTTTCCTCAA
ATATACTTTGAGAGCACAATATCCTTACTGGTCTTTTAATAATCCATGTTAGGCAAAATGAATTTTGGAC
CTAACTCAACAGTTTTGCTCAAGTGATTTCGCAATATGTGCATGTATTACAAAAGTTTACTCGGGTGAGA
TGAGGATCTTCTAGGGCCATATAAAGAGACTACAGCTTATGCCCTCAATCAGTGTGGGACTCTTAACAAT
ATTCGTATTTCCTTCTTCCCCTAAATATCAGCAGCCTAGAGTTCTCTCCGGATTTTGTACTTCTATAGTT
GATTTTAAGTTGTTTTGTAGTAGAGTTTACGGTAGTCCTTTGCCCTAAGTAATCCCTTTCTTAAAATTGA
TGGACAATTTATATTGTTGAATATTACCACTAGCTTGTCTGATAAATGAAATATGTCGTACAATGCGACA
AAAGACCTAAAATAGAAGCTGAATTGCTACTAAAAGAAAGTTGCAGTAACACAAGATATGCCCTCTAATC
CATGTATAAAGATGAACTAGTCGTTTGTGCTCTAACTGAAAACAACTAGTTTTGATACTACATATGAAGC
ACAGATTAATAAAGATTAGTCCCACATGATACATTTCTTATTGAAGGACTGAACTCTAATTTACCGCAAT
TTCACTAGTGAAATATTGTAATATGCTTGACACTTAACCTCAATTTGTTTTTCTGGTTCTATGCTTTAAT
TATTAGTCTCGTCCTGATATGGACCCTGAGAAGGAACAATGGATGATAGGAATAATGGTTTCTGTCACTG
TGGTCAAGTTTATGCTTCTGATCTACTGCCGAAGATTCAAAAATGAAATTGTAAGGGCCTATGCTCAAGA
TCATTTCTTTGATGTCATTACCAACTCAATCGGATTAATGGCAGCAGTCTTAGCCATCCATTTCTACTGG
TGGATTGATCCTACTGGAGCTATAATTGTGAGTTCAGAATAACACCACATAGTTCTTTTATTTGTATACC
TTGTCTGTTGTTGCAATTGAGATGTTTTTGCATTTCCTATGGAGAACTGATCATCCTTTGTTACTGCAAC
AGCTTTTTAAAGTAGTAGTATTTGTTTAGTTTAAGCAATTAATTAGCATTTTGAAGAATAAAGTAGCATA
TCTTTATTAATTAATCTTATTAGTCTCTGTTGTGTGTTTCAGATAGCACTTTACACAATGAGCACATGGG
CAAAGACAGTGATGGAAAATGTGTGGTCACTTATTGGAAGAACAGCTCCACCCGAATTTCTAGCAAAGTT
AACATATCTTATATGGAATCACCATGAAAGGATCAAACACATTGATACTGTTAGAGCATATAACTTTAGAATAC
TATTCT
ACCACTGGACCATTGGTATATTTTATTTTAAGACTGTCTTTTATTTGATTTATACACTTTAATTGTATTT
TCGTATGAAAATAACCGATCAAAGTTGGTCAGTTTTTTAAAATTATCAACCGAATTAACCGACCAACTTT
GGTCGGTTTTTTTAATATTAATTTTTATTTATTTTAATTGAAAAACCGACCAAAGTTGGTTGGTTTCTTG
AAAAATAAATTTTGCGGGACTCAAAAATCGTTTCCCGCATTTTTGCGCCAAAGAAAAACGACCAAAGTTG
GTCGGTTTTGTAAAACAAAATTTAAAAATAAAATATTTGAAAAACCGACCAACTTTGGTCGGTTTTTTG
GCCGGTTTTTTGATCGACCAAAGTTGGTCGGTCGACCTTGGTCAGTTTTTGCCGAAACACAATCTATGGG
AGCGAGTTGAATGTTTGTCACTAGATGATATTTAATGAAGAATATTGCCTAGTATTAAATAGGCAGCCGT
TGCAGAGAATTTGGGCATTCATGACCTGTCGTTTCATGTTCATCAATGACTCCTTTTATTGTAATTTAAG
AGGGGCTTGATCCTAGGATCTTGTTTCCTAGGTATAGCTATAAATAGTAGCTTCAACAACCATTGTAGAC
AGAGAAAATATCTCGCAAAAACTTATGCTACACTTTATTCTCAAGCTAAACAATACAAATTTACTTTCCA
TATGATATTGCTCTTATTTCTGTCCTCGGAAGCATTGCTCCCGGAGCTAGGCCTGCCATTTCCTTTGGTT
TTAACGCTAAGTCTTATTTTTAATCTAATTTACTTATTATTTTGGGTTAAATCAGTTTGCTTGTCTATAA
ACCACATAACGAATACAACTGTACCGTTTTACAGGTAAACAGTTTGGCGCCCCACCGCGGGTCTTAGACA
ACTGCATAATTAAGTTGATCCTTGCATATATTACTAACTCGTTTGATTCTTTATTTCTTAGAAAAAATAG
CACACAACATTGAGGCACACCAAAATCTACCTCAACATGAGGATTCAATCAGTGATACCCGCAATGAGAG
AGATGTGGAAACTCCGGTCCATGGCAGACAATATCGCCGACACGTGCGGG

FIG. 21

SEQ ID No. 17

ATGGAAATCAGTCGCAGTAATGAGAGTGTCACACTGGACGACAGTTTTAGGACGGAGTTGCTGTCTCCCG
CTGCTCAGGCGGTGGTTGATCACTCCATGTCTCTGGGGCCGACATGGAAGCTCAACACAACTGACTTCCA
TCTTCCCCAACTCCGCTCCTCTGATCATCAATCTTTCAGTTTCCTCCGTCTCCTACGAGCTTTCAGGAAT
CAGAAAAAAGTTGCTGAATACTACAAAAAGCAAGAAAGGCTGCTTGAAGGATTCAATGAGATGGACACAA
TTAATGAATGTGGTTATTTACCTGGAAATCTAACTGAGGATGAAATGAAGCAACATGCTAAGAGCGAACG
AATGGCTATTCATGCGTCAAACATAGCAAATATGGTTCTTTTCATTGCTAAAGTCTACGCTTCTATTGAC

FIG. 21 (Continued)

AGCAGATCGCTGGCTGTAATTTCATCGACCTTAGACTCGCTATTAGACCTCTTATCTGGATTTATTCTGT
GGTTCACTTCTCATGCAATGAAAACGCCAAACCAGTACCGCTATCCAATTGGAAAGAAGAGAATGCAGCC
AGTGGGTATAGTTGTTTTTGCATCCGTAATGGCGACCCTAGGATTACAAATATTGTTCGAGTCTGGTAAA
GAACTCATAACTAAGTCTCGTCCTGATATGGACCCTGAGAAGGAACAATGGATGATAGGAATAATGGTTT
CTGTCACTGTGGTCAAGTTTATGCTTCTGATCTACTGCCGAAGATTCAAAAATGAAATTGTAAGGGCCTA
TGCTCAAGATCATTTCTTTGATGTCATTACCAACTCAATCGGATTAATGGCAGCAGTCTTAGCCATCCAT
TTCTACTGGTGGATTGATCCTACTGGAGCTATAATTATAGCACTTTACACAATGAGCACATGGGCAAAGA
CAGTGATGGAAAATGTGTGGTCACTTATTGGAAGAACAGCTCCACCCGAATTTCTAGCAAAGTTAACATA
TCTTATATGGAATCACCATGAAAGGATCAAACACATTGATACTGTTAGAGCATATAACTTTAGAATACTA
TTCTACCACTGGACCATTGGTATATTTTATTTTAAGACTGTCTTTTATTTGA

FIG. 22

SEQ ID No. 18

MEISRSNESVTLDDSFRTELLSPAAQAVVDHSMSLGPTWKLNTTDFHLPQLRSSDHQSFSFLRLLRAFRN
QKKVAEYYKKQERLLEGFNEMDTINECGYLPGNLTEDEMKQHAKSERMAIHASNIANMVLFIAKVYASID
SRSLAVISSTLDSLLDLLSGFILWFTSHAMKTPNQYRYPIGKKRMQPVGIVVFASVMATLGLQILFESGK
ELITKSRPDMDPEKEQWMIGIMVSVTVVKFMLLIYCRRFKNEIVRAYAQDHFFDVITNSIGLMAAVLAIH
FYWWIDPTGAIIIALYTMSTWAKTVMENVWSLIGRTAPPEFLAKLTYLIWNHHERIKHIDTVRAYNFEYY
STTGPLVYFILRLSFI

FIG. 23

SEQ ID No. 19

CATTTTTAGTTCCACTTTCCTTGTTCAAAAAAGTTCCGCCATATAAAGCCTCTACAACTACCCACCCAAA
GAACTCCAAATTACATAAAGGTCCCTGGAGTTCATCAAATTTACGCACTTTACCACTCCCCTGCGGCTCC
TTCAAGTAGGTGCCTCCAGTTTTTTTACCTAGTGTTTTCAACTGTTTTTTTCCCTATTTTCCGGTGACCG
GAAAATGTTGGAAGTAGTACCTCTTCACGGCGGCGATCACGGCGCCGGCACCGAAGAGGAGCTTTTATTG
CTGGAGACAAACAATGCCGACCGGTCATGGAGATTAAACTTCGACGAGTTGCGGTTGTCGTCTGAATCCA
AAGAGAAGCCTCCACGTGGCCTCCATGATTGCCTTGGAGTTTTAAGTACATTCTCCACCTCTCTATGCGA
CGTCGTTTTTTGTTATTCTCTGCTAATTTCTTAACTAGTTGCATTAGGTTGACGTAAGAGAGACACCACT
TGAATAGAGCGGAATTTATATAAAGGAATTATACAGCTGATTCCTATTAAATACTTGACTGATATTCTGT
TGTGCGTAGGATTTTACTAATTGCGGAAATTTTCAAACACTAAGCTTACTCCTTTAGTTGGTTAATTAGT
GGGGACTCTTTTTATACTTTTCAGTTTCAGAAAGTATTTTCTTGCCACGTGGGTTCAATTTTCTGAAGAA
CAAAATGATTCTTGTATGGATGGTGTAAATTTGCTAAAGATGTTAAGCTATATTCACTTTTTATTGTTCT
CTGGACAATTGAACATGCTTATGGGCAGTTCACTGGTTTGGAGCAAATTGGCATATATTTGTATGTAGAT
GGATGATTCTTTTTGGATAAGTTTTAGATGGATAATTTTTGTTATAAGAACATGAGCTTTAGAGCTCAAA
TTTAATGCGTTTCAGCACTTCAGTTTACTGAAAATAAGAAGGGAACTTTAGCTGAGTGCGCTCGCCAGGT
AAGTTTATGTGGTTAGGTCAGTGTAATAAAACCAGAGGCAGACCTATGTTAATATGTGAGGGTGCACTGG
CACCCTGTAGTTTCCGATGAAACTATATGGAGTATATAAAATTCTTATAACACTACTATGTATTTTAGGT
GGCAATTGCAATGACAAAGTAGCGGTAGGAGGATTTGTTAAAATATGTGTTTTTACCTGAGTTGTTGTCT
TCTCATATTGAATACTTACATAATTGAACCAAATTAATGCAATACCATCAAACGAACTTAATGCACTTTA
GATGATATGACTTGTTCGAATCTTTAGTGCACCGGCAACCTTCACTTGGTGTGTGTGTGTTTGCATGTGA
CATGAGCCAGTCAAAAGATTGTTCCAAGAGGCTACTTTTGCATTCTGTTGAATTGTTAAGTTGTCATATG
AGAATGTATGTTTGGAATTGATAATGGTACTTTGACAATTTATAATCGGCTTTGGTATGAGTGGTGGACT
CTAAATGCAGGTCAGCCTTGGTTCTCATCAACTCTTTGGTTTAGTACTTATAGGAGGCTATAGTGCTATA
TAGAGATGCATGTAGAATGGATTTACTGAATGCTTTCACTGTAAGACATGGGGTGTTCTTGAAGGGACGG
ATTATGACGCTGTGTTTTTCTTTGGTGCTTACAGGTCAAGAAGACAACATTGCTGAGTACTACCAGCAAC
AGGTAGAAATGCTCGAGGGCTTCAATGAAATGGACGCCTTGACCGATCGCGGTTTTGTACCTGGGATGTC
AAAGGTTTTGATAGCTTCTTCTTTATGTATAAGACCAACCATTTGTTTCTTCTCTAGATGTATCATTCTT

FIG. 23 (Continued)

ATCTTATTATATAACTTGATGACCTGATCATCTAATTAAAAAAGAATGTTACTCAAAGCTTGGACTGACA
AGCTCAATTAATTTGATTGCAGGAAGAGAGGGAAAAAACGGCTAGAAATGAAACATTTGCCATTAGGATA
TCAAATGTTGCAAACATGGTTCTCTTTGCCGCTAAAGTATATGCGTCAGTCAAGAGTGGTTCATTGGCCA
TCATAGCATCCACATTGGATTCGCTGCTTGATCTTCTCTCTGGTTTCATATTATGGTTTACAGCTTTCTC
CATGCAGACACCAAACCCATATCAATATCCTATTGGAAAAAAACGTATGCAGCCGTTGGTTAGTGCTGCT
GCTTTTATTCTTAAGTTTTTTGCATCTTCTATGCCTTCAATCGGGCCAATTTGCATTCTGCACTTGTCAC
TTGCTATTGGGCTAATACTCATGACTGCATATAATAACAATTTCCTTGCTTTTTCATGCGTTTAAAAATT
GTCTAACAAGGTAATTGTACTATGCATTCTTGTCACATTTGATTCTAAAGGGACCTTAAGTTCTGCCACT
GCTATTTTTATGTTGTGGTCATGGTAAGCCTTAACATTCGTTTTGTTTGTTGATGCAGAGGCAATTTAGC
CTTCTTCTTGAGTTCAATCTCTAATCATCACATGTTGTAGTCCAAAAATAAAGGAATAATTTTCACCTAA
AAGTATGGAACCACGAGAAATTCAAACTTAATGCATCTAAGACAAATTAAATGAATTAAAACAACATCAT
ATCTGATAGTAACCATCTATAAAAGGTTGAAATAAAAGAAAAGATGTGCAGAATTTTAATAATGTCCTCT
AGCAGACAGCTTACATGACTGCATTAAAACCTACAGAGATTCAAATCTTCAGCATCTCTTTCTCCAATAG
TTGTCTTTTAGGTGTAGCCTCAGTGGAGAACCACACATGTTTCTGAGATAGAAAGGTGAGAGAAGATAGC
TGATGGCAGGGGAAGGGGAAAGAGAGAGATGAGACCAGAAGGGAAGGCCACATAGATTGAAGCTGATTTG
GCAGAGAGAATTGAGTGAGATGATGAAACACTGGCTGCTGTGAGTGGCAGTATAGAATTAGAGAGGGTGG
GGTTACGGGGAGATTATGAAGTGTCTATTAGTAATTTTACAAGATTTAGTTGTTTTGTTTTTACTGTGGA
GGGATGAATATGGTCCTTGTTTATGATCTGTGATGGATACCGGAGCTTATAACCTCCCATATGCACCATT
TTCTCCCACATCAGGTTAGGTTGATAGCCATTGCGTTCGCTCTAAGTAGCGATCCTCAAATTCAATTAAT
TAATCGTATTATGGTGATGTTGATATAGACATCTAGACTGTCACTCCTGATGTTACCTATCAAAAAAAAA
AACTATCATCTCCTAGATGTTTCTATTAATCCAATGTCTGTACATAACTAAGGAGGGATCCTAGACTTGA
GTTACACAGAGATTCTTACATAGTCTTTGTTGCTGTTCATCTCTTCCTGTTATCTCATTTTCATTATCAA
AATTGACAGTAAGCACTTGCTCCGTGAATGTAACTAGTCTGGGCATGAATTTGGTGTAGTACTCATAACA
GTTGCATTTAGTTTGGAAGCTTAGAGAGTAGTGCTTTCTAGTGTGGTGGTTTGATGATTATTTTGCGTAA
TATCTGTAAATAAATACCTCTGTGAAGTTTTACTTTGGTGCTAAGTACTTAAATTGCAATCGTGGAGATA
CTATTATCTATTCAGATAACTTTGACGTTCTGGTTTAAATCAGTTGATAATTCCTTAGGATACTAGGATG
ATCCCACTGTAAGTATTATGAGCTTATTTTGATATTTGAGATCTTTATTGACCATTATACATCCATAAAA
GTTCCCGTACTTTGGCAGAAGGAGACTTTTCTTCTGTTTCTAGAGAACCATTTGCAGAAGACTGTCATTT
TTCAATTACATGATTTAAAAGATATGGTTTTCTTCTTCCATCATTTGTTGCTAACAGAAAAAAAGAAGTG
GAAATTTTGATTTAGATCTGAGACTCTATGTAACTTCCACTATGTTGCTGAATGTTGTGTAGAAAAAGAT
CTAGTCTGCAAACAAGTTTTGCCCTGTATGCTGGCTGATCCTATGAAGTTGACATGATTTTACTTATCTT
TTGATTTTTCATGGAGGTAGAGCAAACTGCAGGTCTATGGCTATCTTCATAGTGCATGTTGTGTAATTCC
CAGTGGGTTCAAAATGAACTGTGTTTTAACTTTCAGTTTTACTTGTATTTCTAAATATCTGGTGATAACA
TCGTACAGGCATGAATAGAAATATTGTATGATTGTTTTCTATTCTTCCTTGGGAGCTGGTCCAATTTAAC
TTGAAAAATGATACACAGGGAATCCTTGTTTTTGCTTCTGTCATGGCGACTTTGGGACTGCAGATAATTC
TGGAGTCTATGCGTACACTAATATCTGATGTAAGTTGTGGCTCCTAAGATAAGTTTATTGCTTTATTATG
TTGTATTGTCTGGTTGAAAATTACATGCATGGATTCTTATAATTATTCCTTGACCCTGTACAACGGCAAA
TGTTATAAACATTGACCTTCTCACAGGAGTCTGATTTCAACCTCACCAAGGAGCAGGAGAGATGGGTTGT
TGGGATTATGGTCTTTGTGACTTTGGTGAAACTAGTTTTAATGTTGTATTGCCGGTCTTTTACCAATGAG
ATTGTGAAAGCATATGCCCAGGATCATTTCTTTGATGTTATCACAAACATCATTGGTCTCATTGCAGCAT
TGCTTGCTAACTACATTACCGACTGGATAGATCCCGTTGGAGCTATGATTGTAAGTTCTATCTCCCTGAT
TCTGTTCCACCAATCAGGATTGGAAAGAAAAGGGAAAAGTTTTAATGTGGCTGTCAATCCTCTCGCTTTA
ACCAAGGTTAGTGGCTTTAAGCAATTTTCCCTCTGCTGCAGCTTGCATTGTATACCATTCGAACTTGGTC
AATGACTGTATTGGAGAATGTGAACTCTCTCGTCGGCAAGTCTGCTGCACCAGAATACTTACAGAAGCTG
ACTTACCTCTGCTGGAACCATCACAAGGCCATAAGGCATATAGATACCGTGAGGGCTTATACATTTGGTT
CGCACTACTTTGTTGAAGTTGATATCGTCCTGCCTGCGGACATGCCTTTGCAAGAGGCACATGATATTGG
TGAGTCGTTGCAGGAGAAGCTTGAACTATTGCCTGAGATTGAGCGTGCCTTCGTTCATCTTGACTATGAA
TACAGCCATAAACCTGAACATGCTCAGGCATACCAATAGTCAAAAGGATTTTGTGACATCTTCTCTAGCC
AATGTACCTAATACCTCTGCATAGTGAACTCTGATATGCTGTTCGAGATCGGCTAATCTGGTGATTGCTC
TTTAAAAGAAAATCTGGGAAAGAAAAGGCTGCTATGATCTGGATGTTCCCTAGAACAAGTAATATGAATT
ATTATTTTGTTAAATTTTACCTTGCCTATTCATATATATAACATGATTTCTCAGTTTGCTTGCTCCTGGT

FIG. 24

SEQ ID No. 20

ATGTTGGAAGTAGTACCTCTTCACGGCGGCGATCACGGCGCCGGCACCGAAGAGGAGCTTTTATTGCTGG
AGACAAACAATGCCGACCGGTCATGGAGATTAAACTTCGACGAGTTGCGGTTGTCGTCTGAATCCAAAGA
GAAGCCTCCACGTGGCCTCCATGATTGCCTTGGAGTTTTAAGTCAAGAAGACAACATTGCTGAGTACTAC
CAGCAACAGGTAGAAATGCTCGAGGGCTTCAATGAAATGGACGCCTTGACCGATCGCGGTTTTGTACCTG
GGATGTCAAAGGAAGAGAGGGAAAAAACGGCTAGAAATGAAACATTTGCCATTAGGATATCAAATGTTGC
AAACATGGTTCTCTTTGCCGCTAAAGTATATGCGTCAGTCAAGAGTGGTTCATTGGCCATCATAGCATCC
ACATTGGATTCGCTGCTTGATCTTCTCTCTGGTTTCATATTATGGTTTACAGCTTTCTCCATGCAGACAC
CAAACCCATATCAATATCCTATTGGAAAAAAACGTATGCAGCCGTTGGGAATCCTTGTTTTTGCTTCTGT
CATGGCGACTTTGGGACTGCAGATAATTCTGGAGTCTATGCGTACACTAATATCTGATGAGTCTGATTTC
AACCTCACCAAGGAGCAGGAGAGATGGGTTGTTGGGATTATGGTCTTTGTGACTTTGGTGAAACTAGTTT
TAATGTTGTATTGCCGGTCTTTTACCAATGAGATTGTGAAAGCATATGCCCAGGATCATTTCTTTGATGT
TATCACAAACATCATTGGTCTCATTGCAGCATTGCTTGCTAACTACATTACCGACTGGATAGATCCCGTT
GGAGCTATGATTCTTGCATTGTATACCATTCGAACTTGGTCAATGACTGTATTGGAGAATGTGAACTCTC
TCGTCGGCAAGTCTGCTGCACCAGAATACTTACAGAAGCTGACTTACCTCTGCTGGAACCATCACAAGGC
CATAAGGCATATAGATACCGTGAGGGCTTATACATTTGGTTCGCACTACTTTGTTGAAGTTGATATCGTC
CTGCCTGCGGACATGCCTTTGCAAGAGGCACATGATATTGGTGAGTCGTTGCAGGAGAAGCTTGAACTAT
TGCCTGAGATTGAGCGTGCCTTCGTTCATCTTGACTATGAATACAGCCATAAACCTGAACATGCTCAGGC
ATACCAATAG

FIG. 25

SEQ ID No. 21

MLEVVPLHGGDHGAGTEEELLLLETNNADRSWRLNFDELRLSSESKEKPPRGLHDCLGVLSQEDNIAEYY
QQQVEMLEGFNEMDALTDRGFVPGMSKEEREKTARNETFAIRISNVANMVLFAAKVYASVKSGSLAIIAS
TLDSLLDLLSGFILWFTAFSMQTPNPYQYPIGKKRMQPLGILVFASVMATLGLQIILESMRTLISDESDF
NLTKEQERWVVGIMVFVTLVKLVLMLYCRSFTNEIVKAYAQDHFFDVITNIIGLIAALLANYITDWIDPV
GAMILALYTIRTWSMTVLENVNSLVGKSAAPEYLQKLTYLCWNHHKAIRHIDTVRAYTFGSHYFVEVDIV
LPADMPLQEAHDIGESLQEKLELLPEIERAFVHLDYEYSHKPEHAQAYQ

FIG. 26

SEQ ID No. 22

CATTTTTAGTTCCACTTTCCTTGTTCAAAAAAGTTCCGCCATATATAGCCTCCACAACTACCCACCACTA
AGAACTCCAAATTACATAAAGGTCCCTCGAGTTTCATCAAATTTACTCACTTTACCACTTTCTGCGGCTC
CTTCAAGTAGGTGCCGCCAGTTTTTTACCTAGTGTATTCAACTGGTTTTTTCCTGTTTTCCGGTGACCGG
AAAATGTTAGAAGTAGTACCTCTTCACGGCGGCGATCAAGGCGTCGGCGCCGAAGAGGAGCTTTTATTGC
TGGAGACAAACAATGCCGACCGATCATGGAGATTAAACTTCGACGAGTTGCGGTTATCGTCTGAAACCAA
AGAGAAGCCTCCACGTGGCCTCCATGATTGCCTTGGGGTTTTAAGTACATTCTCCACCTCTCTATGCGAC
GCCGCTTTGAGTGTTATTCTCTGCTAATTTCTTAACTAGTTGCATTAGGATAGTAAATTAGTGGAGACAC
CACTTGAATGGAGTGGAATTTATATAAAGGATTTATACAGCTGATTCCTATTAATCAGTGATGGAGAAAT
ACTTGACTGATATTCTGTTGTGCGTAGGAAGTTTACTAATTGTGGAAATTTTCTAACACTAAGCTTACTT
CTTTAGTTGAGTTATTAGGGGGCTCTTTTTAATACTTTTCAGTGTCAGAAAGTATTCATGCCACGTGGAT
TCAATTTTCGGAAGAACAAAATGATTCTTGTATGGATGGTGTAAATTTGCTAAAGATATTAAGCTATATT
CACTTTTTATTGTTCTCTGGACAATTGAACATGCTTATGGGCAGTTCACTGGTTTGGAGCAAATTGGCAT
ATATTTTGTATGTAGATGGATGATTCTTTTTGGATAAGTTTTAGATGGATAATTATTGTTATAAGAGCAT
GAGCGTTAAAGCTTAAATTTAATGCGTTTCAGCACTTCAGTTTACTGAAAATAAGAAGAAAACTTTAGCT

FIG. 26 (Continued)

GAGTGCACTCACCAGGTAAGTCTATGTGGTTAGGTCAGTGTAATAGAACCAGAGGCAGATCTATGTTAAT
ATGTGAGGGTGCACTGGCACCCGAGTATATAAAATTCTTATAAAACTACTACTCATGTATTTTAGGTGGC
AACCTCAATTACAAAGTAGCGGTAGGAGGATTTGTTAAAATATGTGTTTTTACCTGAGTTGTTGTCTTCT
CATATTGAATACTTACAAAGTTGAATCAAATTAATGCAATACCATCAAACCAACTGAATGCACTTTAGAC
GACATGACTTGTTCGAAGCTTTAGTGCACCGGCAACCTTCAATTCCTTGATATGCCTCTGAATAGAACAG
GTTAATTGGTGCGCGTGTGTGTTTGCATGTGACATGAGCCAGTCAACAGATTGTTTCAAGAGGCTACTTT
TGCATTCTGTTGAATTGTTAAATTGTCATATGAGAATGTATGTTTCGAATTGATAATGGTACTTTAACAA
TTTATAATTGGTTTTGGTACGAGTGGTGGCCTTTAAATGCAGGTCACCCTTGGTTCCCATCAACTCTTTG
GTTTAGTACTTATAGGGGGCTATAGTGAGGGATTTACTGAATGCTTTCACCGTAAGACATGGGGTGTTCT
TGAAGGCACGGATTATGACACTGTGTTTTTCTTTGGTGCTTATAGGTCAAGAAGACAACATTGCTGAGTA
CTACCAGCAACAGGTAGAAATGCTCGAGGGCTTCAATGAAATGGACACCTTGACTGATCGTGGTTTTGTA
CCTGGGATGTCAAAGGTTTTGATAGTTTTTATCTGCTTCTTCTTTATGTATAAGACCAAGCATTTGTTTC
TTCTCTAGATGTAATCATTCTTATATTATTATAAGCTTGGACTGACAAGGTCAATTAATTTGGTTGCAGG
AAGAGAGGGAAAAAACTGCTAGAAATGAAACATTTGCCATTAGGATATCAAATGTTGCAAACATGGTTCT
CTTTGCTGCTAAAGTATATGCATCAGTCAAGAGTGGTTCATTGGCCATCATAGCATCCACATTGGATTCG
CTGCTTGATCTTCTCTCTGGTTTCATATTATGGTTTACAGCTTTCTCCATGCAGACACCAAACCCATATC
AATATCCTATTGGAAAGAAACGTATGCAGCCGTTGGTTAGTGCTGCTGCTTTTGTTCTCTAAGTTTTTTA
CATTTTCTATGCCTTTAATCAGGGCATTTTTGCACTTGTCACTTGCTATTGGGCTAATGTTGATTACTGC
ATATAATAACAATGTTCATGGATTTAAAAGTTGTCTAACAAGGTAATTATACTATGCGTTCTTGTCATAT
TTGATTTTAAAGGGACCTTAAACTCTGGCGCTGCTATTTTTATTTTGTGGTCATGGTAAGCCTTAATATT
CATTTTGTTTGTTGATGCAGAGGCAACTTAGCCTTCTTCTTGAGATCAATCTCTAATCATCACATGACGT
AGTCCAAAAAACAAAGGAATAATTTTCACCTAAAGTATGGAACCACGAGAAATGCAAACTTAATGCATCT
AATAGCATGTTTGGCCAAGCCTTTTTTTGGGCCAAAAGTGTTTTTTTTTCAAAAATTAAGGTGTTTTTTT
TCAAAAAGTGTTTGGCCAAGCTTTTAGAAGGAAAAAATTGTGCTTTTGAGGAGACGCAGAAGTAGTTTTT
GAGAAGCAAAAAAAAGTAGCTTATCTCCAAAAGCACTTTTCTGAGAAGCACTTTTGAGAAAAATACACAT
AGATGCAGTTTTTAAAAGCTTGGCCAAACGCTAATTACTGCTCAAAAGTGCTTTTCAAATTAATTAGCCA
AACACAAACTGCTTATCACCAAAAACACTTTTTTGAAAAGTACTTTTGAGAAAAGTACTTCTCAAAATAA
GCTGATTTTAGAAGCTTGGCCAAACAGGCTATAAGACAAATTAAATGAATTAAAACAACATAATATTTGA
TAGTAACCAACTATAAAAGGTTGAAATAAAAGAAACGACGTGCAAACTTTCAATAATGACCTCTAGCAGA
CAGCTTACATGACTGCAATAAAACCTACAGAGATGCAAATCTTCAGCATCTCTTTCTCCAATAGTTGTCT
TCTAAGTGTAGCCTCAGTGGCGAACCACACTGAGAATGTTTGTGAGACAGAAAGAGAGAGAGAGCAGTGG
CTGCTGTTACTGACAGTATAGAATGAGAGAGGGTGGGGTTACAGGAAGATTATTAAGCGTCTATTAGTAA
TTTGGCAAAAATTTAGGTGTTCTGTTTTTACTGTGGAGGGATGAATATGGTCTCTGTTTATGATCTGTCA
TGGATATTGGAGCTTCTAGCCTCCCATATGGACCATTTTCTCCCACATCAGGTTAGGTTGATAGCCATTG
TGCTCGCTTTAAGTAGCGATCCTCAAATTCAATTAGTTAATCGTGTTTTGGTGATATGCATATAGACATC
TAGATTATCACTCCTGATGTTACCTATAAAAAGAACTATTATCTCCTGATGTTTCTACTAGTCCAATGTC
TGAACATAACTAAGGAGGTAACATAGACTTGAGTTACACTTGGATTCTTGCATAGTCTTTCTTGCCGTTC
ATGTATTCCTGTTATCTCATTTGGATTATCAAAATTGACAACAATCACTTACTCTTTTATTGTTCCATGA
ATAATTAGTTTGGGCATGAATTTGGTGTAGTACTCATAACAGTTGCATTTAGTTAGTAAGCTTAGGATGC
ACATCTTAAGGAGGAGGAGTGTTTTCTAGCTTCTTGGTTTGAAGATAATTTGCCTAATATCTGTAAATAA
ATAACTCCGAGAAGTTTTACTTTGGTGCTAAGTACTTAAATTGCCATCGTGGAGATACTAGTTCATTTAA
TTTGTGTTATCTATTCAGATTTTTGACCTTCTGGTTTAAATCAGTTGATAATTCCTTAGGATACAGGGAT
GATCCCACTGTAAAAATCTAGTCTGCAAACAAGTTTTGCCCTGCATGCTGGCTGATCCTATGAAGTTGAA
TGATTTTACATGTTTGATATTTTCATGTAGCTAGAGCAAAGTGCAGGTCTATGGCTATCTTCAAAGTGCA
TGTTGTGTAATTCCCAATGGGTTCAAAGTGAACTGTGTTTTAACTTTCAGTTTTACTTGTATTTCTACAT
ATCTGGTGATAACAACTTACCGGCATGAATAGAGATATTGTATGATTGTTTTCTTTTCTTCCTTGGGAGC
TGGTCCAATTTAACTTTGAAAAATGATACACAGGGAATCCTTGTTTTTGCTTCTGTCATGGCGACTTTGG
GACTGCAGATAATTCTGGAGTCTATGCGTACACTAATATCTGATGTAAGTTGTGGCTTCTATGATTGCAA
ATTTCTGCTCTATTTATGCTGTATTGTCTGGTTGAAAATTACATGGATTGTTATAATTATTCCTTGATCC
TGCACAACGACAAATGTTAACATTGACCTTCTCACAGGAGTCTGATTTCAACCTTACCAAGGAGCAGGAG
AGATGGGTTGTTGGGATTATGGTCTTTGTGACTTTGGTGAAACTAGTTTTAATGTTGTATTGCCGGTCTT

FIG. 26 (Continued)

TTACCAATGAGATTGTGAAAGCATATGCCCAGGATCATTTCTTTGATGTTATCACAAACATAATTGGTCT
CATTGCAGCATTGCTTGCTAACTACATCACCGACTGGATAGATCCCGTTGGAGCTATGATTGTAAGTTCT
ATCTCTAGATTCTATTCCACCAACAACCTCCTCCCTTAAAAGAAATGTGCAAAGAAAAAGGAAAAGTTTT
AATGGGGCTGTCAATCCTCTCACTTTAAACAAGGTTAGTTGAACAAAGTTAGTGGCTTTAAACTATTTTC
CCTCTGCTGCAGCTCGCACTGTATACCATTCGAACTTGGTCAATGACTGTATTGGAGAATGTGAACTCTC
TCGTCGGCAAGTCAGCTGCACCAGAATATCTACAGAAGCTGACTTACCTTTGCTGGAATCATCACAAGGC
CGTAAGGCATATAGATACCGTGAGGGCTTATACATTTGGTTCTCACTACTTTGTTGAAGTTGATATCGTC
CTGCCTGCGGACATGCCTTTGCAAGAGGCACATGATATTGGCGAGTCGTTGCAGGAGAAGCTTGAACTAT
TGCCTGAGATTGAGCGGGCCTTCGTTCATCTTGACTACGAATACAGCCACAAACCTGAACATGCACAGGC
ATACCAATAGTCAAAAGGATATTGTGACATCTTATCTAACCAATGTACCTAATACCTCTGCATAAGTGAA
CTCTGATATGCTGTTCGAGATCGGTTGATCTGGTGATTGCTCCTTAAAAGAAAATATGGAAAAGAAAAGG
CTGCTATGATCTGGATGTTCCCTAGAACAAGTAATATGAATTATTATTATTTTTTTAATTTACTTTGCCT
ATTCATATATATAACATGATTCCTCAGTTTGCTTGCTCCTGGTATATTGCTAACTTATATTAGAGGAATT
TGGGTTTC

FIG. 27

SEQ ID No. 23

ATGTTAGAAGTAGTACCTCTTCACGGCGGCGATCAAGGCGTCGGCGCCGAAGAGGAGCTTTTATTGCTGG
AGACAAACAATGCCGACCGATCATGGAGATTAAACTTCGACGAGTTGCGGTTATCGTCTGAAACCAAAGA
GAAGCCTCCACGTGGCCTCCATGATTGCCTTGGGGTTTTAAGTCAAGAAGACAACATTGCTGAGTACTAC
CAGCAACAGGTAGAAATGCTCGAGGGCTTCAATGAAATGGACACCTTGACTGATCGTGGTTTTGTACCTG
GGATGTCAAAGGAAGAGAGGGAAAAAACTGCTAGAAATGAAACATTTGCCATTAGGATATCAAATGTTGC
AAACATGGTTCTCTTTGCTGCTAAAGTATATGCATCAGTCAAGAGTGGTTCATTGGCCATCATAGCATCC
ACATTGGATTCGCTGCTTGATCTTCTCTCTGGTTTCATATTATGGTTTACAGCTTTCTCCATGCAGACAC
CAAACCCATATCAATATCCTATTGGAAAGAAACGTATGCAGCCGTTGGGAATCCTTGTTTTTGCTTCTGT
CATGGCGACTTTGGGACTGCAGATAATTCTGGAGTCTATGCGTACACTAATATCTGATGAGTCTGATTTC
AACCTTACCAAGGAGCAGGAGAGATGGGTTGTTGGGATTATGGTCTTTGTGACTTTGGTGAAACTAGTTT
TAATGTTGTATTGCCGGTCTTTTACCAATGAGATTGTGAAAGCATATGCCCAGGATCATTTCTTTGATGT
TATCACAAACATAATTGGTCTCATTGCAGCATTGCTTGCTAACTACATCACCGACTGGATAGATCCCGTT
GGAGCTATGATTCTCGCACTGTATACCATTCGAACTTGGTCAATGACTGTATTGGAGAATGTGAACTCTC
TCGTCGGCAAGTCAGCTGCACCAGAATATCTACAGAAGCTGACTTACCTTTGCTGGAATCATCACAAGGC
CGTAAGGCATATAGATACCGTGAGGGCTTATACATTTGGTTCTCACTACTTTGTTGAAGTTGATATCGTC
CTGCCTGCGGACATGCCTTTGCAAGAGGCACATGATATTGGCGAGTCGTTGCAGGAGAAGCTTGAACTAT
TGCCTGAGATTGAGCGGGCCTTCGTTCATCTTGACTACGAATACAGCCACAAACCTGAACATGCACAGGC
ATACCAATAG

FIG. 28

SEQ ID NO. 24

MLEVVPLHGGDQGVGAEEELLLLETNNADRSWRLNFDELRLSSETKEKPPRGLHDCLGVLSQEDNIAEYY
QQQVEMLEGFNEMDTLTDRGFVPGMSKEEREKTARNETFAIRISNVANMVLFAAKVYASVKSGSLAIIAS
TLDSLLDLLSGFILWFTAFSMQTPNPYQYPIGKKRMQPLGILVFASVMATLGLQIILESMRTLISDESDF
NLTKEQERWVVGIMVFVTLVKLVLMLYCRSFTNEIVKAYAQDHFFDVITNIIGLIAALLANYITDWIDPV
GAMILALYTIRTWSMTVLENVNSLVGKSAAPEYLQKLTYLCWNHHKAVRHIDTVRAYTFGSHYFVEVDIV
LPADMPLQEAHDIGESLQEKLELLPEIERAFVHLDYEYSHKPEHAQAYQ

FIG. 29

SEQ ID No. 25

FIG. 29 (Continued)

AGGCAAGACCAAACAAGTCACATTTCTCATGCATGCCACTATTTTTGAGAGCAAAAACATAATCTGAAAA
TTTGGATATCTACGCATTTTCACATGTTTCAAACTCCTTCACTTTGTCAGCACATCAACAGCCAATTTTT
CTCTCTTTGAAAATAAAGGAAAGGGAAAGAAAGGAAAAGGGAAGTTGGGAAACATATGCCAAATCCCCTG
TCCTTTCTTTCCCTAAATAATTCCCATTTCTGGCTGTTTCGATTTCTTGATCTGAGGATCGGAGGAATTG
AATTTTTAAAATTCTGTTATATTCCATCCATTGCCACTTCTTTTCTTGATTGATTTTTGGATAAGAAAAT
AAAGGGATTTTTCAAATAAAAATGGATGTGGAAGAGGCATTGCTGAGGAATGAAGTTCCAAATGTCATAC
CAAAGCGTCGAAACTCAGTTAATTCTATGAGATGTGATTTCTTCTCTAAACTACCTAGAAAGGTTAAGAC
AGGGCTTGATCCTGAAGAACCTTTTCTTTTGGACTTGTCTAAAACCACTGGTTTAATTGAAGGTAAAGCC
TCTTTTAAGCATTTCTAAGTGCATCATCTTTTTGCTCATCTCTTGTTCTAATTTCTATGTTGATTTTGTT
GCTTGATTCTTAGCTCATCTTCTAATGTAGTTATTTATGATCTTATGAATAGGGGAGAAAGAATATTATG
AAAGACAGATTGCAACTTTAAAGTCCTTTGAGGAAGTAGACTCACTTGATTCAGCTGATGTCATTGATGA
AGAACAAGACCTACTAGATCAAGCACAGCATGAAAGAGCAATGAACATTTCCAATTTTGCAAATGTCTTA
TTACTTGCCTTTAAGGTATAACTTCTTTTTCATTGTTTCTATTGTGCAAACTTTTAATGCCTCAAACCTT
CTCCTGAATACACCCCAGGATCCCTTTTATTTCTTTGTTATGAGTATTATCTTTTTACAATTAACCCTTG
TGGCCCGACCTTTTCTCAGACCCCACGCATAGCATATGCAGGAGCTTAGTGCACCCGACTACCCTTTTAT
CTTTTATATAATGGTAGTGTCTGAGCTAACTTGAACGCACCTCAACTATTCAACATCCCACTAACACAAG
TATCAGGTTACATCTGCTCACTAAGGTTTAGGCAAATGGGAAGAAATCACCTATCATTTCTTATCTCTGT
TGAGATTTGAATATTGATCTCTCATGATTTTCACCCACTTTTGGCTTCTAGGCTACATCCCCAAGATCCT
GTTTATTATCTCAAAGAAAAGGAAGACAGCCCTCAGGTTCAGGGCAGGGTAGTTTGAAGTTTGCAATAGC
TAGTTTAGCTACTTAATTTTTTTATTGCTCAAATTATACCACATGTAAGTTTGACATTAATGACATATTG
AATGATCATTGTGAGACAGTAGGTAGTTGTCTCCAATAATGTTCCTTGTAGAGAAAAGAAATGTTGTATA
TTTCATCTACGAGTAGTTAAATTTGCTTAAATCAAACTGAACCCTCGTTAATTTGGACTGTTTGCAGATC
TATGCTACTGTAAAAAGTGGTTCTTTAGCCATTGCAGCGTCGACGTTGGATTCACTACTTGATCTAATGG
CTGGTGGTATTCTTTGGTTCACACACCTGTCAATGAAGAGCATAAACATTTACAAGTACCCTATAGGAAA
GTTAAGAGTTCAACCAGTGGGGATTATCATCTTTGCTGCTGTTATGGCTACTCTTGGTATGTCCTGGTTC
ACCTGTCATATCTTTCTCTTAATTTTGGCAGTCTAGAATTCATGAATAACCCTTGATACTGAAGAAGAGG
ATAAATAACTTCTATCATAAGAATAAGTTCGACCAAAAAGTTCTCCATTGAAGCATTGTGAATTGCAAAA
TGATGGCGAATACCTCTAACCACTTCTTAGCAGTTTATATTTTGTGGATTTAGGTGGTTTAGTGTGGTGT
AAAGATTAAGTATACAAAAAATTGCAAAGAGAAGTGTTTAAAGAGAATTAGCAATTCTAGATGATTGTTT
GTATCGGTCATGATTTCTCTCCTTGTGAAAAAAGAAATGGAAAAGAACAATCTAAAGAAGTTACAATGGA
AGTCTGCATTTTTGTCTCATTCTGATCTGCATTTAGACAGCGCATGTATGGTGATCGTGTCCTATCACAC
TAATTGAGTATCTGCGATTGCATAGGCTTTCAAGTCTTAGTGCAGGCTGTGGAACAACTGATAAAAGATA
CACCCTCAGACAAGATGACTGGGGAGCAACTGGCTTGGCTATATGCAATCATGCTGACAGCCACTGGAGT
GAAGCTCGTCTTATGGATTTATTGCAGAAGTTCAGGAAACAAGATAGTTAGAGCATATGCAAAGGTCCTT
TTTCCCCATATACTCTCCTGAAAAATCTCATTTAATGCAGTGTTATCCTTTCTTTCATCCATTGAGCAAC
ATTTGACAAATTGTGGAACCATGCATGATATCCAGGATCATTACTTCGATGTGGTAACAAATGTTGTCGG
TTTGGTTGCTGCTGTTCTCGGTGATCGATTCTATTGGTGGATCGATCCTGTTGGTGCTATTGTCCTTGCT
GTATATACAATTACAAATTGGTCAGGAACTGTGCTGGAAAATGCAGGTTCTTACTTTTTCCTTTGTCAGC
TAACATGCATTCACAAATGATGCTAATTTGATTTTGGTTTCGAAAGTAATCAACTTACGCGAACAAAAAA
TAATACACCCAAACTCTAATGCTGCAGTTTGCAATTCTTGGATATACTTCTTGGATCTTTTGGCTCTTAT
AGAGTAGAATTTTCCCCTTTTGTGGGGAATGGTCAGTGAATGATTTTGATGTTTATTTGCTATTTACCTA
GCTAACACTTGAATGTTTCTCTCTCCTGCAGTTTCTCTAGTTGGACAATCAGCCCCTCCTGAATTTCTAC
AGAAACTGACATATCTTGTTCTAAGGCATGATCCTCAGATAAAAAGAGTTGATACCGTTCGAGCCTATAC
TTTTGGAGTTCTTTACTTTGTTGAGGTGCGATGTCCACCACTCTGAAGTGCTTTTCTCCTGCACAATTTT
CAATTTTTAATAGTTCATAAAATTGGTTGAAGAGAGCAAGAAAACAACTACGTCTCAATTCAAGCAAGTT
GGAGCCAATTATATGAATACTCACTATCCATGTCACTTCAATTAAGCTCGTCCCCGCTCAACATTATAAA
TTATTAGCTTCTCTAGTAGTATAATTTTGGAAAATTTAGACAACTTCCTTCATAATCTGATAATTGGCAA
TTGTCTGTTTTGTAACAGGTTGACATAGAGCTCCCAGAAGATTTGCCACTGAAAGAAGCCCATGCCATTG
GAGAGTCACTTCAGATTAAGATTGAAGAACTTCCAGAAGTTGAACGTGCTTTTGTCCATCTTGATTATGA
GTGTGATCACAAACCAGAACACTCCATTTTGAGTAGAATTCCCAACAGCCCACCTTAATATTCTAGTCTC

FIG. 29 (Continued)

TCAACTCCGTGTTATTTCTTAGTACTTTTACAATGTAAAATTAAGAGCCCATTTTGCTATGTGGAAGTAT
CATGAAGAGTGAGGCCTGACGTTGTGATATGTATACAGAAAAGAAGGAAACTAATGGTTGGAGAATTCCA
TTTTTCCCTTATGAAGCACCTAATTAGCTTCACATTTCCT

FIG. 30

SEQ ID No. 26

ATGGATGTGGAAGAGGCATTGCTGAGGAATGAAGTTCCAAATGTCATACCAAAGCGTCGAAACTCAGTTA
ATTCTATGAGATGTGATTTCTTCTCTAAACTACCTAGAAAGGTTAAGACAGGGCTTGATCCTGAAGAACC
TTTTCTTTTGGACTTGTCTAAAACCACTGGTTTAATTGAAGGGGAGAAAGAATATTATGAAAGACAGATT
GCAACTTTAAAGTCCTTTGAGGAAGTAGACTCACTTGATTCAGCTGATGTCATTGATGAAGAACAAGACC
TACTAGATCAAGCACAGCATGAAAGAGCAATGAACATTTCCAATTTTGCAAATGTCTTATTACTTGCCTT
TAAGATCTATGCTACTGTAAAAAGTGGTTCTTTAGCCATTGCAGCGTCGACGTTGGATTCACTACTTGAT
CTAATGGCTGGTGGTATTCTTTGGTTCACACACCTGTCAATGAAGAGCATAAACATTTACAAGTACCCTA
TAGGAAAGTTAAGAGTTCAACCAGTGGGGATTATCATCTTTGCTGCTGTTATGGCTACTCTTGGCTTTCA
AGTCTTAGTGCAGGCTGTGGAACAACTGATAAAAGATACACCCTCAGACAAGATGACTGGGGAGCAACTG
GCTTGGCTATATGCAATCATGCTGACAGCCACTGGAGTGAAGCTCGTCTTATGGATTTATTGCAGAAGTT
CAGGAAACAAGATAGTTAGAGCATATGCAAAGGATCATTACTTCGATGTGGTAACAAATGTTGTCGGTTT
GGTTGCTGCTGTTCTCGGTGATCGATTCTATTGGTGGATCGATCCTGTTGGTGCTATTGTCCTTGCTGTA
TATACAATTACAAATTGGTCAGGAACTGTGCTGGAAAATGCAGTTTCTCTAGTTGGACAATCAGCCCCTC
CTGAATTTCTACAGAAACTGACATATCTTGTTCTAAGGCATGATCCTCAGATAAAAAGAGTTGATACCGT
TCGAGCCTATACTTTTGGAGTTCTTTACTTTGTTGAGGTTGACATAGAGCTCCCAGAAGATTTGCCACTG
AAAGAAGCCCATGCCATTGGAGAGTCACTTCAGATTAAGATTGAAGAACTTCCAGAAGTTGAACGTGCTT
TTGTCCATCTTGATTATGAGTGTGATCACAAACCAGAACACTCCATTTTGAGTAGAATTCCCAACAGCCC
ACCTTAA

FIG. 31

SEQ ID No. 27

MDVEEALLRNEVPNVIPKRRNSVNSMRCDFFSKLPRKVKTGLDPEEPFLLDLSKTTGLIEGEKEYYERQI
ATLKSFEEVDSLDSADVIDEEQDLLDQAQHERAMNISNFANVLLLAFKIYATVKSGSLAIAASTLDSLLD
LMAGGILWFTHLSMKSINIYKYPIGKLRVQPVGIIIFAAVMATLGFQVLVQAVEQLIKDTPSDKMTGEQL
AWLYAIMLTATGVKLVLWIYCRSSGNKIVRAYAKDHYFDVVTNVVGLVAAVLGDRFYWWIDPVGAIVLAV
YTITNWSGTVLENAVSLVGQSAPPEFLQKLTYLVLRHDPQIKRVDTVRAYTFGVLYFVEVDIELPEDLPL
KEAHAIGESLQIKIEELPEVERAFVHLDYECDHKPEHSILSRIPNSPP

FIG. 32

SEQ ID No. 28

TAGCAAAAAGACAAAGTTAGCAACTTAAAACAGAAAGTTTGAGACCCAACGCAAAGACAGTTTTTTTTAA
AGAAACAAAATTATCTAATGGTTTGGTAGTACGTACTACGTTTTAATCTTCTTTATATTTTTAATTAGTA
CAACATCTGACTTTGTCTTTTTTCTAATTAAAATAAAAGTTAGATCATACTCGAAGTTATATATATCTAA
TCAATGCAAATAGTGTGAAGCTTAATTACATGATTTGGAGTTTGCATTACTGAAAATATATACTCCTACA
ACTCTTGATAATGGAGGGAGAATTAGAGGCTAACAATATTAATGGAACTAAAACGCCATTGTTGGAGGGG
TGGAAGCTTAGCGGAAGTGGACGGCGGAGCAGCCGGCGTTTCAGCCGGCATAACTCTTTTACGTCGCTCC
GCCGTGATTTCTTGTCTAGGCTTCCAGATAAGGTGATCAACTCTTTTGTTATTGATTCTGAAGCTTCATA
CATCATTAATAACCTCTCCATATCCTCTGACTTAACCAAAGGTTCTTCTCTCTCTCTCAGGTTGTTTGGT
TCCGGACTAAATATGTGGTTAACTGATTATGATATATATAAAGATTATTATATGTTGTATAAAACTATAG
TGCTTGTAATTAATGGATTATGTAAAGTTAAGAATTAGTTTTATCTTGCTATTGTTAATATGCATGTTCT

FIG. 32 (Continued)

TATATATTCCCATGAACATGTTCTTGGCTTGAGAAAAAGTGAAACTTTTTCTTTTCTATGCTAAATTTGG
TGTATAGACTAGGTTCTGTTTGATATTAATTACTCCTATTAAAGGATTCAAACAGAAGCTGTTATACAAT
CGTTTGATCATGTTAATCCAATCACACTGCATATTAAACTCCTTAACATCTTTTAAAGATTAGAAAAGGA
TGACCTGGGATCGAATCCCCCTCAATGCCTTTTGGGTTGAGTCTGTCGCACATGGCTTGCCTAGTGCGGA
TTACCTCTCCTGTGTGGCTTGCAGGCTATTACNNNNNNNNNNNNNNNNGCGGCTGCGGGGTTTTCCCCTCT
TAAACCAAAAAAAAAAAAAAAAAAAAGAAAAAAGGAATATCAATTTTTTTCTTTTTTCTTTTTCCTTTTTT
TTTTTTTTTTATTTTATTTGCAAATAAAGCAAAATTTTGCTGGAAACTACACTAGGGAAATTCAAATATC
TACCGCTAGAAAAGGATATCTTTAACACCCTCAGTCAGTGGCGAAGCCACATGGTTATAAGGATGGTCAA
TTGACCACCCTTCGTCGAAAAATTACACTGTGTATATAGGTAAAATATTACGTTTTAGCGGTATACAACA
CATATTGAACACCCTTTGTCGGGAATTTTTTTTACTTCATTCAAATTTGAACACCTTTGGAAAAAAATTT
AGGTTCGCCACTGCCCTCGGTGCTCCGTTGACTAAGTTTTATGATGATAGGAGAAAAGGAATACTATGAA
AAACAGTTTGAGACTTTGAAGTCATTTGAGGAAGTTGATTCTGCAGTTGCTTCTGATTGCATTGATGAAG
AGGATCTCGAAGAACAAGCTCAACATGAGAGAGCAATGAGAATCTCCAATTATGCAAACATTATACTGCT
TGCTCTCAAGGTGACCAGAAATTACTTAATTGAACTCGTCATTAACATGAGAATGAGAAATCATCTATTA
ATGTGTATGCATTTCTTTGTCCTGCAACATTTTTATATATGCAGTAAAAGTGAAATTCTGGTTTATGTTT
GAATGACCTGGAAAAATGATAAAGATGGTGGTTTATGCCTTTTTGTCACAATAGCAGTATTGACACATAT
CGCGCCTTGCAGATCTATGCCACAGTAAAGAGTGGTTCTTTAGCTATTGCTGCATCTACACTGGATTCAT
TGCTTGACCTCATGGCTGGTGGCATACTATGGTTTACTCATCTTTCAATGAAAAATATTAATGTCTATAA
ATATCCTATTGGAAAATTGAGAGTGCAGCCTGTTGGAATCATCGTCTTTGCTGCTATTATGGCTACACTT
GGTATGTTATCTGCTTTGACTTTGCATTTGAAATTCCATTATCGGGTTAGTGAATACATAGCGACTTTAG
CTTACAGAAGACATGGCCCTTGACAGGAGGATATGGAGGTCGAAGATTAGGGTAGAAGGGTAATAGGTCG
TAGTGTGTTTTTCTAATATGTTCCAGGTTTATTAGCGCGAGCTGACTAGTACATTGTCTTCGATTCTTAG
AGTGCTAGTATTAGGGTTGTTTTCAGTACTATCTTCCGCTTCGGTTTTCTAGTACTTTGTCGTAATACTG
CTTGTTGCTATTGCTTTCTTCCATTTGTTTGTTTTCTCGGTTCATACATTGATAGTATCATTTTCCTGGC
CTTGTTGTTATTACCTTATTCCTATTCTTCCTCTCGAGCCGGGAGTCTTTCGGAAATAGCCTCTCTATCC
CTCAGGGTAGGGGTAAGGTCTGCGTATACATTACTCTCCTCATACCCCACTTGTGGGATTCCATTGGGTT
GTTGTTGTTGGGTTAGTGAATACATGTCAGTTTGGACAGGTGAGAGTGAGGCATTGGAAATAAAAAAAAA
AAAAAACAGGATGACGGCTTTCAAAAGACGAGTAAGAGACGGGGAGATGGAGGCTCTCGAAACCAAATGA
GATTAGAGAGAACAGGGGAATTAGCACCATTCATATGAGAGCTAACCTCTTTGTATATGAAATTCTTCAA
TTTGCATAATCATGTGCATTTCTTTGTAGGCTTTCAGGTGCTGATCCAGGCTGTAGAACAACTAGTTGAA
AATAAAGCTCCTGAAAAGATGACTTTGAATCAGCTCGCATGGTTATATTCCATCATGTTAACTGCCACAG
TAGTAAAACTTGCCCTTTGGCTTTACTGCAGAAGCTCAGGAAACAACATTGTTCGTGCGTATGCAAAGGT
GTGTGTAGTGTCCTTACCTTCTGGTTTCCACATCTTCTCCTGATAATCTCTTTTCCTAATTTGTTGATGT
ATTTGTCAGGATCACTATTTTGATGTGGTTACTAACGTAGTCGGGTTAATAGCAGCTGTACTTGGTGATA
AGTTCTACTGGTGGATTGATCCCGTTGGTGCTCTTATCCTTGCTATTTATACAATCTCAAATTGGTCAGC
CACTGTGATAGAGAATGCAGGTATATACTTACATGTTCCTGTTGAATTTATAGTTCGTCAATAATTCATG
GAAGTTAACAGCGACGTTCAACAAACACAGAACTAGTAACGCAGACTAGAATCTAACCTTGTAAGAAAAA
TTATCCCTTTAGGATGTCTGCAAGAATTATGCTTGTTGGACACCTCAAGTCTGAGCACATAATATATGTT
GTCCAAGCCAACTTGCACGCAGCTCGACTATTCCACCGGTTACCTGCTACCTCTCACCAGTAAACGTATC
GAGTAACTCTGCTCATCAAGGTTTAGGCAGATGGAAAGAAATTAACTAGTGTCTTTTTGCCACCGCTGGG
GTTTGAACTGGAGACCTCATGGTTCTCCTCTCACTTCATTGACCACTAGACCACACCCTGGGATGCAAAA
CTCCGATATTTTCTTGGTGTTATTTATATCAATACATCAAATAAAACTTGAATGAGGTTCTTGATGCAGT
GTCACTGGTAGGACAATCAGCTCCTCCTGAAGTTATGCAGAAGTTAACATATGTTGTTATAAGACATCCT
CAAGTGAAACGTATTGATACAGTTCGAGCATACACCTTTGGTGTCTTGTACTTTGTTGAGGTCAGTCTCC
AATAGCATGAAATCATTTTCCTAAACATCTTTGGTCTGAACTAACTGAATTATTAAGGCATAGCCTTTTC
CAGATCTCTGCTGATTTCAAAATGTTGCTTCCTTTCTTTTAACATAGGTTGATATTGAACTCCCGGAAGA
TTTGCCATTGAAAGAAGCACATATTATCGGAGAGACTCTACAAATAAAGCTCGAGAAACTCCCTGAAGTG
GAACGCGCATTTGTTCATCTTGATTTTGAATGTGAACACAAACCAGAACACTCCGTCCCCAGCAAGCTGC
CCAACAATGAATCTTAAGTGTAGAACACACAAACTAGGAGAAATTTCAATATAAAGAATAGGTCTTTGAT
TGGGAGCTCAGCTGCTCCTGAACCTCTATAAATACTCTTGGTCATGTTTGAGGAATTTGCATGAT

FIG. 33

SEQ ID No. 29

ATGGAGGGAGAATTAGAGGCTAACAATATTAATGGAACTAAAACGCCATTGTTGGAGGGGTGGAAGCTTA
GCGGAAGTGGACGGCGGAGCAGCCGGCGTTTCAGCCGGCATAACTCTTTTACGTCGCTCCGCCGTGATTT
CTTGTCTAGGCTTCCAGATAAGGTGATCAACTCTTTTGTTATTGATTCTGAAGCTTCATACATCATTAAT
AACCTCTCCATATCCTCTGACTTAACCAAAGGAGAAAAGGAATACTATGAAAAACAGTTTGAGACTTTGA
AGTCATTTGAGGAAGTTGATTCTGCAGTTGCTTCTGATTGCATTGATGAAGAGGATCTCGAAGAACAAGC
TCAACATGAGAGAGCAATGAGAATCTCCAATTATGCAAACATTATACTGCTTGCTCTCAAGATCTATGCC
ACAGTAAAGAGTGGTTCTTTAGCTATTGCTGCATCTACACTGGATTCATTGCTTGACCTCATGGCTGGTG
GCATACTATGGTTTACTCATCTTTCAATGAAAAATATTAATGTCTATAAATATCCTATTGGAAAATTGAG
AGTGCAGCCTGTTGGAATCATCGTCTTTGCTGCTATTATGGCTACACTTGGCTTTCAGGTGCTGATCCAG
GCTGTAGAACAACTAGTTGAAAATAAAGCTCCTGAAAAGATGACTTTGAATCAGCTCGCATGGTTATATT
CCATCATGTTAACTGCCACAGTAGTAAAACTTGCCCTTTGGCTTTACTGCAGAAGCTCAGGAAACAACAT
TGTTCGTGCGTATGCAAAGGATCACTATTTTGATGTGGTTACTAACGTAGTCGGGTTAATAGCAGCTGTA
CTTGGTGATAAGTTCTACTGGTGGATTGATCCCGTTGGTGCTCTTATCCTTGCTATTTATACAATCTCAA
ATTGGTCAGCCACTGTGATAGAGAATGCAGTGTCACTGGTAGGACAATCAGCTCCTCCTGAAGTTATGCA
GAAGTTAACATATGTTGTTATAAGACATCCTCAAGTGAAACGTATTGATACAGTTCGAGCATACACCTTT
GGTGTCTTGTACTTTGTTGAGGTTGATATTGAACTCCCGGAAGATTTGCCATTGAAAGAAGCACATATTA
TCGGAGAGACTCTACAAATAAAGCTCGAGAAACTCCCTGAAGTGGAACGCGCATTTGTTCATCTTGATTT
TGAATGTGAACACAAACCAGAACACTCCGTCCCCAGCAAGCTGCCCAACAATGAATCTTAA

FIG. 34

SEQ ID No. 30

MEGELEANNINGTKTPLLEGWKLSGSGRRSSRRFSRHNSFTSLRRDFLSRLPDKVINSFVIDSEASYIIN
NLSISSDLTKGEKEYYEKQFETLKSFEEVDSAVASDCIDEEDLEEQAQHERAMRISNYANIILLALKIYA
TVKSGSLAIAASTLDSLLDLMAGGILWFTHLSMKNINVYKYPIGKLRVQPVGIIVFAAIMATLGFQVLIQ
AVEQLVENKAPEKMTLNQLAWLYSIMLTATVVKLALWLYCRSSGNNIVRAYAKDHYFDVVTNVVGLIAAV
LGDKFYWWIDPVGALILAIYTISNWSATVIENAVSLVGQSAPPEVMQKLTYVVIRHPQVKRIDTVRAYTF
GVLYFVEVDIELPEDLPLKEAHIIGETLQIKLEKLPEVERAFVHLDFECEHKPEHSVPSKLPNNES

FIG. 35

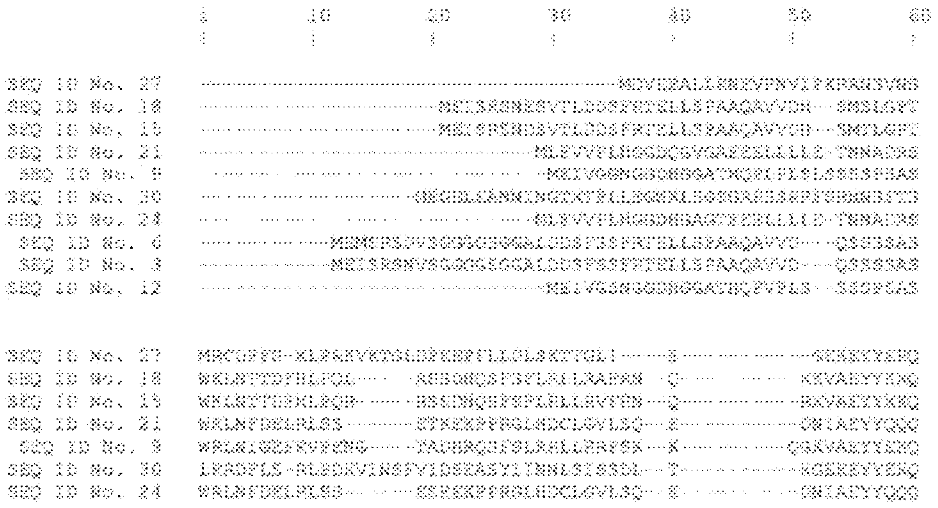

FIG. 35 (Continued)

```
SEQ ID No. 6    WKLNIGEFRLPEEGR----SGSDHHTFSVPALLPTPK--Q-----------GKIAEYYKKQ
SEQ ID No. 3    WRLNIGEFRLPEKGE----SSSDHHSFTVAELLPTPK--Q-----------GKIAEIYKKQ
SEQ ID No. 12   WKLNIGEFRVPEYG-----TGDHHQSFSLPALLAEPSK--K----------QGKVAEYYKKQ

SEQ ID No. 27   IATLKSFNEVDE-LDSADVI------DEEQDLLQQAQHEKAMNIENPANVLLAFKIYATV
SEQ ID No. 18   ERLLEGFNENDT-INECGSLPGNLTEDEMKQHAR-SERMALHASNIAMMVLFIAKVYASI
SEQ ID No. 15   ERLLEGFNEMDT-IDECDYLPGHLTEDELKQHAK-SEPMAILVGNIANMALFIAKIYASI
SEQ ID No. 21   VEMLEGFNENDT-LTDRGFVPG-MDKSEAEKTAE-NETFALRISNVAWMVLFAAKVYASV
SEQ ID No. 9    EALVEGYNENDT-VNEEGFLPGTLTEDEMKQLAK-SERMAIHVSNIANVVLFIAKIYASI
SEQ ID No. 30   FETLKSFEEVD------EAVASDCIDEEDLEEQAQ--EEPAMRISNYAMIILLALKIYATV
SEQ ID No. 24   VENLEGFNEMDA-LTDRGFVPG-MSKEEEEKTAE-NETFAIKISNVAWMVLFAAKVYASV
SEQ ID No. 6    ERLLEGFNENDT-INESGCLPGSLTEDEMKQLAR-SERMALHLGNMANVVLFLAKIYASI
SEQ ID No. 3    ERLLEGFNENDT-INESGCLPGSLTEDEMKQLAR-SERMAIHLSNMANVVLFIAKIYASI
SEQ ID No. 12   ERLLEGSNEMDE-VNESGFLPGSLTEDEMKQLAK-SERMAIHVGNIANLILFIAKIYASI

SEQ ID No. 27   KSGSLAIAASTLDSLLDLMAGGILWFTHLSMKSINIYKYPIGKLRVQPVGIIIFAAVMAT
SEQ ID No. 18   DSRSLAVIASTLDSLLDLLSGFILWFTSHAMKTPNQYRYPIGKKRMQPVGIVVFASVMAT
SEQ ID No. 15   DSRSLAVIASTLDSLLDLLAGFILWFTSHAMKTPNQYCYPIGKKRMQPVGIVVIASVMAT
SEQ ID No. 21   KSGSLAIIASTLDSLLDLLSGFILWFTAFSMQTPNPYQYPIGKKRMQPLGILVFASVMAT
SEQ ID No. 9    ASRSLAVIASTLDSLLDLLSGFILWFTVYAMKNPNQYHYPIGKKRMQPVGIIVFASVMAT
SEQ ID No. 30   KSGSLAIAASTLDSLLDIMAGGILWFTHLSMKNINVYKYPIGKLRVQPVGIIVFAAIMAT
SEQ ID No. 24   KSGSLAIIASTLDSLLDLLSGFILWFTAFSMQTPNPYQYPIGKKRMQPLGILVFASVMAT
SEQ ID No. 6    ESRSLAVIASTLDSLLDLLSGFILWFTSHAMKNPNQYHYPIGKKRMQPVGIIVFASVMAT
SEQ ID No. 3    ESRSLAVIASTLDSLLDLLSGFILWFTSHAMKNPNQYHYPIGKKRMQPLGIIVFASVMAT
SEQ ID No. 12   ASRSLAVIASTLDSLLDLLSGFILWFTVYAMKKPNQYHYPIGKKRMQPVGIIVIASVMAT

SEQ ID No. 27   LGFQVLVQAVEQLIKGTPSDRMTSSQLAWLYAIMLTATSVRLVLWIYCRSSGNKIVRAYA
SEQ ID No. 18   LGLQILPESGKELIT-KSRPDMDPEKSQWMIGIMVSVTVVKFMLLIYCRRFKNEIVRAYA
SEQ ID No. 15   LGLQILFESGKELIT-KSRPDMDPEKSKWMIGIMVSVTVVKFMLLIYCRRFKNEIVRAYA
SEQ ID No. 21   LGLQIILESMRTLISDEEDFNLTKEQEMWVVGIMVFVTLVKLVLMLYCRSFTNEIVRAYA
SEQ ID No. 9    LGLQILFESGKELIE-KSRPNTDPEKSKWMIGIMVSVTVVKFLLMVYCRRFKNEIVRAYA
SEQ ID No. 30   LGFQVLIQAVEQLVENKAPEKMTLEQLAWLYSIMLTATVVKLALWLYCRSSGNRIVRAYA
SEQ ID No. 24   LGLQIILESMRTLISDEEDFNLTKEQEMWVVSIMVFVTLVKLVLMLYCRSFTNEIVRAYA
SEQ ID No. 6    LGLQMLFESAKELIT-KSRPEMDHEKEKWTIGIMVSVTMVKFLLMIYCRRFKNEIVRAYA
SEQ ID No. 3    LGLQILFESAKELIT-KSRPEMDHEKSKWTIGIMVSVTMVKFLLMVYCRRFKNEIVRAYA
SEQ ID No. 12   LGLQILFESGKELIY-KSRPNTDPEKEKWMIGIMVSVTVVKFLLMLYCRRFKNEIVRAYA

SEQ ID No. 27   KDHYFDVVTNVVGLVAAVLGDKFYWWIDPVGAIVLAVYTIINWSGTVLENAVSLVGQSAP
SEQ ID No. 18   QDHFFDVITNSIGLAAAVLAIKFYWWIDPTGAIIIALYTMSTWAKTVMENVWSLIGRTAP
SEQ ID No. 15   QDHFFDVITNSIGLAAAVLAIKFYWWIDPTGAIIIALYTMSTWAKTVMENVWSLIGRTAP
SEQ ID No. 21   QDHFFDVITNIIGLIAALLANYLTDWIDPVGAMILALYTIRTWSMTVLENVNSLVGKSAA
SEQ ID No. 9    QDHLFDVITNSVGLVTAVLAIKFCWWIDPTGAIIIALYTIGTWAKTVIENMRSLIGRTAP
SEQ ID No. 30   KDHYFDVVTNVVGLIAAVLGDKFYWWIDPVGAIILAIYTIGNWSATVIENAVSLVGQSAP
SEQ ID No. 24   QDHFFDVITNIIGLIAALLANYITDWIDPVGAMILALYTIRTWSMTVLENVNSLVGKSAA
SEQ ID No. 6    QDHFFDVITNSVGLVTAVLAVKFYWWIDPTGAIIIAVYTIRTWAKTVAENVWSLIGRTAP
SEQ ID No. 3    QDHFFDVITNSVGLVTAVLAVKFYWWIDPTGAIIIAMYTISTWAKTVAENVWSLIGRTAP
SEQ ID No. 12   QDHFFDVITNSVGLVTAVLAIKFCWWIDPNGAIIIALYTIGTWAKTVIENMRSLIGRTAP

SEQ ID No. 27   PEFLQKLTYLVLRHD-PQIKRVDTVRAYTFGVLYFVEVDIELPEDLPLKEAHAIGESLQI
SEQ ID No. 18   PEFLAKLTYLIWNHR-ERIKHIDTVRAYNF---EVYSTTGELVVFILPLSPI--------
SEQ ID No. 15   PEFLAKLTYLIWNHH-ERIKHIDTVRAYNFGIQYFVEVDIVLPEDMPLRQAHNIGETLQE
SEQ ID No. 21   PEVLQKLTYLCWNHH-KAVRHIDTVRAYTFGSHYFVEVDIVLPADMPLQEAHDIGESLQE
SEQ ID No. 9    PEFLAKLTYLIWNHH-KEIKHIDTVRAYTFGTHYFVEVDIVLPEDMLLSQAHNIGETLQE
SEQ ID No. 30   PEVNQKLTYVVIRH--PQVKRIDTVRAYTFGVLYFVEVDIELPEDLPLKEAHAIGETLQI
SEQ ID No. 24   PEVLQKLTYLCWNHH-KAIRHIDTVRAYTFGSHYFVEVDIVLPADMPLQEAHDIGESLQE
SEQ ID No. 6    PDFLTKLTYLIWNHH-EEIKHIDTVRAYTFGAHYFVEVDIVLPEDMLLNQAHNIGETLQE
SEQ ID No. 3    PDFLTKLTYLIWNHR-EEIKHIDTVRAYTFGAHYFVEVDIVLPEDMLLNKAHNIGETLQE
SEQ ID No. 12   PEFLAKLTYLIWNHH-KEIKHIDTVRAYTFGANYFVEVDIVLPEDMLLSQAHNIGETLQE

SEQ ID No. 27   KLEKLPEVERAFVHLDYECDHKPEHSILSKLPNSEP
SEQ ID No. 18   ------------------------------------
SEQ ID No. 15   KLEQLVEVERAFVHVDFDITHRLEHKGMIK------
SEQ ID No. 21   KLELLPEIERAFVHLDYEYSHKPEHAQAYQ------
SEQ ID No. 9    KLDQLPDVERAFVHVDFEFTHRPEHKTMV-------
SEQ ID No. 30   KLEKLPEVERAFVHLDYECEHKPEHSVPSKLPNNES
SEQ ID No. 24   KLELLPEIERAFVHLDYEYSHKPEHAQAYQ------
SEQ ID No. 6    KLEQLPEVERAFVHIDFEFTHRPEHKTMV-------
SEQ ID No. 3    KLEQLPEVERAFVHIDFEFTHRPEHKTMV-------
SEQ ID No. 12   KLEQLPDVERAFVHVDFEFTHRPEHKTMV-------
```

FIG. 38

SEQ ID No. 31

MEISRSNVSGGGGSGGALDDSFSSFRTELLSPAAQAVVDQSSSSASWRLNISEFRLPERSRSSSDHHSFSVRRLLPTP
RKQGKIAEYYKKQERLLEGFNEMDTINESGCLPGSLTEDEMKQLARSERMAIHLSNMANVVLFIAKIYASIESRSLAV
IASTLDSLLDLLSGFILWFTSHAMKNPNQYHYPIGKKRMQPLGIIVFASVMATLGLQILFESAKELITKSRPEMDHEKE
KWTIGIMVSVTMVKFLLMVYCRRFKNEIVRAYAQDHFFDVITNSVGLVTAVLAVRFYWWIDPTG

FIG. 39

SEQ ID No. 32

ATGGAGATAAGTCGCAGCAATGTTAGTGGTGGTGGCGGCAGCGGCGGCGCTCTGGACGACAGTTTTAGCAG
TTTTAGGACGGAACTGCTGTCTCCGGCTGCTCAGGCGGTGGTGGATCAGTCGTCTTCGTCGGCGTCATGGAGA
CTTAACATTAGCGAATTCCGTCTTCCCGAACGAAGCCGCTCCTCCTCCGATCATCACTCCTTTAGTGTCCGTCGT
CTACTTCCCACTCCCAGGAAACAAGGTAAAATTGCTGAATACTACAAAAAACAAGAAAGGCTGCTTGAAGGGT
TCAATGAGATGGACACCATTAATGAATCTGGTTGTTTACCTGGAAGTCTAACTGAGGATGAAATGAAGCAGCT
TGCAAGAAGTGAAAGGATGGCTATTCATTTATCAAACATGGCTAATGTGGTTCTTTTCATTGCAAAAATCTACG
CTTCTATTGAGAGCAGATCTTTGGCTGTAATCGCGTCAACGTTGGACTCCCTCTTAGACCTCTTATCAGGGTTT
ATACTGTGGTTCACTTCTCATGCCATGAAAAATCCAAACCAGTATCACTATCCTATTGGAAAAAAGAGGATGCA
GCCATTGGGTATTATTGTTTTTGCATCTGTAATGGCGACACTAGGATTACAAATATTGTTCGAGTCAGCTAAAG
AACTCATAACTAAGTCTCGCCCTGAGATGGACCATGAGAAGGAAAAATGGACGATTGGTATTATGGTCTCTGT
CACTATGGTCAAGTTTCTGCTTATGGTCTACTGTCGAAGGTTCAAAAACGAAATCGTAAGAGCCTATGCTCAA
GATCATTTCTTTGATGTCATCACCAACTCAGTTGGATTAGTGACTGCTGTCTTAGCAGTCCGATTCTACTGGTG
GATTGATCCTACGGGAGCTTAA

FIG. 40

SEQ ID No. 33

MEMKQLARSERMAIHLSNMANVVLFIAKIYASIESRSLAVIASTLDSLLDLLSGFILWFTSHAMKNPNQYHYPIGKKR
MQPLGIIVFASVMATLGLQILFESAKELITKSRPEMDHEKEKWTIGIMVSVTMVKFLLMVYCRRFKNEIVRAYAQDH
FFDVITNSVGLVTAVLAVRFYWWIDPTGAIIIAMYTISTWAKTVAENVWSLIGRTAPPDFLTKLTYLIWNHHEEIKHI
DTVRAYTFGAHYFVEVDIVLPEDMLLNKAHNIGETLQEKLEQLPEVERAFVHIDFEFTHRPEHKTMV

FIG. 41

SEQ ID No. 34

ATGGAAATGAAGCAGCTTGCAAGAAGTGAAAGGATGGCTATTCATTTATCAAACATGGCTAATGTGGTTCTTT
TCATTGCAAAAATCTACGCTTCTATTGAGAGCAGATCTTTGGCTGTAATCGCGTCAACGTTGGACTCCCTCTTA
GACCTCTTATCAGGGTTTATACTGTGGTTCACTTCTCATGCCATGAAAAATCCAAACCAGTATCACTATCCTATT
GGAAAAAAGAGGATGCAGCCATTGGGTATTATTGTTTTTGCATCTGTAATGGCGACACTAGGATTACAAATAT
TGTTCGAGTCAGCTAAAGAACTCATAACTAAGTCTCGCCCTGAGATGGACCATGAGAAGGAAAAATGGACGA
TTGGTATTATGGTCTCTGTCACTATGGTCAAGTTTCTGCTTATGGTCTACTGTCGAAGGTTCAAAAACGAAATC
GTAAGAGCCTATGCTCAAGATCATTTCTTTGATGTCATCACCAACTCAGTTGGATTAGTGACTGCTGTCTTAGC
AGTCCGATTCTACTGGTGGATTGATCCTACGGGAGCTATAATTATAGCTATGTACACAATTAGCACGTGGGCG
AAGACAGTGGCAGAAAATGTCTGGTCACTCATTGGAAGAACAGCTCCACCAGATTTTCTTACGAAATTAACCT
ATCTTATATGGAATCATCACGAAGAGATCAAGCACATTGATACTGTTCGAGCATATACTTTTGGTGCTCATTAT
TTTGTAGAGGTTGATATAGTGTTGCCAGAGGACATGCTGTTGAACAAGGCACATAATATTGGTGAGACACTGC
AAGAAAAATTGGAGCAACTCCCTGAAGTTGAGCGAGCTTTTGTTCATATAGACTTCGAGTTCACTCACAGGCC
AGAACACAAAACTATGGTATAA

FIG. 42

SEQ ID No. 36

GTAAAACGACGGCCAG

FIG. 43

SEQ ID No. 37

GTCATAGCTGTTTCCTG

FIG. 44

SEQ ID No. 38

AGCTTGCATGCCTGCAGGTCGAGCTTTTAGGATTCCATAGTGATAAGATATGTTCTTATCTAAACAAAAAAGCA
AGCGTCGGCAAACCATACAGCTGTCCACAAAAAGGAAAGGCTGTAATAACAAGCGGACCCAGCTTCTCAGTG
GAAGATACTTTATCAGACACTGAATAATGGATGGACCCTACCACGATTAAAGAGGAGCGTCTGTCTAAAGTAA
AGTAGATGCGTCTTTAATAATTCATCTACTTTAGACGTCATGCATGACGTTTAACATGCATTGTATCCAGATCCT
CCCTGGCTATATAAAGGGAGTTAAATTTCATTGTTAAGGCATCGAAAAAAAAATTTCAAGTCTATCTCTCAAGA
AAAACTTAGAAAATTACTTTGTCTTAAGGATCCGGGCCCAGCTGTCACAAGTTTGTACAAAAAAGCTGAACGA
GAAACGTAAAATGATATAAATATCAATATATTAAATTAGATTTTGCATAAAAAACAGACTACATAATACTGTAA
AACACAACATATCCAGTCACTATGGCGCCGCATTAGGCACCCCAGGCTTTACACTTTATGCTTCCGGCTCGTAT
AATGTGTGGATTTTGAGTTACGATCCGTCGAGATTTTCAGGAGCTAAGGAAGCTAAAATGGAGAAAAAAATC
ACTGGATATACCACCGTTGATATATCCCAATGGCATCGTAAAGAACATTTTGAGGCATTTCAGTCAGTTGCTCA
ATGTACCTATAACCAGACCGTTCAACTGGATATTACGGCCTTTTTAAAGACCGTAAAGAAAAATAAGCACAAG
TTTTATCCGGCCTTTATTCACATTCTTGCCCGCCTGATGAATGCTCATCCGGAATTTCGTATGGCAATGAAAGAC
GGTGAGCTGGTGATATGGGATAGTGTTCACCCTTGTTACACCGTTTTCCATGAGCAAACTGAAACGTTTTCATC
GCTCTGGAGTGAATACCACGACGATTTCCGGCAGTTTCTACACATATATTCGCAAGATGTGGCGTGTTACGGT
GAAAACCTGGCCTATTTCCCTAAAGGGTTTATTGAGAATATGTTTTTCGTCTCAGCCAATCCCTGGGTGAGTTT
CACCAGTTTTGATTTAAACGTGGCCAATATGGACAACTTCTTCGCCCCCGTTTTCACGATGGGCAAATATTATA
CGCAAGGCGACAAGGTGCTGATGCCGCTGGCGATTCAGGTTCATCATGCCGTTTGTGATGGCTTCCATGTCGG
CAGAATGCTTAATGAATTACAACAGTACTGCGATGAGTGGCAGGGCGGGGCGTAAACGCGACGATCCGGCTT
ACTAAAAGCCAGATAACAGTATGCGTATTTGCGCGCTGATTTTTGCGGTATAAGAATATATACTGATATGTATA
CCCGAAGTATGTCAAAAAGAGGTATGCTATGAAGCAGCGTATTACAGTGACAGTTGACAGCGACAGCTATCA

FIG. 44 (Continued)

GTTGCTCAAGGCATATATGATGTCAATATCTCCGGTCTGGTAAGCACAACCATGCAGAATGAAGCCCGTCGTC
TGCGTGCCGAACGCTGGAAAGCGGAAAATCAGGAAGGGATGGCTGAGGTCGCCCGGTTTATTGAAATGAAC
GGCTCTTTTGCTGACGAGAACAGGGGCTGGTGAAATGCAGTTTAAGGTTTACACCTATAAAAGAGAGAGCCG
TTATCGTCTGTTTGTGGATGTACAGAGTGATATTATTGACACGCCTGGGCGACGGATGGTGATCCCCCTGGCC
AGTGCACGTCTGCTGTCAGATAAAGTCTCCCGTGAACTTTACCCGGTGGTGCATATCGGGGATGAAAGCTGGC
GCATGATGACCACCGATATGGCCAGTGTGCCGGTCTCCGTTATCGGGGAAGAAGTGGCTGATCTCAGCCACC
GCGAAAATGACATCAAAAACGCCATTAACCTGATGTTCTGGGGAATATAAATGTCAGGCTCCCTTATACACAG
CCAGTCTGCACCTCGACCATAGTGACTGGATATGTTGTGTTTTACAGTATTATGTAGTCTGTTTTTTATGCAAAA
TCTAATTTAATATATTGATATTTATATCATTTTACGTTTCTCGTTCAGCTTTCTTGTACAAAGTGGTGCAGCTGAG
ATCTAGGCCTAAGTAAGTAAGATCGTTCAAACATTTGGCAATAAAGTTTCTTTAGATTGAATCCTGTTGCCGGT
CTTGCGATGATTATCATATAATTTCTGTTGAATTACGTTAAGCATGTAGTAATTAACATGTAATGGATGACGTT
ATTTATGAGATGGGTTTTTATGATTAGAGTCCCGCAATTATACATTTAATACGCGATAGAAAACAAAATATAGC
GCGCAAACTAGGATAAATTATCGCGCGCGGTGTCATCTATGTTACTAGATCGAAGGCCTTGTTCTCGAGCAAT
TCACTGGCCGTCGTTTTACAACGTCGTGACTGGGAAAACCCTGGCGTTACCCAACTTAATCGCCTTGCAGCACA
TCCCCCTTTCGCCAGCAGGCGTAATAGCGAAGAGGCCCGCACCGATTGCCCTTCCCAACAGTTGCGCAGCCTG
AATGGCGCCCGCTCCTTTCGCTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAAAACTTGATTTGGGTGATG
GTTCACAAACTATCAGTGTTTGACAGGATATATTGGCGGGTAAACCTAAGAGAAAAGAGCGTTTATTAGAATA
ATCGGATATTTAAAAGGGCGTGAAAAGGTTTATCCGTTCGTCCATTTGTATGTGCATGCCAACCACAGGCTTA
AGAAAACTTGATTTGGGTGATGGTTCACAAACTATCAGTGTTTGACAGGATATATTGGCGGGTAAACCTAAGA
GAAAAGAGCGTTTATTAGAATAATCGGATATTTAAAAGGGCGTGAAAAGGTTTATCCGTTCGTCCATTTGTAT
GTGCATGCCAACCACAGGCTTAAGGTTCTAGACTGGCGCCGGCCAGCGAGACGAGCAAGATTGGCCGCCGCC
CGAAACGATCCGACAGCGCGCCCAGCACAGGTGCGCAGGCAAATTGCACCAACGCATACAGCGCCAGCAGA
ATGCCATAGTGGGCGGTGACCTCGTTCGAGTGAACCAGATCGCGCAGGAGGCCCGGCAGCACCGGCATAATC
AGGCCGATGCCGACAGCGTCGAGCGCGACAGTGCTCAGAATTACGATCAGGGGTATGTTGGGTTTCACGTCT
GGCCTCCGGACCAGCCTCCGCTGGTCCGATTGAACGCGCGGATTCTTTATCACTGATAAGTTGGTGGACATAT
TATGTTTATCAGTGATAAAGTGTCAAGCATGACAAAGTTGCAGCCGAATACAGTGATCCGTGCCGCCCTGGAC
CTGTTGAACGAGGTCGGCGTAGACGGTCTGACGACACGCAAACTGGCGGAACGGTTGGGGGTTCAGCAGCC
GGCGCTTTACTGGCACTTCAGGAACAAGCGGGCGCTGCTCGACGCACTGGCCGAAGCCATGCTGGCGGAGAA
TCATACGCATTCGGTGCCGAGAGCCGACGACGACTGGCGCTCATTTCTGATCGGGAATGCCCGCAGCTTCAGG
CAGGCGCTGCTCGCCTACCGCGATGGCGCGCGCATCCATGCCGGCACGCGACCGGGCGCACCGCAGATGGA
AACGGCCGACGCGCAGCTTCGCTTCCTCTGCGAGGCGGGTTTTTCGGCCGGGGACGCCGTCAATGCGCTGAT
GACAATCAGCTACTTCACTGTTGGGGCCGTGCTTGAGGAGCAGGCCGGCGACAGCGATGCCGGCGAGCGCG
GCGGCACCGTTGAACAGGCTCCGCTCTCGCCGCTGTTGCGGGCCGCGATAGACGCCTTCGACGAAGCCGGTC
CGGACGCAGCGTTCGAGCAGGGACTCGCGGTGATTGTCGATGGATTGGCGAAAAGGAGGCTCGTTGTCAGG
AACGTTGAAGGACCGAGAAAGGGTGACGATTGATGAGGACCGCTGCCGGAGCGCAACCCACTCACTACAGC
AGAGCCATGTAGACAACATCCCCTCCCCCTTTCCACCGCGTCAGACGCCCGTAGCAGCCCGCTACGGGCTTTTT
CATGCCCTGCCCTAGCGTCCAAGCCTCACGGCCGCGCTCGGCCTCTCTGGCGGCCTTCTGGCGCTCGTCGACC
GCTCACTGACTCGCTGCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTC
AAGTCAGAGGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTGGCGCTTTTCCG
CTGCATAACCCTGCTTCGGGGTCATTATAGCGATTTTTTCGGTATATCCATCCTTTTTCGCACGATATACAGGAT
TTTGCCAAAGGGTTCGTGTAGACTTTCCTTGGTGTATCCAACGGCGTCAGCCGGGCAGGATAGGTGAAGTAG
GCCCACCCGCGAGCGGGTGTTCCTTCTTCACTGTCCCTTATTCGCACCTGGCGGTGCTCAACGGGAATCCTGCT
CTGCGAGGCTGGCCGGCTACCGCCGGCGTAACAGATGAGGGCAAGCGGATGGCTGATGAAACCAAGCCAAC
CAGGAAGGGCAGCCCACCTATCAAGGTGTACTGCCTTCCAGACGAACGAAGAGCGATTGAGGAAAAGGCGG
CGGCGGCCGGCATGAGCCTGTCGGCCTACCTGCTGGCCGTCGGCCAGGGCTACAAAATCACGGGCGTCGTGG
ACTATGAGCACGTCCGCGAGCTGGCCCGCATCAATGGCGACCTGGGCCGCCTGGGCGGCCTGCTGAAACTCT
GGCTCACCGACGACCCGCGCACGGCGCGGTTCGGTGATGCCACGATCCTCGCCCTGCTGGCGAAGATCGAAG

FIG. 44 (Continued)

AGAAGCAGGACGAGCTTGGCAAGGTCATGATGGGCGTGGTCCGCCCGAGGGCAGAGCCATGACTTTTTTAGC
CGCTAAAACGGCCGGGGGGTGCGCGTGATTGCCAAGCACGTCCCCATGCGCTCCATCAAGAAGAGCGACTTC
GCGGAGCTGGTGAAGTACATCACCGACGAGCAAGGCAAGACCGAGCGCCTTTGGTACCTCACCGGGCTGGTT
GCCCTCGCCGCTGGGCTGGCGGCCGTCTATGGCCCTGCAAACGCGCCAGAAACGCCGTCGAAGCCGTGTGCG
AGACACCGCCGCCGCCGGCGTTGTGGATACCTCGCGGAAAACTTGGCCCTCACTGACAGATGAGGGGCGGAC
GTTGACACTTGAGGGGCCGACTCACCCGGCGCGGCGTTGACAGATGAGGGGCAGGCTCGATTTCGGCCGGC
GACGTGGAGCTGGCCAGCCTCGCAAATCGGCGAAAACGCCTGATTTTACGCGAGTTTCCCACAGATGATGTG
GACAAGCCTGGGGATAAGTGCCCTGCGGTATTGACACTTGAGGGGCGCGACTACTGACAGATGAGGGGCGC
GATCCTTGACACTTGAGGGGCAGAGTGCTGACAGATGAGGGGCGCACCTATTGACATTTGAGGGGCTGTCCA
CAGGCAGAAAATCCAGCATTTGCAAGGGTTTCCGCCCGTTTTTCGGCCACCGCTAACCTGTCTTTTAACCTGCT
TTTAAACCAATATTTATAAACCTTGTTTTTAACCAGGGCTGCGCCCTGTGCGCGTGACCGCGCACGCCGAAGG
GGGGTGCCCCCCCTTCTCGAACCCTCCCGGCCCGCTAACGCGGGCCTCCCATCCCCCCAGGGGCTGCGCCCCT
CGGCCGCGAACGGCCTCACCCCAAAAATGGCAGCGCTGGCAGTCCTTGCCATTGCCGGGATCGGGGCAGTAA
CGGGATGGGCGATCAGCCCGAGCGCGACGCCCGGAAGCATTGACGTGCCGCAGGTGCTGGCATCGACATTC
AGCGACCAGGTGCCGGGCAGTGAGGGCGGCGGCCTGGGTGGCGGCCTGCCCTTCACTTCGGCCGTCGGGGC
ATTCACGGACTTCATGGCGGGGCCGGCAATTTTTACCTTGGGCATTCTTGGCATAGTGGTCGCGGGTGCCGTG
CTCGTGTTCGGGGGTGACGCGTGAAAATTTTCGATAAACCCAGCGAACCATTTGAGGTGATAGGTAAGATTAT
ACCGAGGTATGAAAACGAGAATTGGACCTTTACAGAATTACTCTATGAAGCGCCATATTTAAAAAGCTACCAA
GACGAAGAGGATGAAGAGGATGAGGAGGCAGATTGCCTTGAATATATTGACAATACTGATAAGATAATATAT
CTTTTATATAGAAGATATGGCCGTATGTAAGGATTTCAGGGGGCAAGGCATAGGCAGCGCGCTTATCAATATA
TCTATAGAATGGGCAAAGCATAAAAACTTGCATGGACTAATGCTTGAAACCCAGGACAATAACCTTATAGCTT
GTAAATTCTATCATAATTGGGTAATGACTCCAACTTATTGATAGTGTTTTATGTTCAGATAATGCCCGATGACTT
TGTCATGCAGCTCCACCGATTTTGAGAACGACAGCGACTTCCGTCCCAGCCGTGCCAGGTGCTGCCTCAGATT
CAGGTTATGCCGCTCAATTCGCTGCGTATATCGCTTGCTGATTACGTGCAGCTTTCCCTTCAGGCGGGATTCAT
ACAGCGGCCAGCCATCCGTCATCCATATCACCACGTCAAAGGGTGACAGCAGGCTCATAAGACGCCCCAGCG
TCGCCATAGTGCGTTCACCGAATACGTGCGCAACAACCGTCTTCCGGAGACTGTCATACGCCTAAAACAGCCA
GCGCTGGCGCGATTTAGCCCCGACATAGCCCCACTGTTCGTCCATTTCCGCGCAGACGATGACGACACTGCCC
GGCTGTATGCGCGAGGTTACCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTCCAGGGGGAAACGCCT
GGTATCTTTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTTGCTCACAT
GTTCTTTCCTGCGTTATCCCCTGATTCTGTGGATAACCGTATTACCGCCTTTGAGTGAGCTGATACCGCTCGCCG
CAGCCGAACGACCGAGCGCAGCGAGTCAGTGAGCGAGGAAGCGGAAGAGCGCCTGATGCGGTATTTTCTCC
TTACGCATCTGTGCGGTATTTCACACCGCATAGTTACCGACTGCGGCCTGAGTTTTTTAAGTGACGTAAAATCG
TGTTGAGGCCAACGCCCATAATGCGGGCTGTTGCCCGGCATCCAACGCCATTCATGGCCATATCAATGATTTTC
TGGTGCGTACCGGGTTGAGAAGCGGTGTAAGTGAACAGCAGTTGCCATGTTTTACGGCAGTGAGAGCAGAG
ATAGCGCTGATGTCCGGCGGTGCTTTTGCCGTTACGCACCACCCCGTCAGTAGCTGAACAGGAGGGACACCTG
ATAGACACAGAAGCCACTGGAGCACCTCAAAAACACCATCATACACTAAATCAGTAAGTTGGCAGCATCACCC
GTTAACATAATTGTGGTTTCAAAATCGGCTCCGTCGATACTATGTTATACGCCAACTTTGAAAACAACTTTGAA
AAAGCTGTTTTCTGGTATTTAAGGTTTTAGAATGCAAGGAACAGTGAATTGGAGTTCGTCTTGTTATAATTAGC
TTCTTGGGGTATCTTTAAATACTGTAGAAAAGAGGAAGGAAATAATAAATGGCTAAAATGAGAATATCACCG
GAATTGAAAAAACTGATCGAAAAATACCGCTGCGTAAAAGATACGGAAGGAATGTCTCCTGCTAAGGTATAT
AAGCTGGTGGGAGAAAATGAAAACCTATATTTAAAAATGACGGACAGCCGGTATAAAGGGACCACCTATGAT
GTGGAACGGGAAAAGGACATGATGCTATGGCTGGAAGGAAAGCTGCCTGTTCCAAAGGTCCTGCACTTTGAA
CGGCATGATGGCTGGAGCAATCTGCTCATGAGTGAGGCCGATGGCGTCCTTTGCTCGGAAGAGTATGAAGAT
GAACAAAGCCCTGAAAAGATTATCGAGCTGTATGCGGAGTGCATCAGGCTCTTTCACTCCATCGACATATCGG
ATTGTCCCTATACGAATAGCTTAGACAGCCGCTTAGCCGAATTGGATTACTTACTGAATAACGATCTGGCCGAT
GTGGATTGCGAAAACTGGGAAGAAGACACTCCATTTAAAGATCCGCGCGAGCTGTATGATTTTTTAAAGACG
GAAAAGCCCGAAGAGGAACTTGTCTTTTCCCACGGCGACCTGGGAGACAGCAACATCTTTGTGAAAGATGGC

FIG. 44 (Continued)

AAAGTAAGTGGCTTTATTGATCTTGGGAGAAGCGGCAGGGCGGACAAGTGGTATGACATTGCCTTCTGCGTC
CGGTCGATCAGGGAGGTTATCGGGGAAGAACAGTATGTCGAGCTATTTTTTGACTTACTGGGGATCAAGCCT
GATTGGGAGAAAATAAAATATTATATTTTACTGGATGAATTGTTTTAGTACCTAGAGAAAATTTTCCTAGGTGT
GGCGCAACGATGCCGGCGACAAGCAGGAGCGCACCGACTTCTTCCGCATCAAGTGTTTTGGCTCTCAGGCCG
AGGCCCACGGCAAGTATTTGGGCAAGGGGTCGCTGGTATTCGTGCAGGGCAAGATTCGGAATACCAAGTACG
AGAAGGACGGCCAGACGGTCTACGGGACCGACTTCATTGCCGATAAGGTGGATTATCTGGACACCAAGGCAC
CAGGCGGGTCAAATCAGGAATAAGGGCACATTGCCCCGGCGTGAGTCGGGGCAATCCCGCAAGGAGGGTGA
ATGAATCGGACGTTTGACCGGAAGGCATACAGGCAAGAACTGATCGACGCGGGGTTTTCCGCCGAGGATGCC
GAAACCATCGCAAGCCGCACCGTCATGCGTGCGCCCCGCGAAACCTTCCAGTCCGTCGGCTCGATGGTCCAGC
AAGCTACGGCCAAGATCGAGCGCGACAGCGTGCAACTGGCTCCCCCTGCCCTGCCCGCGCCATCGGCCGCCG
TGGAGCGTTCGCGTCGTCTCGAACAGGAGGCGGCAGGTTTGGCGAAGTCGATGACCATCGACACGCGAGGA
ACTATGACGACCAAGAAGCGAAAAACCGCCGGCGAGGACCTGGCAAAACAGGTCAGCGAGGCCAAGCAGGC
CGCGTTGCTGAAACACACGAAGCAGCAGATCAAGGAAATGCAGCTTTCCTTGTTCGATATTGCGCCGTGGCCG
GACACGATGCGAGCGATGCCAAACGACACGGCCCGCTCTGCCCTGTTCACCACGCGCAACAAGAAAATCCCG
CGCGAGGCGCTGCAAAACAAGGTCATTTTCCACGTCAACAAGGACGTGAAGATCACCTACACCGGCGTCGAG
CTGCGGGCCGACGATGACGAACTGGTGTGGCAGCAGGTGTTGGAGTACGCGAAGCGCACCCCTATCGGCGA
GCCGATCACCTTCACGTTCTACGAGCTTTGCCAGGACCTGGGCTGGTCGATCAATGGCCGGTATTACACGAAG
GCCGAGGAATGCCTGTCGCGCCTACAGGCGACGGCGATGGGCTTCACGTCCGACCGCGTTGGGCACCTGGAA
TCGGTGTCGCTGCTGCACCGCTTCCGCGTCCTGGACCGTGGCAAGAAAACGTCCCGTTGCCAGGTCCTGATCG
ACGAGGAAATCGTCGTGCTGTTTGCTGGCGACCACTACACGAAATTCATCTGGGAGAAGTACCGCAAGCTGTC
GCCGACGGCCCGACGGATGTTCGACTATTTCAGCTCGCACCGGGAGCCGTACCCGCTCAAGCTGGAAACCTTC
CGCCTCATGTGCGGATCGGATTCCACCCGCGTGAAGAAGTGGCGCGAGCAGGTCGGCGAAGCCTGCGAAGA
GTTGCGAGGCAGCGGCCTGGTGGAACACGCCTGGGTCAATGATGACCTGGTGCATTGCAAACGCTAGGGCCT
TGTGGGGTCAGTTCCGGCTGGGGGTTCAGCAGCCAGCGTGATCACTTTACTGGCATTTCAGGAACAAGCGGG
CACTGCTCGACGCACTTGCTTCGCTCAGTATCGCTCGGGACGCACGGCGCGCTCTACGAACTGCCGATAAACA
GAGGATTAAAATTGACAATTGTGATTAAGGCTCAGATTCGACGGCTTGGAGCGGCCGACGTGCAGGATTTCC
GCGAGATCCGATTGTCGGCCCTGAAGAAAGCTCCAGAGATGTTCGGGTCCGTTTACGAGCACGAGGAGAAAA
AGCCCATGGAGGCGTTCGCTGAACGGTTGCGAGATGCCGTGGCATTCGGCGCCTACATCGACGGCGAGATCA
TTGGGCTGTCGGTCTTCAAACAGGAGGACGGCCCCAAGGACGCTCACAAGGCGCATCTGTCCGGCGTTTTCGT
GGAGCCCGAACAGCGAGGCCGAGGGGTCGCCGGTATGCTGCTGCGGGCGTTGCCGGCGGGTTTATTGCTCG
TGATGATCGTCCGACAGATTCCAACGGGAATCTGGTGGATGCGCATCTTCATCCTCGGCGCACTTAATATTTCG
CTATTCTGGAGCTTGTTGTTTATTTCGGTCTACCGCCTGCCGGGCGGGGTCGCGGCGACGGTAGGCGCTGTGC
AGCCGCTGATGGTCGTGTTCATCTCTGCCGCTCTGCTAGGTAGCCCGATACGATTGATGGCGGTCCTGGGGGC
TATTTGCGGAACTGCGGGCGTGGCGCTGTTGGTGTTGACACCAAACGCAGCGCTAGATCCTGTCGGCGTCGC
AGCGGGCCTGGCGGGGGCGGTTTCCATGGCGTTCGGAACCGTGCTGACCCGCAAGTGGCAACCTCCCGTGCC
TCTGCTCACCTTTACCGCCTGGCAACTGGCGGCCGGAGGACTTCTGCTCGTTCCAGTAGCTTTAGTGTTTGATC
CGCCAATCCCGATGCCTACAGGAACCAATGTTCTCGGCCTGGCGTGGCTCGGCCTGATCGGAGCGGGTTTAAC
CTACTTCCTTTGGTTCCGGGGGATCTCGCGACTCGAACCTACAGTTGTTTCCTTACTGGGCTTTCTCAGCCCCAG
GTCTGGGGTCGATCAGCCGGGGATGCATCAGGCCGACAGTCGGAACTTCGGGTCCCCGACCTGTACCATTCG
GTGAGCAATGGATAGGGGAGTTGAAATCGTCAACGTTCACTTCTAAAGAAATAGCGCCACTCAGCTTCCTCAG
CGGCTTTATCCAGCGATTTCCTATTATGTCGGCATAGTTCTCAAGATCGACAGCCTGTCACGGTTAAGCGAGAA
ATGAATAAGAAGGCTGATAATTCGGATCTCTGCGAGGGAGATGATATTTGATGACAGGCAGCAACGCTCTGT
CATCGTTACAATCAACATGCTACCCTCCGCGAGATCATCCGTGTTTCAAACCCGGCAGCTTAGTTGCCGTTCTTC
CGAATAGCATCGGTAACATGAGCAAAGTCTGCCGCCTTACAACGGCTCTCCCGCTGACTAGTCGTCCCGGAGA
CGTCCTGATGGGCTGCCTGTATCGAGTGGTGATTTTGTGCCGAGCTGCCGGTCGGGGAGCTGTTGGCTGGCT
GGTGGCAGGATATATTGTGGTGTAAACAAATTGACGCTTAGACAACTTAATAACACATTGCGGACGTTTTTAA
TGTACTGGACGTCCTGATGGGCTGCCTGTATCGAGTGGTGATTTTGTGCCGAGCTGCCGGTCGGGGAGCTGTT
GGCTGGCTGGTGGCAGGATATATTGTGGTGTAAACAAATTGACGCTTAGACAACTTAATAACACATTGCGGAC
GTTTTTAATGTACTGGGGTGGTTTTTCTTTTCACCAGTGAGACGGGCAACACGTGATTGCCCTTCACCGCCTGG
CCCTGAGAGAGTTGCAGCAAGCGGTCCACGCTGGTTTGCCCCAGCAGGCGAAAATCCTGTTTGATGGTGGTTC
CGAAATCGGCAAAATCCCTTATAAATCAAAAGAATAGCCCGAGATAGGGTTGAGTGTTGTTCCAGTTTGGAAC

FIG. 44 (Continued)

AAGAGTCCACTATTAAAGAACGTGGACTCCAACGTCAAAGGGCGAAAAACCGTCTATCAGGGCGATGGCCCA
CAAACTGAAGGCGGCCGCAAACGATATCAATCTCATCATGAGCGGAGAATTAAGGGAGTCACGTTATGACCC
CCGCCGATGACGCGGGACAAGCCGTTTTACGTTTGGAACTGACAGAACCGCAACGTTGAAGGAGCCACTCAG
CCGCCGGTTTCTGGAGTTTAATGAGCTAAGCACATACGTCAGAAACCATTATTGCGCGTTCAAAAGTCGCCTA
AGGTCACTATCAGCTAGCAAATATTTCTTGTCAAAAATGCTCCACTGACGTTCCATAAATTCCCCTCGGTATCCA
ATTAGAGTCTCATATTCACTCTCAATCCAAATAATCTGCACCGGATCTGGATCGTTTCGCATGATTGAACAAGA
TGGATTGCACGCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAAGACCGACCTG
TCCGGTGCCCTGAATGAACTCCAGGACGAGGCAGCGCGGCTATCGTGGCTGGCCACGACGGGCGTTCCTTGC
GCTGCTGTGCTCGACGTTGTCACTGAAGCGGGAAGGGACTGGCTGCTATTGGGCGAAGTGCCGGGGCAGGA
TCTCCTGTCATCTCACCTTGCTCCTGCCGAGAAAGTATCCATCATGGCTGATGCAATGCGGCGGCTGCATACGC
TTGATCCGGCTACCTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACTGTTCGCCAGGCT
CAAGGCGCGCATGCCCGACGGCGATGATCTCGTCGTGACCCATGGCGATGCCTGCTTGCCGAATATCATGGT
GGAAAATGGCCGCTTTTCTGGATTCATCGACTGTGGCCGGCTGGGTGTGGCGGACCGCTATCAGGACATAGC
GTTGGCTACCCGTGATATTGCTGAAGAGCTTGGCGGCGAATGGGCTGACCGCTTCCTCGTGCTTTACGGTATC
GCCGCTCCCGATTCGCAGCGCATCGCCTTCTATCGCCTTCTTGACGAGTTCTTCTGAGCGGGACTCTGGGGTTC
GAAATGACCGACCAAGCGACGCCCAACCTGCCATCACGAGATTTCGATTCCACCGCCGCCTTCTATGAAAGGT
TGGGCTTCGGAATCGTTTTCCGGGACGCCGGCTGGATGATCCTCCAGCGCGGGGATCTCATGCTGGAGTTCTT
CGCCCACGGGATCTCTGCGGAACAGGCGGTCGAAGGTGCCGATATTATTACGACAGCAACGGCCGACAAGCA
CAACGCCACGATCCTGAGCGACAATATGATCGGACCCGGCGTCCACATCAACGGCGTCGGCGGCGACTGCCC
AGGCAAGACCGAGATGCACCGCGATATATTGCTGCGTTCGGATATTTTCGTGGAGTTCCCGCCACAGACCCGG
ATGATCCCCGACCGTTCAAACATTTGGCAATAAAGTTTCTAAAGATTGAATCCTGTTGCCGGTCTTGCGATGAT
TATCATATAATTTCTGTTGAATTACGTTAAGCATGTAATAATTAACATGTAATGCATGACGTTATTTATGAGATG
GGTTTTTATGATTAGAGTCCCGCAATTATACATTTAATACGCGATAGAAAACAAAATATAGCGCGCAAACTAG
GATAAATTATCGCGCGCGGTGTCATCTATGTTACTAGATCGGGCCTCCTGATATCAATGCTGCAGCGGCGGCT
CTGGTGGTGGTTCTGGTGGCGGCTCTGAGGGTGGTGGCTCTGAGGGTGGCGGTTCTGAGGGTGGCGGCTCT
GAGGGAGGCGGTTCCGGTGGTGGCTCTGGTTCCGGTGATTTTGATTATGAAAAGATGGCAAACGCTAATAAG
GGGGCTATGACCGAAAATGCCGATGAAAACGCGCTACAGTCTGACGCTAAAGGCAAACTTGATTCTGTCGCT
ACTGATTACGGTGCTGCTATGATGGTTTCATTGGTGACGTTTCCGGCCTTGCTAATGGTAATGGTGCTACTGGT
GATTTTGCTGGCTCTAATTCCCAAATGGCTCAAGTCGGTGACGGTGATAATTCACCTTTAATGAATATTTCCGT
CAATATTTACCTTCCCTCCCTCAATCGGTTGAATGTCGCCCTTTTGTCTTTGGCCCAATACGCAAACCGCCTCTC
CCCGCGCGTTGGCCGATTCATTATGCACTGGCACGACAGGTTTCCCGACTGGAAAGCGGGCAGTGAGCGCAA
CGCAATTATGTGAGTTAGCTCACTCATTAGGCACCCCAGGCTTTACACTTTATGCTTCCGGCTCGTATGTTGTGT
GGAATTGTGAGCGGATAACAATTTCACACAGGAAACAGCTATGACCATGATTACGCCAAGCTGGCGCCA

FIG. 45

SEQ ID No. 39

TCAAAAAGCTCGCTCAACTTCAGGGAGTTGCTCCAATTTTTCTTGCAGTGTCTCACCAATATTATGTGCCTTGTT
CAACAGCATGTCCTCTGGCAACACTATATCAACCTCTACAAAATAATGAGCACCAAAAGTATATGCTCGAACA
GTATCAATGTGCTTGATCTCTTCGTGATGATTCCATATAAGATAGGTTAATTTCGTAAGAAAATCTGGTGGAGC
TGTTCTTCCAATGAGTGACCAGACATTTTCTGCCACTGTCTTCGCCCACGTGCTAATTGTGTACATAGCTATAAT
TATAGCTCCCGTAGGATCAATCCACCAGTAGAATCGGACTGCTAAGACAGCAGTCACTAATCCAACTGAGTTG
GTGATGACATCAAAGAAATGATCTTGAGCATAGGCTCTTACGATTTCGTTTTTGAACCTTCGACAGTAGACCAT
AAGCAGAAACTTGACCATAGTGACAGAGACCATAATACCAATCGTCCATTTTTCCTTCTCATGGTCCATCTCAG
GGCGAGACTTAGTTATGAGTTCTTTAGCTGACTCGAACAATATTTGTAATCCTAGTGTCGCCATTACAGATGCA
AAAACAATAATACCCAATGGCTGCATCCTCTTTTTTCCAATAGGATAGTGATACTGGTTTGGATTTTTCATGGC
ATGAGAAGTGAACCACAGTATAAACCCTGATAAGAGGTCTAAGAGGGAGTCCAACGTTGACGCGATTACAGC
CAAAGATCTGCTCTCAATAGAAGCGTAGATTTTTGCAATGAAAAGAACCACATTAGCCATGTTTGATAAATGA
ATAGCCATCCTTTCACTTCTTGCAAGCTGCTTCATTTCATCCTCAGTTAGACTTCCAGGTAAACAACCAGATTCA

FIG. 45 (Continued)

TTAATGGTGTCCATCTCATTGAACCCTTCAAGCAGCCTTTCTTGTTTTTTGTAGTATTCAGCAATTTTACCTTGTT
TCCTGGGAGTGGGAAGTAGACGACGGACACTAAAGGAGTGATGATCGGAGGAGGAGCGGCTTCGTTCGGG
AAGACGGAATTCGCTAATGTTAAGTCTCCATGACGCCGACGAAGACGACTGATCCACCACCGCCTGAGCAGCC
GGAGACAGCAGTTCCGTCCTAAAACTGCTAAAACTGTCGTCCAGAGCGCCGCCGCTGCCGCCACCACCACTAA
CATTGCTGCGACTTATCTCCAT

FIG. 46

SEQ ID No. 40

TGTACAAAAAAGCAGGCTCAtcaaaaagctcgctcaacttc

FIG. 47

SEQ ID No. 41

TGTACAAGAAAGCTGGGTatggagataagtcgcagcaat

FIG. 48

SEQ ID No. 42

GGGGACAAGTTTGTACAAAAAAGCAGGCT

FIG. 49

SEQ ID No. 43

GGGGACCACTTTGTACAAGAAAGCTGGGT

FIG. 50

SEQ ID No. 44

ATGGAAGACGCCAAAAACATAAAGAAAGGCCCGGCGCCATTCTATCCGCTGGAAGATGGAACCGCTGGAGA
GCAACTGCATAAGGCTATGAAGAGATACGCCCTGGTTCCTGGAACAATTGCTTTTACAGATGCACATATCGAG
GTGGACATTACGTACGCTGAGTACTTCGAAATGTCCGTTCGGTTGGCAGAAGCTATGAAACGATATGGGCTG
AATACAAATCACAGAATCGTCGTATGCAGTGAAAACTCTCTTCAATTCTTTATGCCGGTGTTGGGCGCGTTATT
TATCGGAGTTGCAGTTGCGCCCGCGAACGACATTTATAATGAACGTGAATTGCTCAACAGTATGGGCATTTCG
CAGCCTACCGTGGTGTTCGTTTCCAAAAAGGGGTTGCAAAAAATTTTGAACGTGCAAAAAAAGCTCCCAATCA
TCCAAAAAATTATTATCATGGATTCTAAAACGGATTACCAGGGATTTCAGTCGATGTACACGTTCGTCACATCT
CATCTACCTCCCGGTTTTAATGAATACGATTTTGTGCCAGAGTCCTTCGATAGGGACAAGACAATTGCACTGAT
CATGAACTCCTCTGGATCTACTGGTCTGCCTAAAGGTGTCGCTCTGCCTCATAGAACTGCCTGCGTGAGATTCT
CGCATGCCAGAGATCCTATTTTTGGCAATCAAATCATTCCGGATACTGCGATTTTAAGTGTTGTTCCATTCCATC
ACGGTTTTGGAATGTTTACTACACTCGGATATTTGATATGTGGATTTCGAGTCGTCTTAATGTATAGATTTGAA
GAAGAGCTGTTTCTGAGGAGCCTTCAGGATTACAAGATTCAAAGTGCGCTGCTGGTGCCAACCCTATTCTCCTT
CTTCGCCAAAAGCACTCTGATTGACAAATACGATTTATCTAATTTACACGAAATTGCTTCTGGTGGCGCTCCCCT
CTCTAAGGAAGTCGGGGAAGCGGTTGCCAAGAGGTTCCATCTGCCAGGTATCAGGCAAGGATATGGGCTCAC
TGAGACTACATCAGCTATTCTGATTACACCCGAGGGGGATGATAAACCGGGCGCGGTCGGTAAAGTTGTTCC
ATTTTTTGAAGCGAAGGTTGTGGATCTGGATACCGGGAAAACGCTGGGCGTTAATCAAAGAGGCGAACTGTG
TGTGAGAGGTCCTATGATTATGTCCGGTTATGTAAACAATCCGGAAGCGACCAACGCCTTGATTGACAAGGAT
GGATGGCTACATTCTGGAGACATAGCTTACTGGGACGAAGACGAACACTTCTTCATCGTTGACCGCCTGAAGT
CTCTGATTAAGTACAAAGGCTATCAGGTGGCTCCCGCTGAATTGGAATCCATCTTGCTCCAACACCCCAACATC

FIG. 50 (Continued)

TTCGACGCAGGTGTCGCAGGTCTTCCCGACGATGACGCCGGTGAACTTCCCGCCGCCGTTGTTGTTTTGGAGC
ACGGAAAGACGATGACGGAAAAAGAGATCGTGGATTACGTCGCCAGTCAAGTAACAACCGCGAAAAAGTTG
CGCGGAGGAGTTGTGTTTGTGGACGAAGTACCGAAAGGTCTTACCGGAAAACTCGACGCAAGAAAAATCAG
AGAGATCCTCATAAAGGCCAAGAAGGGCGGAAAGATCGCCGTGTAA

FIG. 51

SEQ ID No. 45

TGTACAAAAAAGCAGGCTCAatggagataagtcgcagcaat

FIG. 52

SEQ ID No. 46

TGTACAAGAAAGCTGGGTTttaagctcccgtaggatcaat

FIG. 53

SEQ ID No. 47

TGTACAAAAAAGCAGGCTCAatggaaatgaagcagcttgca

FIG. 54

SEQ ID No. 48

TGTACAAGAAAGCTGGGTTtataccatagttttgtgttctg

FIG. 55

SEQ ID No. 49

TACTCCAAAAATGTCAAAGATACAGTCTCAGAAGACCAAAGGGCTATTGAGACTTTTCAACAAAGGGTAATTT
CGGGAAACCTCCTCGGATTCCATTGCCCAGCTATCTGTCACTTCATCGAAAGGACAGTAGAAAAGGAAGGTG
GCTCCTACAAATGCCATCATTGCGATAAAGGAAAGGCTATCATTCAAGATGCCTCTGCCGACAGTGGTCCCAA
AGATGGACCCCCACCCACGAGGAGCATCGTGGAAAAAGAAGACGTCCCAACCACGTCTTCAAAGCAAGTGGA
TTGATGTGACATCTCCACTGACGTAAGGGATGACGCACAATCCCACTATCCTTCGCAAGACCCTTCTTCTATAT
AAGGAAGTTCATTTCATTTGGAGAGGACAGCCCAAGCTTTCTAGAGGATCCATAAAACATTTCAATCCTTTGAA
CGCGGTAGAACGTGCTAATTGGATTTTGGTGAGAACGCGGTAGAACGTACTTATCACCTACAGTTTTATTTTGT
TTTTCTTTTTGGTTTAATCTATCCAGCTTAGTACCGAGTGGGGGAAAGTGACTGGTGTGCCTAAAACCTTTTCTT
TGATACTTTGTAAAAATACATACAGATACAATGGCGAACGGTAACTTCAAGTTGTCTCAATTGCTCAATGTGGA
CGAGATGTCTGCTGAGCAGAGGAGTCATTTCTTTGACTTGATGCTGACTAAACCTGATTGTGAGATCGGGCAA
ATGATGCAAAGAGTTGTTGTTGATAAAGTCGATGACATGATTAGAGAAAGAAAGACTAAAGATCCAGTGATT
GTTCATGAAGTTCTTTCTCAGAAGGAACAGAACAAGTTGATGGAAATTTATCCTGAATTCAATATCGTGTTTAA
AGACGACAAAAACATGGTTCATGGGTTTGCGGCTGCTGAGCGAAAACTACAAGCTTTATTGCTTTTAGATAGA
GTTCCTGCTCTGCAAGAGGTGGATGACATCGGTGGTCAATGGTCGTTTTGGGTAACTAGAGGTGAGAAAAGG
ATTCATTCCTGTTGTCCAAATCTAGATATTCGGGATGATCAGAGAGAAATTTCTCGACAGATATTTCTTACTGCT
ATTGGTGATCAAGCTAGAAGTGGTAAGAGACAGATGTCGGAGAATGAGCTGTGGATGTATGACCAATTTCGT
GAAAATATTGCTGCGCCTAACGCGGTTAGGTGCAATAATACATATCAGGGTTGTACATGTAGGGGTTTTTCTG

FIG. 55 (Continued)

ATGGTAAGAAGAAAGGCGCGCAGTATGCGATAGCTCTTCACAGCCTGTATGACTTCAAGTTGAAAGACTTGAT
GGCTACTATGGTTGAGAAGAAAACTAAAGTGGTTCATGCTGCTATGCTTTTTGCTCCTGAAAGTATGTTAGTG
GACGAAGGTCCATTACCTTCTGTTGACGGTTACTACATGAAGAAGAACGGGAAGATCTATTTCGGTTTTGAGA
AAGATCCTTCCTTTTCTTACATTCATGACTGGGAAGAGTACAAGAAGTATCTACTGGGGAAGCCAGTGAGTTA
CCAAGGGAATGTGTTCTACTTCGAACCGTGGCAGGTGAGAGGAGACACAATGCTTTTTTCGATCTACAGGATA
GCTGGAGTTCCGAGGAGGTCTCTATCATCGCAAGAGTACTACCGAAGAATATATATCAGTAGATGGGAAAGC
ATGGTTGTTGTCCCAATTTTCGATCTGGTCGAATCAACGCGAGAGTTGGTCAAGAAAGACCTGTTTGTAAGAA
ACAATTCATGGACAAGTGTTTGGATTACATAGCTAGGTTATCTGACCAGCAGCTGACCATAAGCAATGTTAAA
TCATACTTGAGTTCAAATAATTGGGTCTTATTCATAAACGGGGCGGCCGTGAAGAACAAGCAAAGTGTAGATT
CTCGAGATTTACAGTTGTTGGCTCAAACTTTGCTAGTGAAGGAACAAGTGGCGAGACCTGTCATGAGGGAGTT
GCGTGAAGCAATTCTGACTGAGACGAAACCTATCACGTCATTGACTGATGTGCTGGGTTTAATATCAAGAAAA
CTGTGGAAGCAGTTTGCTAACAAGATCGCAGTCGGCGGATTCGTTGGCATGGTTGGTACTCTAATTGGATTCT
ATCCAAAGAAGGTACTAACCTGGGCGAAGGACACACCAAATGGTCCAGAACTATGTTACGAGAACTCGCACA
AAACCAAGGTGATAGTATTTCTGAGTGTTGTGTATGCCATTGGAGGAATCACGCTTATGCGTCGAGACATCCG
AGATGGACTGGTGAAAAAACTATGTGATATGTTTGATATCAAACGGGGGGCCCATGTCTTAGACGTTGAGAA
TCCGTGCCGCTATTATGAAATCAACGATTTCTTTAGCAGTCTGTATTCGGCATCTGAGTCCGGTGAGACCGTTT
TACCAGATTTATCCGAGGTAAAAGCCAAGTCTGATAAGCTATTGCAGCAGAAGAAAGAAATCGCTGACGAGT
TTCTAAGTGCAAAATTCTCTAACTATTCTGGCAGTTCGGTGAGAACTTCTCCACCATCGGTGGTCGGTTCATCT
CGAAGCGGACTGGGTCTGTTGTTGGAAGACAGTAACGTGCTGACCCAAGCTAGAGTTGGAGTTTCAAGAAAG
GTAGACGATGAGGAGATCATGGAGCAGTTTCTGAGTGGTCTTATTGACACTGAAGCAGAAATTGACGAGGTT
GTTTCAGCCTTTTCAGCTGAATGTGAAAGAGGGGAAACAAGCGGTACAAAGGTGTTGTGTAAACCTTTAACGC
CACCAGGATTTGAGAACGTGTTGCCAGCTGTCAAACCTTTGGTCAGCAAAGGAAAAACGGTCAAACGTGTCG
ATTACTTCCAAGTGATGGGAGGTGAGAGATTACCAAAAAGGCCGGTTGTCAGTGGAGACGATTCTGTGGACG
CTAGAAGAGAGTTTCTGTACTACTTAGATGCGGAGAGAGTCGCTCAAAATGATGAAATTATGTCTCTGTATCG
TGACTATTCGAGAGGAGTTATTCGAACTGGAGGTCAGAATTACCCGCACGGACTGGGAGTGTGGGATGTGGA
GATGAAGAACTGGTGCATACGTCCAGTGGTCACTGAACATGCTTATGTGTTCCAACCAGACAAACGTATGGAT
GATTGGTCGGGATACTTAGAAGTGGCTGTTTGGGAACGAGGTATGTTGGTCAACGACTTCGCGGTCGAAAGG
ATGAGTGATTATGTCATAGTTTGCGATCAGACGTATCTTTGCAATAACAGGTAATAATCCTCTCTCTTGATATTT
TTAAATTATAGAATTAATTAGTTTACTTTATTCTTTACTATATGATTTAAATAGTTTAATCTTGTTTTTGAGTAAA
CTATTCGATTTTGATATTTGTATTCGTCCTACAAAGTTGGAAATACTGATGATATTTTCTTTTGAACGTGATACC
TACCAATACTAATCTTACGGAATCTTTTAATAGAGCACTAATCAACATGGAACTAAAGACCAATTCTTAAGTGT
CTCTGTTGTACAGTTCATTTTAGTAGTGCGTTTAAGTATTATTATCTCCCTTCATGCGGGGCAATTATGTAGATT
AAAATCGAAATTATATAAAATTTACATAAGTCTAAGTCTAGGGTCTCCAGCTAATTGTTATTTTTTTAACGATGT
TGACTAAAGCAATAACGACGTTGACTTGTGTTAAACAGGTTGATCTTGGACAATTTAAGTGCCCTGGATCTAG
GACCAGTTAACTGTTCTTTTGAATTAGTTGACGGTGTACCTGGTTGTGGTAAGTCGACAATGATTGTCAACTCA
GCTAATCCTTGTGTCGATGTGGTTCTCTCTACTGGGAGAGCAGCAACCGACGACTTGATCGAGAGATTCGCGA
GCAAAGGTTTTCCATGCAAATTGAAAAGGAGAGTGAAGACGGTTGATTCTTTTTTGATGCATTGTGTCGATGG
TTCTTTAACCGGAGACGTGTTGCATTTCGACGAAGCTCTCATGGCCCATGCTGGTATGGTGTACTTTTGCGCTC
AGATAGCTGGTGCTAAACGATGTATCTGTCAAGGAGATCAGAATCAAATTTCTTTCAAGCCTAGGGTATCTCA
AGTTGATTTGAGGTTTTCTAGTCTGGTCGGAAAGTTTGACATTGTTACAGAAAAAAGAGAAACTTACAGAAGT
CCAGCAGATGTGGCTGCCGTATTGAACAAGTACTATACTGGAGATGTCAGAACACATAACGCGACTGCTAATT
CGATGACGGTGAGGAAGATTGTGTCTAAAGAACAGGTTTCTTTGAAGCCTGGTGCTCAGTACATAACTTTCCT
TCAGTCTGAGAAGAAGGAGTTGGTAAATTTGTTGGCATTGAGGAAAGTGGCAGCTAAAGTGAGTACAGTACA
CGAGTCGCAAGGAGAGACATTCAAAGATGTAGTCCTAGTCAGGACGAAACCTACGGATGACTCAATCGCTAG
AGGTCGGGAGTACTTAATCGTGGCATTGTCGCGTCACACACAATCACTTGTGTATGAAACTGTGAAAGAGGAC

FIG. 55 (Continued)

GATGTAAGCAAAGAGATCAGGGAAAGTGCCGCGCTTACGAAGGCGGCTTTGGCAAGATTTTTTGTTACTGAG
ACCGTCTTATGACGGTTTCGGTCTAGGTTTGATGTCTTTAGACATCATGAAGGGCCTTGCGCCGTTCCAGATTC
AGGTACGATTACGGACTTGGAGATGTGGTACGACGCTTTGTTTCCGGGAAATTCGTTAAGAGACTCAAGCCTA
GACGGGTATTTGGTGGCAACGACTGATTGCAATTTGCGATTAGACAATGTTACGATCAAAAGTGGAAACTGG
AAAGACAAGTTTGCTGAAAAAGAAACGTTTCTGAAACCGGTTATTCGTACTGCTATGCCTGACAAAAGGAAGA
CTACTCAGTTGGAGAGTTTGTTAGCATTGCAGAAAAGGAACCAAGCGGCACCCGATCTACAAGAAAATGTGC
ACGCGACAGTTCTAATCGAAGAGACGATGAAGAAGCTGAAATCTGTTGTCTACGATGTGGGAAAAATTCGGG
CTGATCCTATTGTCAATAGAGCTCAAATGGAGAGATGGTGGAGAAATCAAAGCACAGCGGTACAGGCTAAGG
TAGTAGCAGATGTGAGAGAGTTACATGAAATAGACTATTCGTCTTACATGTATATGATCAAATCTGACGTGAA
ACCTAAGACTGATTTAACACCGCAATTTGAATACTCAGCTCTACAGACTGTTGTGTATCACGAGAAGTTGATCA
ACTCGTTGTTCGGTCCAATTTTCAAAGAAATTAATGAACGCAAGTTGGATGCTATGCAACCACATTTTGTGTTC
AACACGAGAATGACATCGAGTGATTTAAACGATCGAGTGAAGTTCTTAAATACGGAAGCGGCTTACGACTTTG
TTGAGATAGACATGTCTAAATTCGACAAGTCGGCAAATCGCTTCCATTTACAACTGCAGCTGGAGATTTACAG
GTTATTTGGGCTGGATGAGTGGGCGGCCTTCCTTTGGGAGGTGTCGCACACTCAAACTACTGTGAGAGATATT
CAAAATGGTATGATGGCGCATATTTGGTACCAACAAAAGAGTGGAGATGCTGATACTTATAATGCAAATTCAG
ATAGAACACTGTGTGCACTCTTGTCTGAATTACCATTGGAGAAAGCAGTCATGGTTACATATGGAGGAGATGA
CTCACTGATTGCGTTTCCTAGAGGAACGCAGTTTGTTGATCCGTGTCCAAAGTTGGCTACTAAGTGGAATTTCG
AGTGCAAGATTTTTAAGTACGATGTCCCAATGTTTTGTGGGAAGTTCTTGCTTAAGACGTCATCGTGTTACGAG
TTCGTGCCAGATCCGGTAAAAGTTCTGACGAAGTTGGGGAAAAAGAGTATAAAGGATGTGCAACATTTAGCC
GAGATCTACATCTCGCTGAATGATTCCAATAGAGCTCTTGGGAACTACATGGTGGTATCCAAACTGTCCGAGT
CTGTTTCAGACCGGTATTTGTACAAAGGTGATTCTGTTCATGCGCTTTGTGCGCTATGGAAGCATATTAAGAGT
TTTACAGCTCTGTGTACATTATTCCGAGACGAAAACGATAAGGAATTGAACCCGGCTAAGGTTGATTGGAAGA
AGGCACAGAGAGCTGTGTCAAACTTTTACGACTGGTAATATGGAAGACAAGTCATTGGTCACCTTGAAGAAG
AAGACTTTCGAAGTCTCAAAATTCTCAAATCTAGGGGCCATTGAATTGTTTGTGGACGGTAGGAGGAAGAGA
CCGAAGTATTTTCACAGAAGAAGAGAAACTGTCCTAAATCATGTTGGTGGGAAGAAGAGTGAACACAAGTTA
GACGTTTTTGACCAAAGGGATTACAAAATGATTAAATCTTACGCGTTTCTAAAGGTAGTAGGTGTACAACTAG
TTGTAACATCACATCTACCTGCAGATACGCCTGGGTTCATTCAAATCGATCTGTTGGATTCGAGACTTACTGAG
AAAAGAAAGAGAGGAAAGACTATTCAGAGATTCAAAGCTCGAGCTTGCGATAACTGTTCAGTTGCGCAGTAC
AAGGTTGAATACAGTATTTCCACACAGGAGAACGTACTTGATGTCTGGAAGGTGGGTTGTATTTCTGAGGGC
GTTCCGGTCTGTGACGGTACATACCCTTTCAGTATCGAAGTGTCGCTAATATGGGTTGCTACTGATTCGACTAG
GCGCCTCAATGTGGAAGAACTGAACAGTTCGGATTACATTGAAGGCGATTTTACCGATCAAGAGGTTTTCGGT
GAGTTCATGTCTTTGAAACAAGTGGAGATGAAGACGATTGAGGCGAAGTACGATGGTCCTTACAGACCAGCT
ACTACTAGACCTAAGTCATTATTGTCAAGTGAAGATGTTAAGAGAGCGTCTAATAAGAAAAACTCGTCTTAAT
GCATAAAGAAATTTATTGTCAATATGACGTGTGTACTCAAGGGTTGTGTGAATGAAGTCACTGTTCTTGGTCAC
GAGACGTGTAGTATCGGTCATGCTAACAAATTGCGAAAGCAAGTTGCTGACATGGTTGGTGTCACACGTAGG
TGTGCGGAAAATAATTGTGGATGGTTTGTCTGTGTTGTTATCAATGATTTTACTTTTGATGTGTATAATTGTTGT
GGCCGTAGTCACCTTGAAAAGTGTCGTAAACGTGTTGAAACAAGAAATCGAGAAATTTGGAAACAAATTCGA
CGAAATCAAGCTGAAAACATGTCTGCGACAGCTAAAAAGTCTCATAATTCGAAGACCTCTAAGAAGAAATTCA
AAGAGGACAGAGAATTTGGGACACCAAAAAGATTTTTAAGAGATGATGTTCCTTTCGGGATTGATCGTTTGTT
TGCTTTTTGATTTTATTTTATATTGTTATCTGTTTCTGTGTATAGACTGTTTGAGATTGGCGCTTGGCCGACTCAT
TGTCTTACCATAGGGGAACGGACTTTGTTTGTGTTGTTATTTTATTTGTATTTTATTAAAATTCTCAATGATCTG
AAAAGGCCTCGAGGCTAAGAGATTATTGGGGGGTGAGTAAGTACTTTTAAAGTGATGATGGTTACAAAGGCA
AAAGGGGTAAAACCCCTCGCCTACGTAAGCGTTATTACGCCCGGATCCCCCGGGGAGCTCGAATTCGCTGAA
ATCACCAGTCTCTCTCTACAAATCTATCTCTCTCTATTTTTTCCATAAATAATGTGTGAGTAGTTTCCCGATAAGG
GAAATTAGGGTTCTTATAGGGTTTCGCTCATGTGTTGAGCATATAAGAAACCCTTAGTATGTATTTGTATTTGT

FIG. 55 (Continued)

AAAATACTTCTATTATCAATAAAATTTCTAATTCCTAAAACCAAAATCCAGTACTAAAATCCAGATCTCCTAAAG
TCCCTATAGATCTTTGTCGTGAATATAAACCAGACACGAGACGACTAAACCTGGAGCCCAGACGCCGTTCGAA
GCTAGAAGTACCGCTTAGGCAGGAGGCCGTTAGGGAAAAGATGCTAAGGCAGGGTTGGTTACGTTGACTCCC
CCGTAGGTTTGGTTTAAATATGATGAAGTGGACGGAAGGAAGGAGGAAGACAAGGAAGGATAAGGTTGCAG
GCCCTGTGCAAGGTAAGAAGATGGAAATTTGATAGAGGTACGCTACTATACTTATACTATACGCTAAGGGAAT
GCTTGTATTTATACCCTATACCCCCTAATAACCCCTTATCAATTTAAGAAATAATCCGCATAAGCCCCCGCTTAA
AAATTGGTATCAGAGCCATGAATAGGTCTATGACCAAAACTCAAGAGGATAAAACCTCACCAAAATACGAAA
GAGTTCTTAACTCTAAAGATAAAAGATCTTTCAAGATCAAAACTAGTTCCCTCACACCGGAGCATGCGATATCC
TCGACCTGCAGGCATGCAAGCTTGGCGTAATCATGGTCATAGCTGTTTCCTGTGTGAAATTGTTATCCGCTCAC
AATTCCACACAACATACGAGCCGGAAGCATAAAGTGTAAAGCCTGGGGTGCCTAATGAGTGAGCTAACTCAC
ATTAATTGCGTTGCGCTCACTGCCCGCTTTCCAGTCGGGAAACCTGTCGTGCCAGCTGCATTAATGAATCGGCC
AACGCGCGGGGAGAGGCGGTTTGCGTATTGGGCCAAAGACAAAAGGGCGACATTCAACCGATTGAGGGAG
GGAAGGTAAATATTGACGGAAATTATTCATTAAAGGTGAATTATCACCGTCACCGACTTGAGCCATTTGGGAA
TTAGAGCCAGCAAAATCACCAGTAGCACCATTACCATTAGCAAGGCCGGAAACGTCACCAATGAAACCATCGA
TAGCAGCACCGTAATCAGTAGCGACAGAATCAAGTTTGCCTTTAGCGTCAGACTGTAGCGCGTTTTCATCGGC
ATTTTCGGTCATAGCCCCCTTATTAGCGTTTGCCATCTTTTCATAATCAAAATCACCGGAACCAGAGCCACCACC
GGAACCGCCTCCCTCAGAGCCGCCACCCTCAGAACCGCCACCCTCAGAGCCACCACCCTCAGAGCCGCCACCA
GAACCACCACCAGAGCCGCCGCCAGCATTGACAGGAGGCCCGATCTAGTAACATAGATGACACCGCGCGCGA
TAATTTATCCTAGTTTGCGCGCTATATTTTGTTTTCTATCGCGTATTAAATGTATAATTGCGGGACTCTAATCAT
AAAAACCCATCTCATAAATAACGTCATGCATTACATGTTAATTATTACATGCTTAACGTAATTCAACAGAAATTA
TATGATAATCATCGCAAGACCGGCAACAGGATTCAATCTTAAGAAACTTTATTGCCAAATGTTTGAACGATCG
GGGATCATCCGGGTCTGTGGCGGGAACTCCACGAAAATATCCGAACGCAGCAAGATATCGCGGTGCATCTCG
GTCTTGCCTGGGCAGTCGCCGCCGACGCCGTTGATGTGGACGCCGGGCCCGATCATATTGTCGCTCAGGATC
GTGGCGTTGTGCTTGTCGGCCGTTGCTGTCGTAATGATATCGGCACCTTCGACCGCCTGTTCCGCAGAGATCC
CGTGGGCGAAGAACTCCAGCATGAGATCCCCGCGCTGGAGGATCATCCAGCCGGCGTCCCGGAAAACGATTC
CGAAGCCCAACCTTTCATAGAAGGCGGCGGTGGAATCGAAATCTCGTGATGGCAGGTTGGGCGTCGCTTGGT
CGGTCATTTCGAACCCCAGAGTCCCGCTCAGAAGAACTCGTCAAGAAGGCGATAGAAGGCGATGCGCTGCGA
ATCGGGAGCGGCGATACCGTAAAGCACGAGGAAGCGGTCAGCCCATTCGCCGCCAAGCTCTTCAGCAATATC
ACGGGTAGCCAACGCTATGTCCTGATAGCGGTCCGCCACACCCAGCCGGCCACAGTCGATGAATCCAGAAAA
GCGGCCATTTTCCACCATGATATTCGGCAAGCAGGCATCGCCATGGGTCACGACGAGATCATCGCCGTCGGGC
ATGCGCGCCTTGAGCCTGGCGAACAGTTCGGCTGGCGCGAGCCCCTGATGCTCTTCGTCCAGATCATCCTGAT
CGACAAGACCGGCTTCCATCCGAGTACGTGCTCGCTCGATGCGATGTTTCGCTTGGTGGTCGAATGGGCAGGT
AGCCGGATCAAGCGTATGCAGCCGCCGCATTGCATCAGCCATGATGGATACTTTCTCGGCAGGAGCAAGGTG
AGATGACAGGAGATCCTGCCCCGGCACTTCGCCCAATAGCAGCCAGTCCCTTCCCGCTTCAGTGACAACGTCG
AGCACAGCTGCGCAAGGAACGCCCGTCGTGGCCAGCCACGATAGCCGCGCTGCCTCGTCCTGCAGTTCATTCA
GGGCACCGGACAGGTCGGTCTTGACAAAAAGAACCGGGCGCCCCTGCGCTGACAGCCGGAACACGGCGGCA
TCAGAGCAGCCGATTGTCTGTTGTGCCCAGTCATAGCCGAATAGCCTCTCCACCCAAGCGGCCGGAGAACCTG
CGTGCAATCCATCTTGTTCAATCATGCGAAACGATCCAGATCCGGTGCAGATTATTTGGATTGAGAGTGAATA
TGAGACTCTAATTGGATACCGAGGGGAATTTATGGAACGTCAGTGGAGCATTTTTGACAAGAAATATTTGCTA
GCTGATAGTGACCTTAGGCGACTTTTGAACGCGCAATAATGGTTTCTGACGTATGTGCTTAGCTCATTAAACTC
CAGAAACCCGCGGCTGAGTGGCTCCTTCAACGTTGCGGTTCTGTCAGTTCCAAACGTAAAACGGCTTGTCCCG
CGTCATCGGCGGGGGTCATAACGTGACTCCCTTAATTCTCCGCTCATGATCAGATTGTCGTTTCCCGCCTTCAG
TTTAAACTATCAGTGTTTGACAGGATATATTGGCGGGTAAACCTAAGAGAAAAGAGCGTTTATTAGAATAATC
GGATATTTAAAAGGGCGTGAAAAGGTTTATCCGTTCGTCCATTTGTATGTGCATGCCAACCACAGGGTTCCCC
AGATCTGGCGCCGGCCAGCGAGACGAGCAAGATTGGCCGCCGCCCGAAACGATCCGACAGCGCGCCCAGCA

FIG. 55 (Continued)

CAGGTGCGCAGGCAAATTGCACCAACGCATACAGCGCCAGCAGAATGCCATAGTGGGCGGTGACGTCGTTCG
AGTGAACCAGATCGCGCAGGAGGCCCGGCAGCACCGGCATAATCAGGCCGATGCCGACAGCGTCGAGCGCG
ACAGTGCTCAGAATTACGATCAGGGGTATGTTGGGTTTCACGTCTGGCCTCCGGACCAGCCTCCGCTGGTCCG
ATTGAACGCGCGGATTCTTTATCACTGATAAGTTGGTGGACATATTATGTTTATCAGTGATAAAGTGTCAAGCA
TGACAAAGTTGCAGCCGAATACAGTGATCCGTGCCGCCCTGGACCTGTTGAACGAGGTCGGCGTAGACGGTC
TGACGACACGCAAACTGGCGGAACGGTTGGGGGTTCAGCAGCCGGCGCTTTACTGGCACTTCAGGAACAAGC
GGGCGCTGCTCGACGCACTGGCCGAAGCCATGCTGGCGGAGAATCATACGCATTCGGTGCCGAGAGCCGAC
GACGACTGGCGCTCATTTCTGATCGGGAATGCCCGCAGCTTCAGGCAGGCGCTGCTCGCCTACCGCGATGGC
GCGCGCATCCATGCCGGCACGCGACCGGGCGCACCGCAGATGGAAACGGCCGACGCGCAGCTTCGCTTCCTC
TGCGAGGCGGGTTTTTCGGCCGGGGACGCCGTCAATGCGCTGATGACAATCAGCTACTTCACTGTTGGGGCC
GTGCTTGAGGAGCAGGCCGGCGACAGCGATGCCGGCGAGCGCGGCGGCACCGTTGAACAGGCTCCGCTCTC
GCCGCTGTTGCGGGCCGCGATAGACGCCTTCGACGAAGCCGGTCCGGACGCAGCGTTCGAGCAGGGACTCG
CGGTGATTGTCGATGGATTGGCGAAAAGGAGGCTCGTTGTCAGGAACGTTGAAGGACCGAGAAAGGGTGAC
GATTGATCAGGACCGCTGCCGGAGCGCAACCCACTCACTACAGCAGAGCCATGTAGACAACATCCCCTCCCCC
TTTCCACCGCGTCAGACGCCCGTAGCAGCCCGCTACGGGCTTTTTCATGCCCTGCCCTAGCGTCCAAGCCTCAC
GGCCGCGCTCGGCCTCTCTGGCGGCCTTCTGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAAC
GCAGGAAAGAACATGTGAGCAAAAGGCCAGCAAAAGGCCAGGAACCGTAAAAAGGCCGCGTTGCTGGCGTT
TTTCCATAGGCTCCGCCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGACCCTGCCGCTTAC
CGGATACCTGTCCGCCTTTCTCCCTTCGGGAAGCGTGGCGCTTTTCCGCTGCATAACCCTGCTTCGGGGTCATT
ATAGCGATTTTTTCGGTATATCCATCCTTTTTCGCACGATATACAGGATTTTGCCAAAGGGTTCGTGTAGACTTT
CCTTGGTGTATCCAACGGCGTCAGCCGGGCAGGATAGGTGAAGTAGGCCCACCCGCGAGCGGGTGTTCCTTC
TTCACTGTCCCTTATTCGCACCTGGCGGTGCTCAACGGGAATCCTGCTCTGCGAGGCTGGCCGGCTACCGCCG
GCGTAACAGATGAGGGCAAGCGGATGGCTGATGAAACCAAGCCAACCAGGAAGGGCAGCCCACCTATCAAG
GTGTACTGCCTTCCAGACGAACGAAGAGCGATTGAGGAAAAGGCGGCGGCGGCCGGCATGAGCCTGTCGGC
CTACCTGCTGGCCGTCGGCCAGGGCTACAAAATCACGGGCGTCGTGGACTATGAGCACGTCCGCGAGCTGGC
CCGCATCAATGGCGACCTGGGCCGCCTGGGCGGCCTGCTGAAACTCTGGCTCACCGACGACCCGCGCACGGC
GCGGTTCGGTGATGCCACGATCCTCGCCCTGCTGGCGAAGATCGAAGAGAAGCAGGACGAGCTTGGCAAGG
TCATGATGGGCGTGGTCCGCCCGAGGGCAGAGCCATGACTTTTTTAGCCGCTAAAACGGCCGGGGGGTGCGC
GTGATTGCCAAGCACGTCCCCATGCGCTCCATCAAGAAGAGCGACTTCGCGGAGCTGGTGAAGTACATCACC
GACGAGCAAGGCAAGACCGAGCGCCTTTGCGACGCTCACCGGGCTGGTTGCCCTCGCCGCTGGGCTGGCGGC
CGTCTATGGCCCTGCAAACGCGCCAGAAACGCCGTCGAAGCCGTGTGCGAGACACCGCGGCCGCCGGCGTTG
TGGATACCTCGCGGAAAACTTGGCCCTCACTGACAGATGAGGGGCGGACGTTGACACTTGAGGGGCCGACTC
ACCCGGCGCGGCGTTGACAGATGAGGGGCAGGCTCGATTTCGGCCGGCGACGTGGAGCTGGCCAGCCTCGC
AAATCGGCGAAAACGCCTGATTTTACGCGAGTTTCCCACAGATGATGTGGACAAGCCTGGGGATAAGTGCCC
TGCGGTATTGACACTTGAGGGGCGCGACTACTGACAGATGAGGGGCGCGATCCTTGACACTTGAGGGGCAG
AGTGCTGACAGATGAGGGGCGCACCTATTGACATTTGAGGGGCTGTCCACAGGCAGAAAATCCAGCATTTGC
AAGGGTTTCCGCCCGTTTTTCGGCCACCGCTAACCTGTCTTTTAACCTGCTTTTAAACCAATATTTATAAACCTT
GTTTTTAACCAGGGCTGCGCCCTGTGCGCGTGACCGCGCACGCCGAAGGGGGGTGCCCCCCCTTCTCGAACCC
TCCCGGCCCGCTAACGCGGGCCTCCCATCCCCCCAGGGGCTGCGCCCCTCGGCCGCGAACGGCCTCACCCCAA
AAATGGCAGCGCTGGCAGTCCTTGCCATTGCCGGGATCGGGGCAGTAACGGGATGGGCGATCAGCCCGAGC
GCGACGCCCGGAAGCATTGACGTGCCGCAGGTGCTGGCATCGACATTCAGCGACCAGGTGCCGGGCAGTGA
GGGCGGCGGCCTGGGTGGCGGCCTGCCCTTCACTTCGGCCGTCGGGGCATTCACGGACTTCATGGCGGGGCC
GGCAATTTTTACCTTGGGCATTCTTGGCATAGTGGTCGCGGGTGCCGTGCTCGTGTTCGGGGGTGCGATAAAC

FIG. 55 (Continued)

CCAGCGAACCATTTGAGGTGATAGGTAAGATTATACCGAGGTATGAAAACGAGAATTGGACCTTTACAGAAT
TACTCTATGAAGCGCCATATTTAAAAAGCTACCAAGACGAAGAGGATGAAGAGGATGAGGAGGCAGATTGCC
TTGAATATATTGACAATACTGATAAGATAATATATCTTTTATATAGAAGATATCGCCGTATGTAAGGATTTCAG
GGGGCAAGGCATAGGCAGCGCGCTTATCAATATATCTATAGAATGGGCAAAGCATAAAAACTTGCATGGACT
AATGCTTGAAACCCAGGACAATAACCTTATAGCTTGTAAATTCTATCATAATTGGGTAATGACTCCAACTTATT
GATAGTGTTTTATGTTCAGATAATGCCCGATGACTTTGTCATGCAGCTCCACCGATTTTGAGAACGACAGCGAC
TTCCGTCCCAGCCGTGCCAGGTGCTGCCTCAGATTCAGGTTATGCCGCTCAATTCGCTGCGTATATCGCTTGCT
GATTACGTGCAGCTTTCCCTTCAGGCGGGATTCATACAGCGGCCAGCCATCCGTCATCCATATCACCACGTCAA
AGGGTGACAGCAGGCTCATAAGACGCCCCAGCGTCGCCATAGTGCGTTCACCGAATACGTGCGCAACAACCG
TCTTCCGGAGACTGTCATACGCGTAAAACAGCCAGCGCTGGCGCGATTTAGCCCCGACATAGCCCCACTGTTC
GTCCATTTCCGCGCAGACGATGACGTCACTGCCCGGCTGTATGCGCGAGGTTACCGACTGCGGCCTGAGTTTT
TTAAGTGACGTAAAATCGTGTTGAGGCCAACGCCCATAATGCGGGCTGTTGCCCGGCATCCAACGCCATTCAT
GGCCATATCAATGATTTTCTGGTGCGTACCGGGTTGAGAAGCGGTGTAAGTGAACTGCAGTTGCCATGTTTTA
CGGCAGTGAGAGCAGAGATAGCGCTGATGTCCGGCGGTGCTTTTGCCGTTACGCACCACCCCGTCAGTAGCT
GAACAGGAGGGACAGCTGATAGACACAGAAGCCACTGGAGCACCTCAAAAACACCATCATACACTAAATCAG
TAAGTTGGCAGCATCACCCATAATTGTGGTTTCAAAATCGGCTCCGTCGATACTATGTTATACGCCAACTTTGA
AAACAACTTTGAAAAAGCTGTTTTCTGGTATTTAAGGTTTTAGAATGCAAGGAACAGTGAATTGGAGTTCGTC
TTGTTATAATTAGCTTCTTGGGGTATCTTTAAATACTGTAGAAAAGAGGAAGGAAATAATAAATGGCTAAAAT
GAGAATATCACCGGAATTGAAAAAACTGATCGAAAAATACCGCTGCGTAAAAGATACGGAAGGAATGTCTCC
TGCTAAGGTATATAAGCTGGTGGGAGAAAATGAAAACCTATATTTAAAAATGACGGACAGCCGGTATAAAGG
GACCACCTATGATGTGGAACGGGAAAAGGACATGATGCTATGGCTGGAAGGAAAGCTGCCTGTTCCAAAGGT
CCTGCACTTTGAACGGCATGATGGCTGGAGCAATCTGCTCATGAGTGAGGCCGATGGCGTCCTTTGCTCGGAA
GAGTATGAAGATGAACAAAGCCCTGAAAAGATTATCGAGCTGTATGCGGAGTGCATCAGGCTCTTTCACTCCA
TCGACATATCGGATTGTCCCTATACGAATAGCTTAGACAGCCGCTTAGCCGAATTGGATTACTTACTGAATAAC
GATCTGGCCGATGTGGATTGCGAAAACTGGGAAGAAGACACTCCATTTAAAGATCCGCGCGAGCTGTATGAT
TTTTTAAAGACGGAAAAGCCCGAAGAGGAACTTGTCTTTTCCCACGGCGACCTGGGAGACAGCAACATCTTTG
TGAAAGATGGCAAAGTAAGTGGCTTTATTGATCTTGGGAGAAGCGGCAGGGCGGACAAGTGGTATGACATT
GCCTTCTGCGTCCGGTCGATCAGGGAGGATATCGGGGAAGAACAGTATGTCGAGCTATTTTTTGACTTACTGG
GGATCAAGCCTGATTGGGAGAAAATAAAATATTATATTTTACTGGATGAATTGTTTTAGTACCTAGATGTGGC
GCAACGATGCCGGCGACAAGCAGGAGCGCACCGACTTCTTCCGCATCAAGTGTTTTGGCTCTCAGGCCGAGG
CCCACGGCAAGTATTTGGGCAAGGGGTCGCTGGTATTCGTGCAGGGCAAGATTCGGAATACCAAGTACGAGA
AGGACGGCCAGACGGTCTACGGGACCGACTTCATTGCCGATAAGGTGGATTATCTGGACACCAAGGCACCAG
GCGGGTCAAATCAGGAATAAGGGCACATTGCCCCGGCGTGAGTCGGGGCAATCCCGCAAGGAGGGTGAATG
AATCGGACGTTTGACCGGAAGGCATACAGGCAAGAACTGATCGACGCGGGGTTTTCCGCCGAGGATGCCGA
AACCATCGCAAGCCGCACCGTCATGCGTGCGCCCCGCGAAACCTTCCAGTCCGTCGGCTCGATGGTCCAGCAA
GCTACGGCCAAGATCGAGCGCGACAGCGTGCAACTGGCTCCCCCTGCCCTGCCCGCGCCATCGGCCGCCGTG
GAGCGTTCGCGTCGTCTCGAACAGGAGGCGGCAGGTTTGGCGAAGTCGATGACCATCGACACGCGAGGAAC
TATGACGACCAAGAAGCGAAAAACCGCCGGCGAGGACCTGGCAAAACAGGTCAGCGAGGCCAAGCAGGCCG
CGTTGCTGAAACACACGAAGCAGCAGATCAAGGAAATGCAGCTTTCCTTGTTCGATATTGCGCCGTGGCCGGA
CACGATGCGAGCGATGCCAAACGACACGGCCCGCTCTGCCCTGTTCACCACGCGCAACAAGAAAATCCCGCG
CGAGGCGCTGCAAAACAAGGTCATTTTCCACGTCAACAAGGACGTGAAGATCACCTACACCGGCGTCGAGCT
GCGGGCCGACGATGACGAACTGGTGTGGCAGCAGGTGTTGGAGTACGCGAAGCGCACCCCTATCGGCGAGC
CGATCACCTTCACGTTCTACGAGCTTTGCCAGGACCTGGGCTGGTCGATCAATGGCCGGTATTACACGAAGGC
CGAGGAATGCCTGTCGCGCCTACAGGCGACGGCGATGGGCTTCACGTCCGACCGCGTTGGGCACCTGGAATC
GGTGTCGCTGCTGCACCGCTTCCGCGTCCTGGACCGTGGCAAGAAAACGTCCCGTTGCCAGGTCCTGATCGAC

FIG. 55 (Continued)

GAGGAAATCGTCGTGCTGTTTGCTGGCGACCACTACACGAAATTCATATGGGAGAAGTACCGCAAGCTGTCG
CCGACGGCCCGACGGATGTTCGACTATTTCAGCTCGCACCGGGAGCCGTACCCGCTCAAGCTGGAAACCTTCC
GCCTCATGTGCGGATCGGATTCCACCCGCGTGAAGAAGTGGCGCGAGCAGGTCGGCGAAGCCTGCGAAGAG
TTGCGAGGCAGCGGCCTGGTGGAACACGCCTGGGTCAATGATGACCTGGTGCATTGCAAACGCTAGGGCCTT
GTGGGGTCAGTTCCGGCTGGGGGTTCAGCAGCCAGCGCTTTACTGGCATTTCAGGAACAAGCGGGCACTGCT
CGACGCACTTGCTTCGCTCAGTATCGCTCGGGACGCACGGCGCGCTCTACGAACTGCCGATAAACAGAGGATT
AAAATTGACAATTGTGATTAAGGCTCAGATTCGACGGCTTGGAGCGGCCGACGTGCAGGATTTCCGCGAGAT
CCGATTGTCGGCCCTGAAGAAAGCTCCAGAGATGTTCGGGTCCGTTTACGAGCACGAGGAGAAAAAGCCCAT
GGAGGCGTTCGCTGAACGGTTGCGAGATGCCGTGGCATTCGGCGCCTACATCGACGGCGAGATCATTGGGCT
GTCGGTCTTCAAACAGGAGGACGGCCCCAAGGACGCTCACAAGGCGCATCTGTCCGGCGTTTTCGTGGAGCC
CGAACAGCGAGGCCGAGGGGTCGCCGGTATGCTGCTGCGGGCGTTGCCGGCGGGTTTATTGCTCGTGATGAT
CGTCCGACAGATTCCAACGGGAATCTGGTGGATGCGCATCTTCATCCTCGGCGCACTTAATATTTCGCTATTCT
GGAGCTTGTTGTTTATTTCGGTCTACCGCCTGCCGGGCGGGGTCGCGGCGACGGTAGGCGCTGTGCAGCCGC
TGATGGTCGTGTTCATCTCTGCCGCTCTGCTAGGTAGCCCGATACGATTGATGGCGGTCCTGGGGGCTATTTG
CGGAACTGCGGGCGTGGCGCTGTTGGTGTTGACACCAAACGCAGCGCTAGATCCTGTCGGCGTCGCAGCGG
GCCTGGCGGGGGCGGTTTCCATGGCGTTCGGAACCGTGCTGACCCGCAAGTGGCAACCTCCCGTGCCTCTGC
TCACCTTTACCGCCTGGCAACTGGCGGCCGGAGGACTTCTGCTCGTTCCAGTAGCTTTAGTGTTTGATCCGCCA
ATCCCGATGCCTACAGGAACCAATGTTCTCGGCCTGGCGTGGCTCGGCCTGATCGGAGCGGGTTTAACCTACT
TCCTTTGGTTCCGGGGGATCTCGCGACTCGAACCTACAGTTGTTTCCTTACTGGGCTTTCTCAGCCCCAGATCT
GGGGTCGATCAGCCGGGGATGCATCAGGCCGACAGTCGGAACTTCGGGTCCCCGACCTGTACCATTCGGTGA
GCAATGGATAGGGGAGTTGATATCGTCAACGTTCACTTCTAAAGAAATAGCGCCACTCAGCTTCCTCAGCGGC
TTTATCCAGCGATTTCCTATTATGTCGGCATAGTTCTCAAGATCGACAGCCTGTCACGGTTAAGCGAGAAATGA
ATAAGAAGGCTGATAATTCGGATCTCTGCGAGGGAGATGATATTTGATCACAGGCAGCAACGCTCTGTCATCG
TTACAATCAACATGCTACCCTCCGCGAGATCATCCGTGTTTCAAACCCGGCAGCTTAGTTGCCGTTCTTCCGAA
TAGCATCGGTAACATGAGCAAAGTCTGCCGCCTTACAACGGCTCTCCCGCTGACGCCGTCCCGGACTGATGGG
CTGCCTGTATCGAGTGGTGATTTTGTGCCGAGCTGCCGGTCGGGGAGCTGTTGGCTGGCTGGTGGCAGGATA
TATTGTGGTGTAAACAAATTGACGCTTAGACAACTTAATAACACATTGCGGACGTTTTTAATGTACTGGGGTG
GTTTTTCTTTTCACCAGTGAGACGGGCAACAGCTGATTGCCCTTCACCGCCTGGCCCTGAGAGAGTTGCAGCA
AGCGGTCCACGCTGGTTTGCCCCAGCAGGCGAAAATCCTGTTTGATGGTGGTTCCGAAATCGGCAAAATCCCT
AAGAATAGCCCGAGATAGGGTTGAGTGTTGTTCCAGTTTGGAACAAGAGTCCACTATTAAAGA
ACGTGGACTCCAACGTCAAAGGGCGAAAAACCGTCTATCAGGGCGATGGCCCACTACGTGAACCATCACCCA
AATCAAGTTTTTTGGGGTCGAGGTGCCGTAAAGCACTAAATCGGAACCCTAAAGGGAGCCCCCGATTTAGAG
CTTGACGGGGAAAGCCGGCGAACGTGGCGAGAAAGGAAGGGAAGAAAGCGAAAGGAGCGGGCGCCATTCA
GGCTGCGCAACTGTTGGGAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTTGTAAAACGACGGCCAGT
GAATTCGAGCTCGGTACCCCCC

FIG. 56

SEQ ID No. 50

ATAAAACATTGCACCTATGGTGTTGCCCTGGCTGGGGTATGTCAGTGATCGCAGTAGAATGTACTAATTGACA
AGTTGGAGAATACGGTAGAACGTCCTTATCCAACACAGCCTTTATCCCTCTCCCTGACGAGGTTTTTGTCAGTG
TAATATTTCTTTTTGAACTATCCAGCTTAGTACCGTACGGGAAAGTGACTGGTGTGCTTATCTTTGAAATGTTAC
TTTGGGTTTCGGTTCTTTAGGTTAGTAAGAAAGCACTTGTCTTCTCATACAAAGGAAAACCTGAGACGTATCGC
TTACGAAAGTAGCAATGAAAGAAAGGTGGTGGTTTTAATCGCTACCGCAAAAACGATGGGGTCGTTTTAATTA

FIG. 56 (Continued)

ACTTCTCCTACGCAAGCGTCTAAACGGACGTTGGGGTTTTGCTAGTTTCTTTAGAGAAAACTAGCTAAGTCTTT
AATGTTATCATTAGAGATGGCATAAATATAATACTTGTGTCTGCTGATAAGATCATTTTAATTTGGACGATTAG
ACTTGTTGAACTACAGGTTACTGAATCACTTGCGCTAATCAACATGGGAGATATGTACGATGAATCATTTGACA
AGTCGGGCGGTCCTGCTGACTTGATGGACGATTCTTGGGTGGAATCAGTTTCGTGGAAAGATCTGTTGAAGA
AGTTACACAGCATAAAATTTGCACTACAGTCTGGTAGAGATGAGATCACTGGGTTACTAGCGGCACTGAATAG
ACAGTGTCCTTATTCACCATATGAGCAGTTTCCAGATAAGAAGGTGTATTTCCTTTTAGACTCACGGGCTAACA
GTGCTCTTGGTGTGATTCAGAACGCTTCAGCGTTCAAGAGACGAGCTGATGAGAAGAATGCAGTGGCGGGTG
TTACAAATATTCCTGCGAATCCAAACACAACGGTTACGACGAACCAAGGGAGTACTACTACTACCAAGGCGAA
CACTGGCTCGACTTTGGAAGAAGACTTGTACACTTATTACAAATTCGATGATGCCTCTACAGCTTTCCACAAAT
CTCTAACTTCGTTAGAGAACATGGAGTTGAAGAGTTATTACCGAAGGAACTTTGAGAAAGTATTCGGGATTAA
GTTTGGTGGAGCAGCTGCTAGTTCATCTGCACCGCCTCCAGCGAGTGGAGGTCCGATACGTCCTAATCCCTAG
GGATTTAAGGACGTGAACTCTGTTGAGATCTCTGTGAAATTCAGAGGGTGGGTGATACCATATTCACTGATGC
CATTAGCGACATCTAAATAGGGCTAATTGTGACTAATTTGAGGGAATTTCCTTTACCATTGACGTCAGTGTCGT
TGGTAGCATTTGAGTTTCGCAATGCACGAATTACTTAGGAAGTGGCTTGACGACACTAATGTGTTATTGTTAG
ATAATGGTTTGGTGGTCAAGGTACGTAGTAGAGTCCCACATATTCGCACGTATGAAGTAATTGGAAAGTTGTC
AGTTTTTGATAATTCACTGGGAGATGATACGCTGTTTGAGGGAAAAGTAGAGAACGTATTTGTTTTTATGTTCA
GGCGGTTCTTGTGTGTCAACAAAGATGGACATTGTTACTCAAGGAAGCACGATGAGCTTTATTATTACGGACG
AGTGGACTTAGATTCTGTGAGTAAGGTTACCGAATTCTCTAGAAGGCCTCCATGGGGATCCGGTACCGAGCTC
ACGCGTCTCGAGGCCCGGGCATGTCCCGAAGACATTAAACTACGGTTCTTTAAGTAGATCCGTGTCTGAAGTT
TTAGGTTCAATTTAAACCTACGAGATTGACATTCTCGACTGATCTTGATTGATCGGTAAGTCTTTTGTAATTTAA
TTTTCTTTTTGATTTTATTTTAAATTGTTATCTGTTTCTGTGTATAGACTGTTTGAGATCGGCGTTTGGCCGACTC
ATTGTCTTACCATAGGGGAACGGACTTTGTTTGTGTTGTTATTTTATTTGTATTTTATTAAAATTCTCAACGATCT
GAAAAAGCCTCGCGGCTAAGAGATTGTTGGGGGGTGAGTAAGTACTTTTAAAGTGATGATGGTTACAAAGGC
AAAAGGGGTAAAACCCCTCGCCTACGTAAGCGTTATTACGCCCGTCTGTACTTATATCAGTACACTGACGAGT
CCCTAAAGGACGAAACGGGAGAACGCTAGCCACCACCACCACCACCACGTGTGAATTACAGGTGACCAGCTC
GAATTTCCCCGATCGTTCAAACATTTGGCAATAAAGTTTCTTAAGATTGAATCCTGTTGCCGGTCTTGCGATGA
TTATCATATAATTTCTGTTGAATTACGTTAAGCATGTAATAATTAACATGTAATGCATGACGTTATTTATGAGAT
GGGTTTTTATGATTAGAGTCCCGCAATTATACATTTAATACGCGATAGAAAACAAAATATAGCGCGCAAACTA
GGATAAATTATCGCGCGCGGTGTCATCTATGTTACTAGATCGGGAATTAAACTATCAGTGTTTGACAGGATAT
ATTGGCGGGTAAACCTAAGAGAAAAGAGCGTTTATTAGAATAACGGATATTTAAAAGGGCGTGAAAAGGTTT
ATCCGTTCGTCCATTTGTATGTGCATGCCAACCACAGGGTTCCCCTCGGGATCAAAGTACTTTGATCCAACCCC
TCCGCTGCTATAGTGCAGTCGGCTTCTGACGTTCAGTGCAGCCGTCTTCTGAAAACGACATGTCGCACAAGTCC
TAAGTTACGCGACAGGCTGCCGCCCTGCCCTTTTCCTGGCGTTTTCTTGTCGCGTGTTTTAGTCGCATAAAGTA
GAATACTTGCGACTAGAACCGGAGACATTACGCCATGAACAAGAGCGCCGCCGCTGGCCTGCTGGGCTATGC
CCGCGTCAGCACCGACGACCAGGACTTGACCAACCAACGGGCCGAACTGCACGCGGCCGGCTGCACCAAGCT
GTTTTCCGAGAAGATCACCGGCACCAGGCGCGACCGCCCGGAGCTGGCCAGGATGCTTGACCACCTACGCCC
TGGCGACGTTGTGACAGTGACCAGGCTAGACCGCCTGGCCCGCAGCACCCGCGACCTACTGGACATTGCCGA
GCGCATCCAGGAGGCCGGCGCGGGCCTGCGTAGCCTGGCAGAGCCGTGGGCCGACACCACCACGCCGGCCG
GCCGCATGGTGTTGACCGTGTTCGCCGGCATTGCCGAGTTCGAGCGTTCCCTAATCATCGACCGCACCCGGAG
CGGGCGCGAGGCCGCCAAGGCCCGAGGCGTGAAGTTTGGCCCCCGCCCTACCCTCACCCCGGCACAGATCGC
GCACGCCCGCGAGCTGATCGACCAGGAAGGCCGCACCGTGAAAGAGGCGGCTGCACTGCTTGGCGTGCATC
GCTCGACCCTGTACCGCGCACTTGAGCGCAGCGAGGAAGTGACGCCCACCGAGGCCAGGCGGCGCGGTGCC
TTCCGTGAGGACGCATTGACCGAGGCCGACGCCCTGGCGGCCGCCGAGAATGAACGCCAAGAGGAACAAGC
ATGAAACCGCACCAGGACGGCCAGGACGAACCGTTTTTCATTACCGAAGAGATCGAGGCGGAGATGATCGCG
GCCGGGTACGTGTTCGAGCCGCCCGCGCACGTCTCAACCGTGCGGCTGCATGAAATCCTGGCCGGTTTGTCTG

FIG. 56 (Continued)

ATGCCAAGCTGGCGGCCTGGCCGGCCAGCTTGGCCGCTGAAGAAACCGAGCGCCGCCGTCTAAAAAGGTGAT
GTGTATTTGAGTAAAACAGCTTGCGTCATGCGGTCGCTGCGTATATGATGCGATGAGTAAATAAACAAATACG
CAAGGGGAACGCATGAAGGTTATCGCTGTACTTAACCAGAAAGGCGGGTCAGGCAAGACGACCATCGCAACC
CATCTAGCCCGCGCCCTGCAACTCGCCGGGGCCGATGTTCTGTTAGTCGATTCCGATCCCCAGGGCAGTGCCC
GCGATTGGGCGGCCGTGCGGGAAGATCAACCGCTAACCGTTGTCGGCATCGACCGCCCGACGATTGACCGCG
ACGTGAAGGCCATCGGCCGGCGCGACTTCGTAGTGATCGACGGAGCGCCCCAGGCGGCGGACTTGGCTGTG
TCCGCGATCAAGGCAGCCGACTTCGTGCTGATTCCGGTGCAGCCAAGCCCTTACGACATATGGGCCACCGCCG
ACCTGGTGGAGCTGGTTAAGCAGCGCATTGAGGTCACGGATGGAAGGCTACAAGCGGCCTTTGTCGTGTCGC
GGGCGATCAAAGGCACGCGCATCGGCGGTGAGGTTGCCGAGGCGCTGGCCGGGTACGAGCTGCCCATTCTT
GAGTCCCGTATCACGCAGCGCGTGAGCTACCCAGGCACTGCCGCCGCCGGCACAACCGTTCTTGAATCAGAAC
CCGAGGGCGACGCTGCCCGCGAGGTCCAGGCGCTGGCCGCTGAAATTAAATCAAAACTCATTTGAGTTAATG
AGGTAAAGAGAAAATGAGCAAAAGCACAAACACGCTAAGTGCCGGCCGTCCGAGCGCACGCAGCAGCAAGG
CTGCAACGTTGGCCAGCCTGGCAGACACGCCAGCCATGAAGCGGGTCAACTTTCAGTTGCCGGCGGAGGATC
ACACCAAGCTGAAGATGTACGCGGTACGCCAAGGCAAGACCATTACCGAGCTGCTATCTGAATACATCGCGC
AGCTACCAGAGTAAATGAGCAAATGAATAAATGAGTAGATGAATTTTAGCGGCTAAAGGAGGCGGCATGGA
AAATCAAGAACAACCAGGCACCGACGCCGTGGAATGCCCCATGTGTGGAGGAACGGGCGGTTGGCCAGGCG
TAAGCGGCTGGGTTGTCTGCCGGCCCTGCAATGGCACTGGAACCCCCAAGCCCGAGGAATCGGCGTGACGGT
CGCAAACCATCCGGCCCGGTACAAATCGGCGCGGCGCTGGGTGATGACCTGGTGGAGAAGTTGAAGGCCGC
GCAGGCCGCCCAGCGGCAACGCATCGAGGCAGAAGCACGCCCCGGTGAATCGTGGCAAGCGGCCGCTGATC
GAATCCGCAAAGAATCCCGGCAACCGCCGGCAGCCGGTGCGCCGTCGATTAGGAAGCCGCCCAAGGGCGAC
GAGCAACCAGATTTTTTCGTTCCGATGCTCTATGACGTGGGCACCCGCGATAGTCGCAGCATCATGGACGTGG
CCGTTTTCCGTCTGTCGAAGCGTGACCGACGAGCTGGCGAGGTGATCCGCTACGAGCTTCCAGACGGGCACG
TAGAGGTTTCCGCAGGGCCGGCCGGCATGGCCAGTGTGTGGGATTACGACCTGGTACTGATGGCGGTTTCCC
ATCTAACCGAATCCATGAACCGATACCGGGAAGGGAAGGGAGACAAGCCCGGCCGCGTGTTCCGTCCACACG
TTGCGGACGTACTCAAGTTCTGCCGGCGAGCCGATGGCGGAAAGCAGAAAGACGACCTGGTAGAAACCTGC
ATTCGGTTAAACACCACGCACGTTGCCATGCAGCGTACGAAGAAGGCCAAGAACGGCCGCCTGGTGACGGTA
TCCGAGGGTGAAGCCTTGATTAGCCGCTACAAGATCGTAAAGAGCGAAACCGGGCGGCCGGAGTACATCGA
GATCGAGCTAGCTGATTGGATGTACCGCGAGATCACAGAAGGCAAGAACCCGGACGTGCTGACGGTTCACCC
CGATTACTTTTTGATCGATCCCGGCATCGGCCGTTTTCTCTACCGCCTGGCACGCCGCGCCGCAGGCAAGGCA
GAAGCCAGATGGTTGTTCAAGACGATCTACGAACGCAGTGGCAGCGCCGGAGAGTTCAAGAAGTTCTGTTTC
ACCGTGCGCAAGCTGATCGGGTCAAATGACCTGCCGGAGTACGATTTGAAGGAGGAGGCGGGGCAGGCTGG
CCCGATCCTAGTCATGCGCTACCGCAACCTGATCGAGGGCGAAGCATCCGCCGGTTCCTAATGTACGGAGCAG
ATGCTAGGGCAAATTGCCCTAGCAGGGGAAAAAGGTCGAAAAGGTCTCTTTCCTGTGGATAGCACGTACATT
GGGAACCCAAAGCCGTACATTGGGAACCGGAACCCGTACATTGGGAACCCAAAGCCGTACATTGGGAACCG
GTCACACATGTAAGTGACTGATATAAAAGAGAAAAAAGGCGATTTTTCCGCCTAAAACTCTTTAAAACTTATTA
AAACTCTTAAAACCCGCCTGGCCTGTGCATAACTGTCTGGCCAGCGCACAGCCGAAGAGCTGCAAAAAGCGC
CTACCCTTCGGTCGCTGCGCTCCCTACGCCCCGCCGCTTCGCGTCGGCCTATCGCGGCCGCTGGCCGCTCAAAA
ATGGCTGGCCTACGGCCAGGCAATCTACCAGGGCGCGGACAAGCCGCGCCGTCGCCACTCGACCGCCGGCGC
CCACATCAAGGCACCCTGCCTCGCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAGGGCGCGTCAGCGGGTGTTGG
CGGGTGTCGGGGCGCAGCCATGACCCAGTCACGTAGCGATAGCGGAGTGTATACTGGCTTAACTATGCGGCA
TCAGAGCAGATTGTACTGAGAGTGCACCATATGCGGTGTGAAATACCGCACAGATGCGTAAGGAGAAAATAC
CGCATCAGGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGTGAGCAA
AAGGCCAGCAAAAGGCCAGGAACCGTAAAAAGGCCGCGTTGCTGGCGTTTTTCCATAGGCTCCGCCCCCCTG

FIG. 56 (Continued)

ACGAGCATCACAAAAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCTGTCCGCCTTTCTCC
CTTCGGGAAGCGTGGCGCTTTCTCATAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCAGAGCGAGGTATGTA
GGCGGTGCTACAGAGTTCTTGAAGTGGTGGCCTAACTACGGCTACACTAGAAGGACAGTATTTGGTATCTGC
GCTCTGCTGAAGCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGCATTCTAGGTACTAA
AACAATTCATCCAGTAAAATATAATATTTTATTTTCTCCCAATCAGGCTTGATCCCCAGTAAGTCAAAAAATAGC
TCGACATACTGTTCTTCCCCGATATCCTCCCTGATCGACCGGACGCAGAAGGCAATGTCATACCACTTGTCCGC
CCTGCCGCTTCTCCCAAGATCAATAAAGCCACTTACTTTGCCATCTTTCACAAAGATGTTGCTGTCTCCCAGGTC
GCCGTGGGAAAAGACAAGTTCCTCTTCGGGCTTTTCCGTCTTTAAAAAATCATACAGCTCGCGCGGATCTTTAA
ATGGAGTGTCTTCTTCCCAGTTTTCGCAATCCACATCGGCCAGATCGTTATTCAGTAAGTAATCCAATTCGGCT
AAGCGGCTGTCTAAGCTATTCGTATAGGGACAATCCGATATGTCGATGGAGTGAAAGAGCCTGATGCACTCC
GCATACAGCTCGATAATCTTTTCAGGGCTTTGTTCATCTTCATACTCTTCCGAGCAAAGGACGCCATCGGCCTC
ACTCATGAGCAGATTGCTCCAGCCATCATGCCGTTCAAAGTGCAGGACCTTTGGAACAGGCAGCTTTCCTTCCA
GCCATAGCATCATGTCCTTTTCCCGTTCCACATCATAGGTGGTCCCTTTATACCGGCTGTCCGTCATTTTTAAAT
ATAGGTTTTCATTTTCTCCCACCAGCTTATATACCTTAGCAGGAGACATTCCTTCCGTATCTTTTACGCAGCGGT
ATTTTTCGATCAGTTTTTTCAATTCCGGTGATATTCTCATTTTAGCCATTTATTATTTCCTTCCTCTTTTCTACAGT
ATTTAAAGATACCCCAAGAAGCTAATTATAACAAGACGAACTCCAATTCACTGTTCCTTGCATTCTAAAACCTTA
AATACCAGAAAACAGCTTTTTCAAAGTTGTTTTCAAAGTTGGCGTATAACATAGTATCGACGGAGCCGATTTTG
AAACCGCGGTGATCACAGGCAGCAACGCTCTGTCATCGTTACAATCAACATGCTACCCTCCGCGAGATCATCC
GTGTTTCAAACCCGGCAGCTTAGTTGCCGTTCTTCCGAATAGCATCGGTAACATGAGCAAAGTCTGCCGCCTTA
CAACGGCTCTCCCGCTGACGCCGTCCCGGACTGATGGGCTGCCTGTATCGAGTGGTGATTTTGTGCCGAGCTG
CCGGTCGGGGAGCTGTTGGCTGGCTGGTGGCAGGATATATTGTGGTGTAAACAAATTGACGCTTAGACAACT
TAATAACACATTGCGGACGTTTTTAATGTACTGAATTAACGCCGAATTAATTCCTAGGCCACCATGTTGGGCCC
GGCGCGCCAAGCTTGCATGCCTGCAGGTCAACATGGTGGAGCACGACACTCTCGTCTACTCCAAGAATATCAA
AGATACAGTCTCAGAAGACCAGAGGGCTATTGAGACTTTTCAACAAAGGGTAATATCGGGAAACCTCCTCGG
ATTCCATTGCCCAGCTATCTGTCACTTCATCGAAAGGACAGTAGAAAAGGAAGATGGCTTCTACAAATGCCAT
CATTGCGATAAAGGAAAGGCTATCGTTCAAGATGCCTCTACCGACAGTGGTCCCAAAGATGGACCCCCACCCA
CGAGGAACATCGTGGAAAAAGAAGACGTTCCAACCACGTCTTCAAAGCAAGTGGATTGATGTGATGGTCAAC
ATGGTGGAGCACGACACTCTCGTCTACTCCAAGAATATCAAAGATACAGTCTCAGAAGACCAGAGGGCTATTG
AGACTTTTCAACAAAGGGTAATATCGGGAAACCTCCTCGGATTCCATTGCCCAGCTATCTGTCACTTCATCGAA
AGGACAGTAGAAAAGGAAGATGGCTTCTACAAATGCCATCATTGCGATAAAGGAAAGGCTATCGTTCAAGAT
GCCTCTACCGACAGTGGTCCCAAAGATGGACCCCCACCCACGAGGAACATCGTGGAAAAAGAAGACGTTCCA
ACCACGTCTTCAAAGCAAGTGGATTGATGTGATATCTCCACTGACGTAAGGGATGACGCACAATCCCACTATC
CTTCGCAAGACCCTTCCTCTATATAAGGAAGTTCATTTCATTTGGAGAGG

FIG. 57

SEQ ID No. 51

ATTATAGCTATGTACACAATTAGCACGTGGGCGAAGACAGTGGCAGAAAATGTCTGGTCACTCATTGGAAGA
ACAGCTCCACCAGATTTTCTTACGAAATTAACCTATCTTATATGGAATCATCACGAAGAGATCAAGCACATTGA
TACTGTTCGAGCATATACTTTTGGTGCTCATTATTTTGTAGAGGTTGATATAGTGTTGCCAGAGGACATGCTGT

FIG. 57 (Continued)

TGAACAAGGCACATAATATTGGTGAGACACTGCAAGAAAAATTGGAGCAACTCCCTGAAGTTGAGCGAGCTT
TTGTTCAT

FIG. 58

SEQ ID No. 52

CGTCGTCCAACATTATCATGGCCTCGTGAAATCCCGTTAGTAAAAGGTGGTAAACCTGACGTTGTACAAATTGT
TAGGAATTATAATGCTTATCTACGTGCAAGTGATGATTTACCAAAAATGTTTATTGAATCGGACCCAGGATTCT
TTTCCAATGCTATTGTTGAAGGTGCCAAGAAGTTTCCTAATACTGAATTTGTCAAAGTAAAAGGTCTTCATTTTT
CGCAAGAAGATGCACCTGATGAAATGGGAAAATATATCAAATCGTTCGTTGAGCGAGTTCTCAAAAATGAAC
AATAA

FIG. 59

SEQ ID No. 53
AGGGAATATTAAGCTTATGGAGATAAGTCGCAGCAATGT

FIG. 60

SEQ ID No. 54
GTTACTAGTGGATCCTTATACCATAGTTTTGTGTTCTG

FIG. 61

SEQ ID No. 55
AGCTTGCATGCCTGCAGGTCGAGCTTTTAGGATTCCATAGTGATAAGATATGTTCTTATCTAAACAAAAAAGCA
AGCGTCGGCAAACCATACAGCTGTCCACAAAAAGGAAAGGCTGTAATAACAAGCGGACCCAGCTTCTCAGTG
GAAGATACTTTATCAGACACTGAATAATGGATGGACCCTACCACGATTAAAGAGGAGCGTCTGTCTAAAGTAA
AGTAGATGCGTCTTTAATAATTCATCTACTTTAGACGTCATGCATGACGTTTAACATGCATTGTATCCAGATCCT
CCCTGGCTATATAAAGGGAGTTAAATTTCATTGTTAAGGCATCGAAAAAAAAATTTCAAGTCTATCTCTCAAGA
AAAACTTAGAAAATTACTTTGTCTTAAGGATCCGGGCCCAGCTGTCACAAGTTTGTACAAAAAAGCAGGCTAC
TAAAAGCTCGCTCAACTTCAGGGAGTTGCTCCAATTTTTCTTGCAGTGTCTCACCAATATTATGTGCCTTGTTCA
ACAGCATGTCCTCTGGCAACACTATATCAACCTCTACAAAATAATGAGCACCAAAAGTATATGCTCGAACAGTA
TCAATGTGCTTGATCTCTTCGTGATGATTCCATATAAGATAGGTTAATTTCGTAAGAAAATCTGGTGGAGCTGT
TCTTCCAATGAGTGACCAGACATTTTCTGCCACTGTCTTCGCCCACGTGCTAATTGTGTACATAGCTATGATTTC
GTTTTTGAACCTTCGACAGTAGACCATAAGCAGAAACTTGACCATAGTGACAGAGACCATAATACCAATCGTC
CATTTTTCCTTCTCATGGTCCATCTCAGGGCGAGACTGATCGTAAGCATAGAACCACCGAAACAACAAACGTA
GATTAAGATGTCAAGGGTAATGCAATTGTTAGTGAAATTGCAGTAAGTTACAAGTCTATATCCTACAATTGAA
GTAGCACTATGCGAGTTAATCTTCACTTAGCTATGCAACATCAGTAGAAATATCAAAACCAGTCCCTTTTTATTA
GGTAGTATACAGTAGCCTAATTTATCTTATGTAAACATCTTTGGCCTAACTGGTTTGGCTACAACTTCATTTCAG
TAGTAACTCAACCCGTTTTTCGTCTTCTTGTTTCCTATAAATTGCATGTTTTTTTTTGTCTTGATGTAAAAGATTTT
AGAAACTCAAAACTCTACTAACCATAGGAACCTGCTGCTCTGAAAATTCTCAGGATAGTTGAAGTGAAGCAAT
TCACATACCTTAGTTATGAGTTCTTTAGCTGACTCGAACAATATTTGTAATCCTAGTGTCGCCATTACAGATGCA
AAAACAATAATACCCAATGGCTGCATCCTCTTTTTTCCAATAGGATAGTGATACTGGTTTGGATTTTTCATGGC
ATGAGAAGTGAACCACAGTATAAACCCTGATAAGAGGTCTAAGAGGGAGTCCAACGTTGACGCGATTACAGC
CAAAGATCTGCTCTCAATAGAAGCGTAGATTTTTGCAATGAAAAGAACCACATTAGCCATGTTTGATAAATGA
ATAGCCATCCTTTCACTTCTTGCAAGCTGCTTCATTTCATCCTCAGTTAGACTTCCAGGTAAACAACCAGATTCA
TTAATGGTGTCCATCTCATTGAACCCTTCAAGCAGCCTTTCTTGTTTTTTGTAGTATTCAGCAATTTTACCTTGTT
TCCTGGGAGTGGGAAGTAGACGACGGACACTAAAGGAGTGATGATCGGAGGAGGAGCGGCTTCGTTCGGG
AAGACGGAATTCGCTAATGTTAAGTCTCCATGACGCCGACGAAGACGACTGATCCACCACCGCCTGAGCAGCC

FIG. 61 (Continued)

GGAGACAGCAGTTCCGTCCTAAAACTGCTAAAACTGTCGTCCAGAGCGCCGCCGCTGCCGCCACCACCACTAA
CATTGCTGCGACTTATCTCCATACCCAGCTTTCTTGTACAAAGTGGTGCAGCTGAGATCTAGGCCTAAGTAAGT
AAGATCGTTCAAACATTTGGCAATAAAGTTTCTTTAGATTGAATCCTGTTGCCGGTCTTGCGATGATTATCATAT
AATTTCTGTTGAATTACGTTAAGCATGTAGTAATTAACATGTAATGGATGACGTTATTTATGAGATGGGTTTTT
ATGATTAGAGTCCCGCAATTATACATTTAATACGCGATAGAAAACAAAATATAGCGCGCAAACTAGGATAAAT
TATCGCGCGCGGTGTCATCTATGTTACTAGATCGAAGGCCTTGTTCTCGAGCAATTCACTGGCCGTCGTTTTAC
AACGTCGTGACTGGGAAAACCCTGGCGTTACCCAACTTAATCGCCTTGCAGCACATCCCCCTTTCGCCAGCAG
GCGTAATAGCGAAGAGGCCCGCACCGATTGCCCTTCCCAACAGTTGCGCAGCCTGAATGGCGCCCGCTCCTTT
CGCTTTCTTCCCTTCCTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTTGGGTGATGGTTCACAAACTATCAGTG
TTTGACAGGATATATTGGCGGGTAAACCTAAGAGAAAAGAGCGTTTATTAGAATAATCGGATATTTAAAAGG
GCGTGAAAAGGTTTATCCGTTCGTCCATTTGTATGTGCATGCCAACCACAGGCTTAAGAAAACTTGATTTGGGT
GATGGTTCACAAACTATCAGTGTTTGACAGGATATATTGGCGGGTAAACCTAAGAGAAAAGAGCGTTTATTAG
AATAATCGGATATTTAAAAGGGCGTGAAAAGGTTTATCCGTTCGTCCATTTGTATGTGCATGCCAACCACAGG
CTTAAGGTTCTAGACTGGCGCCGGCCAGCGAGACGAGCAAGATTGGCCGCCGCCCGAAACGATCCGACAGCG
CGCCCAGCACAGGTGCGCAGGCAAATTGCACCAACGCATACAGCGCCAGCAGAATGCCATAGTGGGCGGTG
ACCTCGTTCGAGTGAACCAGATCGCGCAGGAGGCCCGGCAGCACCGGCATAATCAGGCCGATGCCGACAGC
GTCGAGCGCGACAGTGCTCAGAATTACGATCAGGGGTATGTTGGGTTTCACGTCTGGCCTCCGGACCAGCCTC
CGCTGGTCCGATTGAACGCGCGGATTCTTTATCACTGATAAGTTGGTGGACATATTATGTTTATCAGTGATAAA
GTGTCAAGCATGACAAAGTTGCAGCCGAATACAGTGATCCGTGCCGCCCTGGACCTGTTGAACGAGGTCGGC
GTAGACGGTCTGACGACACGCAAACTGGCGGAACGGTTGGGGGTTCAGCAGCCGGCGCTTTACTGGCACTTC
AGGAACAAGCGGGCGCTGCTCGACGCACTGGCCGAAGCCATGCTGGCGGAGAATCATACGCATTCGGTGCC
GAGAGCCGACGACGACTGGCGCTCATTTCTGATCGGGAATGCCCGCAGCTTCAGGCAGGCGCTGCTCGCCTA
CCGCGATGGCGCGCGCATCCATGCCGGCACGCGACCGGGCGCACCGCAGATGGAAACGGCCGACGCGCAGC
TTCGCTTCCTCTGCGAGGCGGGTTTTTCGGCCGGGGACGCCGTCAATGCGCTGATGACAATCAGCTACTTCAC
TGTTGGGGCCGTGCTTGAGGAGCAGGCCGGCGACAGCGATGCCGGCGAGCGCGGCGGCACCGTTGAACAG
GCTCCGCTCTCGCCGCTGTTGCGGGCCGCGATAGACGCCTTCGACGAAGCCGGTCCGGACGCAGCGTTCGAG
CAGGGACTCGCGGTGATTGTCGATGGATTGGCGAAAAGGAGGCTCGTTGTCAGGAACGTTGAAGGACCGAG
AAAGGGTGACGATTGATGAGGACCGCTGCCGGAGCGCAACCCACTCACTACAGCAGAGCCATGTAGACAACA
TCCCCTCCCCCTTTCCACCGCGTCAGACGCCCGTAGCAGCCCGCTACGGGCTTTTTCATGCCCTGCCCTAGCGT
CCAAGCCTCACGGCCGCGCTCGGCCTCTCTGGCGGCCTTCTGGCGCTCGTCGACCGCTCACTGACTCGCTGCG
CTCGGTCGTTCGGCTGCGGCGAGCGGTATCAGCTCACTCAAAGGCGGTAATACGGTTATCCACAGAATCAGG
GGATAACGCAGGAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTTCCGCTGCATAACCCTGCTTCGG
GGTCATTATAGCGATTTTTTCGGTATATCCATCCTTTTTCGCACGATATACAGGATTTTGCCAAAGGGTTCGTGT
AGACTTTCCTTGGTGTATCCAACGGCGTCAGCCGGGCAGGATAGGTGAAGTAGGCCCACCCGCGAGCGGGTG
TTCCTTCTTCACTGTCCCTTATTCGCACCTGGCGGTGCTCAACGGGAATCCTGCTCTGCGAGGCTGGCCGGCTA
CCGCCGGCGTAACAGATGAGGGCAAGCGGATGGCTGATGAAACCAAGCCAACCAGGAAGGGCAGCCCACCT
ATCAAGGTGTACTGCCTTCCAGACGAACGAAGAGCGATTGAGGAAAAGGCGGCGGCGGCCGGCATGAGCCT
GTCGGCCTACCTGCTGGCCGTCGGCCAGGGCTACAAAATCACGGGCGTCGTGGACTATGAGCACGTCCGCGA
GCTGGCCCGCATCAATGGCGACCTGGGCCGCCTGGGCGGCCTGCTGAAACTCTGGCTCACCGACGACCCGCG
CACGGCGCGGTTCGGTGATGCCACGATCCTCGCCCTGCTGGCGAAGATCGAAGAGAAGCAGGACGAGCTTG
GCAAGGTCATGATGGGCGTGGTCCGCCCGAGGGCAGAGCCATGACTTTTTTAGCCGCTAAAACGGCCGGGG
GGTGCGCGTGATTGCCAAGCACGTCCCCATGCGCTCCATCAAGAAGAGCGACTTCGCGGAGCTGGTGAAGTA
CATCACCGACGAGCAAGGCAAGACCGAGCGCCTTTGGTACCTCACCGGGCTGGTTGCCCTCGCCGCTGGGCT
GGCGGCCGTCTATGGCCCTGCAAACGCGCCAGAAACGCCGTCGAAGCCGTGTGCGAGACACCGCCGCCGCCG
GCGTTGTGGATACCTCGCGGAAAACTTGGCCCTCACTGACAGATGAGGGGCGGACGTTGACACTTGAGGGGC
CGACTCACCCGGCGCGGCGTTGACAGATGAGGGGCAGGCTCGATTTCGGCCGGCGACGTGGAGCTGGCCAG
CCTCGCAAATCGGCGAAAACGCCTGATTTTACGCGAGTTTCCCACAGATGATGTGGACAAGCCTGGGGATAA

FIG. 61 (Continued)

GTGCCCTGCGGTATTGACACTTGAGGGGCGCGACTACTGACAGATGAGGGGCGCGATCCTTGACACTTGAGG
GGCAGAGTGCTGACAGATGAGGGGCGCACCTATTGACATTTGAGGGGCTGTCCACAGGCAGAAAATCCAGC
ATTTGCAAGGGTTTCCGCCCGTTTTTCGGCCACCGCTAACCTGTCTTTTAACCTGCTTTTAAACCAATATTTATA
AACCTTGTTTTTAACCAGGGCTGCGCCCTGTGCGCGTGACCGCGCACGCCGAAGGGGGGTGCCCCCCCTTCTC
GAACCCTCCCGGCCCGCTAACGCGGGCCTCCCATCCCCCCAGGGGCTGCGCCCCTCGGCCGCGAACGGCCTCA
CCCCAAAAATGGCAGCGCTGGCAGTCCTTGCCATTGCCGGGATCGGGGCAGTAACGGGATGGGCGATCAGCCC
CGAGCGCGACGCCCGGAAGCATTGACGTGCCGCAGGTGCTGGCATCGACATTCAGCGACCAGGTGCCGGGC
AGTGAGGGCGGCGGCCTGGGTGGCGGCCTGCCCTTCACTTCGGCCGTCGGGGCATTCACGGACTTCATGGCG
GGGCCGGCAATTTTTACCTTGGGCATTCTTGGCATAGTGGTCGCGGGTGCCGTGCTCGTGTTCGGGGGTGAC
GCGTGAAAATTTTCGATAAACCCAGCGAACCATTTGAGGTGATAGGTAAGATTATACCGAGGTATGAAAACG
AGAATTGGACCTTTACAGAATTACTCTATGAAGCGCCATATTTAAAAAGCTACCAAGACGAAGAGGATGAAGA
GGATGAGGAGGCAGATTGCCTTGAATATATTGACAATACTGATAAGATAATATATCTTTTATATAGAAGATAT
GGCCGTATGTAAGGATTTCAGGGGGCAAGGCATAGGCAGCGCGCTTATCAATATATCTATAGAATGGGCAAA
GCATAAAAACTTGCATGGACTAATGCTTGAAACCCAGGACAATAACCTTATAGCTTGTAAATTCTATCATAATT
GGGTAATGACTCCAACTTATTGATAGTGTTTTATGTTCAGATAATGCCCGATGACTTTGTCATGCAGCTCCACC
GATTTTGAGAACGACAGCGACTTCCGTCCCAGCCGTGCCAGGTGCTGCCTCAGATTCAGGTTATGCCGCTCAA
TTCGCTGCGTATATCGCTTGCTGATTACGTGCAGCTTTCCCTTCAGGCGGGATTCATACAGCGGCCAGCCATCC
GTCATCCATATCACCACGTCAAAGGGTGACAGCAGGCTCATAAGACGCCCCAGCGTCGCCATAGTGCGTTCAC
CGAATACGTGCGCAACAACCGTCTTCCGGAGACTGTCATACGCCTAAAACAGCCAGCGCTGGCGCGATTTAGC
CCCGACATAGCCCCACTGTTCGTCCATTTCCGCGCAGACGATGACGACACTGCCCGGCTGTATGCGCGAGGTT
ACCTGCTGCCAGTGGCGATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCTACACCGAACTGAGAT
ACCTACAGCGTGAGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCCTATGGAAAAAC
GCCAGCAACGCGGCCTTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCCGAACGACCGAGC
GCAGCGAGTCAGTGAGCGAGGAAGCGGAAGAGCGCCTGATGCGGTATTTTCTCCTTACGCATCTGTGCGGTA
TTTCACACCGCATAGTTACCGACTGCGGCCTGAGTTTTTTAAGTGACGTAAAATCGTGTTGAGGCCAACGCCCA
TAATGCGGGCTGTTGCCCGGCATCCAACGCCATTCATGGCCATATCAATGATTTTCTGGTGCGTACCGGGTTG
AGAAGCGGTGTAAGTGAACAGCAGTTGCCATGTTTTACGGCAGTGAGAGCAGAGATAGCGCTGATGTCCGGC
GGTGCTTTTGCCGTTACGCACCACCCCGTCAGTAGCTGAACAGGAGGGACACCTGATAGACACAGAAGCCAC
TGGAGCACCTCAAAAACACCATCATACACTAAATCAGTAAGTTGGCAGCATCACCCGTTAACATAATTGTGGTT
TCAAAATCGGCTCCGTCGATACTATGTTATACGCCAACTTTGAAAACAACTTTGAAAAAGCTGTTTTCTGGTAT
TTAAGGTTTTAGAATGCAAGGAACAGTGAATTGGAGTTCGTCTTGTTATAATTAGCTTCTTGGGGTATCTTTAA
ATACTGTAGAAAAGAGGAAGGAAATAATAAATGGCTAAAATGAGAATATCACCGGAATTGAAAAAACTGATC
GAAAAATACCGCTGCGTAAAAGATACGGAAGGAATGTCTCCTGCTAAGGTATATAAGCTGGTGGGAGAAAAT
GAAAACCTATATTTAAAAATGACGGACAGCCGGTATAAAGGGACCACCTATGATGTGGAACGGGAAAAGGAC
ATGATGCTATGGCTGGAAGGAAAGCTGCCTGTTCCAAAGGTCCTGCACTTTGAACGGCATGATGGCTGGAGC
AATCTGCTCATGAGTGAGGCCGATGGCGTCCTTTGCTCGGAAGAGTATGAAGATGAACAAAGCCCTGAAAAG
ATTATCGAGCTGTATGCGGAGTGCATCAGGCTCTTTCACTCCATCGACATATCGGATTGTCCCTATACGAATAG
CTTAGACAGCCGCTTAGCCGAATTGGATTACTTACTGAATAACGATCTGGCCGATGTGGATTGCGAAAACTGG
GAAGAAGACACTCCATTTAAAGATCCGCGCGAGCTGTATGATTTTTTAAAGACGGAAAAGCCCGAAGAGGAA
CTTGTCTTTTCCCACGGCGACCTGGGAGACAGCAACATCTTTGTGAAAGATGGCAAAGTAAGTGGCTTTATTG
ATCTTGGGAGAAGCGGCAGGGCGGACAAGTGGTATGACATTGCCTTCTGCGTCCGGTCGATCAGGGAGGTTA
TCGGGGAAGAACAGTATGTCGAGCTATTTTTTGACTTACTGGGGATCAAGCCTGATTGGGAGAAAATAAAAT
ATTATATTTTACTGGATGAATTGTTTTAGTACCTAGAGAAAATTTTCCTAGGTGTGGCGCAACGATGCCGGCGA
CAAGCAGGAGCGCACCGACTTCTTCCGCATCAAGTGTTTTGGCTCTCAGGCCGAGGCCCACGGCAAGTATTTG
GGCAAGGGGTCGCTGGTATTCGTGCAGGGCAAGATTCGGAATACCAAGTACGAGAAGGACGGCCAGACGGT
CTACGGGACCGACTTCATTGCCGATAAGGTGGATTATCTGGACACCAAGGCACCAGGCGGGTCAAATCAGGA
ATAAGGGCACATTGCCCCGGCGTGAGTCGGGGCAATCCCGCAAGGAGGGTGAATGAATCGGACGTTTGACC

FIG. 61 (Continued)

GGAAGGCATACAGGCAAGAACTGATCGACGCGGGGTTTTCCGCCGAGGATGCCGAAACCATCGCAAGCCGC
ACCGTCATGCGTGCGCCCCGCGAAACCTTCCAGTCCGTCGGCTCGATGGTCCAGCAAGCTACGGCCAAGATCG
AGCGCGACAGCGTGCAACTGGCTCCCCCTGCCCTGCCCGCGCCATCGGCCGCCGTGGAGCGTTCGCGTCGTCT
CGAACAGGAGGCGGCAGGTTTGGCGAAGTCGATGACCATCGACACGCGAGGAACTATGACGACCAAGAAGC
GAAAAACCGCCGGCGAGGACCTGGCAAAACAGGTCAGCGAGGCCAAGCAGGCCGCGTTGCTGAAACACACG
AAGCAGCAGATCAAGGAAATGCAGCTTTCCTTGTTCGATATTGCGCCGTGGCCGGACACGATGCGAGCGATG
CCAAACGACACGGCCCGCTCTGCCCTGTTCACCACGCGCAACAAGAAAATCCCGCGCGAGGCGCTGCAAAAC
AAGGTCATTTTCCACGTCAACAAGGACGTGAAGATCACCTACACCGGCGTCGAGCTGCGGGCCGACGATGAC
GAACTGGTGTGGCAGCAGGTGTTGGAGTACGCGAAGCGCACCCCTATCGGCGAGCCGATCACCTTCACGTTC
TACGAGCTTTGCCAGGACCTGGGCTGGTCGATCAATGGCCGGTATTACACGAAGGCCGAGGAATGCCTGTCG
CGCCTACAGGCGACGGCGATGGGCTTCACGTCCGACCGCGTTGGGCACCTGGAATCGGTGTCGCTGCTGCAC
CGCTTCCGCGTCCTGGACCGTGGCAAGAAAACGTCCCGTTGCCAGGTCCTGATCGACGAGGAAATCGTCGTG
CTGTTTGCTGGCGACCACTACACGAAATTCATCTGGGAGAAGTACCGCAAGCTGTCGCCGACGGCCCGACGG
ATGTTCGACTATTTCAGCTCGCACCGGGAGCCGTACCCGCTCAAGCTGGAAACCTTCCGCCTCATGTGCGGAT
CGGATTCCACCCGCGTGAAGAAGTGGCGCGAGCAGGTCGGCGAAGCCTGCGAAGAGTTGCGAGGCAGCGGC
CTGGTGGAACACGCCTGGGTCAATGATGACCTGGTGCATTGCAAACGCTAGGGCCTTGTGGGGTCAGTTCCG
GCTGGGGGTTCAGCAGCCAGCGTGATCACTTTACTGGCATTTCAGGAACAAGCGGGCACTGCTCGACGCACTT
GCTTCGCTCAGTATCGCTCGGGACGCACGGCGCGCTCTACGAACTGCCGATAAACAGAGGATTAAAATTGAC
AATTGTGATTAAGGCTCAGATTCGACGGCTTGGAGCGGCCGACGTGCAGGATTTCCGCGAGATCCGATTGTC
GGCCCTGAAGAAAGCTCCAGAGATGTTCGGGTCCGTTTACGAGCACGAGGAGAAAAAGCCCATGGAGGCGT
TCGCTGAACGGTTGCGAGATGCCGTGGCATTCGGCGCCTACATCGACGGCGAGATCATTGGGCTGTCGGTCT
TCAAACAGGAGGACGGCCCCAAGGACGCTCACAAGGCGCATCTGTCCGGCGTTTTCGTGGAGCCCGAACAGC
GAGGCCGAGGGGTCGCCGGTATGCTGCTGCGGGCGTTGCCGGCGGGTTTATTGCTCGTGATGATCGTCCGAC
AGATTCCAACGGGAATCTGGTGGATGCGCATCTTCATCCTCGGCGCACTTAATATTTCGCTATTCTGGAGCTTG
TTGTTTATTTCGGTCTACCGCCTGCCGGGCGGGGTCGCGGCGACGGTAGGCGCTGTGCAGCCGCTGATGGTC
GTGTTCATCTCTGCCGCTCTGCTAGGTAGCCCGATACGATTGATGGCGGTCCTGGGGGCTATTTGCGGAACTG
CGGGCGTGGCGCTGTTGGTGTTGACACCAAACGCAGCGCTAGATCCTGTCGGCGTCGCAGCGGGCCTGGCG
GGGGCGGTTTCCATGGCGTTCGGAACCGTGCTGACCCGCAAGTGGCAACCTCCCGTGCCTCTGCTCACCTTTA
CCGCCTGGCAACTGGCGGCCGGAGGACTTCTGCTCGTTCCAGTAGCTTTAGTGTTTGATCCGCCAATCCCGAT
GCCTACAGGAACCAATGTTCTCGGCCTGGCGTGGCTCGGCCTGATCGGAGCGGGTTTAACCTACTTCCTTTGG
TTCCGGGGGATCTCGCGACTCGAACCTACAGTTGTTTCCTTACTGGGCTTTCTCAGCCCCAGGTCTGGGGTCGA
TCAGCCGGGGATGCATCAGGCCGACAGTCGGAACTTCGGGTCCCCGACCTGTACCATTCGGTGAGCAATGGA
TAGGGGAGTTGAAATCGTCAACGTTCACTTCTAAAGAAATAGCGCCACTCAGCTTCCTCAGCGGCTTTATCCA
GCGATTTCCTATTATGTCGGCATAGTTCTCAAGATCGACAGCCTGTCACGGTTAAGCGAGAAATGAATAAGAA
GGCTGATAATTCGGATCTCTGCGAGGGAGATGATATTTGATGACAGGCAGCAACGCTCTGTCATCGTTACAAT
CAACATGCTACCCTCCGCGAGATCATCCGTGTTTCAAACCCGGCAGCTTAGTTGCCGTTCTTCCGAATAGCATC
GGTAACATGAGCAAAGTCTGCCGCCTTACAACGGCTCTCCCGCTGACTAGTCGTCCCGGAGACGTCCTGATGG
GCTGCCTGTATCGAGTGGTGATTTTGTGCCGAGCTGCCGGTCGGGGAGCTGTTGGCTGGCTGGTGGCAGGAT
ATATTGTGGTGTAAACAAATTGACGCTTAGACAACTTAATAACACATTGCGGACGTTTTTAATGTACTGGACGT
CCTGATGGGCTGCCTGTATCGAGTGGTGATTTTGTGCCGAGCTGCCGGTCGGGGAGCTGTTGGCTGGCTGGT
GGCAGGATATATTGTGGTGTAAACAAATTGACGCTTAGACAACTTAATAACACATTGCGGACGTTTTTAATGT
ACTGGGGTGGTTTTTCTTTTCACCAGTGAGACGGGCAACACGTGATTGCCCTTCACCGCCTGGCCCTGAGAGA
GTTGCAGCAAGCGGTCCACGCTGGTTTGCCCCAGCAGGCGAAAATCCTGTTTGATGGTGGTTCCGAAATCGGC
AAAATCCCTTATAAATCAAAAGAATAGCCCGAGATAGGGTTGAGTGTTGTTCCAGTTTGGAACAAGAGTCCAC
TATTAAAGAACGTGGACTCCAACGTCAAAGGGCGAAAAACCGTCTATCAGGGCGATGGCCCACAAACTGAAG
GCGGCCGCAAACGATATCAATCTCATCATGAGCGGAGAATTAAGGGAGTCACGTTATGACCCCCGCCGATGA
CGCGGGACAAGCCGTTTTACGTTTGGAACTGACAGAACCGCAACGTTGAAGGAGCCACTCAGCCGCCGGTTT
CTGGAGTTTAATGAGCTAAGCACATACGTCAGAAACCATTATTGCGCGTTCAAAAGTCGCCTAAGGTCACTAT
CAGCTAGCAAATATTTCTTGTCAAAAAATGCTCCACTGACGTTCCATAAATTCCCCTCGGTATCCAATTAGAGTCT
CATATTCACTCTCAATCCAAATAATCTGCACCGGATCTGGATCGTTTCGCATGATTGAACAAGATGGATTGCAC
GCAGGTTCTCCGGCCGCTTGGGTGGAGAGGCTATTCGGCTATGACTGGGCACAACAGACAATCGGCTGCTCT

FIG. 61 (Continued)

GATGCCGCCGTGTTCCGGCTGTCAGCGCAGGGGCGCCCGGTTCTTTTTGTCAAGACCGACCTGTCCGGTGCCC
TGAATGAACTCCAGGACGAGGCAGCGCGGCTATCGTGGCTGGCCACGACGGGCGTTCCTTGCGCTGCTGTGC
TCGACGTTGTCACTGAAGCGGGAAGGGACTGGCTGCTATTGGGCGAAGTGCCGGGGCAGGATCTCCTGTCAT
CTCACCTTGCTCCTGCCGAGAAAGTATCCATCATGGCTGATGCAATGCGGCGGCTGCATACGCTTGATCCGGC
TACCTGCCCATTCGACCACCAAGCGAAACATCGCATCGAGCGAGCACGTACTCGGATGGAAGCCGGTCTTGTC
GATCAGGATGATCTGGACGAAGAGCATCAGGGGCTCGCGCCAGCCGAACTGTTCGCCAGGCTCAAGGCGCG
CATGCCCGACGGCGATGATCTCGTCGTGACCCATGGCGATGCCTGCTTGCCGAATATCATGGTGGAAAATGGC
CGCTTTTCTGGATTCATCGACTGTGGCCGGCTGGGTGTGGCGGACCGCTATCAGGACATAGCGTTGGCTACCC
GTGATATTGCTGAAGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGGTTCGAAATGACCGA
CCAAGCGACGCCCAACCTGCCATCACGAGATTTCGATTCCACCGCCGCCTTCTATGAAAGGTTGGGCTTCGGA
ATCGTTTTCCGGGACGCCGGCTGGATGATCCTCCAGCGCGGGGATCTCATGCTGGAGTTCTTCGCCCACGGGA
TCTCTGCGGAACAGGCGGTCGAAGGTGCCGATATTATTACGACAGCAACGGCCGACAAGCACAACGCCACGA
TCCTGAGCGACAATATGATCGGACCCGGCGTCCACATCAACGGCGTCGGCGGCGACTGCCCAGGCAAGACCG
AGATGCACCGCGATATATTGCTGCGTTCGGATATTTTCGTGGAGTTCCCGCCACAGACCCGGATGATCCCCGA
CCGTTCAAACATTTGGCAATAAAGTTTCTAAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGA
TTAGAGTCCCGCAATTATACATTTAATACGCGATAGAAAACAAAATATAGCGCGCAAACTAGGATAAATTATC
GCGCGCGGTGTCATCTATGTTACTAGATCGGGCCTCCTGATATCAATGCTGCAGCGGCGGCTCTGGTGGTGGT
TCTGGTGGCGGCTCTGAGGGTGGTGGCTCTGAGGGTGGCGGTTCTGAGGGTGGCGGCTCTGAGGGAGGCG
GTTCCGGTGGTGGCTCTGGTTCCGGTGATTTTGATTATGAAAAGATGGCAAACGCTAATAAGGGGGCTATGA
CCGAAAATGCCGATGAAAACGCGCTACAGTCTGACGCTAAAGGCAAACTTGATTCTGTCGCTACTGATTACGG
TGCTGCTATGATGGTTTCATTGGTGACGTTTCCGGCCTTGCTAATGGTAATGGTGCTACTGGTGATTTTGCTGG
CTCTAATTCCCAAATGGCTCAAGTCGGTGACGGTGATAATTCACCTTTAATGAATATTTCCGTCAATATTTACCT
TCCCTCCCTCAATCGGTTGAATGTCGCCCTTTTGTCTTTGGCCCAATACGCAAACCGCCTCTCCCCGCGCGTTGG
CCGATTCATTATGCACTGGCACGACAGGTTTCCCGACTGGAAAGCGGGCAGTGAGCGCAACGCAATTATGTG
AGTTAGCTCACTCATTAGGCACCCCAGGCTTTACACTTTATGCTTCCGGCTCGTATGTTGTGTGGAATTGTGAG
CGGATAACAATTTCACACAGGAAACAGCTATGACCATGATTACGCCAAGCTGGCGCCA

FIG. 62

SEQ ID No. 56
AGGGAATATTAAGCTTatggagataagtcgcagcaat

FIG. 63

SEQ ID No. 57
GTTACTAGTGGATCCttaagctcccgtaggatcaat

FIG. 64

SEQ ID No. 58
ACGGATTAGAAGCCGCCGAGCGGGTGACAGCCCTCCGAAGGAAGACTCTCCTCCGTGCGTCCTCGTCTTCACC
GGTCGCGTTCCTGAAACGCAGATGTGCCTCGCGCCGCACTGCTCCGAACAATAAAGATTCTACAATACTAGCT
TTTATGGTTATGAAGAGGAAAAATTGGCAGTAACCTGGCCCCACAAACCTTCAAATGAACGAATCAAATTAAC
AACCATAGGATGATAATGCGATTAGTTTTTTAGCCTTATTTCTGGGGTAATTAATCAGCGAAGCGATGATTTTT
GATCTATTAACAGATATATAAATGCAAAAACTGCATAACCACTTTAACTAATACTTTCAACATTTTCGGTTTGTA
TTACTTCTTATTCAAATGTAATAAAAGTATCAACAAAAAATTGTTAATATACCTCTATACTTTAACGTCAAGGAG
AAAAAACCCCGGATCGGACTACTAGCAGCTGTAATACGACTCACTATAGGGAATATTAAGCTTGGTACCGAGC
TCGGATCCACTAGTAACGGCCGCCAGTGTGCTGGAATTCTGCAGATATCCAGCACAGTGGCGGCCGCTCGAA
AACCCGCTGATCCTAGAGGGCCGCATCATGTAATTAGTTATGTCACGCTTACATTCACGCCCTCCCCCCACATC
CGCTCTAACCGAAAAGGAAGGAGTTAGACAACCTGAAGTCTAGGTCCCTATTTATTTTTTTATAGTTATGTTAG

FIG. 64 (Continued)

TATTAAGAACGTTATTTATATTTCAAATTTTTCTTTTTTTTCTGTACAGACGCGTGTACGCATGTAACATTATACT
GAAAACCTTGCTTGAGAAGGTTTTGGGACGCTCGAAGGCTTTAATTTGCAAGCTGCGGCCCTGCATTAATGAA
TCGGCCAACGCGCGGGGAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTTATCCACAGAATCAGG
GGATAACGCAGGAAAGAACATGTGAGCAAAAGGCCAGCAAAAGCCCAGGAACCGTAAAAAGGCCGCGTTGC
TGGCGTTTTTCCATAGGCTCCGCCCCCCTGACGAGCATCACAAAAATCGACGCTCAAGTCAGAGGTGGCGAAA
CCCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACGCTGTAGGTAT
CTCAGTTCGGTGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTTCGGAAAAAGAGTTGGTAGCTCTT
GATCCGGCAAACAAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATACGGGAGCGCTTACCATC
TGGCCCCAGTGCTGCAATGATACCGCGAGACCCACGCTCACCGGCTCCAGATTTATCAGCAATAAACCAGCCA
GCCGGAAGGGCCGAGCGCAGAAGTGGTCCTGCAACTTTATCCGCCTCCATCCAGTCTATTAATTGTTGCCGGG
AAGCTAGAGTAAGTAGTTCGCCAGTTAATAGTTTGCGCAACGTTGTTGCCATTGCTACAGGCATCGTGGTGTC
ACGCTCGTCGTTTGGTATGGCTTCATTCAGCTCCGGTTCCCAACGATCAAGGCGAGTTACATGATCCCCCATGT
TGTGCAAAAAAGCGGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTCTGTGACTGGTGAGT
ACTCAACCAAGTCATTCTGAGAATAGTGTATGCGGCGACCGAGTTGCTCTTGCCCGGCGTCAACACGGGATAA
TACCGCGCCACATAGCAGAACTTTAAAAGTGCTCATCATTGGAAAACGTTCTTCGGGGCGAAAACTCTCAAGG
ATCTTACCGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCATGAGCGGATA
CATATTTGAATGTATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCCTTTCGTCTTCAAGA
AATTCGGTCGAAAAAAGAAAAGGAGAGGGCCAAGAGGGAGGGCATTGGTGACTATTGAGCACGTGAGTATA
CGTGATTAAGCACACAAAGGCAGCTTGGAGTATGTCTGTTATTAATTTCACAGGTAGTTCTGGTCCATTGGTG
AAAGTTTGCGGCTTGCAGAGCACAGAGGCCGCAGAATGTGCTCTAGATTCCGATGCTGACTTGCTGGGTATTA
TATGTGTGCCCAATAGAAAGAGAACAATTGACCCGGTTATTGCAAGGAAAATTTCAAGTCTTGTAAAAGCATA
TAAAAATAGTTCAGGCACTCCGAAATACTTGGTTGGCGTGTTTCGTAATCAACCTAAGGAGGATGTTTTGGCT
CTGGTCAATGATTACGGCATTGATATCGTCCAACTGCACGGAGATGAGTCGTGGCAAGAATACCAAGAGTTCC
TCGGTTTGCCAGTTATTAAAAGACTCGTATTTCCAAAAGACTGCAACATACTACTCAGTGCAGCTTCACAGAAA
CCTCATTCGTTTATTCCCTTGTTTGATTCAGAAGCAGGTGGGACAGGTGAACTTTTGGATTGGAACTCGATTTC
TGACTGGGTTGGAAGGCAAGAGAGCCCCGAGAGCTTACATTTTATGTTAGCTGGTGGACTGACGCCAGAAAA
TGTTGGTGATGCGCTTAGATTAAATGGCGTTATTGGTGTTGATGTAAGCGGAGGTGTGGAGACAAATGGTGT
AAAAGACTCTAACAAAATAGCAAATTTCGTCAAAAATGCTAAGAAATAGGTTATTACTGAGTAGTATTTATTTA
AGTATTGTTTGTGCACTTGCCCTAGCTTATCGATGATAAGCTGTCAAAGATGAGAATTAATTCCACGGACTATA
GACTATACTAGATACTCCGTCTACTGTACGATACACTTCCGCTCAGGTCCTTGTCCTTTAACGAGGCCTTACCAC
TCTTTTGTTACTCTATTGATCCAGCTCAGCAAAGGCAGTGTGATCTAAGATTCTATCTTCGCGATGTAGTAAAA
CTAGCTAGACCGAGAAAGAGACTAGAAATGCAAAAGGCACTTCTACAATGGCTGCCATCATTATTATCCGATG
TGACGCTGCAGCTTCTCAATGATATTCGAATACGCTTTGAGGAGATACAGCCTAATATCCGACAAACTGTTTTA
CAGATTTACGATCGTACTTGTTACCCATCATTGAATTTTGAACATCCGAACCTGGGAGTTTTCCCTGAAACAGA
TAGTATATTTGAACCTGTATAATAATATATAGTCTAGCGCTTTACGGAAGACAATGTATGTATTTCGGTTCCTG
GAGAAACTATTGCATCTATTGCATAGGTAATCTTGCACGTCGCATCCCCGGTTCATTTTCTGCGTTTCCATCTTG
CACTTCAATAGCATATCTTTGTTAACGAAGCATCTGTGCTTCATTTTGTAGAACAAAAATGCAACGCGAGAGCG
CTAATTTTTCAAACAAAGAATCTGAGCTGCATTTTTACAGAACAGAAATGCAACGCGAAAGCGCTATTTTACCA

FIG. 64 (Continued)

ACGAAGAATCTGTGCTTCATTTTTGTAAAACAAAAATGCAACGCGACGAGAGCGCTAATTTTTCAAACAAAGA
ATCTGAGCTGCATTTTTACAGAACAGAAATGCAACGCGAGAGCGCTATTTTACCAACAAAGAATCTATACTTCT
TTTTTGTTCTACAAAAATGCATCCCGAGAGCGCTATTTTTCTAACAAAGCATCTTAGATTACTTTTTTTCTCCTTT
GTGCGCTCTATAATGCAGTCTCTTGATAACTTTTTGCACTGTAGGTCCGTTAAGGTTAGAAGAAGGCTACTTTG
GTGTCTATTTTCTCTTCCATAAAAAAAGCCTGACTCCACTTCCCGCGTTTACTGATTACTAGCGAAGCTGCGGG
TGCATTTTTTCAAGATAAAGGCATCCCCGATTATATTCTATACCGATGTGGATTGCGCATACTTTGTGAACAGA
AAGTGATAGCGTTGATGATTCTTCATTGGTCAGAAAATTATGAACGGTTTCTTCTATTTTGTCTCTATATACTAC
GTATAGGAAATGTTTACATTTTCGTATTGTTTTCGATTCACTCTATGAATAGTTCTTACTACAATTTTTTTGTCTA
AAGAGTAATACTAGAGATAAACATAAAAAATGTAGAGGTCGAGTTTAGATGCAAGTTCAAGGAGCGAAAGGT
GGATGGGTAGGTTATATAGGGATATAGCACAGAGATATATAGCAAAGAGATACTTTTGAGCAATGTTTGTGG
AAGCGGTATTCGCAATGGGAAGCTCCACCCCGGTTGATAATCAGAAAAGCCCCAAAAACAGGAAGATTGTAT
AAGCAAATATTTAAATTGTAAACGTTAATATTTTGTTAAAATTCGCGTTAAATTTTTGTTAAATCAGCTCATTTTT
TAACGAATAGCCCGAAATCGGCAAAATCCCTTATAAATCAAAAGAATAGACCGAGATAGGGTTGAGTGTTGTT
CCAGTTTCCAACAAGAGTCCACTATTAAAGAACGTGGACTCCAACGTCAAAGGGCGAAAAAGGGTCTATCAG
GGCGATGGCCCACTACGTGAACCATCACCCTAATCAAGTTTTTTGGGGTCGAGGTGCCGTAAAGCAGTAAATC
GGAAGGGTAAACGGATGCCCCCATTTAGAGCTTGACGGGGAAAGCCGGCGAACGTGGCGAGAAAGGAAGG
GAAGAAAGCGAAAGGAGCGGGGGCTAGGGCGGTGGGAAGTGTAGGGGTCACGCTGGGCGTAACCACCACA
CCCGCCGCGCTTAATGGGGCGCTACAGGGCGCGTGGGGATGATCCACTAGT

FIG. 65

SEQ ID No. 59

AGGGAATATTAAGCTTatggaaatgaagcagcttgca

FIG. 66

SEQ ID No. 60

GTTACTAGTGGATCCttataccatagttttgtgttctg

METHOD FOR REDUCING NORNICOTINE IN TOBACCO

CROSS REFERENCE TO RELATED APPLICATIONS

This is a U.S. National Phase application claiming priority to PCT/GB2019/052165, filed Aug. 1, 2019, the entire contents of which are hereby expressly incorporated by reference in its entirety including, without limitation, the specification, claims, and abstract, as well as any figures, tables, or drawings thereof.

FIELD OF THE INVENTION

The present invention relates to reducing specific nitrosamines or their precursors in tobacco and products derived therefrom (e.g. propagation materials, harvest leaf, processed tobacco and tobacco industry products). In particular, the invention relates to a cation efflux protein and its use in modulating (e.g. reducing) specific nitrosamines or their precursors in tobacco.

BACKGROUND

Tobacco pyridine alkaloids are precursors of tobacco-specific nitrosamines (TSNAs) that form during the post-harvest leaf curing. The four primary TSNAs found in cured tobacco leaves are N'-nitrosonornicotine (NNN), N'nitrosoanatabine (NAT), N'-nitrosoanabasine (NAB) and 4-(methyl nitrosamino)-1-(3-pyridyl)-1-butanone (NNK). TSNAs form when nitrous oxide species (e.g. NO, $NO_2$, $N_2O_3$ and $N_2O_4$) react with tobacco alkaloids (FIG. 1). NAT and NAB are formed via the nitrosation of the secondary alkaloids anatabine and anabasine, respectively. Although early studies claimed that NNN originates from both nicotine and nornicotine, more recent reports have demonstrated that the occurrence of NNN in cured tobacco leaves is correlated with nornicotine content, not nicotine (Bush et al., Rec. Adv. Tob. Sci. 27; 23-46 (2001); Lewis et at, Plant Biotech J. 6: 346-354 (2008)). Nornicotine is the demethylated derivative of nicotine, the major alkaloid in tobacco accounting for 90% of the total alkaloid content (Saitoh et at, 1985 Phytochemistry, 24 pp. 477-480). The precursor/product relationship of NNK formation is less clear. Some studies state that NNK is a nitrosation product of nicotine, but due to the slow reaction rate of nicotine nitrosation, it is likely that an oxidized derivative(s) of nicotine, rather than nicotine itself serves as the direct precursor of NNK (Caldwell et al Ann. N.Y. Acad. Sci. 686, 213-228 (1993)). Identifying the genes responsible of the production and regulation of the TSNA precursors is of high importance.

Although nornicotine typically accounts for only 2-4% of the total pyridine alkaloid content in tobacco plants, the genetic instability that leads to the spontaneous appearance of high nornicotine-containing converter plants is a chronic problem in tobacco production. Maintaining low nornicotine levels may prevent the objectionable flavour and aroma associated with this alkaloid, as well as reducing the formation of N-nitrosonornicotine (NNN) in tobacco industry products, of which nornicotine is the direct precursor.

The gene responsible for the majority of the nicotine to nornicotine conversion is a nicotine demethylase gene CYP82E4, encoding a cytochrome P450 monooxygenase (Siminszky et al., Proc. Natl. Acad. Sci. USA, 102 (2005), pp. 14919-14924; Xu et al., Physiol. Plantarum, 129 (2007), pp. 307-319). The nicotine demethylase gene family in tobacco is extensively characterised, but little is known about other cell processes that can influence nornicotine levels.

There still exists a great need to devise methodologies that can further reduce the levels of TSNAs in tobacco plants and products produced from tobacco plants.

Cation efflux proteins are pumps that remove metal ions such as cadmium (Cd), zinc (Zn), and cobalt (Co) from the cell. These metals are not only essential micronutrients for the plant metabolism, but they also act as secondary messengers influencing several enzymatic reactions and signal transduction cascades. Co, Cd, and Zn increase the activity of N-demethylase, the content of cytochrome P-450 and microsomal heme in mice (Kadiiska et al. E. Arch Toxicol (1985) 56: 167.). It was proposed that these cations exert an enzyme-inducing effect on the hepatic monooxygenases.

Cation efflux proteins typically include an N-terminal cytoplasmic domain often containing metal binding sites, 4-6 transmembrane domains followed by a C-terminal cation efflux domain. It was proposed that the N-terminal cytoplasmic domain exhibits a negative regulation of the protein by interacting with key metal-binding residues in a central cytoplasmic domain, preventing metal transport. When metal concentration in the cell increases to a certain threshold, metal binding to the N-terminal domain induces a conformational change that releases the inhibition on the cytoplasmic binding sites. The cation efflux changes to a high affinity state and metal transport is enabled (Futai et al., Handbook of ATPases: Biochemistry, Cell Biology, Pathophysiology 2004).

SUMMARY OF THE INVENTION

According to one aspect, the present invention provides a method of reducing the content of at least one tobacco specific nitrosamine (TSNA) or a precursor of a TSNA in tobacco comprising expressing a deregulated cation efflux protein in a tobacco plant or plant part thereof or plant cell.

The deregulated cation efflux protein may be a constitutively high affinity cation efflux transporter. The deregulated cation efflux protein may exhibit increased metal ion transport compared to a wild type cation efflux transporter. The deregulated cation efflux protein may lack a functional regulatory domain, preferably the deregulated cation efflux protein lacks at least part of a regulatory domain. The deregulated cation efflux protein may lack a functional cytoplasmic domain, preferably the deregulated cation efflux protein lacks at least part of the cytoplasmic domain. The deregulated cation efflux transporter may be deregulated when compared to a wild-type cation efflux protein comprising the amino acid sequence shown as SEQ ID No. 3, 6, 9, 12, 15, 18, 21, 24, 27 or 30 or a sequence which has at least 70% identity thereto. The deregulated cation efflux transport protein may comprises one or more mutations compared to the amino acid sequence shown as SEQ ID No. 3, 6, 9, 12, 15, 18, 21, 24, 27 or 30 or a sequence which has at least 70% identity thereto. The method may comprise introducing into the genome of said plant or plant cell a mutation within a polynucleotide encoding a cation efflux protein such that the polynucleotide encodes a deregulated cation efflux protein. The mutation which is introduced to the plant genome may produce a deletion, a splice mutant or codon encoding a non-tolerated amino acid substitution in the polynucleotide encoding said protein.

The deregulated cation efflux protein may comprise an amino acid sequence which lacks at least part of the N terminus when compared with an amino acid sequence shown as SEQ ID No. 3, 6, 9, 12, 15, 18, 21, 24, 27 or 30 or a sequence which has at least 70% identity thereto. The method may comprise introducing into the genome of said plant or plant cell an exogenous polynucleotide sequence which encodes a deregulated cation efflux protein.

The deregulated cation efflux protein may be:

a) a truncated cation efflux protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;

b) a truncated cation efflux protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30.

The TSNA is N'-nitrosonornicotine (NNN) and/or the precursor may be nornicotine.

In another aspect, there is provided a method of producing tobacco having a reduced content of a tobacco specific nitrosamine (TSNA) or a precursor of a TSNA, comprising:

a. crossing a donor tobacco plant which produces a reduced content of a tobacco specific nitrosamine (TSNA) or a precursor of a TSNA and comprises a deregulated cation efflux protein with a recipient tobacco plant that does not produce reduced content of a tobacco specific nitrosamine (TSNA) or a precursor of a TSNA and possesses commercially desirable traits;
b. isolating genetic material from a progeny of said donor plant crossed with said recipient plant; and
c. performing molecular marker-assisted selection with a molecular marker comprising:
    i. identifying an introgressed region comprising a mutation in a polynucleotide sequence encoding a protein defined in a.

The deregulated cation efflux protein may comprise the amino acid sequence shown as SEQ ID No. 33, or a sequence which has at least 70%, at least 75%, at least 80%, at least 85%, at least 90%, at least 95%, at least 97%, or at least 99% sequence identity thereto. The deregulated cation efflux protein may be encoded by a polynucleotide comprising the sequence shown as SEQ ID No. 34, or a sequence which has at least 70% sequence identity thereto, preferably at least 75%, at least 80%, at least 85%, at least 90%, at least 95%, at least 97%, or at least 99% sequence identity thereto In another aspect, there is provided an isolated polynucleotide comprising a nucleotide sequence selected from the group consisting of:

a. A nucleotide sequence comprising SEQ ID No. 34;
b. A nucleotide sequence having at least 70% sequence identity to the entirety of the sequence set forth in SEQ ID No. 34, wherein said nucleotide sequence encodes a polypeptide involved in cation efflux in a plant;
c. A nucleotide sequence encoding a polypeptide comprising the amino acid sequence shown herein as SEQ ID No. 33, or a fragment thereof comprising at least 200, or at least 250, or at least 300, or at least 350, or at least 400 contiguous residues of SEQ ID No. 33;
d. A nucleotide sequence encoding a truncated polypeptide which lacks at least amino acids corresponding to 2-25, or 2-50, or 2-75, or 2-100, or 2-114, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;
e. A nucleotide sequence encoding a truncated polypeptide which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;
f. A nucleotide sequence encoding a polypeptide comprising an amino acid sequence which corresponds to amino acids 125-324 of SEQ ID No. 3, 6, 9, 12, 15, 18, 21, 24, 27 or 30 and/or comprising an amino acid sequence which corresponds to amino acids 323-413 of SEQ ID No. 3, 6, 9, 12, 15, 18, 21, 24, 27 or 30 wherein said nucleotide sequence encodes a polypeptide involved in cation efflux in a plant;
g. A nucleotide sequence according to any of preceding items (a) to (f) which further comprises a mutation in said nucleotide sequence, e.g. where said mutation produces a deletion, a splice mutant or codon encoding a non-tolerated amino acid substitution in the polynucleotide encoding said protein; or
h. A nucleotide sequence that is complementary to the sequence according any of preceding items (a) to (g).

In a further aspect, there is provided an isolated polypeptide comprising an amino acid sequence selected from the group consisting of:

a. An amino acid sequence comprising SEQ ID No. 33;
b. An amino acid sequence that is at least 70% identical to an amino acid sequence set forth in SEQ ID No. 33;
c. An amino acid sequence comprising amino acids which correspond to amino acids 125-324 of SEQ ID No. 3, 6, 9, 12, 15, 18, 21, 24, 27 or 30 and/or comprising amino acids which correspond to amino acids 323-413 of SEQ ID No. 3, 6, 9, 12, 15, 18, 21, 24, 27 or 30 wherein said polypeptide is involved in cation efflux in a plant;
d. An amino acid sequence which is a fragment of SEQ ID No. 3, 6, 9, 12, 15, 18, 21, 24, 27 or 30 comprising at least 200, or at least 250, or at least 300, or at least 350, or at least 400 contiguous residues of SEQ ID No. 3, 6, 9, 12, 15, 18, 21, 24, 27 or 30;
e. An amino acid which is a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

f. An amino acid which is a truncated amino acid sequence which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30; or g. An amino acid sequence having at least 70% sequence identity to the entirety of the sequence set forth in SEQ ID No. 33.

In a further aspect, there is provided a construct or vector comprising a polynucleotide according to the present invention or a polynucleotide encoding a polypeptide according to the present invention.

In another aspect, there is provided a tobacco plant or part thereof:

a. which has been modified to achieve a reduction in a TSNA or a precursor of a TSNA compared with an unmodified plant, wherein the modified plant or part thereof comprises a deregulated cation efflux protein;

b. which has a mutation within a gene of the plant encoding a cation efflux protein which mutation deregulates said cation efflux protein, wherein the gene prior to mutation comprises the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 70% sequence identity thereto;

c. comprising an exogenous gene which encodes a deregulated cation efflux protein wherein said protein comprises a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

d. comprising a deregulated cation efflux protein which comprises the amino acid sequence set forth in SEQ ID No. 33 or a sequence with at least 70% identity thereto, or a polynucleotide sequence set forth in SEQ ID No. 34 or a sequence with at least 70% identity thereto; or e. comprising a construct or vector according to the present invention.

In another aspect, there is provided a cell:

a. comprising a deregulated cation efflux protein;

b. which has a mutation within a gene encoding a cation efflux protein which mutation deregulates said cation efflux protein, wherein the gene prior to mutation comprises the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 70% sequence identity thereto;

c. obtained or obtainable by the method according to the present invention;

d. comprising an exogenous gene which encodes a deregulated cation efflux protein wherein said protein comprises a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

e. comprising a deregulated cation efflux protein which comprises the amino acid sequence set forth in SEQ ID No. 33 or a sequence with at least 70% identity thereto, or a polynucleotide sequence set forth in SEQ ID No. 34 or a sequence with at least 70% identity thereto; or f. comprising a construct or vector according to the present invention.

The cell may be a plant cell (e.g. tobacco plant cell) or a yeast cell.

In a further aspect, there is provided a cell culture comprising a cell or population of cells according to the present invention.

In another embodiment there is provided a plant propagation material (e.g. a plant seed) obtainable from a plant according to the present invention.

The plant for use in the present invention may be from the species *Nicotiana tabacum* or *Nicotiana rustica.*

In another aspect, there is provided the use of a cell according to the present invention, or of a tobacco plant or tobacco plant part thereof according to the present invention, or cell culture according to the present invention, or a deregulated cation efflux protein as defined herein, for the production of a tobacco industry product.

In yet another aspect, there is provided the use of a tobacco plant according to the present invention or a plant propagation material according to the present invention to breed a tobacco plant.

In a further aspect, there is provided the use of a tobacco plant according to the present invention or a plant propagation material according to the present invention to grow a crop.

In another aspect, there is provided the use of a tobacco plant according to the present invention or a plant propagation material according to the present invention to produce a processed (preferably cured) tobacco leaf.

In another aspect, there is provided a harvested leaf of a tobacco plant according to the present invention or obtainable from a tobacco plant propagated from a propagation material according to the present invention or obtainable from a tobacco plant obtainable by a method according to the present invention or obtainable by a use according to the present invention. In one aspect, there is provided a harvested leaf of a tobacco plant according to the present invention wherein the harvested leaf is a cut harvested leaf.

In a further aspect, there is provided a processed tobacco leaf (preferably a non-viable processed tobacco leaf):

a. comprising a plant cell according to the present invention;
b. obtainable from processing a tobacco plant according to the present invention;
c. obtainable from a tobacco plant propagated from a plant propagation material according to the present invention; or
d. obtainable by processing a harvested leaf according to the present invention;

The processed tobacco leaf may be processed by curing, fermentation, pasteurising or combinations thereof. The processed tobacco leaf may be a cut processed tobacco leaf. In yet another aspect, the present invention provides cured tobacco material made from a plant or a part thereof according to the present invention or is obtained (or obtainable) from the plant propagation material according the present invention or obtained (or obtainable) by the method according to the present invention.

In one aspect there is provided a tobacco blend comprising cured tobacco material according to the present invention.

In another aspect there is provided a tobacco industry product:

a. prepared from a tobacco plant according to the present invention or a part thereof;
b. prepared from a tobacco plant or a part thereof (preferably the leaves harvested from the plant) obtained or obtainable by the method according to the present invention;
c. prepared from the plant (preferably the leaves) propagated from a plant propagation material according to the present invention;
d. prepared from a harvested leaf according to the present invention;
e. prepared from a processed leaf according to the present invention;
f. prepared from a cell according to the present invention;
g. or prepared from a cell culture according to the present invention;
h. prepared from a cured tobacco material according to the present invention; or
i. prepared from a tobacco blend according to the present invention.

The tobacco industry product may be a combustible smoking article or a smokeless tobacco industry product or a non-combustible aerosol provision system, such as a tobacco heating device (e.g. an aerosol-generating device).

In another aspect, there is provided a combustible smoking article, non-combustible aerosol provisioning system, smokeless tobacco industry product or tobacco heating device comprising a plant or a portion thereof from the species *Nicotiana tabacum* or *Nicotiana rustica* according to the present invention, or obtainable (e.g. obtained) from a plant propagation product according to the present invention, or obtainable (e.g. obtained) from a method according to the present invention.

In another aspect there is provided the use of a nucleotide sequence encoding a deregulated cation efflux protein comprising the amino acid sequence shown as SEQ ID No. 33, or sequence which has at least 70% identity thereto, or a nucleotide sequence which encodes a deregulated cation efflux protein wherein said protein comprises a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30 to select a plant having modified content of a TSNA or a precursor of a TSNA.

In yet another aspect there is provided a mutant of a plant carrying a heritable mutation in a nucleotide sequence of at least one gene encoding a deregulated cation efflux protein comprising the amino acid sequence shown as SEQ ID No. 33, or sequence which has at least 70% identity thereto, or a nucleotide sequence which encodes a deregulated cation efflux protein wherein said protein comprises a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30; wherein said heritable mutation decreases the content of at least one TSNA or a precursor of a TSNA relative to a comparable plant which does not carry said heritable mutation.

In a further aspect, there is provided progeny or seed of a mutant plant which carries the heritable mutation according to the present invention.

In another aspect, there is provided a harvested leaf, a processed leaf or cured tobacco material produced from a plant comprising a mutation in a nucleotide sequence encoding a deregulated cation efflux protein comprising the amino acid sequence shown as SEQ ID No. 33, or sequence which has at least 70% identity thereto, or a nucleotide sequence which encodes a deregulated cation efflux protein wherein said protein comprises a truncated amino acid sequence which lacks at least amino acids corresponding to 2-25, or 2-50, or 2-75, or 2-100, or 2-114, or 2-117, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30; wherein said harvested leaf, processed leaf or cured tobacco has decreased content of at least one TSNA or a precursor of a TSNA relative to a comparable plant which does not carry said modification.

In another aspect, there is provided a method, a tobacco leaf, a tobacco plant, a tobacco plant propagation material, a harvested leaf, a processed tobacco, a tobacco industry product, a cell, a cell culture, a use or a combination thereof substantially as described herein with reference to the description and drawings.

BRIEF DESCRIPTION OF THE DRAWINGS

Embodiments of the invention will now be described, by way of example only, with reference to accompanying drawings, in which:

FIG. 5 shows the genomic sequence—SEQ ID No. 1—encoding a protein according to the present invention.

FIG. 6 shows the cDNA sequence—SEQ ID No. 2—encoding a protein according to the present invention.

FIG. 7 shows the polypeptide sequence SEQ ID No. 3 of a protein in according to the present invention—the polypeptide sequence comprises cation efflux transmembrane domain (amino acids 125-324) and a cation efflux cytoplasmic domain (amino acids 323-413).

FIG. 8 shows the genomic sequence—SEQ ID No. 4—encoding a homologous protein from *Nicotiana tabacum.*

FIG. 9 shows the cDNA sequence—SEQ ID No. 5—encoding a homologous protein from *Nicotiana tabacum.*

FIG. 10 shows the polypeptide sequence—SEQ ID No. 6—encoding a homologous protein from *Nicotiana tabacum.*

FIG. 11 shows the genomic sequence—SEQ ID No. 7—encoding a homologous protein from *Nicotiana tabacum.*

FIG. 12 shows the cDNA sequence—SEQ ID No. 8—encoding a homologous protein from *Nicotiana tabacum.*

FIG. 13 shows the polypeptide sequence—SEQ ID No. 9—encoding a homologous protein from *Nicotiana tabacum.*

FIG. 14 shows the genomic sequence—SEQ ID No. 10—encoding a homologous protein from *Nicotiana tabacum.*

FIG. 15 shows the cDNA sequence—SEQ ID No. 11—encoding a homologous protein from *Nicotiana tabacum.*

FIG. 16 shows the polypeptide sequence—SEQ ID No. 12—encoding a homologous protein from *Nicotiana tabacum.*

FIG. 17 shows the genomic sequence—SEQ ID No. 13—encoding a homologous protein from *Nicotiana tabacum.*

FIG. 18 shows the cDNA sequence—SEQ ID No. 14—encoding a homologous protein from *Nicotiana tabacum.*

FIG. 19 shows the polypeptide sequence—SEQ ID No. 15—encoding a homologous protein from *Nicotiana tabacum.*

FIG. 20 shows the genomic sequence—SEQ ID No. 16—encoding a homologous protein from *Nicotiana tabacum.*

FIG. 21 shows the cDNA sequence—SEQ ID No. 17—encoding a homologous protein from *Nicotiana tabacum.*

FIG. 22 shows the polypeptide sequence—SEQ ID No. 18—encoding a homologous protein from *Nicotiana tabacum.*

FIG. 23 shows the genomic sequence—SEQ ID No. 19—encoding a homologous protein from *Nicotiana tabacum.*

FIG. 24 shows the cDNA sequence—SEQ ID No. 20—encoding a homologous protein from *Nicotiana tabacum.*

FIG. 25 shows the polypeptide sequence—SEQ ID No. 21—encoding a homologous protein from *Nicotiana tabacum.*

FIG. 26 shows the genomic sequence—SEQ ID No. 22—encoding a homologous protein from *Nicotiana tabacum.*

FIG. 27 shows the cDNA sequence—SEQ ID No. 23—encoding a homologous protein from *Nicotiana tabacum.*

FIG. 28 shows the polypeptide sequence—SEQ ID No. 24—encoding a homologous protein from *Nicotiana tabacum.*

FIG. 29 shows the genomic sequence—SEQ ID No. 25—encoding a homologous protein from *Nicotiana tabacum.*

FIG. 30 shows the cDNA sequence—SEQ ID No. 26—encoding a homologous protein from *Nicotiana tabacum.*

FIG. 31 shows the polypeptide sequence—SEQ ID No. 27—encoding a homologous protein from *Nicotiana tabacum.*

FIG. 32 shows the genomic sequence—SEQ ID No. 28—encoding a homologous protein from *Nicotiana tabacum.*

FIG. 33 shows the cDNA sequence—SEQ ID No. 29—encoding a homologous protein from *Nicotiana tabacum.*

FIG. 34 shows the polypeptide sequence—SEQ ID No. 30—encoding a homologous protein from *Nicotiana tabacum.*

FIG. 35 shows an alignment SEQ ID No. 3 and homologous protein sequences from *Nicotiana tabacum.*

FIG. 38 shows a polypeptide sequence of a mutated cation efflux protein based on SEQ ID No. 3, wherein the last 117 amino acids of the C-terminal domain have been deleted (SEQ ID No. 31).

FIG. 39 shows the cDNA sequence of a mutated cation efflux protein based on SEQ ID No. 3, wherein the last 117 amino acids of the C-terminal domain have been deleted (SEQ ID No. 32).

FIG. 40 shows a polypeptide sequence of a mutated cation efflux protein based on SEQ ID No. 3, wherein the first 117 amino acids (i.e. from the N-terminal domain) have been deleted (SEQ ID No. 33).

FIG. 41 shows the cDNA sequence of a mutated cation efflux protein based on SEQ ID No. 3, wherein the first 117 amino acids (i.e. from the N-terminal domain) have been deleted (SEQ ID No. 34).

FIG. 42 shows the sequence of primer M13.fw (SEQ ID No. 36).

FIG. 43 shows the sequence of primer M13.rv (SEQ ID No. 37).

FIG. 44 shows the sequence of the Gateway Destination Binary (GDB) expression vector (SEQ ID No. 38).

FIG. 45 shows the sequence of cation efflux antisense (AS) (SEQ ID No. 39).

FIG. 46 shows the sequence of primer AS.fw (SEQ ID No. 40).

FIG. 47 shows the sequence of primer AS.rv (SEQ ID No. 41)

FIG. 48 shows the sequence of primer attB1 (SEQ ID No. 42).

FIG. 49 shows the sequence of primer attB2 (SEQ ID No. 43).

FIG. 50 shows the sequence of the luciferase control sequence (SEQ ID No. 44).

FIG. 51 shows the sequence of primer delta 117C fw (SEQ ID No. 45).

FIG. 52 shows the sequence of primer delta 117C ry (SEQ ID No. 46).

FIG. 53 shows the sequence of primer delta 117N fw (SEQ ID No. 47).

FIG. 54 shows the sequence of primer delta 117N ry (SEQ ID No. 48).

FIG. 55 shows the sequence of tobacco rattle virus (TRV) RNA1 (SEQ ID No. 49).

FIG. 56 shows the sequence of TRV RNA2 (SEQ ID No. 50).

FIG. 57 shows the sequence of the virus-induced gene silencing (VIGS) target sequence (SEQ ID No. 51).

FIG. 58 shows the sequence of the VIGS control sequence (SEQ ID No. 52).

FIG. 59 shows the sequence of yeast Fw primer (SEQ ID No. 53) used in Example 5.

FIG. 60 shows the sequence of yeast Rv primer (SEQ ID No. 54) used in Example 5.

FIG. 61 shows the sequence of the modified pTES3 vector pYES3/UT.1 (SEQ ID No. 55) used in Example 5.

FIG. 62 shows the sequence of the Δ117C Fw primer (SEQ ID No. 56) used in Example 5.

FIG. 63 shows the sequence of the Δ117C Rv primer (SEQ ID No. 57) used in Example 5.

FIG. 64 shows the sequence of the pTES3 vector pYES3/UT.2 (SEQ ID No. 58) used in Example 5.

FIG. 65 shows the sequence of the Δ117N Fw primer (SEQ ID No. 59) used in Example 5.

FIG. 66 shows the sequence of the Δ117N Rv primer (SEQ ID No. 60) used in Example 5.

DETAILED DESCRIPTION

Figure 1:
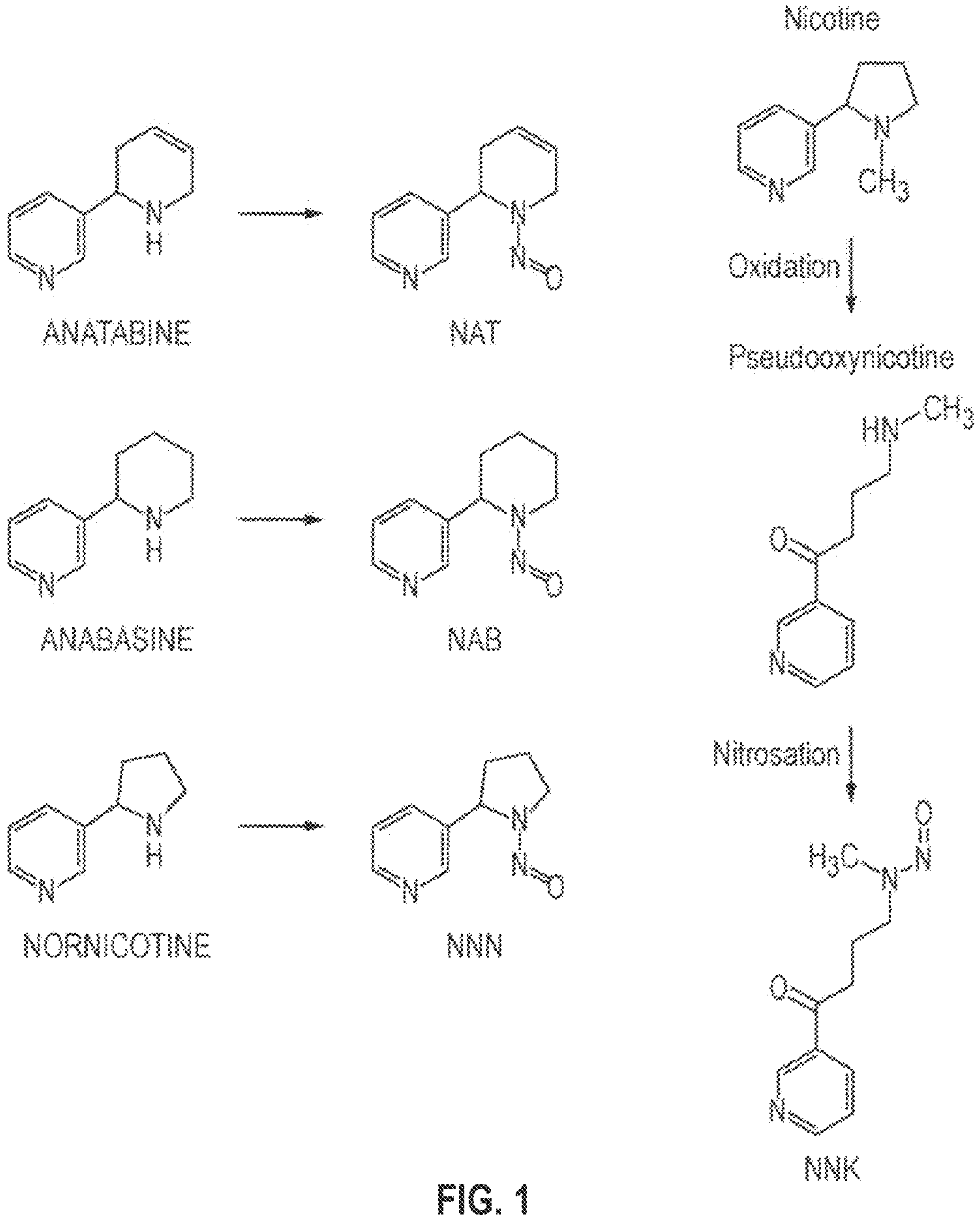
FIG. 1 shows the formation of tobacco-specific nitrosamines (TSNA) from precursors such as nicotine and nornicotine via a nitrosation reaction in tobacco smoke.

A seminal finding of the present invention is that deregulated cation efflux proteins can be used to modulate at least one tobacco-specific nitrosamine (TSNA) or a precursor thereto in tobacco.

Based on this finding a deregulated (e.g. a constitutively high affinity cation efflux transporter) can be used to reduce the content of a TSNA or a precursor or a TSNA in tobacco. In one embodiment the TSNA is N'nitrosonornicotine (NNN) and/or the precursor is nornicotine.

Cation efflux proteins are pumps that remove metal ions such as cadmium, zinc, and cobalt from the cell. These metals are not only essential micronutrients for the plant metabolism, but they also act as secondary messengers initiating components of intracellular signal transduction cascades.

Based on these surprising findings, there is provided a method of reducing or decreasing the content of a tobacco specific nitrosamine (TSNA) or a precursor of a TSNA in tobacco comprising expressing a deregulated cation efflux protein in a tobacco plant or plant part thereof or plant cell. Suitably, the reduction in the TSNA content or precursor of a TSNA is compared to a tobacco plant or part thereof which does not comprise a deregulated cation efflux protein. In other words, the reduction in the TSNA content or precursor of a TSNA is compared to a tobacco plant or part thereof which has not been modified to express a deregulated cation efflux protein.

In one embodiment, the concentration and/or total content of nicotine in a tobacco plant or part thereof, such as a leaf (e.g. cured leaf), is not decreased by the method of reducing the content of a tobacco specific nitrosamine (TSNA) or a precursor of a TSNA in a tobacco plant or plant part thereof according to the present invention.

In one embodiment, the concentration and/or total content of nicotine in a tobacco plant or part thereof, such as a leaf (e.g. cured leaf), is unaltered (e.g. is not significantly altered for example is altered by less than 10%, less than 5%, less than 3%, less than 2%, less than 1%) by the method of reducing the content of a tobacco specific nitrosamine (TSNA) or a precursor of a TSNA in a tobacco plant or plant part thereof according to the present invention. In one embodiment, the concentration and/or total content of nicotine in a tobacco plant or part thereof, such as a leaf (e.g.

cured leaf), may be increased by the method of reducing the content of a tobacco specific nitrosamine (TSNA) or a precursor of a TSNA in a tobacco plant or plant part thereof according to the present invention.

In a preferred embodiment the content of a TSNA or a precursor thereof in tobacco (e.g. in a tobacco leaf) is reduced by expressing a deregulated cation efflux protein in a tobacco plant or plant part thereof or plant cell.

In one embodiment the method of the present invention comprises introducing into the genome of said plant or part thereof or plant cell a mutation within a polynucleotide encoding a cation efflux protein. Suitably said mutation results the mutated polynucleotide encoding a deregulated cation efflux protein.

As used herein, a "mutation" may be a modification selected from a deletion, an insertion, a substitution.

In a preferred embodiment the mutation is a deletion. In another embodiment the mutation may be a substitution with a non-natural amino acid.

In one embodiment the method of the present invention comprises introducing into the genome of said plant a mutation within a polynucleotide encoding a protein comprising the sequence shown as SEQ I D No. 3, 6, 9, 12, 15, 18, 21, 24, 27 or 30 or a sequence which has at least 70% identity thereto.

In one embodiment the method of the present invention comprises introducing into the genome of said plant a mutation within a polynucleotide encoding a protein comprising the sequence shown as SEQ ID No. 3, 6, 9, 12, 15, 18, 21, 24, 27 or 30 or a sequence which has at least 75%, at least 80%, at least 85%, at least 90%, at least 95%, at least 97%, or at least 99% sequence identity hereto.

In one embodiment the method of the present method comprises introducing into the genome of a tobacco plant a mutation within a polynucleotide comprising the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29 or a sequence which has at least 70% sequence identity thereto.

In one embodiment the method of the present method comprises introducing into the genome of a tobacco plant a mutation within a polynucleotide comprising the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 75%, at least 80%, at least 85%, at least 90%, at least 95%, at least 97%, or at least 99% sequence identity thereto.

In one embodiment the protein comprising the sequence shown as SEQ ID No. 3, 6, 9, 12, 15, 18, 21, 24, 27 or 30 or a sequence which has at least 70% identity thereto is encoded by a polynucleotide comprising the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 70% sequence identity thereto.

In one embodiment the protein comprising the sequence shown as SEQ ID No. 3, 6, 9, 12, 15, 18, 21, 24, 27 or 30 or a sequence which has at least 70% identity thereto is encoded by a polynucleotide comprising the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 75%, at least 80%, at least 85%, at least 90%, at least 95%, at least 97%, or at least 99% sequence identity thereto.

The mutation may be any mutation which results in the expression of a deregulated cation efflux protein.

In one embodiment the mutation may produce a deletion, a splice mutant or codon encoding a non-tolerated amino acid substitution in the polynucleotide encoding said protein. Suitably, the mutant may comprise a deletion, such as deletion of at least part of a domain or deletion of an entire domain. Suitably, the mutant may comprise a deletion of at least part of the cytoplasmic domain.

In one embodiment, the mutation (e.g. deletion) may be in the N-terminal cytoplasmic domain of the protein. Suitably, the mutation may comprise deletion of at least part of the N terminus when compared with an amino acid sequence shown as SEQ ID No. 3, 6, 9, 12, 15, 18, 21, 24, 27 or 30 or a sequence which has at least 70% identity thereto.

Suitably, the mutation may comprise deletion of at least part of the N terminus when compared with an amino acid sequence shown as SEQ ID No. 3, or a sequence which has at least 70% identity thereto.

Suitably, the mutation may be in amino acids corresponding to at least amino acids 2-25, or 2-50, or 2-75, or 2-100, 2-114, 2-117, 2-120, 2-125, 2-128, or 2-130 of SEQ ID No. 3. Preferably, the mutation is in amino acids corresponding to amino acids 2-117 of SEQ ID No. 3. Preferably the mutation is a deletion.

In one embodiment, the method of the present invention comprises expressing in a tobacco plant or plant part thereof or plant cell:

a) a truncated protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, at least 98% or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;

b) a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30.

Suitably, the method may comprise expressing in a tobacco plant or plant part thereof or plant cell a truncated protein which lacks at least amino acids corresponding to amino acids 2-117 from the N-terminal side of SEQ ID No.

3, 6, 9, 12, 15, 18, 21, 24, 27 or 30, or a protein which has at least 70% (preferably at least 75%, at least 80%, at least 85%, at least 90%, at least 95%, at least 97%, at least 98% or at least 99%) sequence identity to a truncated protein which lacks at least amino acids corresponding to amino acids 2-117 of SEQ ID No. 3, 6, 9, 12, 15, 18, 21, 24, 27 or 30.

Suitably, the method may comprise expressing in a tobacco plant or plant part thereof or plant cell a truncated protein which lacks at least amino acids corresponding to amino acids 2-117 from the N-terminal side of SEQ ID No. 3, or a protein which has at least 70% (preferably at least 75%, at least 80%, at least 85%, at least 90%, at least 95%, at least 97%, at least 98% or at least 99%) sequence identity to a truncated protein which lacks at least amino acids corresponding to amino acids 2-117 of SEQ ID No. 3.

In one embodiment, a method according to the present invention comprises expressing a protein comprising (or having or consisting of) the amino acid sequence shown as SEQ ID No. 33, or a sequence which has at least 70% or at least 75%, at least 80%, at least 85%, at least 90%, at least 95%, at least 97%, or at least 98%, or at least 99% sequence identity thereto in a tobacco plant or plant part thereof or plant cell.

In another embodiment, a method according to the present invention comprises expressing a protein encoded by a polynucleotide comprising the sequence shown as SEQ ID No. 34, or a sequence which has at least 70% sequence identity, or at least 75%, at least 80%, at least 85%, at least 90%, at least 95%, at least 97%, or at least 99% sequence identity thereto in a tobacco plant or plant part thereof or plant cell.

The tobacco plant or part thereof or plant cell may express said protein using any method known in the art.

Suitably, the method according to the present invention may comprise introducing a nucleotide sequence to a plant or part thereof or plant cell which encodes said protein. This may be achieved for example by introducing a construct or vector which encodes said protein. Suitably, the method may comprise introducing a construct or vector according to the present invention to a plant or part thereof or plant cell.

Alternatively, the method may comprise gene editing the endogenous nucleotide sequence to encode the variant protein.

In one embodiment the TSNA may be one or more of group selected from: N'-nitrosonornicotine (NNN), N'nitrosoanatabine (NAT), N'-nitrosoanabasine (NAB) and 4-(methyl nitrosamino)-1-(3-pyridyl)-1-butanone (NNK).

In a preferred embodiment the TSNA is N'-nitrosonornicotine (NNN).

The TSNA may be measured in a processed tobacco, e.g. cured tobacco or reconstituted tobacco. In one embodiment the TSNA content is measured and/or modified (e.g. reduced) in a cured tobacco plant or part thereof (e.g. in cured tobacco leaf).

The term "tobacco-specific nitrosamine" or "TSNA" as used herein has its usual meaning in the art, namely a nitrosamine which is found only in tobacco products or other nicotine-containing products. Suitably the at least one tobacco-specific nitrosamine may be 4-(methylnitrosamino)-1-(3-pyridyl)-1-butanone (NNK), N'-nitrosonornicotine (NNN), N'-nitrosoanatabine (NAT) or N-nitrosoanabasine (NAB).

More suitably the at least one tobacco-specific nitrosamine may be NNK or NNN. In one embodiment the tobacco-specific nitrosamine is NNN.

The term "precursor thereto" when used in relation to at least one tobacco-specific nitrosamine refers to one or more chemicals or compounds of a tobacco plant that give rise to the formation of a tobacco-specific nitrosamine or are involved in the nitrosation reaction leading to tobacco-specific nitrosamine production. Suitably the term "precursor thereto" may refer to nitrate, nitrite or nitric oxide.

In one embodiment the precursor of the TSNA is one or more of the group selected from nornicotine, anabasine, anatabine, and an oxidised derivative of nicotine such as pseudooxynicotine (PON).

In one embodiment, the TSNA precursor is the direct precursor to the TSNA.

In one embodiment, a direct precursor of a TSNA is one or more of the group selected from nornicotine, anabasine, anatabine, and an oxidised derivative of nicotine such as pseudooxynicotine (PON).

In a preferred embodiment the precursor of the TSNA is nornicotine.

In one embodiment, the precursor of the TSNA is PON.

In one embodiment, the TSNA precursor is not nicotine.

The precursor of the TSNA (e.g. NNN, NNK, NAB and/or NAT) may be measured in green tobacco leaf, e.g. prior to processing, e.g. prior to curing. In one embodiment the precursor of the TSNA (e.g. NNN, NNK, NAB and/or NAT) is measured and/or modified (e.g. reduced) in a green tobacco leaf, e.g. prior to processing, e.g. prior to curing.

In one embodiment carrying out a method and or use of the invention results in a reduction of at least one TSNA or a precursor thereto in the modified tobacco plant (or part thereof) when compared to a tobacco plant (or part thereof) which has not been modified in accordance with the present invention.

The terms "reducing at least one TSNA or precursor thereto" or "reduction of at least one TSNA or precursor thereto" are used herein to mean that the concentration and/or total content of the at least one TSNA or precursor thereto in the product, method or use of the invention is lower in relation to a comparable product, method or use. For example, a comparable tobacco industry product would be derived from a tobacco plant which had not been modified according to the present invention, but in which all other relevant features were the same (e.g. plant species, growing conditions, method of processing tobacco, etc).

The term "a comparable product" as defined herein may mean a tobacco plant or a part thereof, such as a tobacco leaf, a harvested leaf, a cut harvested leaf, a processed tobacco leaf or tobacco plant propagation material, or a tobacco industry product or combinations thereof obtainable or obtained from a tobacco plant which has not been altered to express a deregulated cation efflux protein.

In one embodiment, a comparable product is obtainable or obtained from a tobacco plant which does not express a truncated protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30.

In another embodiment, a comparable product is obtainable or obtained from a tobacco plant which does not express protein comprising the amino acid sequence shown as SEQ ID No. 33, or a sequence which has at least 70% or at least 75%, at least 80%, at least 85%, at least 90%, at least 95%, at least 97%, or at least 99% sequence identity thereto.

Suitably, the comparable product may be obtainable or obtained from a tobacco plant which does not express a protein encoded by a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

The term "unmodified plant" as defined herein would be a tobacco plant which had not been modified according to the present invention, to express a deregulated cation efflux protein. In another embodiment, an unmodified plant would be a tobacco plant which had not been modified according to the present invention to express a truncated protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30 and in which all other relevant features were the same (e.g. plant species, growing conditions, method of processing tobacco, etc.).

Any method known in the art for determining the concentration and/or levels of at least one TSNA or precursor thereto may be used. In particular a method may comprise the addition of deuterium labelled internal standard, an aqueous extraction and filtration, followed by analysis using reversed phase high performance liquid chromatography with tandem mass spectrometry (LC-MS/MS). Other examples for determining the concentration and/or level of a precursor to a tobacco-specific nitrosamine include a method such as the one detailed in CORESTA recommended method CRM-72: Determination of Tobacco Specific Nitrosamines in Tobacco and Tobacco Products by LC-MS/MS; CRM being developed into ISO/DIS 21766 or Wagner et al. Analytical Chemistry (2005), 77(4), 1001-1006 all of which are incorporated herein by reference.

Suitably the concentration and/or total content of the at least one tobacco-specific nitrosamine or precursor thereto may be reduced by carrying out a method and/or use of the present invention. Suitably the concentration and/or level of the at least one tobacco-specific nitrosamine or precursor thereto may be reduced in a tobacco plant of the invention (e.g. obtainable or obtained by a method and/or use of the invention) when compared to the concentration and/or level of the at least one tobacco-specific nitrosamine(s) or precursor thereto in a tobacco plant which has not been modified in accordance with present invention. The concentration and/or total content of the at least one tobacco-specific nitrosamine(s) or precursor thereto may be reduced in a tobacco leaf, harvested leaf, processed tobacco leaf, tobacco industry product or combinations thereof obtainable or obtained from a tobacco plant (or part of a tobacco plant) of the invention when compared with a tobacco leaf, harvested leaf, processed tobacco leaf, tobacco industry product or combinations thereof obtainable or obtained from a tobacco plant (or part of a tobacco plant) which has not been modified in accordance with the present invention.

Suitably the concentration and/or total content of the at least one tobacco-specific nitrosamine or precursor thereto may be reduced in a processed tobacco leaf.

Suitably the concentration and/or level of the at least one tobacco-specific nitrosamine or precursor thereto may be reduced in a tobacco industry product.

In one embodiment the at least one tobacco-specific nitrosamine or precursor thereto may be reduced by at least about 1%, at least about 3%, at least about 5%, at least about 10%, at least about 20%, at least about 30%, at least about 40%, at least about 50%, at least about 60%, at least about 70%, at least about 80% or at least about 90%. In some embodiments the at least one tobacco-specific nitrosamine or precursor thereto may be reduced by between about 5% and about 95%, by between about 10% and about 90%, by between 20% and about 80%, by between 30% and about 70%, or by between about 40% and 60%.

In relation to processed tobacco leaf (e.g. cured or reconstituted), the at least one tobacco-specific nitrosamine or precursor thereto may be reduced by between about 5000 ng/g and about 50 ng/g, by between about 4000 ng/g and about 100 ng/g, by between about 3000 ng/g and 500 ng/g or by between 2000 ng/g and 1000 ng/g. In some embodiments the at least one tobacco-specific nitrosamine or precursor thereto may be reduced by at least about 5000 ng/g, at least about 4000 ng/g, at least about 3000 ng/g, at least about 2000 ng/g, at least about 1000 ng/g, at least about 500 ng/g, at least about 100 ng/g or at least about 50 ng/g.

Cation Efflux Protein

Cation efflux proteins are pumps that remove metal ions such as cadmium, zinc, and cobalt from the cell. These metals are not only essential micronutrients for the plant metabolism, they also act as secondary messengers initiating components of intracellular signal transduction cascades.

In one embodiment a wild type cation efflux protein comprises an amino acid sequence shown as SEQ ID No. 3, 6, 9, 12, 15, 18, 21, 24, 27 or 30, or a sequence which has at least 90% identity thereto (preferably at least 75%, at least 80%, at least 85%, at least 90%, at least 95%, at least 97%, or at least 99% identity thereto).

Suitably, a wild type cation efflux protein according to the present invention may comprise an amino acid sequence shown as SEQ ID No. 3, or a sequence which has at least 90% identity thereto (preferably at least 95%, at least 97%, or at least 99% identity thereto).

Suitably, a wild type cation efflux protein may comprise an amino acid sequence shown as SEQ ID No. 6, or a sequence which has at least 90% identity thereto (preferably at least 95%, at least 97%, or at least 99% identity thereto).

Suitably, a wild type cation efflux protein may comprise an amino acid sequence shown as SEQ ID No. 9, or a sequence which has at least 90% identity thereto (preferably at least 95%, at least 97%, or at least 99% identity thereto).

Suitably, a wild type cation efflux protein may comprise an amino acid sequence shown as SEQ ID No. 12, or a sequence which has at least 90% identity thereto (preferably at least 95%, at least 97%, or at least 99% identity thereto).

Suitably, a wild type cation efflux protein may comprise an amino acid sequence shown as SEQ ID No. 15, or a sequence which has at least 90% identity thereto (preferably at least 95%, at least 97%, or at least 99% identity thereto).

Suitably, a wild type cation efflux protein may comprise an amino acid sequence shown as SEQ ID No. 18, or a sequence which has at least 90% identity thereto (preferably at least 95%, at least 97%, or at least 99% identity thereto).

Suitably, a wild type cation efflux protein may comprise an amino acid sequence shown as SEQ ID No. 21, or a sequence which has at least 90% identity thereto (preferably at least 95%, at least 97%, or at least 99% identity thereto).

Suitably, a wild type cation efflux protein according to the present invention may comprise an amino acid sequence shown as SEQ ID No. 24, or a sequence which has at least 90% identity thereto (preferably at least 95%, at least 97%, or at least 99% identity thereto).

Suitably, a wild type cation efflux protein according to the present invention may comprise an amino acid sequence shown as SEQ ID No. 27, or a sequence which has at least 90% identity thereto (preferably at least 95%, at least 97%, or at least 99% identity thereto).

Suitably, a wild type cation efflux protein according to the present invention may comprise an amino acid sequence shown as SEQ ID No. 30, or a sequence which has at least 90% identity thereto (preferably at least 95%, at least 97%, or at least 99% identity thereto).

In one embodiment the wild type cation efflux protein comprises an amino acid sequence selected from: SEQ ID No. 3, 6, 9, 12, 15, 18, 21, 24, 27 or 30.

Suitably, the cation efflux protein may be from *Nicotiana tabacum.*

In one embodiment the wild type cation efflux protein is encoded by a polynucleotide sequence wherein the gene (prior to mutation) comprises the sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a sequence which has at least 70% sequence identity thereto.

Suitably, the wild type protein for use according to the present invention may be encoded by a polynucleotide sequence wherein the gene (prior to mutation) comprises the sequence shown as SEQ ID No. 1, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 2, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 4, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 5, or a sequence which has at least 90% sequence identity thereto. Suitably, the protein for use according to the present invention may be encoded by a polynucleotide sequence wherein the gene (prior to mutation) comprises the sequence shown as SEQ ID No. 7, or a sequence which has at least 90% sequence identity thereto.

Suitably, the wild type protein for use according to the present invention may be encoded by a polynucleotide sequence wherein the gene (prior to mutation) comprises the sequence shown as SEQ ID No. 8, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 10, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 11, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 13, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 14, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 16, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 17, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 19, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 20, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 22, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 23, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 25, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 26, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 28, or a sequence which has at least 90% sequence identity thereto. Suitably, the wild type protein for use according to the present invention may be encoded by a polynucleotide sequence wherein the gene (prior to mutation) comprises the sequence shown as SEQ ID No. 29, or a sequence which has at least 90% sequence identity thereto.

In one embodiment the wild type cation efflux protein is encoded by a polynucleotide sequence wherein the gene (prior to mutation) is selected from: SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29.

Suitably, the wild type protein for use according to the present invention may be encoded by a polynucleotide sequence from *Nicotiana tabacum*.

Deregulated Cation Efflux Protein

In one embodiment the protein for use according to the present invention is a deregulated cation efflux protein.

As used herein "cation efflux protein" has its usual meaning in the art and refers to a protein which transports cations, for example transports cations out of a cell.

Cation efflux proteins are usually integral membrane proteins which increase tolerance to divalent metal ions, such as zinc, cadmium and cobalt. Cation efflux proteins may act as efflux pumps to remove these ions from cells.

The cation efflux protein may be capable of transporting zinc, cobalt, cadmium or nickel.

In one embodiment, the cation efflux protein is capable of transporting zinc. In one embodiment, the cation efflux protein is a zinc transporter.

As used herein, "deregulated cation efflux protein" means that a cation efflux protein for use in accordance with the present invention does not respond to or exhibits a reduction in response to the concentration of metal ions in a cell when compared to a wild type cation efflux protein found in a tobacco plant, i.e. a cation efflux protein that is not deregulated.

In other words such a cation efflux protein is of reduced sensitivity to or no longer responsive to changes in metal ion concentration within a cell.

For example, the deregulated cation efflux protein is not capable of undergoing a conformational change upon modulation of metal ion concentration (i.e. from low metal ion concentration to high metal ion concentration) within the cell.

A cation efflux protein which is no longer capable of changing conformation in response to the metal ion concentration within the cell may be referred to herein as a deregulated cation efflux protein.

In one embodiment, the deregulated cation efflux protein for use according to the present invention is a constitutively high affinity cation efflux transporter.

As used herein the term "high affinity cation efflux protein" or "high affinity cation efflux transporter" refers to a protein which is in an open conformation which allows metal ion transport. For example, the protein may be in a constitutively open conformation.

In one embodiment the high affinity cation efflux protein is in a conformation which allows metal binding to the cytoplasmic binding sites between the transmembrane domains. See FIG. 4*a*. In other words, in the high affinity cation efflux protein the cytoplasmic binding sites between the transmembrane domains are not obscured by the cytoplasmic regulatory domain.

In one embodiment, a deregulated cation efflux protein is a protein which transports cations (such as zinc ions) out of a cell at a higher rate than a comparable, wild-type cation efflux protein. Suitably the wild-type cation protein may have an amino acid sequence as set forth in SEQ ID No. 3, 6, 9, 12, 15, 18, 21, 24, 27 or 30.

In one embodiment, the deregulated cation efflux protein exhibits increased metal ion transport compared to a wild type cation efflux transporter. The deregulated cation efflux protein may exhibit at least about 1%, at least about 3%, at least about 5%, at least about 10%, at least about 20%, at least about 30%, at least about 40%, at least about 50%, at least about 60%, at least about 70%, at least about 80% or at least about 90% more metal ion transport compared to a wild type cation efflux transporter. Suitably, metal ion transport may be measured under comparable conditions.

The activity of a cation efflux transporter (such as metal ion transport) may be measured using any method known in the art.

For example metal ion transport may be measured using fluorescent cation sensors, such as fluorescent $Zn^{2+}$ sensors, fluorescence microscopy (described by Carpenter et al., Arch Biochem Biophys. 2016 Dec. 1; 611: 20-29 which is incorporated herein by reference). In one embodiment, a cell which expresses the deregulated cation efflux protein exhibits a lower concentration of intracellular metal ions (such as a lower intracellular concentration of zinc ions) compared to a cell which does not express the deregulated cation efflux protein, for example compared to a cell which only expresses the wild type cation efflux transporter.

Suitably the wild-type cation protein may have an amino acid sequence as set forth in SEQ ID No. 3, 6, 9, 12, 15, 18, 21, 24, 27 or 30.

A cell which expresses a deregulated cation efflux protein may exhibit a reduction in intracellular cation concentration (such as intracellular zinc concentration) of at least about 5%, at least about 10%, at least about 20%, at least about 30%, at least about 40%, at least about 50%, at least about 60%, at least about 70%, at least about 80% or at least about 90% more ion transport compared to a wild type cation efflux transporter.

The concentration of cations (such as zinc) in a cell may be measured by first washing a cell, removing extracellular matrix and lysing the cell then measuring the concentration of cations (such as zinc). A cell which expresses a deregulated cation efflux protein according to the invention may have a lower intracellular concentration of cations (such as zinc) compared to a cell which does not express a deregulated cation efflux protein i.e. a cell which only expresses wild-type cation efflux proteins.

In one embodiment, the deregulated cation efflux protein increases tolerance of a cell to divalent metal ions (such as zinc).

Without wishing to be bound by theory, the deregulated cation efflux protein may reduce the intracellular concentration of cations (such as zinc), thereby increasing tolerance to divalent metal ions. Suitably, the deregulated cation efflux protein may allow a cell to tolerate higher concentrations of divalent metal ions (such as zinc) than a cell which does not express a deregulated cation efflux protein.

The deregulated cation efflux protein may increase tolerance to divalent metal ions (such as zinc) at least about 5%, at least about 10%, at least about 20%, at least about 30%, at least about 40%, at least about 50%, at least about 60%, at least about 70%, at least about 80% or at least about 90% compared to a wild type cation efflux transporter.

Figure 69A:
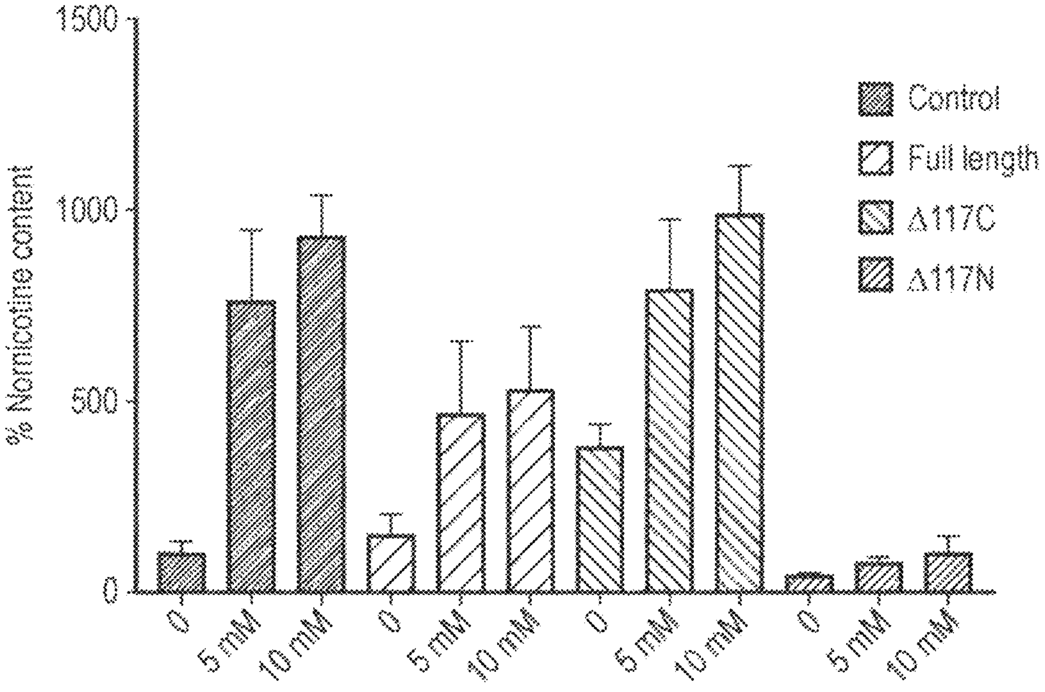
FIG. 69*a* shows the nornicotine content of tobacco plants expressing the full-length zinc transporter, the Δ117C and Δ117N variants upon treatment with the indicated concentrations of zinc.
Figure 69B:
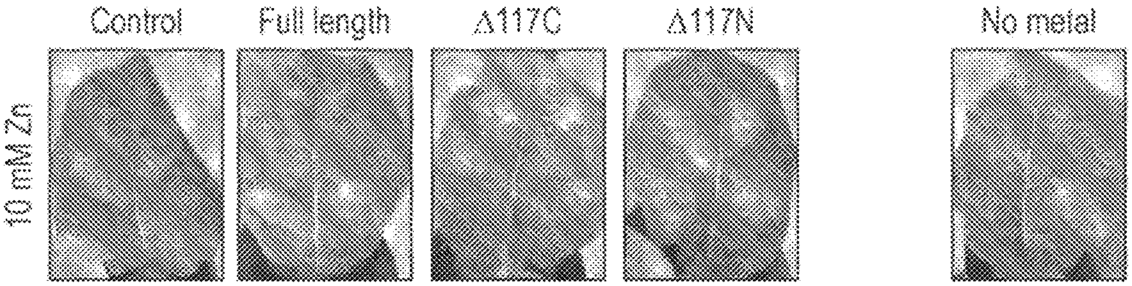
FIG. 69*b* shows the phenotypes of tobacco leaves expressing the indicated constructs upon treatment with 10 mM zinc.

Increased tolerance to metal ions (such as zinc) may be measured using any method in the art. For example, tolerance may be measured by determining leaf quality, such as chlorophyll intensity of leaves treated with metal ions as shown in FIG. 69*b*. Without wishing to be bound by theory, the leaves of plants which express a deregulated cation efflux protein exhibit tolerance to treatment with metal ions because the cation efflux protein reduces the intracellular concentration of said metal ion.

Figure 69C:
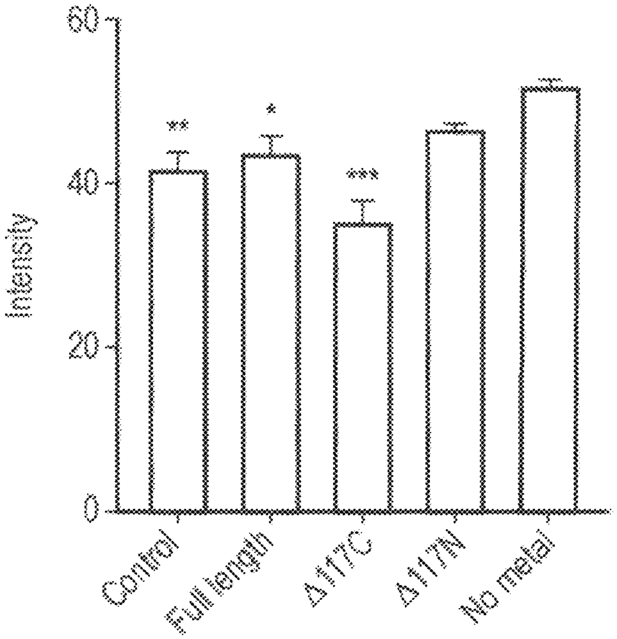
FIG. 69*c* shows the chlorophyll intensity of treated leaf areas in FIG. 69*b*. Values are shown as means±SEM. Asterisks indicate statistical significance of P value ≤0.001 upon comparison to the no metal samples and analysis with one-way ANOVA and Tukey's multiple-comparison post-test.

In one embodiment, upon treatment with a metal ion (such as zinc) a cell expressing the deregulated cation efflux protein exhibits a similar leaf phenotype (such as chlorophyll intensity) to a leaf which has not been treated with a metal ion (such as zinc)—see for example FIG. 69*c*. Suitably, a cell expressing the deregulated cation efflux protein may exhibit a reduction in chlorophyll intensity which is not statistically significant when compared to a leaf which has not been treated with said metal ion, for example using one-way ANOVA and Tukey's multiple-comparison post-test.

A cell expressing the deregulated cation efflux protein may exhibit a decrease in chlorophyll intensity of less than 15%, less than 10%, less than 5% when treated with metal ions compared to a leaf which has not been treated with said metal ions.

In one embodiment, the deregulated cation efflux protein may lack a functional regulatory domain; preferably the deregulated cation efflux protein lacks at least part of a regulatory domain.

The term "regulatory domain" as used herein has its usual meaning in the art namely a conserved part of a protein sequence which controls the activity of the protein. Regulatory domains include activation domains, repression domains and epigenetic effector domains.

In one aspect, the regulatory domain according to the present invention is the cytoplasmic domain.

In one aspect, the regulatory domain is a sensor of metal ion content in the cell.

Figure 4A:
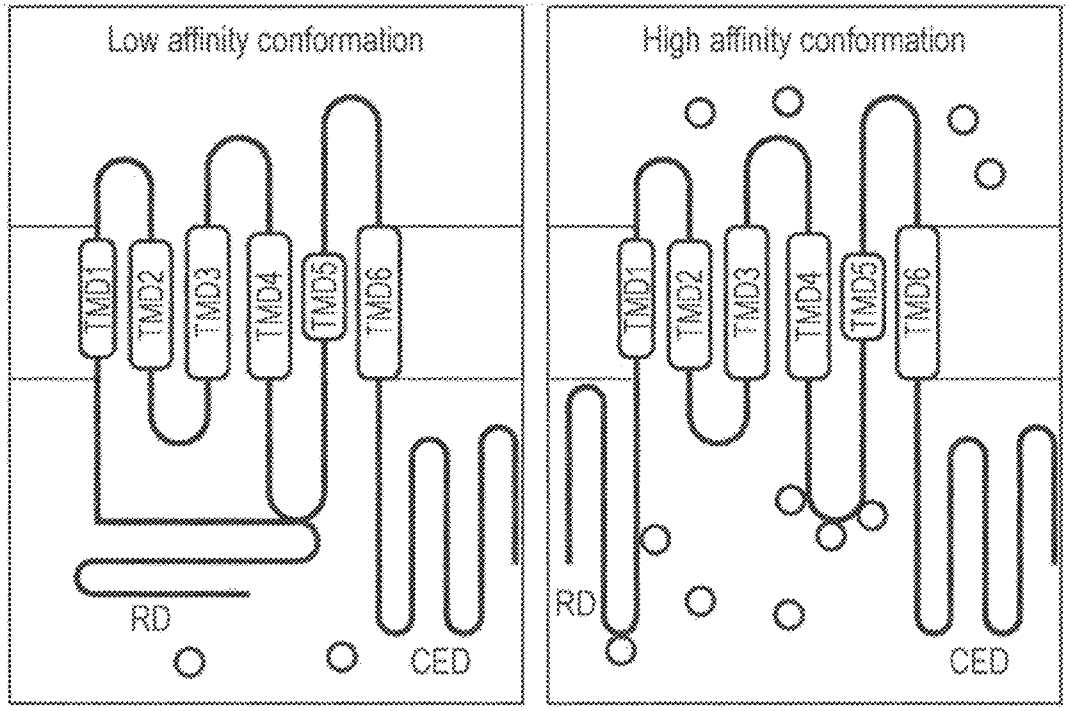
FIG. 4*a* shows a schematic of a proposed mechanism of low affinity and high affinity confirmations of a cation efflux transporter.

When a protein lacks a functional regulatory domain according to the present invention, the activity of said protein is no longer capable of being regulated by that regulatory domain. In one aspect, a cation efflux protein which lacks a functional regulatory domain is not capable of switching between low affinity and high affinity conformations (as shown in FIG. 4*a*).

Suitably, the deregulated cation efflux protein may lack a functional cytoplasmic domain.

In one embodiment the cytoplasmic domain may be rendered non-functional by mutation. In another embodiment, the cytoplasmic domain may be rendered non-functional by deletion. Suitably, the deregulated cation efflux protein may lack at least part of the cytoplasmic domain when compared to a wild type protein. Suitably, the deregulated cation efflux protein may lack at least part of the N terminal when compared to a wild type protein.

The term "cytoplasmic domain" as used herein has its usual meaning in the art, and describes the topology of a protein domain as an intracellular domain which interacts with the interior of the cell.

Topological domains of proteins including cytoplasmic domains may be annotated based on predictions provided by algorithms such as the program TMHMM provided by the Technical University of Denmark (DTU) Department of Bio and Health Informatics; services.healthtech.dtu.dk/services/TMHMM-2.0/.

Alternatively, cytoplasmic domains may be annotated or predicted by amino acid sequence comparison with known protein structures. For example, cytoplasmic domains of cation efflux proteins may be identified by sequence alignment against SEQ ID No. 3, wherein amino acid resides 1-128 of SEQ ID No. 3 indicate a cytoplasmic domain.

In one embodiment, a cytoplasmic domain is a region of a protein which corresponds to amino acid 1 to 128 of the N terminus of SEQ ID No. 3. In one embodiment, a cytoplasmic domain is a region of a protein which corresponds to amino acid 2 to 128 of the N terminus of SEQ ID No. 3.

In one embodiment the first amino acid (amino acid number 1) is not counted as part of the N terminus. The first amino acid (amino acid number 1) is always required for translation of the protein.

In the context of the present invention, the cytoplasmic domain regulates the activity of the cation efflux protein. The cytoplasmic domain contains metal binding sites. When metal concentration in the cell increases to a threshold, metal binding to the N-terminal domain induces a conformational change in the cation efflux protein (see FIG. 4).

In one embodiment, the deregulated cation efflux transporter is deregulated when compared to a wild type cation efflux protein.

In one embodiment a wild type cation efflux protein comprises an amino acid sequence shown as SEQ ID No. 3, 6, 9, 12, 15, 18, 21, 24, 27 or 30 or a sequence which has at least 70% identity thereto (preferably at least 75%, at least 80%, at least 85%, at least 90%, at least 95%, at least 97%, or at least 99% identity thereto).

In one embodiment, a wild type cation efflux protein is encoded by a polynucleotide sequence shown as SEQ ID No. 1, SEQ ID No. 2, SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a nucleic acid sequence which has at least 70% identity thereto (preferably at least 75%, at least 80%, at least 85%, at least 90%, at least 95%, at least 97%, or at least 99% identity thereto).

Suitably, the method according to the present invention may comprise modifying an endogenous wild type sequence to encode a deregulated cation efflux protein. The endogenous sequence may be modified for example by gene editing.

In one embodiment, the deregulated cation efflux protein comprises one or more mutations compared to the amino acid sequence shown as SEQ ID No. 3, 6, 9, 12, 15, 18, 21, 24, 27 or 30 or a sequence which has at least 70% identity thereto.

The mutation may be a deletion, a splice mutant or codon encoding a non-tolerated amino acid substitution. The mutation may be in the cytoplasmic domain. The mutation may be in the N terminus.

In one embodiment the deregulated cation efflux protein comprises an amino acid sequence which lacks at least part of the N terminus when compared with an amino acid sequence shown as SEQ ID No. 3, 6, 9, 12, 15, 18, 21, 24, 27 or 30 or a sequence which has at least 70% identity thereto.

In another embodiment, the deregulated cation efflux protein comprises:

a) a truncated protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30; or b) a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30. IN one embodiment the deregulated cation efflux protein comprises the amino acid sequence shown as SEQ ID No. 33, or a sequence which has at least 70% or at least 75%, at least 80%, at least 85%, at least 90%, at least 95%, at least 97%, or at least 99% sequence identity thereto.

In another embodiment the deregulated cation efflux protein is encoded by a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

In one embodiment, a deregulated cation efflux protein comprises an amino acid sequence shown as SEQ ID No. 3, 6, 9, 12, 15, 18, 21, 24, 27 or 30, or a sequence which has at least 90% identity thereto (preferably at least 75%, at least 80%, at least 85%, at least 90%, at least 95%, at least 97%, or at least 99% identity thereto) wherein upon alignment with the amino acid sequence SEQ ID No. 3, the deregulated cation efflux protein comprises:

a methionine at amino acid position number three;

an aspartic acid residue at amino acid position number seven: and/or a threonine residue at amino acid residue number 68, wherein the amino acid numbering is with reference to SEQ ID No. 3.

In some embodiments, the invention provides a cation efflux protein which is deregulated.

The deregulated cation efflux protein may be modified relative to a wild-type cation efflux protein to promote the formation of or stabilize dimers (such as homodimers) or oligomers. In one embodiment, a deregulated cation efflux protein according to the invention forms more stable dimers (such as homodimers) or other oligomers relative to a wild-type cation efflux protein. Suitably, mutations in the amino acid sequence may promote dimerization (such as homodimerisation) or oligomerisation of the deregulated cation efflux protein.

In some embodiments, the deregulated cation efflux protein may comprise one or more modified transmembrane domains (for example, relative to a wild-type cation efflux protein). Suitably, the deregulated cation efflux protein may comprise additional transmembrane domains or may comprise stabilized transmembrane domains.

Sequence Identity

Sequence identity comparisons can be conducted by eye, or more usually, with the aid of readily available sequence comparison programs. These commercially available computer programs can calculate % identity between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % identity when a global alignment is performed. Consequently, most sequence comparison methods are designed to produce optimal alignments that take into consideration possible insertions and deletions without penalising unduly the overall identity score. This is achieved by inserting "gaps" in the sequence alignment to try to maximise local identity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed-Chapter 18), BLAST 2 (see FEMS Microbiol Lett 1999 174(2): 247-50; FEMS Microbiol Lett 1999 177(1): 187-8 and tatiana@ncbi.nlm.nih.qov) FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage identities may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % sequence identity. The software typically does this as part of the sequence comparison and generates a numerical result.

Should Gap Penalties be used when determining sequence identity, the following parameters may be used for pairwise alignment:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, BLAST may be used with the gap penalty and gap extension set as defined above.

In one embodiment, CLUSTAL may be used with the gap penalty and gap extension set as defined above.

In some embodiments the gap penalties used for BLAST or CLUSTAL alignment may be different to those detailed above. The skilled person will appreciate that the standard parameters for performing BLAST and CLUSTAL alignments may change periodically and will be able to select appropriate parameters based on the standard parameters detailed for BLAST or CLUSTAL alignment algorithms at the time.

Suitably, the degree of identity with regard to a nucleotide sequence or an amino acid sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least 60 contiguous nucleotides/amino acids, preferably over at least 100 contiguous nucleotides/amino acids.

Suitably, the degree of identity with regard to a nucleotide sequence or the amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid, 7-amino heptanoic acid*, L-methionine sulfone[#]*, L-norleucine*, L-norvaline*, p-nitro-L-phenylalanine*, L-hydroxyproline[#], L-thioproline*, methyl derivatives of phenylalanine (Phe) such as 4-methyl-Phe*, pentamethyl-Phe*, L-Phe (4-amino)[#], L-Tyr (methyl)*, L-Phe (4-isopropyl)*, L-Tic (1,2,3,4-tetrahydroisoquinoline-3-carboxyl acid)*, L-diaminopropionic acid[#] and L-Phe (4-benzyl)*.

The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Norwell D C, *Trends Biotechnol.* (1995) 13(4), 132-134.

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also relates to nucleotide sequences that can hybridise to the nucleotide sequences of the present invention (including complementary sequences of those presented herein).

Preferably, hybridisation is determined under stringent conditions (e.g. 50° C. and 0.29×SSC {1×SSC=0.15 M NaCl, 0.015 M $Na_3$citrate pH 7.0}).

More preferably, hybridisation is determined under high stringent conditions (e.g. 65° C. and 0.1×SSC {1×SSC=0.15 M NaCl, 0.015 M $Na_3$citrate pH 7.0}).

Reducing or Preventing Expression and/or Function

In one aspect the present invention provides a method of decreasing the concentration and/or total content of the at least one tobacco-specific nitrosamine or precursor thereto in tobacco comprising expressing a deregulated cation efflux protein in a tobacco plant or plant part thereof or plant cell.

In another aspect the present invention provides a method of decreasing the concentration and/or total content of the at least one tobacco-specific nitrosamine or precursor thereto in tobacco comprising expressing in a tobacco plant or plant part thereof or plant cell:

a) a truncated cation efflux protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;

b) a truncated cation efflux protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, in a tobacco plant or plant part thereof or plant cell;

c) a protein comprising the amino acid sequence shown as SEQ ID No. 33, or a sequence which has at least 70%, at least 75%, at least 80%, at least 85%, at least 90%, at least 95%, at least 97%, or at least 99% sequence identity thereto; or d) a protein encoded by a polynucleotide comprising the sequence shown as SEQ ID No. 34, or a sequence which has at least 70%, at least 75%, at least 80%, at least 85%, at least 90%, at least 95%, at least 97%, or at least 99% sequence identity thereto. Any method known in the art for expressing a protein may be used in the present method.

By way of example, the present method may comprise:

providing a mutation (e.g. deletion) in a nucleic acid sequence which encodes a protein comprising the amino acid sequence shown as SEQ ID No. 3, 6, 9, 12, 15, 18, 21, 24, 27 or 30 or an amino acid sequence which has at least 70% sequence identity thereto;

providing a mutation in a regulatory region (e.g. cytoplasmic domain) of a protein comprising the amino acid sequence shown as SEQ ID No. 3, 6, 9, 12, 15, 18, 21, 24, 27 or 30 or an amino acid sequence which has at least 70% sequence identity thereto;

providing a mutation (e.g. deletion) in a regulatory region (e.g. a cytoplasmic domain, preferably an N-terminal cytoplasmic domain) of a protein comprising the amino acid sequence shown as SEQ ID No. 3, 6, 9, 12, 15, 18, 21, 24, 27 or 30 or an amino acid sequence which has at least 70% sequence identity thereto;

providing a nucleic acid sequence which encodes the amino acid sequence shown as SEQ ID No. 33, or a sequence which has at least 70% or at least 75%, at least 80%, at least 85%, at least 90%, at least 95%, at least 97%, or at least 99% sequence identity thereto;

providing a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

Each of the above approaches result in the decrease of the content of at least one TSNA or a precursor of a TSNA in tobacco. Suitably, each of the above approaches may result in the expression of a deregulated cation efflux protein.

As used herein, the term "mutation" encompasses a natural genetic variant or an engineered variant. In particular, the term "mutation" refers to a variation in the nucleotide sequence encoding the amino acid sequence or in the amino acid sequence compared to the sequence shown as SEQ ID No. 3, 6, 9, 12, 15, 18, 21, 24, 27 or 30 or an amino acid sequence which has at least 70% sequence identity thereto. Suitably the mutation may reduce the content of at least one TSNA or a precursor of a TSNA in tobacco.

In one embodiment, a method according to the present invention may comprise providing a nucleic acid sequence according to the present invention to a plant or part thereof or plant cell. Suitably said nucleic acid sequence may be introduced to the plant or part thereof or cell. Suitably an endogenous nucleic acid sequence in the plant or part thereof or cell may be modified to encode the polypeptide according to the present invention (e.g. by gene editing). In a preferred embodiment, each copy of a nucleic acid sequence encoding a protein comprising a sequence shown as SEQ ID No. 3, 6, 9, 12, 15, 18, 21, 24, 27 or 30 or a sequence which has at least 70% sequence identity thereto which is present in the plant is modified e.g. mutated as defined herein (e.g. each genomic copy of a gene encoding said protein in a plant is mutated). For example, each copy of the gene in the allotetraploid genome of *N. tabacum* may be mutated.

In a preferred embodiment, all homologues of the cation efflux protein are modified e.g. mutated. Suitably, all of SEQ ID No. 3, 6, 9, 12, 15, 18, 21, 24, 27 or 30 or corresponding sequences which have at least 70% sequence identity thereto are modified e.g. mutated.

In a preferred embodiment the plant or plant cell according to the present invention is homozygous. Suitably, the plant or plant cell may be homozygous for the modification e.g. mutation.

In one embodiment preferably the plant or plant cell according to the present invention expresses only the modified e.g. mutated nucleic acid. In other words, in some embodiments no endogenous (or endogenous and functional protein) is present in the plant according to the present invention. In other words, if any endogenous protein is present it is preferably in an inactive form.

In one embodiment the present method may comprise providing a mutation in the sequence shown as SEQ ID No. 1, SEQ ID No. 2 or SEQ ID No. 4, SEQ ID No. 5, SEQ ID No. 7, SEQ ID No. 8, SEQ ID No. 10, SEQ ID No. 11, SEQ ID No. 13, SEQ ID No. 14, SEQ ID No. 16, SEQ ID No. 17, SEQ ID No. 19, SEQ ID No. 20, SEQ ID No. 22, SEQ ID No. 23, SEQ ID No. 25, SEQ ID No. 26, SEQ ID No. 28 or SEQ ID No. 29, or a nucleic acid sequence which has at least 70% identity thereto.

The mutation may alter the plant genome such that a nucleic acid sequence encoding a protein comprising the amino acid sequence shown as SEQ ID No. 3, 6, 9, 12, 15, 18, 21, 24, 27 or 30 or an amino acid sequence which has at least 70% sequence identity thereto is completely or partially deleted or otherwise made non-functional.

The nucleic acid sequence may comprise one or more nucleotide change(s) that reduce or prevent expression of the protein or affect protein trafficking. For example, expression of the protein may be reduced or prevented by introduction of one or more of a frame shift, a splice mutant or a non-tolerated amino acid substitution in the open reading frame.

A frame-shift mutation (also called a framing error or a reading frame shift) is a mutation caused by indels (insertions or deletions) of a number of nucleotides in a nucleic acid sequence that is not divisible by three. Due to the triplet nature of gene expression by codons, the insertion or deletion can change the reading frame, resulting in a completely different translation from the original. A frameshift mutation will often cause the reading of the codons after the mutation to code for different amino acids. The frameshift mutation will commonly result in the introduction of a premature stop codon.

A splice mutant inserts, deletes or changes a number of nucleotides in the specific site at which splicing takes place during the processing of precursor messenger RNA into mature messenger RNA. The deletion of the splicing site results in one or more introns remaining in mature mRNA and may lead to the production of abnormal proteins.

A non-tolerated amino acid substitution refers to a mutation which causes a non-synonymous amino acid substitution in the protein which results in reduced or ablated function of the protein.

Any method known in the art for providing a mutation in a nucleic acid sequence may be used in the present method. For example, homologous recombination may be used, in which a vector is created in which the relevant nucleic acid sequence(s) are mutated and used to transform plants or plant cells. Recombinant plants or plant cells expressing the mutated sequence may then be selected.

The nucleic acid sequence may be wholly or partially deleted. The deletion may be continuous, or may comprise a plurality of sections of sequence. The deletion preferably removes a sufficient amount of nucleotide sequence such that the nucleic acid sequence no longer encodes a functional protein.

The deletion may remove at least part of one or more domains of the cation efflux protein.

The deletion may, for example, remove at least 10%, 20%, 30%, 40%, 50%, 60%, 70%, 80% or 90% of the coding portion of the nucleic acid sequence of at least one domain.

The deletion may, for example, remove at least 10%, 20%, 30%, 40%, 50%, 60%, 70%, 80% or 90% of the coding portion of the nucleic acid sequence.

Figure 37:
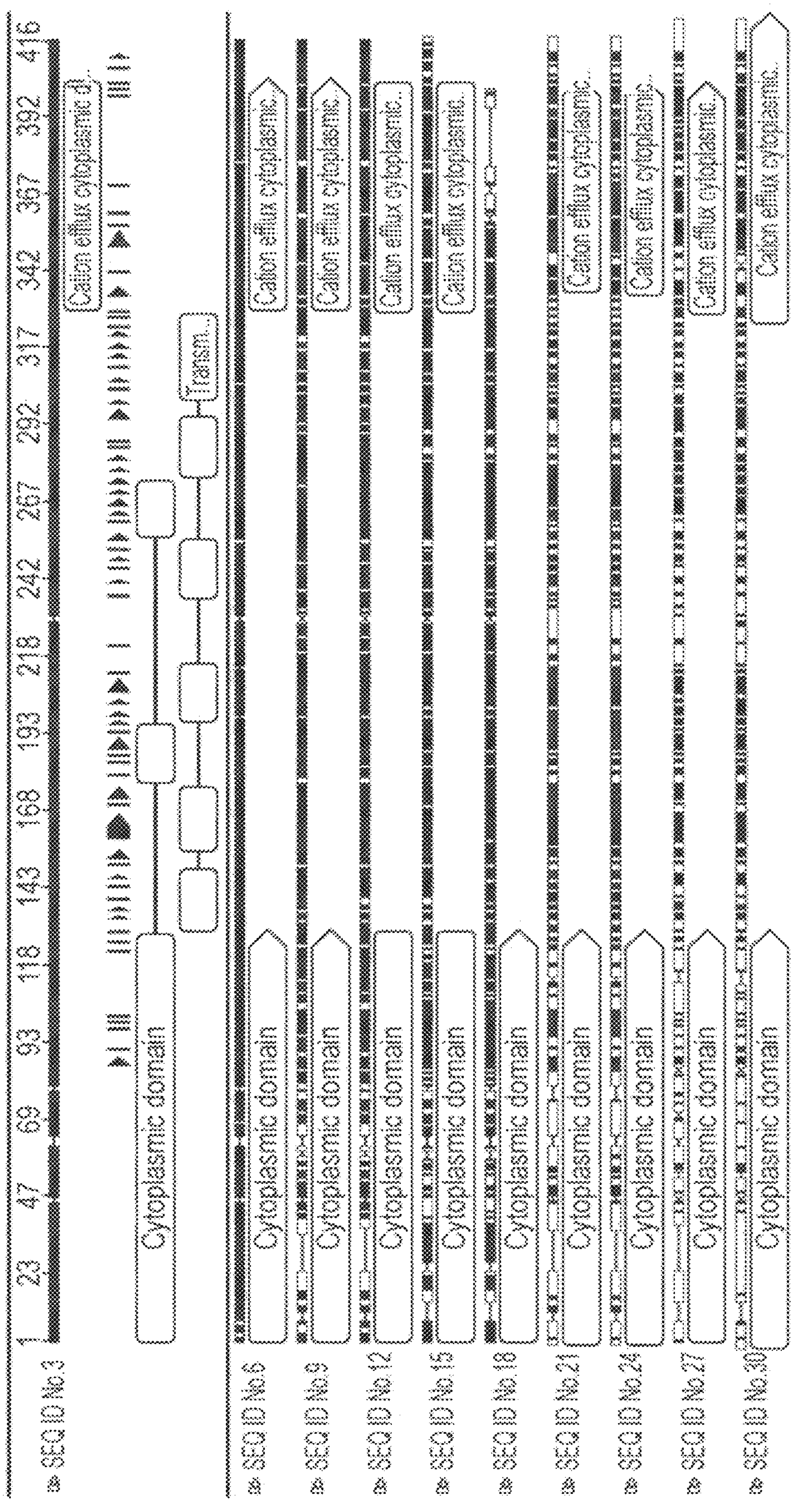
FIG. 37 shows an alignment of SEQ ID No. 3 and homologous protein sequences from *Nicotiana tabacum.*
Figure 67:
FIG. 67 shows the predicted 3D structure of SEQ ID No.3. The homodimer is predicted to contain two zinc docking sites.

The N terminal regulatory cytoplasmic domain is shown in FIG. 37. The N terminal regulatory cytoplasmic domain may be identified by sequence alignment with SEQ ID NO. 3.

In one embodiment, the amino acids encoding N-terminal regulatory cytoplasmic domain correspond to amino acids 1-128 of when aligned with SEQ ID No. 3.

Suitably, at least part of the N terminal regulatory cytoplasmic domain may be deleted. The deletion may, for example, remove at least 10%, 20%, 30%, 40%, 50%, 60%, 70%, 80% or 90% of the coding portion of the cytoplasmic domain. Suitably, the deletion may remove the entire N terminal regulatory cytoplasmic domain.

Figure 36:
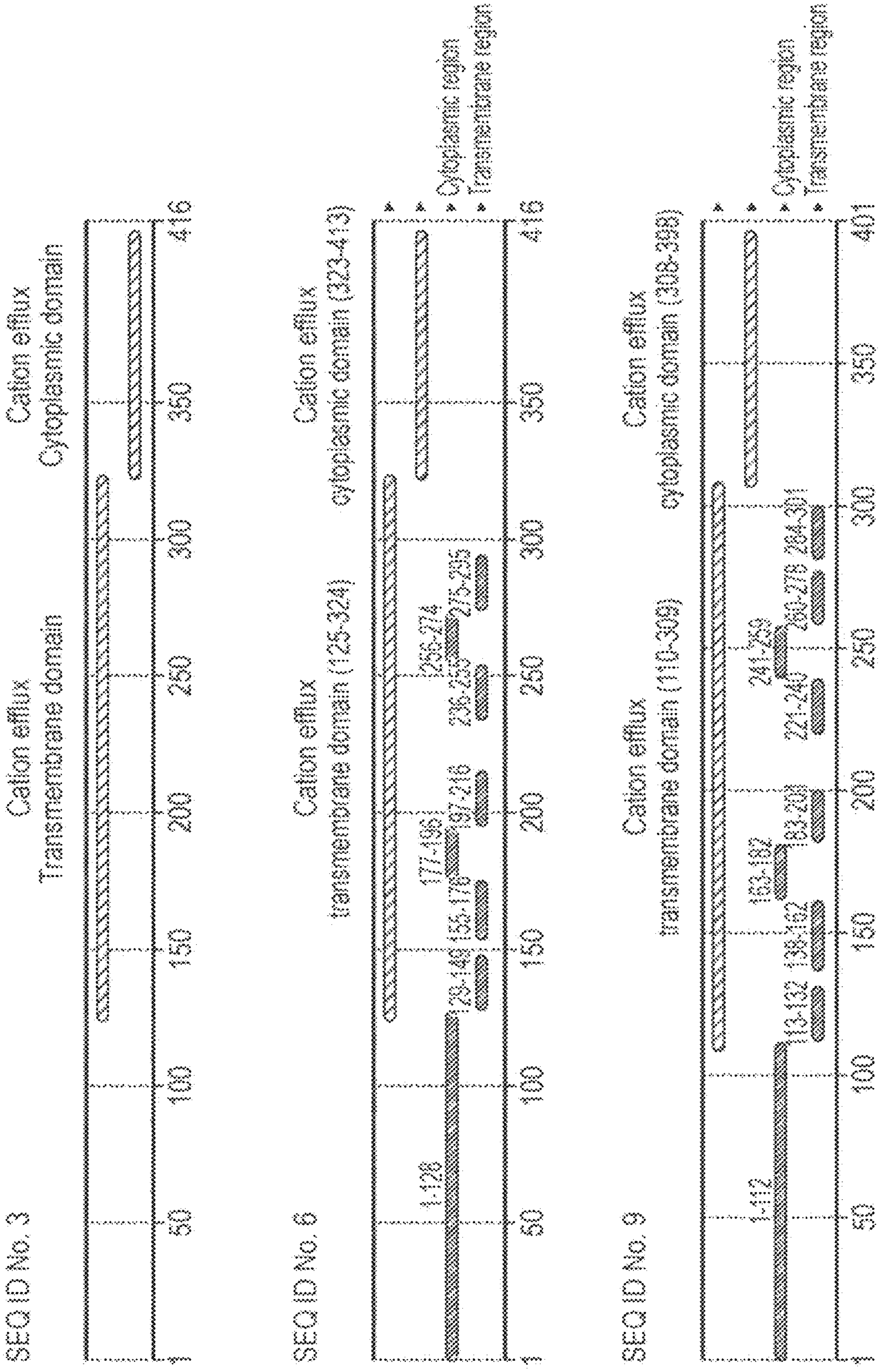
FIG. 36 shows the transmembrane domain and the cytoplasmic domain of SEQ ID No. 3 and of homologous protein sequences from *Nicotiana tabacum*. The protein sequence of SEQ ID No. 3 indicates the presence of a cation efflux transmembrane domain (amino acid positions 125-324) and a cation efflux cytoplasmic domain (amino acid positions 323-413).
Figure 36:
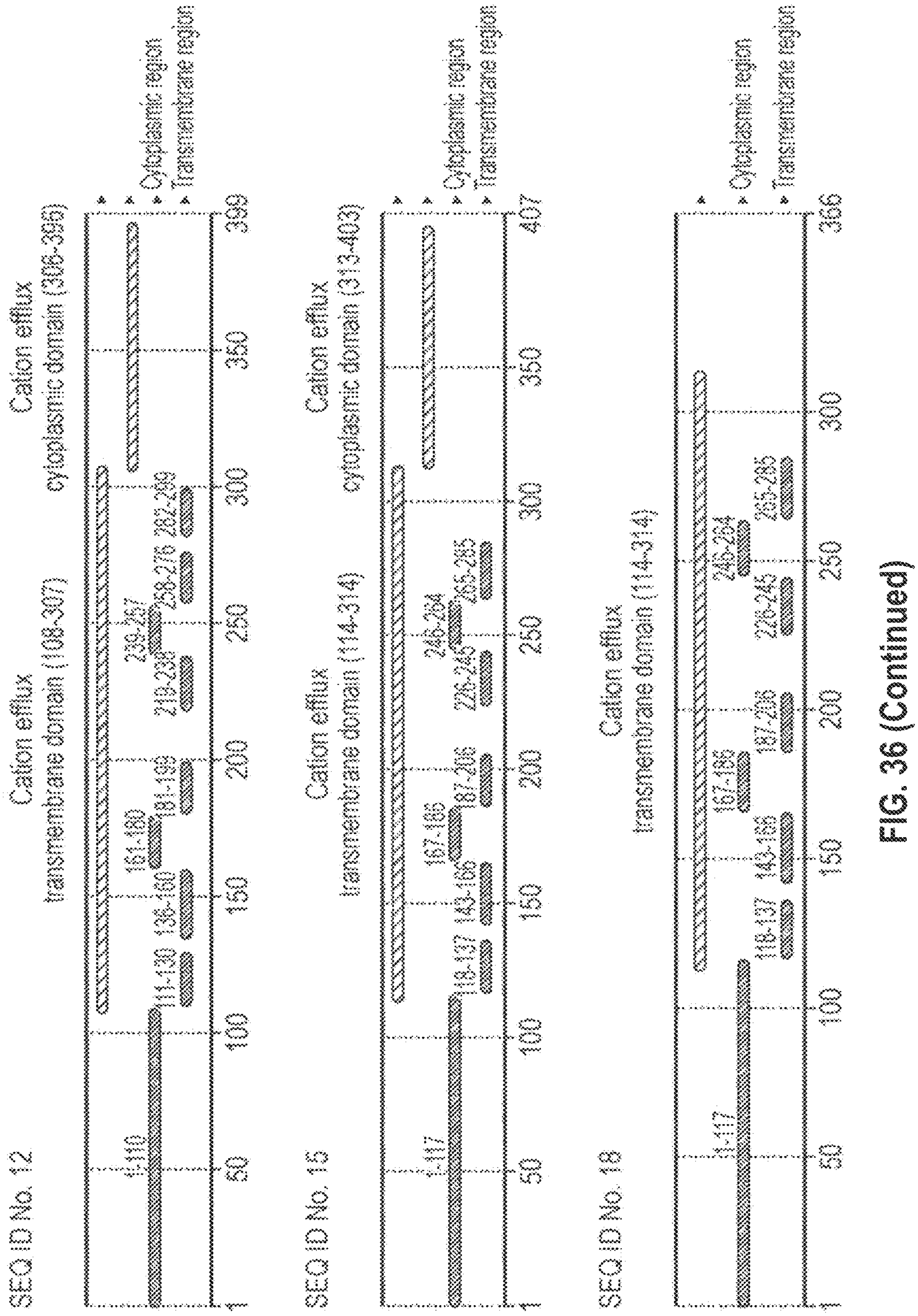
Figure 36:
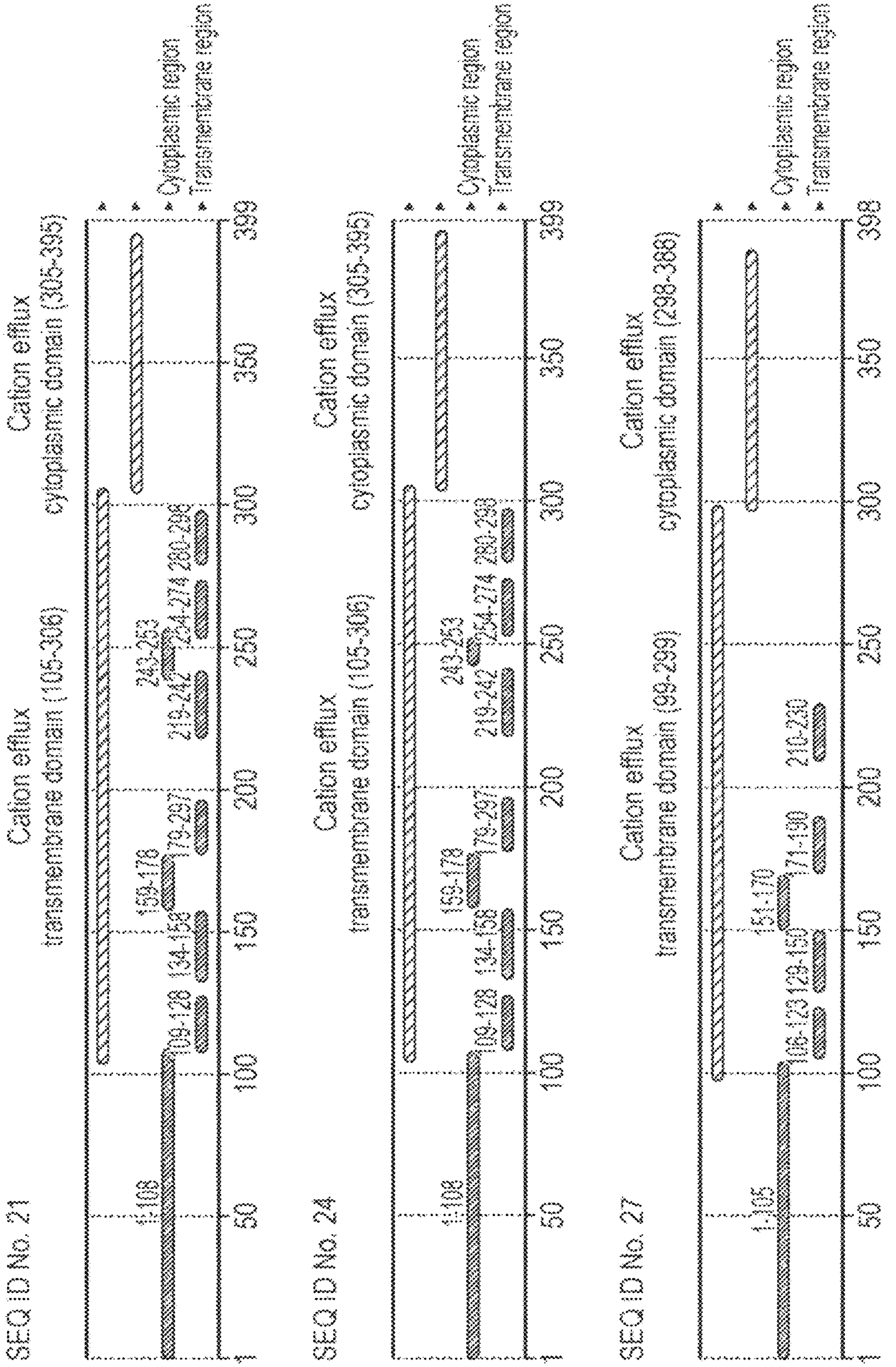
Figure 36:
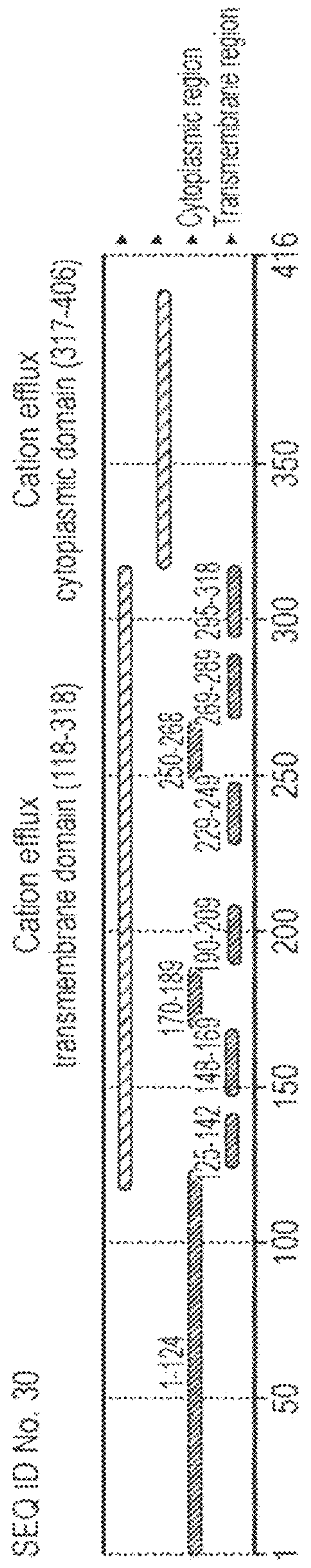

The cation efflux transmembrane domain and the cation efflux cytoplasmic domains are shown in FIG. 36.

Suitably, at least part of the cation efflux transmembrane domain may be deleted. The deletion may, for example, remove at least 10, 20, 30, 40, 50, 60, 70, 80 or 90% of the coding portion of the cation efflux transmembrane domain.

Suitably, at least part of the cation efflux cytoplasmic domains may be deleted. The deletion may, for example, remove at least 10, 20, 30, 40, 50, 60, 70, 80 or 90% of the coding portion of the cation efflux cytoplasmic domain.

Methods for deletion of nucleic acid sequences in plants are known in the art. For example, homologous recombination may be used, in which a vector is created in which the relevant nucleic acid sequence(s) are missing and used to transform plants or plant cells. Recombinant plants or plant cells expressing the new portion of sequence may then be selected.

Plant cells transformed with a vector as described above may be grown and maintained in accordance with well-known tissue culturing methods such as by culturing the cells in a suitable culture medium supplied with the necessary growth factors such as amino acids, plant hormones, vitamins, etc.

Modification of the nucleic acid sequence may be performed using targeted mutagenesis methods (also referred to as targeted nucleotide exchange (TNE) or oligo-directed mutagenesis (ODM)). Targeted mutagenesis methods include, without limitation, those employing zinc finger nucleases, TALENs (see WO2011/072246 and WO2010/079430), Cas9-like, Cas9/crRNA/tracrRNA, Cas9/gRNA, or other CRISPR systems (see WO 2014/071006 and WO2014/093622), meganucleases (see WO2007/047859 and WO2009/059195), or targeted mutagenesis methods employing mutagenic oligonucleotides, possibly containing chemically modified nucleotides for enhancing mutagenesis with sequence complementarity to the gene, into plant protoplasts (e.g., KeyBase® or TALENs). Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which comprise a gene encoding a protein having a mutation. TILLING uses traditional chemical mutagenesis (e.g. ethyl methanesulfonate (EMS) mutagenesis, which produces random mutations) followed by high-throughput screening for mutations. Thus, plants, seeds and tissues comprising a gene having the desired mutation may be obtained.

The method may comprise the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may, for example, be radiated or chemically treated and the plants may be screened for a modified phenotype.

Fast neutron deletion mutagenesis may be used in a reverse genetics sense (i.e. with PCR) to identify plant lines carrying a deletion in the endogenous gene. See for example Ohshima et al. (1998) Virology 213:472-481; Okubara et al. (1994) Genetics 137:867-874; and Quesada et al. (2000) Genetics 154:421-4315 which are incorporated herein by reference.

In another approach, dominant mutants may be used to trigger RNA silencing due to gene inversion and recombination of a duplicated gene locus. See for example Kusaba et al. (2003) Plant Cell 15:1455-1467 (incorporated herein by reference).

Modified plants may be distinguished from non-modified plants, i.e., wild type plants, by molecular methods, such as the mutation(s) present in the DNA, and by the modified phenotypic characteristics. The modified plants may be homozygous or heterozygous for the mutation.

In one embodiment the method of reducing the content of at least one tobacco specific nitrosamine (TSNA) or a precursor of a TSNA in tobacco does not comprise treating the plant with a chemical (e.g. an agrochemical).

Other ways of reducing or preventing the expression or activity will be apparent to one skilled in the art and include the use of micro RNA silencing, RNAi, antisense, tDNA insertions, virus-induced gene silencing (VIGs), or dominant negative constructs (or antimorphic mutations).

In one embodiment the nucleic acid encoding a protein comprising the amino acid sequence shown as SEQ ID No. 3, 6, 9, 12, 15, 18, 21, 24, 27 or 30 or an amino acid sequence which has at least 70% sequence identity thereto may be modified or mutated by a targeted mutagenesis based system.

In one embodiment the nucleic acid encoding a protein comprising the amino acid sequence shown as SEQ ID No. 3, 6, 9, 12, 15, 18, 21, 24, 27 or 30 or an amino acid sequence which has at least 70% sequence identity thereto may be modified (e.g. mutated or at least partially deleted) by gene editing such as a CRISPR based system.

In one embodiment the nucleic acid encoding a protein comprising the amino acid sequence shown as SEQ ID No. 3, 6, 9, 12, 15, 18, 21, 24, 27 or 30 or an amino acid sequence which has at least 70% sequence identity thereto may be modified (e.g. mutated or at least partially deleted) by zinc finger nuclease, TALENs, meganucleases, mutagenic oligonucleotides or TILLING.

Measurement of the level or amount of a gene product may be carried out by any suitable method, for example including comparison of mRNA transcript levels, protein or peptide levels, and/or phenotype of a plant, between a modified plant and comparable plant which has not been modified according to the present invention.

The ability of a protein to function as a cation efflux protein may be determined using any method known in the art for example including plant assays (such as those described by Lang et al, 2011. Journal of Experimental Botany, Volume 62, Issue 13 pages 4467-4480 (incorporated herein by reference)) or yeast complementation assays (such as those described by Pervans et al. 2001, PNAS, vol. 98 no. 17 (incorporated herein by reference)). In one embodiment, the ability of a protein to function as a cation efflux protein may be determined using a plant assay.

Suitably, shoot biomass production of a plant comprising the polynucleotide of interest may be measured under metal stress and compared to shoot biomass production of a wild-type plant. An increase in shoot biomass production under metal stress relative to the shoot biomass production of a wild-type plant is indicative of the polynucleotide of interest having cation efflux transporter functionality.

Suitably, transcript expression of the polynucleotide of interest may be measured under metal stress (such as Zn, Cd, Co, Ni) and compared to basal levels of wild type plants. An increase in transcript level of the polynucleotide of interest under metal stress compared to shoot biomass production of a wild-type plant is indicative of the polynucleotide of interest having a cation efflux transporter functionality.

In one embodiment, the ability of a protein to function as a cation efflux protein may be measured using a yeast complementation assay, such as the assay described herein.

Suitably, the cDNA of the polynucleotide of interest may be cloned into a yeast expression vector and transformed into a cot1zrc1 double mutant yeast strain (sensitive to Co, Ni, Cd, and Zn). Suitably, the yeast are on plates around cation-soaked filter discs, An assay may be conducted by comparing the zone of yeast strain growth inhibition for yeast comprising the polynucleotide of interest compared to yeast comprising a control vector. When the area of zone of inhibition for yeast comprising the polynucleotide of interest is smaller than the area of zone of inhibition for yeast comprising a control vector, this is indicative of the polynucleotide of interest having a cation efflux transporter functionality.

In one aspect, the present invention provides a method for decreasing the concentration and/or total content of a tobacco specific nitrosamine (TSNA) or a precursor of a TSNA in a tobacco plant.

The method may comprise expressing within the plant a polynucleotide (e.g. an exogenous polynucleotide) comprising:

a) a truncated cation efflux protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;

b) a truncated cation efflux protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;

c) a protein comprising the amino acid sequence shown as SEQ ID No. 33, or a sequence which has at least 70% or at least 75%, at least 80%, at least 85%, at least 90%, at least 95%, at least 97%, or at least 99% sequence identity thereto; or d) a protein encoded by a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

In one aspect, the present invention provides a method for increasing the concentration and/or total content of nicotine in a tobacco plant. Suitably said method may be used to produce nicotine for use in non-combustible systems.

The method may comprise expressing within the plant a polynucleotide (e.g. an exogenous polynucleotide) comprising:

a) a truncated cation efflux protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;

b) a truncated cation efflux protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;

c) a protein comprising the amino acid sequence shown as SEQ ID No. 33, or a sequence which has at least 70% or at least 75%, at least 80%, at least 85%, at least 90%, at least 95%, at least 97%, or at least 99% sequence identity thereto; or d) a protein encoded by a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

Promoters

The nucleic acid sequence may be operably linked to with a heterologous promoter for directing transcription of said nucleic acid sequence in said plant.

For example, in some embodiments, a promoter may be operably linked to nucleotide sequence in a construct or vector which is used to decrease the concentration and/or total content of a tobacco specific nitrosamine (TSNA) or a precursor of a TSNA in a tobacco plant or part thereof.

In one embodiment, a promoter is operably linked to a nucleic acid sequence which encodes a deregulated cation efflux protein according to the present invention.

Suitably, a promoter may be operably linked to:

a. A nucleotide sequence comprising SEQ ID No. 34;

b. A nucleotide sequence having at least 70% sequence identity to the entirety of the sequence set forth in SEQ ID No. 34, wherein said nucleotide sequence encodes a polypeptide involved in cation efflux in a plant;

c. A nucleotide sequence encoding a polypeptide comprising the amino acid sequence shown herein as SEQ ID No. 33, or a fragment thereof comprising at least 200, or at least 250, or at least 300, or at least 350, or at least 400 contiguous residues of SEQ ID No. 33;

d. A nucleotide sequence encoding a truncated polypeptide which lacks at least amino acids corresponding to 2-25, or 2-50, or 2-75, or 2-100, or 2-114, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

e. A nucleotide sequence encoding a truncated polypeptide which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;

f. A nucleotide sequence encoding a polypeptide comprising an amino acid sequence which corresponds to amino acids 125-324 of SEQ ID No. 3, 6, 9, 12, 15, 18, 21, 24, 27 or 30 and/or comprising an amino acid sequence which corresponds to amino acids 323-413 of SEQ ID No. 3, 6, 9, 12, 15, 18, 21, 24, 27 or 30 wherein said nucleotide sequence encodes a polypeptide involved in cation efflux in a plant.

In some embodiments, a promoter may be operably linked to nucleotide sequence in a construct or vector which is used to increase the concentration and/or total content of nicotine in a cell or cell culture or tobacco plant or part thereof.

In some embodiments the promoter may be selected from the group consisting of: a constitutive promoter, a tissue-specific promoter, a developmentally-regulated promoter and an inducible promoter.

In one embodiment the promoter may be a constitutive promoter.

A constitutive promoter directs the expression of a gene throughout the various parts of a plant continuously during plant development, although the gene may not be expressed at the same level in all cell types. Examples of known constitutive promoters include those associated with the cauliflower mosaic virus 35S transcript (Odell J T, Nagy F, Chua N H. (1985). Identification of DNA sequences required for activity of the cauliflower mosaic virus 35S promoter. Nature. 313 810-2), the rice actin 1 gene (Zhang W, McElroy D, Wu R. (1991). Analysis of rice Act1 5' region activity in transgenic rice plants. Plant Cell 3 1155-65) and the maize ubiquitin 1 gene (Cornejo M J, Luth D, Blankenship K M, Anderson O D, Blechl A E. (1993). Activity of a maize ubiquitin promoter in transgenic rice. Plant Molec. Biol. 23 567-81). Constitutive promoters such as the Carnation Etched Ring Virus (CERV) promoter (Hull R, Sadler J, Longstaff M (1986) (CaMV/35S), figwort mosaic virus 35S promoter. The sequence of carnation etched ring virus DNA: comparison with cauliflower mosaic virus and retroviruses. EMBO Journal, 5(2):3083-3090).

The constitutive promoter may be selected from a: a carnation etched ring virus (CERV) promoter, a cauliflower mosaic virus (CaMV 35S promoter), a promoter from the rice actin 1 gene or the maize ubiquitin 1 gene.

The promoter may be a tissue specific promoter. A tissue-specific promoter is one which directs the expression of a gene in one (or a few) parts of a plant, usually throughout the lifetime of those plant parts. The category of tissue-specific promoter commonly also includes promoters whose specificity is not absolute, i.e. they may also direct expression at a lower level in tissues other than the preferred tissue. Tissue specific promoters include the phaseolin-promoter, legumin b4-promoter, usp-promoter, sbp-promoter, ST-LS1 promoter, B33 (patatin class I promoter).

In another embodiment the promoter may be a developmentally-regulated promoter.

A developmentally-regulated promoter directs a change in the expression of a gene in one or more parts of a plant at a specific time during plant development. The gene may be expressed in that plant part at other times at a different (usually lower) level, and may also be expressed in other plant parts.

In one embodiment the promoter may be an inducible promoter.

An inducible promoter is capable of directing the expression of a gene in response to an inducer. In the absence of the inducer the gene will not be expressed. The inducer may act directly upon the promoter sequence, or may act by counteracting the effect of a repressor molecule. The inducer may be a chemical agent such as a metabolite, a protein, a growth regulator (such as auxin and salicylic acid which activate the OCS promoter), or a toxic element, a physiological stress such as heat, light (such as the soybean SSU promoter), wounding (e.g. the nos, nopaline synthase promoter), or osmotic pressure, or an indirect consequence of the action of a pathogen or pest. A developmentally-regulated promoter might be described as a specific type of inducible promoter responding to an endogenous inducer produced by the plant or to an environmental stimulus at a particular point in the life cycle of the plant. Examples of known inducible promoters include those associated with wound response, such as described by Warner S A, Scott R, Draper J. ((1993) Plant J. 3 191-201), temperature response as disclosed by Benfey & Chua (1989) (Benfey, P. N., and Chua, N-H. ((1989) Science 244 174-181), and chemically induced, as described by Gatz ((1995) Methods in Cell Biol. 50 411-424).

The present invention also provides a construct or vector comprising a nucleic acid sequence encoding a protein according to the present invention.

In one embodiment, the construct or vector according to the present invention may comprise:

a. A nucleotide sequence comprising SEQ ID No. 34;

b. A nucleotide sequence having at least 70% sequence identity to the entirety of the sequence set forth in SEQ ID No. 34, wherein said nucleotide sequence encodes a polypeptide involved in cation efflux in a plant;

c. A nucleotide sequence encoding a polypeptide comprising the amino acid sequence shown herein as SEQ ID No. 33, or a fragment thereof comprising at least 200, or at least 250, or at least 300, or at least 350, or at least 400 contiguous residues of SEQ ID No. 33;

d. A nucleotide sequence encoding a truncated polypeptide which lacks at least amino acids corresponding to 2-25, or 2-50, or 2-75, or 2-100, or 2-114, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

e. A nucleotide sequence encoding a truncated polypeptide which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;

f. A nucleotide sequence encoding a polypeptide comprising an amino acid sequence which corresponds to amino acids 125-324 of SEQ ID No. 3, 6, 9, 12, 15, 18, 21, 24, 27 or 30 and/or comprising an amino acid sequence which corresponds to amino acids 323-413 of SEQ ID No. 3, 6, 9, 12, 15, 18, 21, 24, 27 or 30 wherein said nucleotide sequence encodes a polypeptide involved in cation efflux in a plant.

The present invention further provides the use of a nucleic acid sequence according to the present invention reduce the content of a tobacco specific nitrosamine (TSNA) or a precursor of a TSNA in tobacco.

The present invention also provides a chimeric construct comprising a promoter operably linked to a nucleic acid sequence according to the present invention.

A suitable promoter sequence may be constitutive, non-constitutive, tissue-specific, developmentally-regulated or inducible/repressible.

In one embodiment a suitable promoter may be a promoter selected from the group consisting of: the cauliflower mosaic virus 35S promoter, the Carnation Etch Ring Virus (CERV) promoter, the pea plastocyanin promoter, the rubisco promoter, the nopaline synthase promoter, the chlorophyll a/b binding promoter, the high molecular weight glutenin promoter, the α, β-gliadin promoter, the hordein promoter, the patatin promoter, or a senescence-specific promoter.

The construct may be comprised in a vector. Suitably the vector may be a plasmid.

Exogenous polynucleotides may be introduced into plants according to the present invention by means of suitable vector, e.g. plant transformation vectors. A plant transformation vector may comprise an expression cassette comprising 5'-3' in the direction of transcription, a promoter sequence, a gene of interest (e.g. nucleic acid sequence encoding a protein according to the present invention) coding sequence, optionally including introns, and, optionally a 3' untranslated, terminator sequence including a stop signal for RNA polymerase and a polyadenylation signal for polyadenylase. The promoter sequence may be present in one or more copies, and such copies may be identical or variants of a promoter sequence as described above. The terminator sequence may be obtained from plant, bacterial or viral genes. Suitable terminator sequences are the pea rbcS E9 terminator sequence, the nos terminator sequence derived from the nopaline synthase gene of *Agrobacterium tumefaciens* and the 35S terminator sequence from cauliflower mosaic virus, for example. A person skilled in the art will be readily aware of other suitable terminator sequences.

The expression cassette may also comprise a gene expression enhancing mechanism to increase the strength of the promoter. An example of such an enhancer element is one derived from a portion of the promoter of the pea plastocyanin gene, and which is the subject of International patent Application No. WO 97/20056. Suitable enhancer elements may be the nos enhancer element derived from the nopaline synthase gene of *Agrobacterium tumefaciens* and the 35S enhancer element from cauliflower mosaic virus, for example. These regulatory regions may be derived from the same gene as the promoter DNA sequence or may be derived from different genes, for example from a plant of the family Solanaceae. All of the regulatory regions should be capable of operating in cells of the tissue to be transformed.

The promoter DNA sequence may be derived from the same gene as the gene of interest (e.g. the gene the promoter is going to direct, for instance a gene encoding a the modification of a plant to increase the activity or expression of a protein comprising the sequence shown as SEQ ID No. 3, 6, 9, 12, 15, 18, 21, 24, 27 or 30 or an amino acid sequence which has at least 70% sequence identity thereto) coding sequence used in the present invention or may be derived from a different gene, from for example from a plant of the family Solanaceae.

The expression cassette may be incorporated into a basic plant transformation vector, such as pBIN 19 Plus, pBI 101, or other suitable plant transformation vectors known in the art. In addition to the expression cassette, the plant transformation vector will contain such sequences as are necessary for the transformation process. These may include the

*Agrobacterium virgenes*, one or more T-DNA border sequences, and a selectable marker or other means of identifying transgenic plant cells.

The term "plant transformation vector" means a construct capable of in vivo or in vitro expression. Preferably, the expression vector is incorporated in the genome of the organism.

The term "incorporated" preferably covers stable incorporation into the genome.

Techniques for transforming plants are well known within the art and include *Agrobacterium*-mediated transformation, for example. The basic principle in the construction of genetically modified plants is to insert genetic information in the plant genome so as to obtain a stable maintenance of the inserted genetic material. A review of the general techniques may be found in articles by Potrykus (Annu Rev Plant Physiol Plant Mol Biol [1991] 42:205-225) and Christon (AgroFood-Industry Hi-Tech March/Apri11994 17-27).

Typically, in *Agrobacterium*-mediated transformation a binary vector carrying a foreign DNA of interest, is transferred from an appropriate *Agrobacterium* strain to a target plant by the co-cultivation of the *Agrobacterium* with explants from the target plant. Transformed plant tissue is then regenerated on selection media, which selection media comprises a selectable marker and plant growth hormones. An alternative is the floral dip method (Clough & Bent, 1998) whereby floral buds of an intact plant are brought into contact with a suspension of the *Agrobacterium* strain containing the chimeric gene, and following seed set, transformed individuals are germinated and identified by growth on selective media. Direct infection of plant tissues by *Agrobacterium* is a simple technique which has been widely employed and which is described in Butcher D. N. et al., (1980), Tissue Culture Methods for Plant Pathologists, eds.: D. S. Ingrams and J. P. Helgeson, 203-208.

Further suitable transformation methods include direct gene transfer into protoplasts using polyethylene glycol or electroporation techniques, particle bombardment, micro-injection and the use of silicon carbide fibres for example.

Transforming plants using ballistic transformation, including the silicon carbide whisker technique are taught in Frame B R, Drayton P R, Bagnaall S V, Lewnau C J, Bullock W P, Wilson H M, Dunwell J M, Thompson J A & Wang K (1994). Production of fertile transgenic maize plants by silicon carbide whisker-mediated transformation is taught in The Plant Journal 6: 941-948) and viral transformation techniques is taught in for example Meyer P, Heidmmm I & Niedenhof I (1992). The use of cassava mosaic virus as a vector system for plants is taught in Gene 110: 213-217. Further teachings on plant transformation may be found in EP-A-0449375.

In a further aspect, the present invention relates to a vector system which carries a nucleotide sequence encoding a gene of interest (e.g. a nucleic acid sequence according to the present invention) and introducing it into the genome of an organism, such as a plant. The vector system may comprise one vector, but it may comprise two vectors. In the case of two vectors, the vector system is normally referred to as a binary vector system. Binary vector systems are described in further detail in Gynheung Anetal, (1980), Binary Vectors, Plant Molecular Biology Manual A3, 1-19.

One extensively employed system for transformation of plant cells uses the Ti plasmid from *Agrobacterium tumefaciens* or a Ri plasmid from *Agrobacterium rhizogenes* Anetal., (1986), Plant Physiol. 81, 301-305 and Butcher D. N. et al., (1980), Tissue Culture Methods for Plant Pathologists, eds.: D. S. Ingrams and J. P. Helgeson, 203-208. After each introduction method of the desired exogenous gene according to the present invention in the plants, the presence and/or insertion of further DNA sequences may be necessary. The use of T-DNA for the transformation of plant cells has been intensively studied and is described in EP-A-120516; Hoekema, in: The Binary Plant Vector System Offset-drukkerij Kanters B. B., Amsterdam, 1985, Chapter V; Fraley, et al., Crit. Rev. Plant Sci., 4:1-46; and Anetal., EMBO J (1985) 4:277-284.

Plant cells transformed with an exogenous gene encoding a protein of interest (e.g. a protein according to the present invention) may be grown and maintained in accordance with well-known tissue culturing methods such as by culturing the cells in a suitable culture medium supplied with the necessary growth factors such as amino acids, plant hormones, vitamins, etc.

The term "transgenic plant" in relation to the present invention includes any plant that comprises an exogenous gene encoding a gene of interest, e.g. a protein according to the present invention, as described herein. Preferably the exogenous gene is incorporated in the genome of the plant.

The terms "transgenic plant" and "exogenous gene" do not cover native nucleotide coding sequences in their natural environment when they are under the control of their native promoter which is also in its natural environment.

Thus in one embodiment the present invention relates to a method for producing a transgenic plant comprising introducing, into an unmodified plant, an exogenous gene (chimeric construct or vector) encoding a protein according to the present invention.

In one embodiment the present invention relates to a method for producing a transgenic plant comprising transforming a plant cell with a construct or vector (e.g. a chimaeric construct) comprising a nucleic acid encoding a protein according to the present invention; and regenerating a plant from the transformed plant cell.

In another aspect there is provided the use of an exogenous nucleic acid sequence (construct or vector or chimaeric construct) in accordance with the present invention for decreasing the content of a tobacco specific nitrosamine (TSNA) or a precursor of a TSNA in a tobacco plant, e.g. by transformation of the plant with the exogenous nucleic acid sequence (construct or vector or chimaeric construct).

In one embodiment the present invention further relates to a host cell comprising an exogenous nucleic acid sequence (construct or vector or chimaeric construct) in accordance with the present invention.

In one embodiment, a mutation in the amino acid sequence shown as SEQ ID No. 3, 6, 9, 12, 15, 18, 21, 24, 27 or 30 or a sequence which has at least 70% sequence identity thereto may deregulate the protein in relation to a protein shown as SEQ ID No. 3, 6, 9, 12, 15, 18, 21, 24, 27 or 30 or a sequence which has at least 70% sequence identity thereto.

In some embodiments the mutation in the amino acid sequence shown as SEQ ID No. 3, 6, 9, 12, 15, 18, 21, 24, 27 or 30 or a sequence which has at least 70% sequence identity thereto may not alter the level or expression but may decrease the activity of the protein in relation to a protein shown as SEQ ID No. 3, 6, 9, 12, 15, 18, 21, 24, 27 or 30 ora sequence which has at least 70% sequence identity thereto.

Biomass Production

In one aspect, the present invention provides a method of producing a biomass comprising: growing a cell which has been engineered to express a deregulated cation efflux protein under conditions to produce a biomass.

In one embodiment, the present invention provides a method of producing a biomass having modified (e.g. increased) concentration and/or total content of nicotine, comprising growing a cell which have been engineered to:

a) express a deregulated cation efflux protein;
b) express a truncated protein which lacks at least amino acids corresponding to 2-25, or 2-50, or 2-75, or 2-100, 2-114, 2-117, 2-120, 2-125, 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, 2-114 or 2-117 of SEQ ID No. 3, 6, 9, 12, 15, 18, 21, 24, 27 or 30;
c) express a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;
d) express a protein comprising the amino acid sequence shown as SEQ ID No. 33, or a sequence which has at least 70% or at least 75%, at least 80%, at least 85%, at least 90%, at least 95%, at least 97%, or at least 99% sequence identity thereto;
e) express a protein encoded by a polynucleotide comprising the sequence shown as SEQ ID No. 34, or a sequence which has at least 70% sequence identity thereto or at least 75%, at least 80%, at least 85%, at least 90%, at least 95%, at least 97%, or at least 99% sequence identity thereto.

Suitably, the biomass may contain a higher concentration and/or total content of nicotine compared with the biomass produced by a comparable cell which has not been modified in accordance with the present invention.

Suitably the cell for use in biomass production may be a plant cell, such as a tobacco cell. Suitably the cell for use in biomass production may be a yeast cell.

In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell). The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltransferase or S-adenosyl-L-methionine:putrescine N-methyltransferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification of in this way may be taught in US2016032299 for example, which is incorporated herein by reference.

Commercially Desirable Traits

The term "commercially desirable traits" will include traits such as yield, quality (e.g. leaf quality, suitably cured leaf quality), abiotic (for instance drought) stress tolerance, herbicide tolerance and/or biotic (for instance insect, bacteria or fungus) stress tolerance and/or disease tolerance.

Leaf quality may be measured based on colour, texture and aroma of the cured leaf, for example according to United States Department of Agriculture (USDA) grades and standards.

Tobacco grades are evaluated based on factors including, but not limited to, the leaf stalk position, leaf size, leaf colour, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast.

Leaf grade can be determined using standard methods known in the art, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania SeedleafTobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida ShadeGrown Cigar-Wrapper Tobacco (U.S. Type 62), Effective April 1971. A USDA grade index value can be determined according to an industry accepted grade index. See, e.g., Bowman et al, Tobacco Science, 32:39-40 (1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated herein in their entirety).

In one aspect, a USDA grade index is a 0-100 numerical representation of federal grade received and is a weighted average of all stalk positions. A higher grade index indicates higher quality. Alternatively, leaf grade may be determined via hyper-spectral imaging. See e.g., WO 2011/027315 (which is incorporated herein by reference).

In one embodiment, a tobacco plant of the present invention provides tobacco of commercially acceptable grade.

Suitably, the tobacco plant of the present invention provides cured tobacco of commercially acceptable grade.

In one embodiment, a tobacco plant of the present invention is capable of producing leaves having a USDA grade index value of at least about 70% of the USDA grade index value of leaves of a comparable plant when grown in similar growth conditions. Suitably, tobacco plants disclosed herein may be capable of producing leaves having a USDA grade index value of at least about 65%, at least about 70%, at least about 75%, at least about 80%, at least about 85%, at least about 90%, at least about 95%, or at least about 98% of the USDA grade index value of a control plant when grown in similar growth conditions. Suitably, tobacco plants disclosed herein may be capable of producing leaves having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a comparable plant.

In one aspect, the tobacco plant of the present invention is capable of producing leaves having a USDA grade index value of at least 50. Suitably, tobacco plants disclosed herein may be capable of producing leaves having a USDA grade index value of 55 or more, 60 or more, 65 or more, 70 or more, 75 or more, 80 or more, 85 or more, 90 or more, and 95 or more.

Unless specified otherwise, used herein, tobacco yield refers to cured leaf yield which is calculated based on the weight of cured tobacco leaves per acre under standard field conditions following standard agronomic and curing practice.

In one aspect, a tobacco plant of the present invention has a yield between 50% and 150%, between 55% and 145%, between 60% and 140%, between 65% and 135%, between 70% and 130%, between 75% and 125%, between 80% and 120%, between 85% and 115%, between 90% and 110%, between 95% and 105%, 50% and 100%, between 55% and 100%, between 60% and 100%, between 65% and 100%, between 70% and 100%, between 75% and 100%, between 80% and 100%, between 85% and 100%, between 90% and 100%, between 95% and 100%, between 100% and 150%, between 105% and 150%, between 110% and 150%, between 115% and 150%, between 120% and 150%, between 125% and 150%, between 130% and 150%, between 135% and 150%, between 140% and 150%, or between 145% and 150% of the yield of a comparable plant when grown in similar field conditions.

In another aspect, the yield of a tobacco plant of the present invention is approximately 1.5, 1.6, 1.7, 1.8, 1.9, 2.0, 2.1, 2.2, 2.3, 2.4, 2.5, 2.6, 2.7, 2.8, 2.9, or 3.0 times of the yield of the a comparable plant when grown in similar field conditions.

In another aspect, the yield of a tobacco plant of the present invention is comparable to the yield of a cured comparable plant when grown in similar field conditions.

In one aspect, a tobacco plant of the present invention provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre.

In another aspect, a tobacco plant of the present invention provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre.

In a further aspect, a tobacco plant of the present invention provides a yield selected from the group consisting of about between 1200 and 3500, between 1200 and 3400, between 1200 and 3300, between 1200 and 3200, between 1200 and 3100, between 1200 and 3000, between 1200 and 2900, between 1200 and 2800, between 1200 and 2700, between 1200 and 2600, between 1200 and 2500, between 1200 and 2400, between 1200 and 2300, between 1200 and 2200, between 1200 and 2100, between 1200 and 2000, between 1200 and 1900, between 1200 and 1800, between 1200 and 1700, between 1200 and 1600, between 1200 and 1500, and between 1200 and 1400 lbs/acre.

Plant Breeding

In one embodiment the present invention provides a method of producing a tobacco plant having reduced content of a tobacco specific nitrosamine (TSNA) or a precursor of a TSNA, comprising:

a. crossing a donor tobacco plant which produces a reduced content of a tobacco specific nitrosamine (TSNA) or a precursor of a TSNA and comprises a deregulated cation efflux protein with a recipient tobacco plant that does not produce reduced content of a tobacco specific nitrosamine (TSNA) or a precursor of a TSNA and possesses commercially desirable traits;
b. isolating genetic material from a progeny of said donor plant crossed with said recipient plant; and
c. performing molecular marker-assisted selection with a molecular marker comprising:
d. identifying an introgressed region comprising a mutation in a polynucleotide sequence encoding a protein defined in a.

The molecular marker assisted selection may comprise performing PCR to identify a introgressed nucleic acid sequence comprising a. A nucleotide sequence comprising SEQ ID No. 34;
b. A nucleotide sequence having at least 70% sequence identity to the entirety of the sequence set forth in SEQ ID No. 34, wherein said nucleotide sequence encodes a polypeptide involved in cation efflux in a plant;
c. A nucleotide sequence encoding a polypeptide comprising the amino acid sequence shown herein as SEQ ID No. 33, or a fragment thereof comprising at least 200, or at least 250, or at least 300, or at least 350, or at least 400 contiguous residues of SEQ ID No. 33;
d. A nucleotide sequence encoding a truncated polypeptide which lacks at least amino acids corresponding to 2-25, or 2-50, or 2-75, or 2-100, or 2-114, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;
e. A nucleotide sequence encoding a truncated polypeptide which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30;
f. A nucleotide sequence encoding a polypeptide comprising an amino acid sequence which corresponds to amino acids 125-324 of SEQ ID No. 3, 6, 9, 12, 15, 18, 21, 24, 27 or 30 and/or comprising an amino acid sequence which corresponds to amino acids 323-413 of SEQ ID No. 3, 6, 9, 12, 15, 18, 21, 24, 27 or 30 wherein said nucleotide sequence encodes a polypeptide involved in cation efflux in a plant;

Tobacco Plant and Part Thereof

The term "tobacco plant" as used herein refers to a plant in the genus *Nicotiana* that is used in the production of tobacco industry products. Non-limiting examples of suitable tobacco plants include *N. tabacum* and *N. rustica* (for example, LA B21, LN KY171, TI 1406, Basma, Galpao, Perique, Beinhart 1000-1, and Petico).

Thus, in one embodiment a tobacco plant does include *Nicotiana plumbaginifolia.*

The tobacco material can be derived from varieties of *Nicotiana tabacum* species, commonly known as Burley varieties, flue or bright varieties, dark varieties and oriental/Turkish varieties. In some embodiments, the tobacco material is derived from a Burley, Virginia, flue-cured, air-cured, fire-cured, Oriental, or a dark tobacco plant. The tobacco plant may be selected from Maryland tobacco, rare tobacco, specialty tobacco, expanded tobacco or the like.

The use of tobacco cultivars and elite tobacco cultivars is also contemplated herein. The tobacco plant for use herein may therefore be a tobacco variety or elite tobacco cultivar.

Particularly useful *Nicotiana tabacum* varieties include Burley type, dark type, flue-cured type, and Oriental type tobaccos.

In some embodiments, the tobacco plant may be, for example, selected from one or more of the following varieties: N. tabacum AA 37-1, N. tabacum B 13P, *N. tabacum* Xanthi (Mitchell-Mor), *N. tabacum* KT D #3 Hybrid 107, N. tabacum Bel-W3, N. tabacum 79-615, N. tabacum Samsun Holmes NN, F4 from cross N. tabacum BU21×N. tabacum Hoja Parado, line 97, *N. tabacum* KTRDC #2 Hybrid 49, *N. tabacum* KTRDC #4 Hybrid 1 10, *N. tabacum Burley* 21, *N. tabacum* PM016, *N. tabacum* KTRDC #5 KY 160 SI, *N. tabacum* KTRDC #7 FCA, *N. tabacum* KTRDC #6 TN 86 SI, *N. tabacum* PM021, *N. tabacum* K 149, *N. tabacum* K 326, *N. tabacum* K 346, *N. tabacum* K 358, *N. tabacum* K 394, *N. tabacum* K 399, *N. tabacum* K 730, *N. tabacum* KY 10, *N. tabacum* KY 14, *N. tabacum* KY 160, *N. tabacum* KY 17, *N. tabacum* KY 8959, *N. tabacum* KY 9, *N. tabacum* KY 907, *N. tabacum* MD 609, *N. tabacum* McNair 373, *N. tabacum* NC 2000, *N. tabacum* PG 01, *N. tabacum* PG 04, *N. tabacum* P01, *N. tabacum* P02, *N. tabacum* P03, *N. tabacum* RG 11, *N. tabacum* RG 17, *N. tabacum* RG 8, *N. tabacum* Speight G-28, *N. tabacum* TN 86, *N. tabacum* TN 90, *N. tabacum* VA 509, *N. tabacum* AS44, *N. tabacum* Banket A1, *N. tabacum* Basma Drama B84/31, *N. tabacum* Basma I Zichna ZP4/B, *N. tabacum* Basma Xanthi BX 2A, *N. tabacum* Batek, *N. tabacum* Besuki Jember, *N. tabacum* C104, *N. tabacum* Coker 319, *N. tabacum* Coker 347, *N. tabacum* Criollo Misionero, *N. tabacum* PM092, *N. tabacum* Delcrest, *N. tabacum* Djebel 81, *N. tabacum* DVH 405, *N. tabacum* Galpao Comum, *N. tabacum* HBO4P, *N. tabacum* Hicks Broadleaf, *N. tabacum* Kabakulak Elassona, *N. tabacum* PM102, *N. tabacum* Kutsage E1, *N. tabacum* KY 14xL8, *N. tabacum* KY 171, *N. tabacum* LA BU 21, *N. tabacum* McNair 944, *N. tabacum* NC 2326, *N. tabacum* NC 71, *N. tabacum* NC 297, *N. tabacum* NC 3, *N. tabacum* PVH 03, *N. tabacum* PVH 09, *N. tabacum* PVH 19, *N. tabacum* PVH 21 10, *N. tabacum* Red Russian, *N. tabacum* Samsun, *N. tabacum* Saplak, *N. tabacum* Simmaba, *N. tabacum* Talgar 28, *N. tabacum* PM132, *N. tabacum* Wislica, *N. tabacum* Yayaldag, *N. tabacum* NC 4, *N. tabacum* TR Madole, *N. tabacum* Prilep HC-72, *N. tabacum* Prilep P23, *N. tabacum* Prilep PB 156/1, *N. tabacum* Prilep P12-2/1, *N. tabacum* Yaka JK-48, *N. tabacum* Yaka JB 125/3, *N. tabacum* TI-1068, *N. tabacum* KDH-960, *N. tabacum* TI-1070, *N. tabacum* TW136, *N. tabacum* PM204, *N. tabacum* PM205, *N. tabacum* Basma, *N. tabacum* TKF 4028, *N. tabacum* L8, *N. tabacum* TKF 2002, *N. tabacum* TN90, *N. tabacum* GR141, *N. tabacum* Basma xanthi, *N. tabacum* GR149, *N. tabacum* GR153, and *N. tabacum* Petit Havana.

Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF91 1, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371 LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC 'Periq'e' tobacco, PVH03, PVH09, PVH19, PVH50, PVH51, R 610, R 630, R 7-1 1, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, V A 309, VA359, AA 37-1, B 13P, Xanthi (Mitchell-Mor), Bel-W3, 79-615, Samsun Holmes N N, KTRDC number 2 Hybrid 49, Burley 21, KY 8959, KY 9, MD 609, PG 01, PG 04, P01, P02, P03, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HBO4P, Hicks Broadleaf, Kabakulak Elassona, Kutsage E1, LA BU 21, NC 2326, NC 297, PVH 21 10, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka J B 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

In one embodiment the tobacco plant is a Burley type tobacco plant, suitably a Burley PH2517.

In one embodiment the plant propagation material may be obtainable from a tobacco plant of the invention.

A "plant propagation material" as used herein refers to any plant matter taken from a plant from which further plants may be produced. Suitably, a plant propagation material may be selected from a seed, plant calli and plant clumps.

Suitably the plant propagation material may be a seed. Suitably, a plant propagation material may be plant calli. Suitably the plant propagation material may be plant clumps.

In one embodiment the cell (e.g. tobacco cell), tobacco plant and/or plant propagation material may be obtainable (e.g. obtained) by a method according to the invention. In one embodiment the cell (e.g., tobacco cell), tobacco plant and/or plant propagation material of the invention may comprise:

A nucleic acid sequence encoding a deregulated cation efflux protein;

a nucleotide sequence comprising SEQ ID No. 34;

a nucleotide sequence having at least 70% sequence identity to the entirety of the sequence set forth in SEQ ID No. 34, wherein said nucleotide sequence encodes a polypeptide involved in cation efflux in a plant;

a nucleotide sequence encoding a polypeptide comprising the amino acid sequence shown herein as SEQ ID No. 33, or a fragment thereof comprising at least 200, or at least 250, or at least 300, or at least 350, or at least 400 contiguous residues of SEQ ID No. 33;

a nucleotide sequence encoding a truncated polypeptide which lacks at least amino acids corresponding to 2-25, or 2-50, or 2-75, or 2-100, or 2-114, or 2-117, or 2-120, or 2-125, or 2-128, or 2-130 from the N-terminal side of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which lacks at least amino acids corresponding to amino acids 2-25, or 2-50, or 2-75, or 2-100, or 2-114, or 2-117, or 2-117, or 2-120, or 2-125, or 2-128, or 2-130 of SEQ ID No. 3, 6, 9, 12, 15, 18, 21, 24, 27 or 30;

a nucleotide sequence encoding a truncated polypeptide which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30, or a protein which has at least 70% (preferably at least 75%, at least 80%, at least 85%, at least 90%, at least 95%, at least 97%, or at least 99%) sequence identity to a truncated protein which consists essentially of or consists of at least 375, at least 350, or at least 300, or at least 250, or at least 200, or at least 150 amino acids from the C-terminal of SEQ ID No. 3, 6, 9, 12, 15, 18, 21, 24, 27 or 30; or a nucleotide sequence encoding a polypeptide comprising an amino acid sequence which corresponds to amino acids 125-324 of SEQ ID No. 3, 6, 9, 12, 15, 18, 21, 24, 27 or 30 and/or comprising an amino acid sequence which corresponds to amino acids 323-413 of SEQ ID No. 3, 6, 9, 12, 15, 18, 21, 24, 27 or 30 wherein said nucleotide sequence encodes a polypeptide involved in cation efflux in a plant.

Suitably a tobacco plant according to the present invention may have a e.g. reduced content of a tobacco specific nitrosamine (TSNA) or a precursor of a TSNA when compared to an unmodified tobacco plant, wherein the modification is the expression of a deregulation cation efflux protein according to the present invention or the expression of a nucleic acid sequence according to the present invention.

In one embodiment the tobacco plant in accordance with the present invention comprises a tobacco cell of the invention.

In another embodiment the plant propagation material may be obtainable (e.g. obtained) from a tobacco plant of the invention.

In one embodiment there is provided the use of a tobacco plant as described herein to breed a tobacco plant.

The present invention also provides in another embodiment the use of a tobacco plant of the foregoing embodiments for the production of a tobacco industry product.

In another embodiment there is provided the use of a tobacco plant of the invention to grow a crop.

In one embodiment there is provided the use of a cell as provided for in the foregoing embodiments for production of a tobacco industry product.

In one embodiment the present invention provides a cell culture (e.g. in in vitro culture).

The tobacco cell culture may be a cell suspension culture. These cells cultured in vitro may be incorporated into a tobacco industry product, e.g. as a substitute for conventional tobacco particles, shreds, fine cut or long cut tobacco lamina, as an additive ingredient or as both a substitute and an additive. Suitably, the cell culture may produce nicotine.

In one embodiment there is provided the use of a cell culture, e.g. a harvested and/or processed cell culture according to the present invention for the production of a tobacco industry product.

The cells harvested from an in vitro culture may be dried, e.g. freeze-dried, for example to produce a powder.

In one embodiment, the cell culture is a tobacco cell culture.

The skilled person will be aware of known methods for establishing in vitro cultures of tobacco cells. By way of example only the following method may be used: collecting seeds form a tobacco plant of interest and sterilising their exterior to eliminate unwanted organisms, planting said seeds to grown a tobacco plant of interest, removing tissue from the tobacco plant (for example, from the tobacco stem) for use as an explant, establishing a callus culture form the tobacco explant, establishing a cell suspension culture from the callus culture, and harvesting culture material (e.g. including tobacco cells) to produce a tobacco cell culture.

The tobacco cells can be harvested by various methods, including filtration, e.g. vacuum filtration. The sample may be washed in the filter by adding water and the remaining liquid removed with the filtration, e.g. vacuum filtration.

The harvested tobacco cell culture may be further processed, e.g. dried, such as air-dried and/or freeze-dried. The harvested tobacco cell culture or dried harvested tobacco cell culture may be incorporated into tobacco industry products according to the present invention.

In one embodiment, the cell culture is a yeast cell culture. In one embodiment the cell (e.g. yeast cell) may be further modified to comprise one or more sequences that increases nicotinic alkaloid biosynthesis. Suitably these one or more sequences may be incorporated into a nucleic acid construct that is suitable for cell (e.g. yeast cell) transformation. The one or more sequences may be overexpressed in the cell (e.g. yeast cell). The sequences may be selected from one or more of the following genes: MPO (or Methylputrescine Oxidase or MPO1 or MPO2); A622 (or Isoflavone reductase-like protein or Isoflavone reductase homolog or Isoflavone reductase-like protein); BBL (or Berberine bridge enzyme or Berberine bridge enzyme-like or BBE or NBB1); PMT (or Putrescine N-Methyltransferase or putrescine methyltransferase or S-adenosyl-L-methionine:putrescine N-methyltransferase or PMT or PMT1 or PMT2 or PMT3 or PMT4) and QPT (or quinolinate phosphoribosyltransferase). In one embodiment the sequences may be selected from one or more of the following genes: BBL, A622, PMT and MPO (MPO1 or MPO2). Genes suitable for modification of in this way may be taught in US2016032299 for example, which is incorporated herein by reference.

Products

The present invention also provides for products obtainable or obtained from tobacco according to the present invention.

In one embodiment there is provided the use of a tobacco plant of the invention to produce a tobacco leaf.

Suitably the tobacco leaf may be subjected to downstream applications such as processing. Thus in one embodiment the use of the foregoing embodiment may provide a processed tobacco leaf. Suitably the tobacco leaf may be subjected to curing, fermenting, pasteurising or combinations thereof. In another embodiment the tobacco leaf may be cut. In some embodiments the tobacco leaf may be cut before or after being subjected to curing, fermenting, pasteurising or combinations thereof.

In one embodiment the present invention provides a harvested leaf of a tobacco plant of the invention.

In a further embodiment the harvested leaf may be obtainable (e.g. obtained) from a tobacco plant propagated from a propagation material of the present invention.

In another embodiment there is provided a harvest leaf obtainable from a method or use of the present invention.

Suitably the harvested leaf may be a cut harvested leaf.

In some embodiments the harvested leaf may comprise viable tobacco cells. In other embodiments the harvested leaf may be subjected to further processing.

There is also provided a processed tobacco leaf.

The processed tobacco leaf may be obtainable from a tobacco plant of the invention.

Suitably the processed tobacco leaf may be obtainable from a tobacco plant obtained in accordance with any of the methods and/or uses of the present invention.

In another embodiment the processed tobacco leaf may be obtainable from a tobacco plant propagated form a tobacco plant propagation material according to the present invention.

The processed tobacco leaf of the present invention may be obtainable by processing a harvested leaf of the invention.

The term "processed tobacco leaf" as used herein refers to a tobacco leaf that has undergone one or more processing steps to which tobacco is subjected to in the art. A "processed tobacco leaf" comprises no or substantially no viable cells.

The term "viable cells" refers to cells which are able to grow and/or are metabolically active.

Thus, if a cell is said to not be viable, also referred to as "non-viable" then a cell does not display the characteristics of a viable cell.

The term "substantially no viable cells" means that less than about 5% of the total cells are viable. Preferably, less than about 3%, more preferably less than about 1%, even more preferably less than about 0.1% of the total cells are viable.

In one embodiment the processed tobacco leaf may be processed by one or more of: curing, fermenting and/or pasteurising.

Suitably the processed tobacco leaf may be processed by curing.

Tobacco leaf may be cured by any method known in the art. In one embodiment tobacco leaf may be cured by one or more of the curing methods selected from the group consisting of: air curing, fire curing, flue curing and sun curing.

Suitably the tobacco leaf may be air cured.

Typically air curing is achieved by hanging tobacco leaf in well-ventilated barns and allowing to dry. This is usually carried out over a period of four to eight weeks. Air curing is especially suitable for burley tobacco.

Suitably the tobacco leaf may be fire cured. Fire curing is typically achieved by hanging tobacco leaf in large barns where fires of hardwoods are kept on continuous or intermittent low smoulder and usually takes between three days and ten weeks, depending on the process and the tobacco.

In another embodiment the tobacco leaf may be flue cured. Flue curing may comprise stringing tobacco leaves onto tobacco sticks and hanging them from tier-poles in curing barns. The barns usually have a flue which runs from externally fed fire boxes. Typically this results in tobacco that has been heat-cured without being exposed to smoke. Usually the temperature will be raised slowly over the course of the curing with the whole process taking approximately 1 week.

Suitably the tobacco leaf may be sun cured. This method typically involves exposure of uncovered tobacco to the sun.

Suitably the processed tobacco leaf may be processed by fermenting.

Fermentation can be carried out in any manner known in the art. Typically during fermentation, the tobacco leaves are piled into stacks (a bulk) of cured tobacco covered in e.g. burlap to retain moisture. The combination of the remaining water inside the leaf and the weight of the tobacco generates a natural heat which ripens the tobacco. The temperature in the centre of the bulk is monitored daily. In some methods every week, the entire bulk is opened. The leaves are then removed to be shaken and moistened and the bulk is rotated so that the inside leaves go outside and the bottom leaves are placed on the top of the bulk. This ensures even fermentation throughout the bulk. The additional moisture on the leaves, plus the actual rotation of the leaves themselves, generates heat, releasing the tobacco's natural ammonia and reducing nicotine, while also deepening the colour and improving the tobacco's aroma. Typically the fermentation process continues for up to 6 months, depending on the variety of tobacco, stalk position on the leaf, thickness and intended use of leaf.

Suitably the processed tobacco leaf may be processed by pasteurising. Pasteurising may be particularly preferred when the tobacco leaf will be used to make a smokeless tobacco industry product, most preferably snus.

Tobacco leaf pasteurisation may be carried out by any method known in the art. For example pasteurisation may be carried out as detailed in J Foulds, L Ramstrom, M Burke, K Fagerstrom. Effect of smokeless tobacco (snus) on smoking and public health in Sweden. Tobacco Control (2003) 12: 349-359, the teaching of which is incorporated herein by reference.

During the production of snus pasteurisation is typically carried out by a process in which the tobacco is heat treated with steam for 24-36 hours (reaching temperatures of approximately 100° C.). This results in an almost sterile product and without wishing to be bound by theory one of the consequences of this is believed to be a limitation of further TSNA formation.

In one embodiment the pasteurisation may be steam pasteurisation.

In some embodiments the processed tobacco leaf may be cut. The processed tobacco leaf may be cut before or after processing. Suitably, the processed tobacco leaf may be cut after processing.

In one embodiment, the use of the foregoing embodiment may provide reconstituted tobacco. "Reconstituted" as used herein may also be referred to as recon, recycled or homogenized sheet tobacco and refers to tobacco material generated from remnants of tobacco leaf after processing. Reconstituted tobacco allows the production of a consistent, high quality blend and allows the adjustment of the ratio of individual components.

Reconstituted tobacco may be nano fibre recon (nanofibers can be extracted in solid or liquid form), paper making recon (which uses stems, scraps, and midribs, etc. as the raw material) or slurry type recon (which uses a mixture of fines and tobacco stems, ground to power, mixed with water and vegetable binding agent. The soluble residue is formed to sheets by extracting the water.)

Any method known in the art may be used for making reconstituted tobacco, for example see CORESTA Congress, Sapporo, 2012, Smoke Science/Product Technology Groups, SSPT 12 (incorporated herein by reference).

In some embodiments the tobacco plant, harvested leaf of a tobacco plant and/or processed tobacco leaf may be used to extract nicotine. The extraction of nicotine can be achieved using any method known in the art. For example a method for extracting nicotine from tobacco is taught in U.S. Pat. No. 2,162,738 which is incorporated herein by reference.

In one aspect, the present invention provides cured tobacco material made from a tobacco plant or part thereof according to the invention.

In another aspect, the present invention provides a tobacco blend comprising tobacco material made from a tobacco plant or part thereof according to the present invention, or from a tobacco cell culture according to the present invention. In one aspect, the present invention provides a tobacco blend comprising cured tobacco material according to the present invention.

Suitably, the tobacco blend according to the present invention may comprise approximately 10%, 20%, 30%, 40%, 50%, 60%, 70%, 80% or 90% tobacco from a tobacco plant or part thereof according to the present invention, or from a tobacco cell culture according to the present invention. Suitably, the tobacco blend may comprise approximately 10% tobacco from a tobacco plant or part thereof according to the present invention, or from a tobacco cell culture according to the present invention. Suitably, the tobacco blend may comprise approximately 20% tobacco from a tobacco plant or part thereof according to the present invention, or from a tobacco cell culture according to the present invention. Suitably, the tobacco blend may comprise approximately 30% tobacco from a tobacco plant or part thereof according to the present invention, or from a tobacco cell culture according to the present invention. Suitably, the tobacco blend may comprise approximately 40% tobacco from a tobacco plant or part thereof according to the present invention, or from a tobacco cell culture according to the present invention. Suitably, the tobacco blend may comprise approximately 50% tobacco from a tobacco plant or part thereof according to the present invention, or from a tobacco cell culture according to the present invention. Suitably, the tobacco blend may comprise approximately 60% tobacco from a tobacco plant or part thereof according to the present invention, or from a tobacco cell culture according to the present invention. Suitably, the tobacco blend may comprise approximately 70% tobacco from a tobacco plant or part thereof according to the present invention, or from a tobacco cell culture according to the present invention. Suitably, the tobacco blend may comprise approximately 80% tobacco from a tobacco plant or part thereof according to the present invention, or from a tobacco cell culture according to the present invention. Suitably, the tobacco blend may comprise approximately 90% tobacco from a tobacco plant or part thereof according to the present invention, or from a tobacco cell culture according to the present invention.

In one aspect, a tobacco blend product of the present invention comprises at least about 5, 10, 20, 30, 40, 50, 60, 70, 80, 90, or 95 percent by dry weight of tobacco cured from a tobacco plant or part thereof according to the present invention, or a tobacco cell culture according to the present invention.

Suitably, the cured tobacco material may be air cured. Suitably, the cured tobacco material may be flue cured. Suitably, the cured tobacco material may be sun cured. Suitably, the cured tobacco material may be fire cured.

A tobacco industry product or smoking article according to the present invention may comprise the tobacco material (e.g. cured tobacco material or reconstituted tobacco material) according to the present invention.

In another aspect the present invention provides a tobacco industry product.

In one embodiment the tobacco industry product according to the present invention may be a blended tobacco industry product. Suitably, the tobacco blend may comprise cured tobacco material according to the present invention.

In one embodiment the tobacco industry product may be prepared from a tobacco plant of the invention or a part thereof.

Suitably the tobacco plant or part thereof may be propagated from a tobacco plant propagation material according to the .present invention.

The term "part thereof" as used herein in the context of a tobacco plant refers to a portion of the tobacco plant. Suitably, the "part thereof" may be a leaf, root or stem of a tobacco plant or the flowers. Suitably, the "part thereof" may be a leaf, root or stem of a tobacco plant.

Tobacco Industry Product

As used herein, the term "tobacco industry product" is intended to include combustible smoking articles such as cigarettes, cigarillos, cigars, tobacco for pipes or for roll-your-own cigarettes, (whether based on tobacco, tobacco derivatives, expanded tobacco, reconstituted tobacco, tobacco substitutes or other smokable material), non-combustible aerosol provision systems such as heating products that release compounds from substrate materials without burning such as electronic cigarettes, tobacco heating products, and hybrid systems to generate aerosol from a combination of substrate materials, for example hybrid systems containing a liquid or gel or solid substrate, as well as aerosolizable substrate materials used within these aerosol provision systems; and aerosol-free delivery articles such as lozenges, gums, patches, articles comprising breathable powders and smokeless tobacco industry products such as snus and snuff, which aerosol-free delivery articles may or may not deliver nicotine.

In one embodiment the tobacco industry product may be prepared from (e.g. may comprise) a tobacco plant of the invention or a part thereof.

Suitably the tobacco plant or part thereof may be propagated from a tobacco plant propagation material according to the present invention.

The term "part thereof" as used herein in the context of a tobacco plant refers to a portion of the tobacco plant. Preferably the "part thereof" is a leaf of a tobacco plant.

In another embodiment the tobacco industry product may be prepared from a harvested leaf of the invention.

In a further embodiment the tobacco industry product may be prepared from a processed tobacco leaf of the invention.

Suitably the tobacco industry product may be prepared from a tobacco leaf processed by one or more of: curing, fermenting and/or pasteurising.

Suitably the tobacco industry product may comprise a cut tobacco leaf, optionally processed as per the foregoing embodiment.

In another embodiment, the tobacco industry product may be prepared from a tobacco cell culture according to the present invention.

In another embodiment, the tobacco industry product may be prepared from (e.g. may comprise) a cured tobacco material according to the present invention.

In another embodiment, the tobacco industry product may be prepared from (e.g. may comprise) a tobacco blend according to the present invention.

In one embodiment the tobacco industry product may be a smoking article.

As used herein, the term "smoking article" can include smokeable products, such as rolling tobacco, cigarettes, cigars and cigarillos whether based on tobacco, tobacco derivatives, expanded tobacco, reconstituted tobacco or tobacco substitutes.

In another embodiment the tobacco industry product may be a smokeless tobacco industry product.

The term "smokeless tobacco industry product" as used herein refers to a tobacco industry product that is not intended to be smoked and/or subjected to combustion.

Smokeless tobacco industry products (including heat-not-burn materials) may contain tobacco in any form, including dried particles, shreds, granules, powders, or slurry, deposited on, mixed in, surrounded by, or combined with other ingredients in any format, such as flakes, films, tabs, foams, or beads.

In one embodiment a smokeless tobacco industry product may include snus, snuff, chewing tobacco or the like.

In one embodiment, the tobacco industry product is a combustible smoking article, selected from the group consisting of a cigarette, a cigarillo and a cigar.

In one embodiment, the tobacco industry product comprises one or more components of a combustible smoking article, such as a filter, a filter rod, a filter rod segments, tobacco, a tobacco rod, a tobacco rod segment, a spill, an additive release component such as a capsule, a thread, beads, a paper such as a plug wrap, a tipping paper or a cigarette paper.

In one embodiment, the tobacco industry product is a non-combustible aerosol provision system.

In one embodiment, the tobacco industry product comprises one or more components of a non-combustible aerosol provision system, such as a heater and an aerosolizable substrate.

In one embodiment, the aerosol provision system is an electronic cigarette also known as a vaping device.

In one embodiment the electronic cigarette comprises a heater, a power supply capable of supplying power to the heater, an aerosolizable substrate such as a liquid or gel, a housing and optionally a mouthpiece.

In one embodiment the aerosolizable substrate is contained in a substrate container. In one embodiment the substrate container is combined with or comprises the heater.

In one embodiment, the tobacco industry product is a heating product which releases one or more compounds by heating, but not burning, a substrate material. The substrate material is an aerosolizable material which may be for example tobacco or other non-tobacco products, which may or may not contain nicotine. In one embodiment, the heating product is a tobacco heating product.

In one embodiment, the heating product is an electronic device.

In one embodiment, the tobacco heating product comprises a heater, a power supply capable of supplying power to the heater, an aerosolizable substrate such as a solid or gel material.

In one embodiment the heating product is a non-electronic article.

In one embodiment the heating product comprises an aerosolizable substrate such as a solid or gel material and a heat source which is capable of supplying heat energy to the aerosolizable substrate without any electronic means, such as by burning a combustion material, such as charcoal.

In one embodiment the heating product also comprises a filter capable of filtering the aerosol generated by heating the aerosolizable substrate.

In some embodiments the aerosolizable substrate material may comprise a vapour or aerosol generating agent or a humectant, such as glycerol, propylene glycol, triacetin or diethylene glycol.

In one embodiment, the tobacco industry product is a hybrid system to generate aerosol by heating, but not burning, a combination of substrate materials. The substrate materials may comprise for example solid, liquid or gel which may or may not contain nicotine. In one embodiment, the hybrid system comprises a liquid or gel substrate and a solid substrate. The solid substrate may be for example tobacco or other non-tobacco products, which may or may not contain nicotine. In one embodiment, the hybrid system comprises a liquid or gel substrate and tobacco.

In a further embodiment the tobacco industry product may be a tobacco heating device or hybrid device or e-cigarette or the like.

Typically in tobacco heating devices or hybrid devices, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user.

Aerosol-generating articles and devices for consuming or smoking tobacco heating devices are known in the art. They can include, for example, electrically heated aerosol-generating devices in which an aerosol is generated by the transfer of heat from one or more electrical heating elements of the aerosol-generating device to the aerosol-forming substrate of a tobacco heating device.

Suitably the tobacco heating device may be an aerosol-generating device.

Preferably the tobacco heating device may be a heat-not-burn device. Heat-not-burn devices are known in the art and release compounds by heating, but not burning, tobacco. An example of a suitable, heat-not-burn device may be one taught in WO2013/034459 or GB2515502 which are incorporated herein by reference.

In one embodiment the aerosol-forming substrate of a tobacco heating device may be a tobacco industry product in accordance with the present invention.

In one embodiment the tobacco heating device may be a hybrid device.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a protein" or "a nucleic acid sequence" includes a plurality of such candidate agents and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Figures and Examples.

EXAMPLES

Example 1

Methods and Materials

Plant Material

Plant material from *Nicotiana* including *Nicotiana tabacum* e.g.: Burley and Virginia varieties and other species e.g. *Nicotiana rustica.*

Bacterial Strains

The *Escherichia coli* (*E. coli*) strain TOP10 F-[F-mcrA Δ (mrr-hsdRMS-mcrBC) Φ80lacZΔM15 Δ lacX74 recA1 araD139 Δ(araleu)7697 galU galK rpsL (StrR) endA1 nupG] were used for cloning and plasmid DNA production. *E. coli* strain TOP10 were transformed by means of a chemical method.

*Agrobacterium tumefaciens* strain GV3101::pMP90 was used for transformation of binary vectors for in planta assays.

Alkaloid Measurement

Relative content of pyridine alkaloids was determined by reversed phase high performance liquid chromatography with tandem mass spectrometry (LC-MS/MS). Chromatographic separation is achieved using a Gemini-NX column (100 mm×3.0 mm, particle size 3 μm, Phenomenex) and gradient chromatographic separation using 6.5 mM ammonium acetate buffer (aq) (pH10) and Methanol.

Mass Spectrometer operates in electrospray (ESI) positive mode using scheduled MRM data acquisition. Two MRM transitions are monitored for each analyte and one for the isotope labelled internal standard.

| Analyte | Precursor Ion | Daughter Ion (quant/confirm) |
|---|---|---|
| Nicotine | 163.1 | 130/106 |
| Nicotine d4 | 167.1 | 134.1 |
| Anabasine | 163.1 | 80/120 |
| Anatabine | 161.1 | 144/80 |
| Nornicotine | 149.1 | 80/130 |
| Nornicotine d4 | 153.1 | 84.1 |
| PON | 176.1 | 106.0/148 |
| PON d4 | 183.1 | 110.0 |

Statistical Analysis

Statistical significances based on one-way ANOVA analyses is performed with Prism 5.01 software (GraphPad Software).

Virus-Induced Gene Silencing (VIGS)

The TRV vector comprising both SEQ ID No. 49 (TRV RNA1) and SEQ ID No. 50 (TRV RNA2) comprising SEQ ID No. 51 (targeted nucleotide sequence) were separately propagated in *A. tumefaciens*. These cultures were mixed (1:1) and syringe-infiltration into 2-week-old tobacco plants. The silencing effect was assessed two weeks post-virus infection by assessing the expression level of the target gene.

Results

Figure 2:
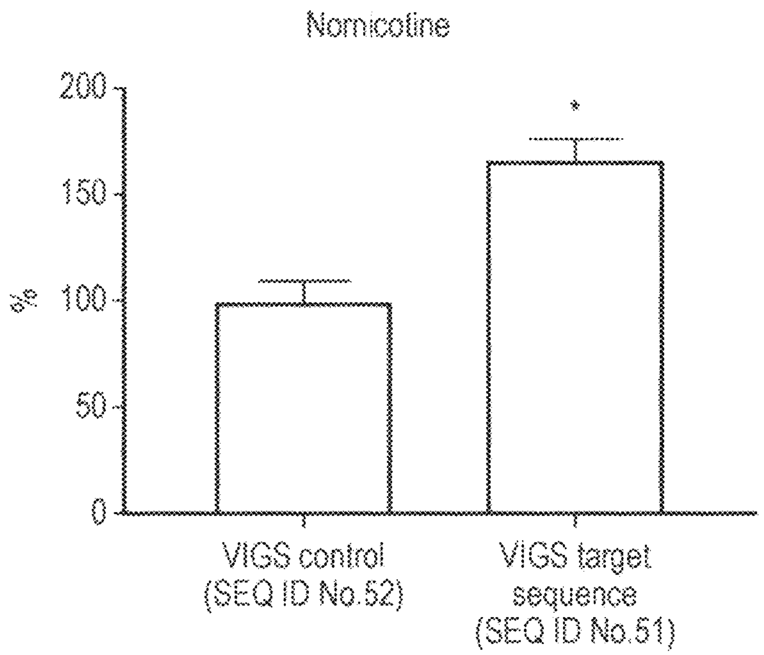
FIG. 2 shows the nornicotine content of 5 week old tobacco leaves which have been modified by virus-induced gene silencing of the cation efflux protein.

Nornicotine content of 5-week-old tobacco leaves expressing the VIGS target sequence (SEQ ID No. 51) and the VIGS control sequence (SEQ ID No. 52) is shown in FIG. 2. The nornicotine content is represented relative to a control (SEQ ID No. 52) and comprises three biological replicates analysed by one-way ANOVA and Tukey's multiple-comparison post-test. Values are shown as means±SEM. Asterisks indicate statistical significance of P value ≤0.001.

Conclusions

Silencing of a cation efflux protein encoded by SEQ ID No. 2 results in an increase in nornicotine content.

Example 2

Methods and Materials

Cloning

GDB-Cation Efflux Expression Vector

The gene sequence (SEQ ID No. 2) was amplified from a Gateway™ compatible cDNA library using primers (M13.fw [SEQ ID No. 36] and M13.rv [SEQ ID No. 37]) located outside the attB1 and attB2 sites flanking the gene sequence. The gene sequence was then transferred to the GDB expression vector (SEQ ID No. 38).

GDB-Cation Efflux_AS Expression Vector

AS construct (SEQID No. 39) was generated by two-step amplification and Gateway™ cloning, using the GDB-Cation efflux expression vector as template, a first set of gene-specific primers (Cation efflux_AS.fw [SEQ ID No. 40] and Cation efflux_AS.rv [SEQ ID No. 41]) and a second set of Gateway™ compatible primers (attB1 [SEQ ID No. 42] and attB2 [SEQ ID No. 43]). The amplification product was inserted into the Gateway™ pDONR™/Zeo vector (ThermoFisher Scientific). The sequence is then transferred to the GDB expression vector (SEQ ID No. 38).

GDB-Cation Efflux_Δ117C Expression Vector

The Δ117C variant (SEQ ID No. 32) is generated by two-step PCR amplification and Gateway™ cloning, using the GDB-Cation efflux expression vector as template, a first set of gene-specific primers (Cation efflux_Δ117C.fw [SEQ ID No. 45] and Cation efflux_Δ117C.rv [SEQ ID No. 46]) and a second set of Gateway™ compatible primers (attB1 [SEQ ID No. 42] and attB2 [SEQ ID No. 43]). The amplification product was inserted into the Gateway™ pDONR™/Zeo vector (ThermoFisher Scientific). The sequence is then transferred to the GDB expression vector (SEQ ID No. 38).

GDB-Cation Efflux_Δ117N Expression Vector

The Δ117N variant (SEQ ID No. 34) was generated by two-step PCR amplification and Gateway™ cloning, using the GDB-Cation efflux expression vector as template, a first set of gene-specific primers (Cation efflux_Δ117N.fw [SEQ ID No. 47] and Cation efflux_Δ117N.rv [SEQ ID No. 46]) and a second set of Gateway™ compatible primers (attB1 [SEQ ID No. 42] and attB2 [SEQ ID No. 43]). The amplification product was inserted into the Gateway™ pDONR™/Zeo vector (ThermoFisher Scientific). The sequence was then transferred to the GDB expression vector (SEQ ID No. 38).

The resulting plasmids were sequenced and transformed into *Agrobacterium tumefaciens* GV3101pMP90 by heat shock and transiently expression in TN90 leaves.

Transient Gene Expression

*Agrobacterium tumefaciens* GV3101 strains carrying the construct of interest were grown overnight in Luria-Bertani (LB) medium supplemented with appropriate antibiotics. Cultures are spun down and re-suspended in buffer containing 10 mM MgCl2, 10 mM MES pH 5.6 and 100 μM acetosyringone to OD600=0.6 and incubated for one hour at room temperature. Infiltration is performed with a needleless syringe into TN90 leaves. Samples are taken 5 days post-infiltration.

Tests were performed in two biological replicates comprising twelve technical replicates each.

Statistical Analysis

Statistical significances based on one-way ANOVA analyses is performed with Prism 5.01 software (GraphPad Software).

Results

Figure 3:
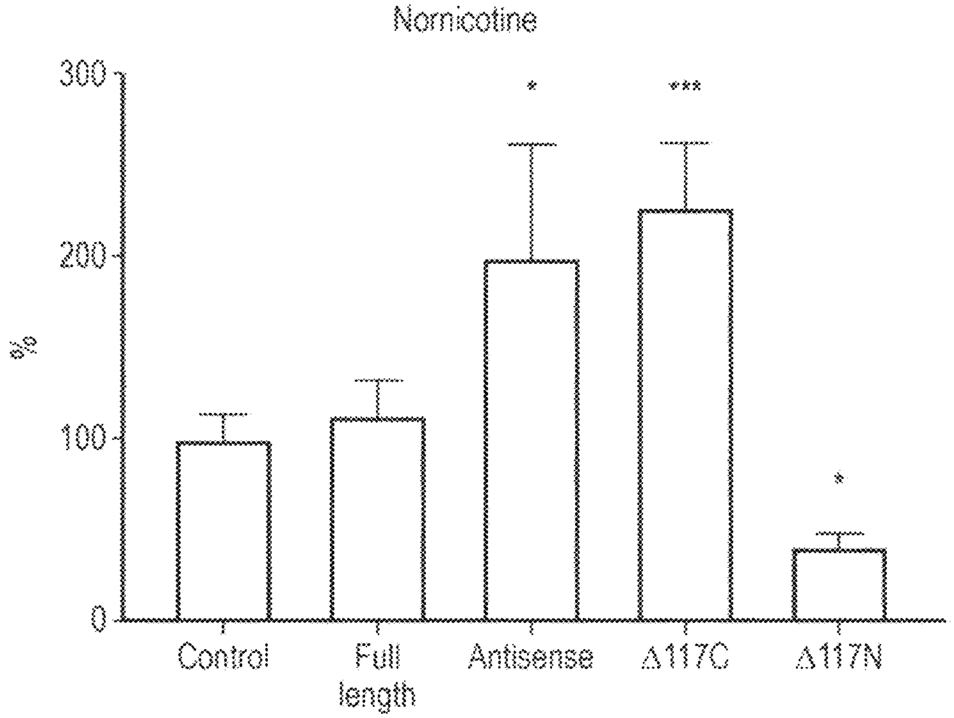
FIG. 3 shows the nornicotine content of 5 week old tobacco leaves which have been modified to express a luciferase control (SEQ ID No. 44), the wild-type sequence (SEQ ID No. 2), an anti-sense (SEQ ID No. 39), cation efflux_Δ117C variant (SEQ ID No. 32) or cation efflux_Δ117N variant (SEQ ID No. 34).

Nornicotine content of 5-week-old TN90 leaves expressing the Indicated constructs is shown in FIG. 3. The nornicotine content is represented relative to a luciferase control (SEQ ID No. 44) and results comprise three biological replicates analysed by t-test. Values are shown as means±SEM. Asterisks indicate statistical significance of P value 0.05.

Conclusions

Figure 4B:
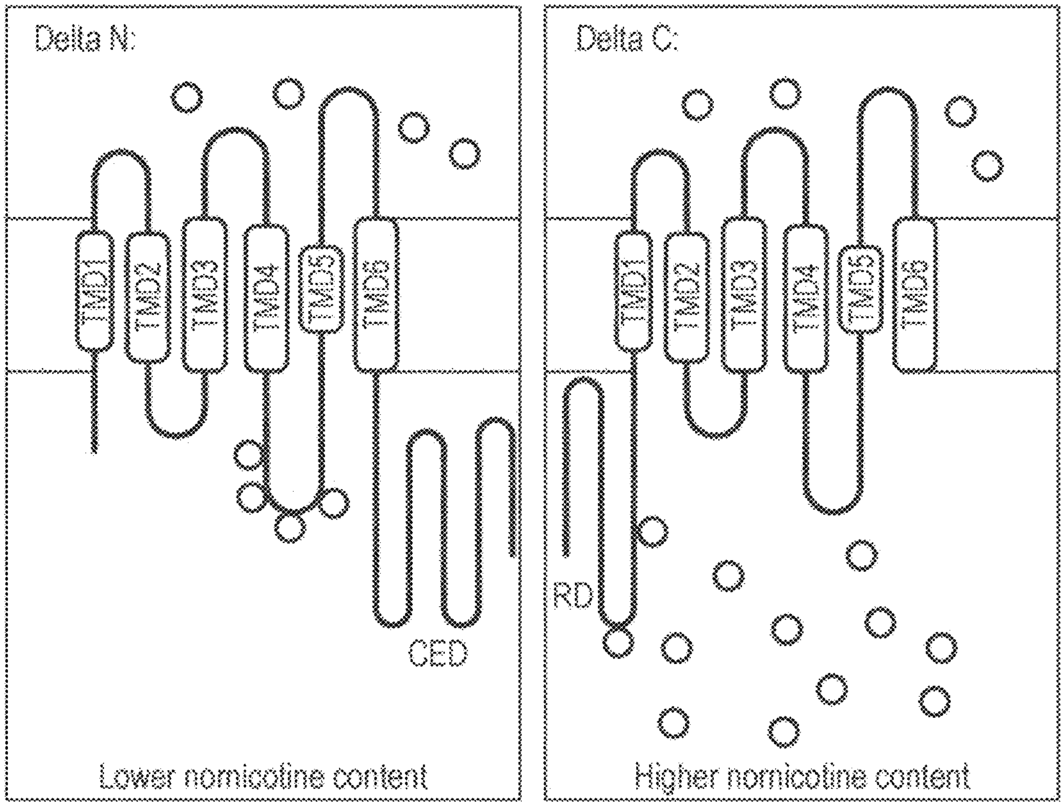
FIG. 4*b* shows a schematic of a proposed mechanism for cation efflux_Δ117C and cation efflux_Δ117N expression.

Deletion of the N-terminal domain results in a decrease in nornicotine content. A proposed mechanism for cation efflux_Δ117C and cation efflux_Δ117N expression is shown in FIG. 4.

Example 3

In order to determine the ligand transported by SEQ ID No.3, 3D modelling of the protein structure was performed using Phyre2 (Kelley L A et al. Nature Protocols 10, 845-858 (2015) incorporated herein by reference) and Swiss-Model. Phyre2 uses the alignment of Hidden Markov Models (HMM) via HHsearch (Soding, J. Bioinformatics 21, 951-960 (2005) incorporated herein by reference) to significantly determine accuracy of alignment and detection rate. Material and methods used by Swiss-Model are described on swissmodel.expasy.org Results Protein modelling using Phyre$^2$ indicated Zinc transport with 100% confidence. Protein modelling using evolutionary related structures matching SED ID No. 3 indicates two Zn ion binding sites upon formation of homodimers (Swiss-Model, see for example, FIG. 4*c*).

Conclusions

These results indicate that SEQ ID No.3 is likely to be involved in zinc efflux.

Example 4

To assess the correlation between the substrate of the identified metal transporter and nornicotine content in planta, transgenic tobacco plants overexpressing the wild type cation efflux (encoded by SEQ ID No. 2), cation efflux Δ117C variant (SEQ ID No. 32), and cation efflux Δ117N variant (SEQ ID No. 34) were treated with various concentrations of the substrate metal: Zn (3 mM, 5 mM, 10 mM), as well as Cd (70 μM, 100 μM, 150 μM), or Ni (50 μM, 300 μM, 1 mM) and nornicotine levels were measured as described in Example 2.

Results

Figure 68:
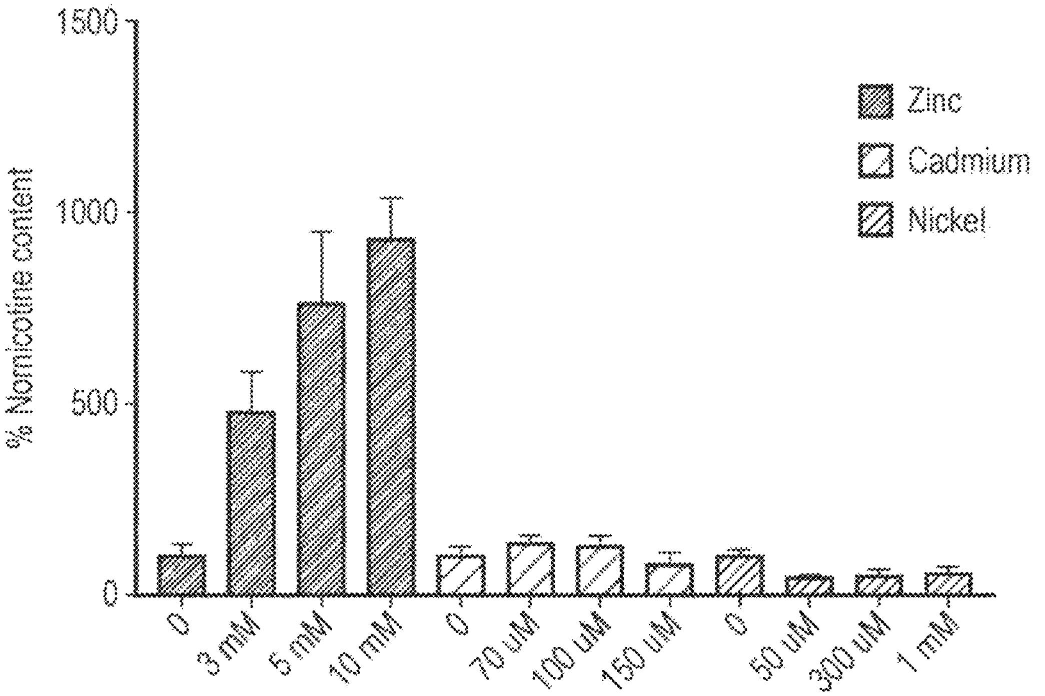
FIG. 68 shows the nornicotine content of tobacco plants treated with the indicated concentrations of zinc, cadmium, or nickel.

The nornicotine content of tobacco plants treated with the indicated concentrations of zinc, cadmium or nickel is shown in FIG. 68.

Zinc treatment induces an increase in nornicotine levels. This effect is reverted upon expression of a constitutive high affinity Δ117N zinc transporter as shown in FIGS. 69*a-c*.

Conclusions

Zinc levels correlate with nornicotine levels, indicating that zinc acts as a regulator in nicotine conversion. This is further evidenced by the insensitivity to zinc and the reduced symptoms to zinc treatment when expressing a constitutive high affinity Δ117N zinc transporter, which detoxifies cytoplasmic zinc ions via efflux.

Example 5

Since zinc acts as catalytic or structural cofactor for many proteins, depletion of intracellular zinc content, resulting in zinc deficiency, induces retarded growth and apoptosis in severe cases (Siklar et al., 2003 J Trop Pediatr. 49(3):187-8; Eide 2009 Journal of Biological Chemistry 10; 284(28): 18565-18569). Zinc starvation is reported to strongly impair yeast growth and induces autophagy (Kawamata et al. 2017 J Biol Chem. 2017 May 19; 292(20):8520-8530).

To confirm that Δ117N acts as a constitutive high affinity zinc transporter, the cation efflux protein, the Δ117C and the Δ117N variants according to the present invention were engineered into yeast and the colony growth was monitored.

Yeast

For yeast expression, BY4742 strain is transformed by means of a chemical method.

Cloning

Cation Efflux Yeast Expression Vector

The gene sequence (SEQ ID No. 2) was amplified from a Gateway™ compatible cDNA library using In-Fusion PCR primers (SEQ ID No. 50 and SEQ ID No. 51), which allow In-Fusion cloning into a pYES2 vector (pYES3/UT.1 [SEQ ID No. 52]) (Thermo Fisher Scientific). Prior to In-Fusion cloning the vector is digested with HindIII and BamHI restriction enzymes (Promega).

Cation Efflux_Δ117C Yeast Expression Vector

The Cation efflux_Δ117C yeast expression vector was generated by In-Fusion cloning using the GDB-Cation efflux expression vector as template and In-Fusion PCR primers (SEQ ID No. 53 and SEQ ID No. 54), which allow In-Fusion cloning into a pYES2 vector (SEQ ID No. 55). Prior to In-Fusion cloning the vector is digested with HindIII and BamHI restriction enzymes (Promega).

Cation Efflux_Δ117N Yeast Expression Vector

The Cation efflux_Δ117N yeast expression vector was generated by In-Fusion cloning using the GDB-Cation efflux expression vector as template and In-Fusion PCR primers (SEQ ID No. 56 SEQ ID No. 57), which allow In-Fusion cloning into a pYES2 vector (SEQ ID No. 55). Prior to In-Fusion cloning the vector is digested with HindIII and BamHI restriction enzymes (Promega).

Activity of a cation efflux protein is measured using a yeast metal tolerance assay.

Yeast Metal Tolerance Assays

Yeast wild type strains were transformed with the constructs of interest. Yeast transformation was performed using S.c. EasyComp™ Transformation Kit (Thermo Fisher).

Positive colonies were selected on synthetic dropout (SD) plates containing the appropriate selective markers. Yeast strains expressing empty vector, wild-type cation transporter (Seq ID No. 2), or mutated variants (Δ117C and Δ117N) were pre-cultured in SD liquid medium containing the appropriate selective markers at 28° C. for 16 h. The optical density was normalized to 0.5, and the strains were grown for 4 hours with selective media+galactose 2% to induce gene expression 5 μL of three 10-fold dilutions of the culture (of optical density at 600 nm of 0.005 0.0005, and 0.00005) are spotted onto SD-agar plates containing the appropriate selective markers, galactose, and ZnCl2 (3 mM and 5 mM)

Results

Figure 70:
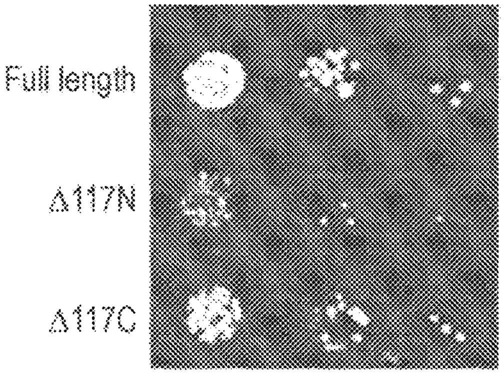
FIG. 70 shows the expression of Δ117N metal efflux variant induces growth retardation in yeast.

Growth of wild type yeast expressing the indicated constructs is shown in FIG. 70.

Conclusions

Expression of the Δ117N cation efflux variant in yeast leads to reduced growth. The Δ117N cation efflux variant is therefore identified as a deregulated, constitutive high affinity transporter.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A tobacco plant or part thereof or tobacco plant propagation material:

which has been modified to achieve a reduction in nornicotine compared with an unmodified tobacco plant or part thereof or tobacco plant propagation material, wherein the modified tobacco plant or part thereof or tobacco plant propagation material comprises a deregulated zinc cation efflux protein which results in said reduction in nornicotine, and wherein the deregulated zinc cation efflux protein comprises the amino acid sequence of SEQ ID NO:33 or a sequence which has at least 95% sequence identity thereto.

2. The tobacco plant or part thereof or plant propagation material according to claim 1, wherein the plant is from the species *Nicotiana tabacum* or *Nicotiana rustica*.

3. A harvested leaf or a cut harvested leaf of the tobacco plant according to claim 1.

* * * * *

SEQUENCE LISTING

```
<160> NUMBER OF SEQ ID NOS: 60

<210> SEQ ID NO 1
<211> LENGTH: 3406
<212> TYPE: DNA
<213> ORGANISM: Artificial Sequence
<220> FEATURE:
<223> OTHER INFORMATION: genomic sequence encoding protein of the
      invention

<400> SEQUENCE: 1

attatttttt cctatataaa cattaatcat acgactacaa ccagaggaat taatcgttca      60
```

```
aatataacta actactcctc taaacatgga gataagtcgc agcaatgtta gtggtggtgg    120
cggcagcggc ggcgctctgg acgacagttt tagcagtttt aggacggaac tgctgtctcc    180
ggctgctcag gcggtggtgg atcagtcgtc ttcgtcggcg tcatggagac ttaacattag    240
cgaattccgt cttcccgaac gaagccgctc ctcctccgat catcactcct ttagtgtccg    300
tcgtctactt cccactccca gtatgtgtat atatatatat atatatatat atattcctca    360
cttcacttgt ctttacaatg tattaaacct ttctacttcc tttgaacttc ttcggatttg    420
ttaattaatg ttaagagatt tgagggaagc cttggcttac tggtaaagtg atggcatgtg    480
acttcccagt cacatgttta agccgtgtta aagttgttgg catgtgacct cctggtcaca    540
ggtttaagcc gtggaaatag actttcgtag aaatacaggt aaagaaatgc aggtaaggtt    600
gcgtacttgt gatctggccc tttctcgaat ctcgcacata aatgaagctt agtgcctttt    660
tttaaggtta atagtttttt agtcagaata gtaccaaaat tagactagaa gattcatagt    720
tctaatattg gtaaaccaaa atttacgact tatatatatt tacataaatg ggcgaggaat    780
ctttattctt atcatgccat agtccatgga acgtactgag cctttaattt ctatttgcta    840
ttgctgggaa atgaatcaga tggccaattt tcttatgtat acatattctc actggtatgg    900
gatcgaatcg gcgacagaac tccaagttag aggattcttt ttcattaagt cattacttat    960
tttaagttca agtaacagca ctggaagttc aactaagagt tgataaacat gatcagtgaa   1020
actcacaatt gtttgtccta aattttggat ctttacttgg aaagtgtaga tgttagtata   1080
tgcttatgct atactggcca gcagtgctcg taacagtatc tatgagtact aataggctta   1140
tgctatatta ctgtatttat aatgctaatc agctaatgag atatgataac tcatatatga   1200
caactacagt aggaaattca gataaccata ttcatttttt cagtagtctc agttttgagt   1260
tttgcttttc ccttgcctga gtttacctaa tggaatcatt tgaaattcat ccgtagggaa   1320
acaaggtaaa attgctgaat actacaaaaa acaagaaagg ctgcttgaag ggttcaatga   1380
gatggacacc attaatgaat ctggttgttt acctggaagt ctaactgagg tgtgtttctg   1440
gaatctggat actgttttca attgatgata agtatgtgaa tttttgtatc gaccgatcat   1500
gtttgttcag gatgaaatga agcagcttgc aagaagtgaa aggatggcta ttcatttatc   1560
aaacatggct aatgtggttc ttttcattgc aaaaatctac gcttctattg agagcagatc   1620
tttggctgta atcgcgtcaa cgttggactc cctcttagac ctcttatcag ggtttatact   1680
gtggttcact tctcatgcca tgaaaaatcc aaaccagtat cactatccta ttggaaaaaa   1740
gaggatgcag ccattggtga gtcttcaaat atatgtgaca tcccttaaaa gaattatctc   1800
tggcatttgt tctgtttcgt gtctgcgata aaatgacctt aatgttcaat tcatggatca   1860
tattttacct tgtttctgta gaaccctttt tactcattag atgcaatttg ttcagggtat   1920
tattgttttt gcatctgtaa tggcgacact aggattacaa atattgttcg agtcagctaa   1980
agaactcata actaaggtat gtgaattgct tcacttcaac tatcctgaga attttcagag   2040
cagcaggttc ttatggttag tagagttttg agtttctaaa atcttttaca tcaagacaaa   2100
aaaaaacatg caatttatag gaaacaagaa gacgaaaaac gggttgagtt actactgaaa   2160
tgaagttgta gccaaaccag ttaggccaaa gatgtttaca taagataaat taggctactg   2220
tatactacct aataaaaagg gactggtttt gatatttcta ctgatgttgc atagctaagt   2280
gaagattaac tcgcatagtg ctacttcaat tgtaggatat agacttgtaa cttactgcaa   2340
tttcactaac aattgcatta cccttgacat cttaatctac gtttgttgtt tcggtggttc   2400
```

```
tatgcttacg atcagtctcg ccctgagatg gaccatgaga aggaaaaatg gacgattggt   2460

attatggtct ctgtcactat ggtcaagttt ctgcttatgg tctactgtcg aaggttcaaa   2520

aacgaaatcg taagagccta tgctcaagat catttctttg atgtcatcac caactcagtt   2580

ggattagtga ctgctgtctt agcagtccga ttctactggt ggattgatcc tacgggagct   2640

ataattgtga gttcacaatc acaactcaaa tatttcaatt agtaagcttg taaatatata   2700

ctccaacctt gtttcacact gctggtgatg ttaagagtct aatacatctt gcatattcag   2760

atagctatgt acacaattag cacgtgggcg aagacagtgg cagaaaatgt ctggtcactc   2820

attggaagaa cagctccacc agatttcttt acgaaattaa cctatcttat atggaatcat   2880

cacgaagaga tcaagcacat tgatactgtt cgagcatata cttttggtgc tcattatttt   2940

gtagaggttg atatagtgtt gccagaggac atgctgttga acaaggcaca taatattggt   3000

gagacactgc aagaaaaatt ggagcaactc cctgaagttg agcgagcttt tgttcatata   3060

gacttcgagt tcactcacag gccagaacac aaaactatgg tataatgaca ccagaattta   3120

aactctatgt gttcaacctt aaagattttt agcgttgaat caatcatatt tttaaagtta   3180

tgggttcatt tctactattt gttgcaattt taataatttt tacgcataaa tttgtatttc   3240

gcgtcgaaag tactaggttc acatgaatcc ggtatcaaag ggctagatcc gccccctgac   3300

tacacatcat ttacggtgtt tctttttgta actcaaaata attttaatgg tgcttcttag   3360

agttgaatct gtgaattagt cgcaccttta aggcttatga gatggg                  3406
```

```
<210> SEQ ID NO 2
<211> LENGTH: 1251
<212> TYPE: DNA
<213> ORGANISM: Artificial Sequence
<220> FEATURE:
<223> OTHER INFORMATION: cDNA sequence encoding protein of the invention

<400> SEQUENCE: 2

atggagataa gtcgcagcaa tgttagtggt ggtggcggca gcggcggcgc tctggacgac     60

agttttagca gttttaggac ggaactgctg tctccggctg ctcaggcggt ggtggatcag    120

tcgtcttcgt cggcgtcatg gagacttaac attagcgaat tccgtcttcc cgaacgaagc    180

cgctcctcct ccgatcatca ctcctttagt gtccgtcgtc tacttcccac tcccaggaaa    240

caaggtaaaa ttgctgaata ctacaaaaaa caagaaaggc tgcttgaagg gttcaatgag    300

atggacacca ttaatgaatc tggttgttta cctggaagtc taactgagga tgaaatgaag    360

cagcttgcaa gaagtgaaag gatggctatt catttatcaa acatggctaa tgtggttctt    420

ttcattgcaa aaatctacgc ttctattgag agcagatctt tggctgtaat cgcgtcaacg    480

ttggactccc tcttagacct cttatcaggg tttatactgt ggttcacttc tcatgccatg    540

aaaaatccaa accagtatca ctatcctatt ggaaaaaaga ggatgcagcc attgggtatt    600

attgtttttg catctgtaat ggcgacacta ggattacaaa tattgttcga gtcagctaaa    660

gaactcataa ctaagtctcg ccctgagatg gaccatgaga aggaaaaatg gacgattggt    720

attatggtct ctgtcactat ggtcaagttt ctgcttatgg tctactgtcg aaggttcaaa    780

aacgaaatcg taagagccta tgctcaagat catttctttg atgtcatcac caactcagtt    840

ggattagtga ctgctgtctt agcagtccga ttctactggt ggattgatcc tacgggagct    900

ataattatag ctatgtacac aattagcacg tgggcgaaga cagtggcaga aaatgtctgg    960

tcactcattg gaagaacagc tccaccagat ttcttacga aattaaccta tcttatatgg   1020

aatcatcacg aagagatcaa gcacattgat actgttcgag catatacttt tggtgctcat   1080
```

tattttgtag aggttgatat agtgttgcca gaggacatgc tgttgaacaa ggcacataat 1140
attggtgaga cactgcaaga aaaattggag caactccctg aagttgagcg agcttttgtt 1200
catatagact tcgagttcac tcacaggcca gaacacaaaa ctatggtata a 1251

<210> SEQ ID NO 3
<211> LENGTH: 416
<212> TYPE: PRT
<213> ORGANISM: Artificial Sequence
<220> FEATURE:
<223> OTHER INFORMATION: polypeptide sequence of protein of the invention

<400> SEQUENCE: 3

Met Glu Ile Ser Arg Ser Asn Val Ser Gly Gly Gly Gly Ser Gly Gly
1 5 10 15

Ala Leu Asp Asp Ser Phe Ser Ser Phe Arg Thr Glu Leu Leu Ser Pro
20 25 30

Ala Ala Gln Ala Val Val Asp Gln Ser Ser Ser Ser Ala Ser Trp Arg
35 40 45

Leu Asn Ile Ser Glu Phe Arg Leu Pro Glu Arg Ser Arg Ser Ser Ser
50 55 60

Asp His His Ser Phe Ser Val Arg Arg Leu Leu Pro Thr Pro Arg Lys
65 70 75 80

Gln Gly Lys Ile Ala Glu Tyr Tyr Lys Lys Gln Glu Arg Leu Leu Glu
85 90 95

Gly Phe Asn Glu Met Asp Thr Ile Asn Glu Ser Gly Cys Leu Pro Gly
100 105 110

Ser Leu Thr Glu Asp Glu Met Lys Gln Leu Ala Arg Ser Glu Arg Met
115 120 125

Ala Ile His Leu Ser Asn Met Ala Asn Val Val Leu Phe Ile Ala Lys
130 135 140

Ile Tyr Ala Ser Ile Glu Ser Arg Ser Leu Ala Val Ile Ala Ser Thr
145 150 155 160

Leu Asp Ser Leu Leu Asp Leu Leu Ser Gly Phe Ile Leu Trp Phe Thr
165 170 175

Ser His Ala Met Lys Asn Pro Asn Gln Tyr His Tyr Pro Ile Gly Lys
180 185 190

Lys Arg Met Gln Pro Leu Gly Ile Ile Val Phe Ala Ser Val Met Ala
195 200 205

Thr Leu Gly Leu Gln Ile Leu Phe Glu Ser Ala Lys Glu Leu Ile Thr
210 215 220

Lys Ser Arg Pro Glu Met Asp His Glu Lys Glu Lys Trp Thr Ile Gly
225 230 235 240

Ile Met Val Ser Val Thr Met Val Lys Phe Leu Leu Met Val Tyr Cys
245 250 255

Arg Arg Phe Lys Asn Glu Ile Val Arg Ala Tyr Ala Gln Asp His Phe
260 265 270

Phe Asp Val Ile Thr Asn Ser Val Gly Leu Val Thr Ala Val Leu Ala
275 280 285

Val Arg Phe Tyr Trp Trp Ile Asp Pro Thr Gly Ala Ile Ile Ile Ala
290 295 300

Met Tyr Thr Ile Ser Thr Trp Ala Lys Thr Val Ala Glu Asn Val Trp
305 310 315 320

Ser Leu Ile Gly Arg Thr Ala Pro Pro Asp Phe Leu Thr Lys Leu Thr

```
                325                 330                 335

Tyr Leu Ile Trp Asn His His Glu Glu Ile Lys His Ile Asp Thr Val
            340                 345                 350

Arg Ala Tyr Thr Phe Gly Ala His Tyr Phe Val Glu Val Asp Ile Val
        355                 360                 365

Leu Pro Glu Asp Met Leu Leu Asn Lys Ala His Asn Ile Gly Glu Thr
    370                 375                 380

Leu Gln Glu Lys Leu Glu Gln Leu Pro Glu Val Glu Arg Ala Phe Val
385                 390                 395                 400

His Ile Asp Phe Glu Phe Thr His Arg Pro Glu His Lys Thr Met Val
                405                 410                 415


<210> SEQ ID NO 4
<211> LENGTH: 3691
<212> TYPE: DNA
<213> ORGANISM: Nicotiana tabacum

<400> SEQUENCE: 4

ataaacatta atcatacgac tataaccaga ggaattaatt gttcaaatat tagaaactac      60

tcctctaaac atggagatga gtcggagtga cgttagtggt ggcggcggca gcggcggcgc     120

tttggacgac agttttagca gttttaggac ggaactactg tctccggctg ctcaggcggt     180

ggtggatcag tcgtcttctt cggcgtcatg gagacttaac attagcgaat tccgtcttcc     240

cgaacgaagc cgctcctcct ccgatcatca cacctttagt gtccgtcgcc tacttcccac     300

tcccagtatg tatgtgtata tatatatata ttatattcct ctcttcactt gtctttacaa     360

tgtattaaac ctttctactc tttgaacttc ttcggctttg ttaattagtg ttgagagttt     420

tgaaaggtag cctgacgtaa ctggtaaagt tgtcgccatg tgacctcctg gtcacaggtt     480

agaaatagtc tcttgcgtaa atgcagggta tgactgcgta caatatttat atgaaataaa     540

tatgaagtac aagaacccag actctctcaa aacaccacgc atagctggaa cttagtgcac     600

tagccacgct ttttaatgtt aagagttttc tactcagaat agtaccaaaa ttagactaga     660

agattcatag ttctaatatt ggcaaaccaa aatttacgac ttatatatat ttacataaat     720

gggcgatgaa tctttattct tatcatgcca tagtccatgg aacatactaa gcctttaatt     780

tctactccct ccgtttcaat tcatgtgaac tcatttgatc gggcacggaa tttaagaaaa     840

gagagaaaac ttttgaactt ctggtgtaaa tgaggcacat atattttatg tggctataaa     900

ttattgcata aagataaatt gtttccaaat agggaaatga ctcattcttt ttggtatgta     960

ctaaaaagga aatagggaaa cggagggagt atttgctatt gctgggaaat gaatcagatg    1020

gccaattttc ttatgtatat atacatattc tcactggcat gggatcaaat cggcgacaga    1080

actccaagtt agaggactct ttttcatgaa gtcattactt aatttaagtt caagtaacag    1140

cagtggaagt tcaactaaga gttgataaac atgatcagtg aaactcacaa ttgttcgtcc    1200

aaatttcgga tattcacttg gaaggtgtag atgttagtat atgcttatgc tatattggcc    1260

agcagtactc gtagcagtat ctatgagtac taaaatgctt atgctatatt actgtatttg    1320

taatgttaat gagatatgat tactcatata tatgacaact acagggggag attcagataa    1380

ccaagttcat ttcagtctgt aattcagtct cagttttgag ttttgctttt ctcttgggtg    1440

agtttacctg atgaaattat tttaaattca tccgtaggaa aacaaggtaa aattgctgaa    1500

tactacaaaa aacaagaaag gctgcttgaa gggttcaatg agatggacac cattaatgaa    1560

tctggctgtt tacctggaag tctaactgag gttggtttct gaaatctgga tactatttgc    1620
```

```
aattgacgaa taagtatgtg aatttttgta tcgaccgacc atgtttttc aggatgaaat   1680
gaagcagcta gcaaggagtg aaaggatggc tattcattta tcaaacatgg ctaatgtggt   1740
tcttttcatt gcaaaaatct acgcttctat tgagagcaga tctttggctg taatcgcgtc   1800
aacgttggac tccctcttag acctcttatc agggtttata ctgtggttca cttctcatgc   1860
catgaaaaat ccaaaccagt atcactatcc tattggaaaa aagaggatgc agccagtggt   1920
gagtcttcaa atatatgtaa catcctgaaa ttattatctc tggcttttgt tctgtcttcg   1980
tttatttgca aaaatgacct taatgttcaa tacatagatc acattttaca tttgaccttc   2040
acattttttc ctttgctgtt gctgatacat tgtctctttc cttcttgtgc cgagggtcta   2100
ccgaaaacag cctctctact cctccggagt aggggtaagg tctgcgtaca cactaccctc   2160
cccagactca acttgtggga tctcattggg ttgttgttgt ctgtagaact gttttataga   2220
tcacatttta ccttgtttcc gttgaaccgt ttttactcat tagttgcatt ttcttcaggg   2280
tattattgtt tttgcatctg tgatggcgac actaggatta caaatgttgt tcgagtctgc   2340
taaggaactc ataactaagg tatgtgaatt ggttcacctc aactatcctg agaattttca   2400
gagcagcagg ttcttatggc tgtattagta gagttttgag tttctataat ctttaacatc   2460
aagatgaaaa accatgcaat ttataggaaa caagaagacg aaaaaggggt tgagttacta   2520
ctgaaatgaa gttgcagtca aaacagttaa gccaaagatg tttacataag ataaattagg   2580
ctactgtata ctactaataa aagtgactgg ttttgatatt tctattgatg ttgcatagct   2640
taataaagat tatctcgcat agtgctactt ctattgtagg atatagactt gtaagttatt   2700
gcattttcac taacaattgc attacgcttg acatcttaac ctatgtttgt tgtttcgatg   2760
gttctatgct tacgatcagt ctcgccctga gatggatcat gagaaggaaa aatggacaat   2820
tgggattatg gtctctgtca ctatggtcaa gtttctgctt atgatctact gtcgaaggtt   2880
caaaaacgaa atcgtaagag cctatgctca agatcatttc tttgatgtca tcactaactc   2940
agttggatta gtgacggctg tcttagcagt acgattctac tggtggattg atcctacagg   3000
agctataatt gtgagttcac aatcacaact caaaaactta cacaattagc aatcacactt   3060
ctggtaatgt caatagtcta atatattttg catatccaga tagctgtgta cacaattagc   3120
acgtgggcga agacagtggc tgaaaatgtc tggtcgctca ttggaagaac agctccacca   3180
gattttctta cgaaattaac ctatcttata tggaatcatc acgaagagat caagcacatt   3240
gatactgtta gagcatatac ttttggtgcg cattactttg tggaggttga tatagtgttg   3300
ccagaggaca tgctgttgaa tcaggcacat aatattggtg agacactgca agaaaaattg   3360
gagcaactcc ctgaagttga gcgagctttt gttcatatag actttgagtt cactcacagg   3420
ccagaacaca aaaccatggt ataatgacat agtggttgca acaagtacgc acataggcgg   3480
atccaagctt taaactctat acgtacaacc tttaagattt ttagcgttga actgatcata   3540
tttttaaagt tatggcttca tatctactac tatttgttgc aattttaata aattttttta   3600
cataaatttg tattctacat cgaaagtact gggttcagat aaacttggtg accaaagggc   3660
tggatccgcc cctgactaca cattatttac a                                 3691
```

<210> SEQ ID NO 5
<211> LENGTH: 1251
<212> TYPE: DNA
<213> ORGANISM: Nicotiana tabacum

<400> SEQUENCE: 5

```
atggagatga gtcggagtga cgttagtggt ggcggcggca gcggcggcgc tttggacgac     60
```

```
agttttagca gttttaggac ggaactactg tctccggctg ctcaggcggt ggtggatcag    120

tcgtcttctt cggcgtcatg gagacttaac attagcgaat tccgtcttcc cgaacgaagc    180

cgctcctcct ccgatcatca cacctttagt gtccgtcgcc tacttcccac tcccagaaaa    240

caaggtaaaa ttgctgaata ctacaaaaaa caagaaaggc tgcttgaagg gttcaatgag    300

atggacacca ttaatgaatc tggctgttta cctggaagtc taactgagga tgaaatgaag    360

cagctagcaa ggagtgaaag gatggctatt catttatcaa acatggctaa tgtggttctt    420

ttcattgcaa aaatctacgc ttctattgag agcagatctt tggctgtaat cgcgtcaacg    480

ttggactccc tcttagacct cttatcaggg tttatactgt ggttcacttc tcatgccatg    540

aaaaatccaa accagtatca ctatcctatt ggaaaaaaga ggatgcagcc agtgggtatt    600

attgtttttg catctgtgat ggcgacacta ggattacaaa tgttgttcga gtctgctaag    660

gaactcataa ctaagtctcg ccctgagatg gatcatgaga aggaaaaatg gacaattggg    720

attatggtct ctgtcactat ggtcaagttt ctgcttatga tctactgtcg aaggttcaaa    780

aacgaaatcg taagagccta tgctcaagat catttctttg atgtcatcac taactcagtt    840

ggattagtga cggctgtctt agcagtacga ttctactggt ggattgatcc tacaggagct    900

ataattatag ctgtgtacac aattagcacg tgggcgaaga cagtggctga aaatgtctgg    960

tcgctcattg gaagaacagc tccaccagat tttcttacga aattaaccta tcttatatgg   1020

aatcatcacg aagagatcaa gcacattgat actgttagag catatacttt tggtgcgcat   1080

tactttgtgg aggttgatat agtgttgcca gaggacatgc tgttgaatca ggcacataat   1140

attggtgaga cactgcaaga aaaattggag caactccctg aagttgagcg agcttttgtt   1200

catatagact ttgagttcac tcacaggcca gaacacaaaa ccatggtata a            1251
```

<210> SEQ ID NO 6
<211> LENGTH: 416
<212> TYPE: PRT
<213> ORGANISM: Nicotiana tabacum

<400> SEQUENCE: 6

```
Met Glu Met Ser Arg Ser Asp Val Ser Gly Gly Gly Gly Ser Gly Gly
1               5                   10                  15

Ala Leu Asp Asp Ser Phe Ser Ser Phe Arg Thr Glu Leu Leu Ser Pro
            20                  25                  30

Ala Ala Gln Ala Val Val Asp Gln Ser Ser Ser Ser Ala Ser Trp Arg
        35                  40                  45

Leu Asn Ile Ser Glu Phe Arg Leu Pro Glu Arg Ser Arg Ser Ser Ser
    50                  55                  60

Asp His His Thr Phe Ser Val Arg Arg Leu Leu Pro Thr Pro Arg Lys
65                  70                  75                  80

Gln Gly Lys Ile Ala Glu Tyr Tyr Lys Lys Gln Glu Arg Leu Leu Glu
                85                  90                  95

Gly Phe Asn Glu Met Asp Thr Ile Asn Glu Ser Gly Cys Leu Pro Gly
            100                 105                 110

Ser Leu Thr Glu Asp Glu Met Lys Gln Leu Ala Arg Ser Glu Arg Met
        115                 120                 125

Ala Ile His Leu Ser Asn Met Ala Asn Val Val Leu Phe Ile Ala Lys
    130                 135                 140

Ile Tyr Ala Ser Ile Glu Ser Arg Ser Leu Ala Val Ile Ala Ser Thr
145                 150                 155                 160
```

```
Leu Asp Ser Leu Leu Asp Leu Leu Ser Gly Phe Ile Leu Trp Phe Thr
                165                 170                 175

Ser His Ala Met Lys Asn Pro Asn Gln Tyr His Tyr Pro Ile Gly Lys
            180                 185                 190

Lys Arg Met Gln Pro Val Gly Ile Ile Val Phe Ala Ser Val Met Ala
        195                 200                 205

Thr Leu Gly Leu Gln Met Leu Phe Glu Ser Ala Lys Glu Leu Ile Thr
    210                 215                 220

Lys Ser Arg Pro Glu Met Asp His Glu Lys Glu Lys Trp Thr Ile Gly
225                 230                 235                 240

Ile Met Val Ser Val Thr Met Val Lys Phe Leu Leu Met Ile Tyr Cys
                245                 250                 255

Arg Arg Phe Lys Asn Glu Ile Val Arg Ala Tyr Ala Gln Asp His Phe
            260                 265                 270

Phe Asp Val Ile Thr Asn Ser Val Gly Leu Val Thr Ala Val Leu Ala
        275                 280                 285

Val Arg Phe Tyr Trp Trp Ile Asp Pro Thr Gly Ala Ile Ile Ile Ala
    290                 295                 300

Val Tyr Thr Ile Ser Thr Trp Ala Lys Thr Val Ala Glu Asn Val Trp
305                 310                 315                 320

Ser Leu Ile Gly Arg Thr Ala Pro Pro Asp Phe Leu Thr Lys Leu Thr
                325                 330                 335

Tyr Leu Ile Trp Asn His His Glu Glu Ile Lys His Ile Asp Thr Val
            340                 345                 350

Arg Ala Tyr Thr Phe Gly Ala His Tyr Phe Val Glu Val Asp Ile Val
        355                 360                 365

Leu Pro Glu Asp Met Leu Leu Asn Gln Ala His Asn Ile Gly Glu Thr
    370                 375                 380

Leu Gln Glu Lys Leu Glu Gln Leu Pro Glu Val Glu Arg Ala Phe Val
385                 390                 395                 400

His Ile Asp Phe Glu Phe Thr His Arg Pro Glu His Lys Thr Met Val
                405                 410                 415
```

<210> SEQ ID NO 7
<211> LENGTH: 4523
<212> TYPE: DNA
<213> ORGANISM: Nicotiana tabacum

<400> SEQUENCE: 7

```
acagtttgag cctatttttc ctctcattat atctatgtgt tatctttcct caaaagtatc     60

tttaactaaa cctatcttta gaagagtcct tttgcgtctc cctacttcga cttactagta    120

tacaactata gataaatatc aaaacacaag tacattgtca ttcgtacaaa tatttagtaa    180

caattttcat ggaaatcgtt ggcggtaacg gtggtgatca tggcggcgcc actcatcagc    240

cgttgccgtt gtcgttatct tcctcttcgc cgtcggcgtc gtggaggctg aatatagggg    300

agtttcgtgt ccctgaaaat ggcactgctg atcatcgtca atctttcagt ttacgtcgac    360

tcttacgtcg cccttctagt aattttcctt ccttttatct tttatatttc ttctatgata    420

ttgtttgcta gctttattgc acttgtcgaa aaaaaaaaaa ctacttggaa atcattgcat    480

tttaatggta tttgaatcca ttcaaccatc tcctagcaaa ttactcccac cgttttattt    540

tatgtgaatt tgtttgactg aaaacaaaat ttaagaaagg aattactact ttggaacttg    600

tagtattaaa catttcacca ccttaatttg tatgtaaaat aaaaataatt aatgttaaat    660

tatttctaaa tatagaaaga tcgtcttttt ttgaaagcaa gattaaaaaa taattgtgtg    720
```

```
ttttaagtac aactcacttc aaccaattgt tttaagttct aactttggtt tggatatcct    780
tttttttctt ttgtcttcaa gaactactta actaagaaaa tagtttttat aaattttcta    840
ttacctatct tagttttcag cctgtcaaca tccattattt gtaaggattt tatcttttat    900
cttacaaatc attttcatat atatctctat atatagaaaa acaaggcaaa gtagctgaat    960
attacgagaa gcaagaaagg ttggttgaag ggttcaatga gatggacact gttcatgaat   1020
ctggcttttt acctggaact ctaaccgagg ttcgtctctt ttcctcaata ataaactgat   1080
aatgaaagaa tttatacgtc acttaaaaat tcacacaaga tatgatatat aggccggtgc   1140
ataaagtatt ctgtatccac gcagggtctt ggaagtatca ccgcaccacc tcaagaagtg   1200
tgatgtagac agccgaccta atgcaaatat tagtggttgc ttttacggct cgaacccgtg   1260
acctgtaggt cacacgacaa ctttattatt tttttagtca tgagtctcat gacctatatg   1320
tcacttaaaa atatattact gttaaatatt tataataaga aaaattaata acctggaaaa   1380
taagtcaaac agcctcgtag gatatatata ttaatagtgt aatttttttt ttatagtcaa   1440
tatttggcct cagtatcaca gcttggggat atgatgtcgg ggcatgtgtc ccctaacttt   1500
tctaagttta atttcctact cttaggaaat gtcaaatttt tggaaatttt gctttagtga   1560
aaattcttct tctccttctt tccttgtaaa agtgtcctac tcttcagaag ttttgtgttt   1620
ttggcataag tttacttgtg ggaggtcaac tttactattt ttcaagttcg ttacttcact   1680
tattatagat ggttagttta agttatcttt caagtgacat atagtagtag aaaattttta   1740
gattgttaat gcataaaagg ttaaaagtta aactcaaaaa aagagcataa cttataaaca   1800
acaattactt tttttaaac ctttgttag gtcacttaac agataattac aagtcacggt   1860
ctataatata taagtgagac tagtaatctt aacaaattct gataacttgc tacaacaggt   1920
caaaatagtc taactaataa agtaggatta atctcacttt tattctctac aactcaatat   1980
ttgtcaggat gaaatgaagc agcttgctaa gagtgagagg atggcaattc atgtatcaaa   2040
catagcaaat gtggttcttt tcattgcaaa aatctatgct tctattgcaa gtagatcttt   2100
ggctgtgatt gcatcaactt tggactcact cttagactta ttgtctggat ttattctgtg   2160
gttcactgta tatgcaatga aaaatccaaa ccaataccac tatccaattg gtaaaaagag   2220
aatgcagcct gtggtgagtc ttcaaaaata acgttgtgac attttgatat ttgttacatt   2280
cattctatac tttgtgtcag tctgatatga gttttatagc caaataaaat atttatatgt   2340
aatatttata gggtattatt gtttttgcat cggtgatggc aacccttgga ttacaaatac   2400
tatttgagtc tggtaaagaa ctcatacata aggtacgtga ctcggttctc taaagtcttt   2460
ttttagaaaa aaaaaggaat ttctaaattt aacttttcaa aataatacaa aatgatgaaa   2520
actgttctcc tatatcatga tctttctctt ggacttcaag acgcagttgt ttatgctaca   2580
ttatttggct attagatgaa gtattgacca atatctttat gcacgttagt tgacttttat   2640
gtactcatag tataaaaaag atatttatac aatttggtct tatataacgt gatatatgta   2700
actttgatga taagcattac tccatttgtt taattaatat gacggtattt cactaaatat   2760
ggagttcaag aaacaaaaaa aaaggagact tctgcaactt gtgttcatac atgccatgaa   2820
attttgtggc tataaaatca tgtcattaag gataaaatgc aagatgagga gtaattggta   2880
aatatttagt actatcacag attaaactac actaatgtca gtttattgtt tcttcttgtt   2940
caatgcttat catatcagtc tcgtcctaat acggatcctg agaaggaaaa atggatgatt   3000
gggatcatgg tctctgtcac tgttgttaag tttctgctta tggtttattg tcgaagattc   3060
```

```
aagaatgaaa ttgtaagagc ctatgctcaa gaccatttat ttgatgtcat taccaactct   3120

gttggattag tgactgcagt tttagcaatt cgattctgct ggtggattga tcctacggga   3180

gctatattgg tgagttcaca atcatcactt atacttcttt tgcttttatc tacttattta   3240

ataggcatct cgatgcataa cgtatttccc gttcatacat gattcgggaa aagccgcacc   3300

taaaaggtat gatatagata tcctacccta atgcaagcat taatgattgc tttcacggtt   3360

cgaaccatat agtggtgttc gcatcaactt gcgcagcacc tcaactattt cacttagtac   3420

atgtaatctc tcactaaaaa atttaccgga caccttgtta ctccccaagg ctttggcgtg   3480

tgggaataac ttgtattttt tgtctctact agaaaaggaa tcctaatttc aacctttata   3540

tcaattttat tgatcactaa gtcatactct tgggtgcacg tgcacacaca tacgacacta   3600

catctgtctc aatttactaa gtactatttc ctttttgttt tcttttgtcc tgaaagattg   3660

atatctttat agctttagaa actccaaaca tttatttata tttttatatc aagattgaca   3720

cctttatgta tatatggtat ttctgactta ttaagcatat taaacttcta tgtcagagat   3780

ctcttttatt ttttaaactt catgtctagt caaaggatgc taaaccaatt gtggtggacg   3840

actatcacta aatgattgag caaataaaat gagtagaaat tttcaaagac atccctccaa   3900

attttccatt attattaagg ataacattat gtatttgcag atagcactat acacaattgg   3960

tacgtgggca aagacagtaa tcgaaaatat gcgatcactc atcggaagaa cagctccacc   4020

agaatttctg gcgaaattaa catatcttat atggaatcat cacaaagaaa tcaagcacat   4080

tgatactgtg agagcataca catttggtac aaattacttt gtggaagttg atatagtttt   4140

gccagaggac atgcttctaa gccaagcaca taatattggt gaaacattgc aagaaaaatt   4200

agagcagctt cctgatgttg agagagcttt tgtgcatgtt gatttcgagt tcactcatag   4260

accagagcac aagactatgg tctaatgaca taaataaact aggtaattaa taattaaaaa   4320

ttagtttgag cttgaacttt gttgttgggc actgtttcct tgcacctgga gtagtaactt   4380

accaaaaaaa aaagttcttt aatgtggaga acccaaccat gttgaaactt gttgaatttg   4440

cattctcaaa atttatgtaa cctaatgttt atttttaact caagatgcct catgagtcat   4500

gaacgacaag tatataccta cgt                                           4523
```

<210> SEQ ID NO 8
<211> LENGTH: 1206
<212> TYPE: DNA
<213> ORGANISM: Nicotiana tabacum

<400> SEQUENCE: 8

```
atggaaatcg ttggcggtaa cggtggtgat catggcggcg ccactcatca gccgttgccg     60

ttgtcgttat cttcctcttc gccgtcggcg tcgtggaggc tgaatatagg ggagtttcgt    120

gtccctgaaa atggcactgc tgatcatcgt caatctttca gtttacgtcg actcttacgt    180

cgcccttcta aaaaacaagg caaagtagct gaatattacg agaagcaaga aaggttggtt    240

gaagggttca atgagatgga cactgttcat gaatctggct ttttacctgg aactctaacc    300

gaggatgaaa tgaagcagct tgctaagagt gagaggatgg caattcatgt atcaaacata    360

gcaaatgtgg ttcttttcat tgcaaaaatc tatgcttcta ttgcaagtag atctttggct    420

gtgattgcat caactttgga ctcactctta gacttattgt ctggatttat tctgtggttc    480

actgtatatg caatgaaaaa tccaaaccaa taccactatc caattggtaa aaagagaatg    540

cagcctgtgg gtattattgt ttttgcatcg gtgatggcaa cccttggatt acaaatacta    600

tttgagtctg gtaaagaact catacataag tctcgtccta atacggatcc tgagaaggaa    660
```

```
aaatggatga ttgggatcat ggtctctgtc actgttgtta agtttctgct tatggtttat    720

tgtcgaagat tcaagaatga aattgtaaga gcctatgctc aagaccattt atttgatgtc    780

attaccaact ctgttggatt agtgactgca gttttagcaa ttcgattctg ctggtggatt    840

gatcctacgg gagctatatt gatagcacta tacacaattg gtacgtgggc aaagacagta    900

atcgaaaata tgcgatcact catcggaaga acagctccac cagaatttct ggcgaaatta    960

acatatctta tatggaatca tcacaaagaa atcaagcaca ttgatactgt gagagcatac   1020

acatttggta caaattactt tgtggaagtt gatatagttt tgccagagga catgcttcta   1080

agccaagcac ataatattgg tgaaacattg caagaaaaat tagagcagct tcctgatgtt   1140

gagagagctt ttgtgcatgt tgatttcgag ttcactcata gaccagagca caagactatg   1200

gtctaa                                                              1206
```

```
<210> SEQ ID NO 9
<211> LENGTH: 401
<212> TYPE: PRT
<213> ORGANISM: Nicotiana tabacum

<400> SEQUENCE: 9

Met Glu Ile Val Gly Gly Asn Gly Gly Asp His Gly Gly Ala Thr His
1               5                   10                  15

Gln Pro Leu Pro Leu Ser Leu Ser Ser Ser Ser Pro Ser Ala Ser Trp
            20                  25                  30

Arg Leu Asn Ile Gly Glu Phe Arg Val Pro Glu Asn Gly Thr Ala Asp
        35                  40                  45

His Arg Gln Ser Phe Ser Leu Arg Arg Leu Leu Arg Arg Pro Ser Lys
    50                  55                  60

Lys Gln Gly Lys Val Ala Glu Tyr Tyr Glu Lys Gln Glu Arg Leu Val
65                  70                  75                  80

Glu Gly Phe Asn Glu Met Asp Thr Val His Glu Ser Gly Phe Leu Pro
                85                  90                  95

Gly Thr Leu Thr Glu Asp Glu Met Lys Gln Leu Ala Lys Ser Glu Arg
            100                 105                 110

Met Ala Ile His Val Ser Asn Ile Ala Asn Val Val Leu Phe Ile Ala
        115                 120                 125

Lys Ile Tyr Ala Ser Ile Ala Ser Arg Ser Leu Ala Val Ile Ala Ser
    130                 135                 140

Thr Leu Asp Ser Leu Leu Asp Leu Leu Ser Gly Phe Ile Leu Trp Phe
145                 150                 155                 160

Thr Val Tyr Ala Met Lys Asn Pro Asn Gln Tyr His Tyr Pro Ile Gly
                165                 170                 175

Lys Lys Arg Met Gln Pro Val Gly Ile Ile Val Phe Ala Ser Val Met
            180                 185                 190

Ala Thr Leu Gly Leu Gln Ile Leu Phe Glu Ser Gly Lys Glu Leu Ile
        195                 200                 205

His Lys Ser Arg Pro Asn Thr Asp Pro Glu Lys Glu Lys Trp Met Ile
    210                 215                 220

Gly Ile Met Val Ser Val Thr Val Val Lys Phe Leu Leu Met Val Tyr
225                 230                 235                 240

Cys Arg Arg Phe Lys Asn Glu Ile Val Arg Ala Tyr Ala Gln Asp His
                245                 250                 255

Leu Phe Asp Val Ile Thr Asn Ser Val Gly Leu Val Thr Ala Val Leu
            260                 265                 270
```

```
Ala Ile Arg Phe Cys Trp Trp Ile Asp Pro Thr Gly Ala Ile Leu Ile
        275                 280                 285

Ala Leu Tyr Thr Ile Gly Thr Trp Ala Lys Thr Val Ile Glu Asn Met
    290                 295                 300

Arg Ser Leu Ile Gly Arg Thr Ala Pro Pro Glu Phe Leu Ala Lys Leu
305                 310                 315                 320

Thr Tyr Leu Ile Trp Asn His His Lys Glu Ile Lys His Ile Asp Thr
                325                 330                 335

Val Arg Ala Tyr Thr Phe Gly Thr Asn Tyr Phe Val Glu Val Asp Ile
            340                 345                 350

Val Leu Pro Glu Asp Met Leu Leu Ser Gln Ala His Asn Ile Gly Glu
        355                 360                 365

Thr Leu Gln Glu Lys Leu Glu Gln Leu Pro Asp Val Glu Arg Ala Phe
    370                 375                 380

Val His Val Asp Phe Glu Phe Thr His Arg Pro Glu His Lys Thr Met
385                 390                 395                 400

Val
```

<210> SEQ ID NO 10
<211> LENGTH: 6216
<212> TYPE: DNA
<213> ORGANISM: Nicotiana tabacum
<220> FEATURE:
<221> NAME/KEY: misc_feature
<222> LOCATION: (1259)..(1840)
<223> OTHER INFORMATION: n is a, c, g, or t

<400> SEQUENCE: 10

```
tatagaagag tccttttgct tctccctact tgcaaatgat aaatatcaaa acacaagtac     60

attttcactc gtacaaatac tagtaacaat tttcatggag atcgttggca gcaacggcgg    120

tgatcatggc ggcgccaccc atcagccggt gccgttatct tcctcttcac cgtcggcgtc    180

gtggaggctg aatatagggg agtttcgtgt ccctgaatat ggcactggtg atcatcgtca    240

atctttcagt ttacgtcgac tcttgcgtcg cccttctagt aattttcctt caatttatct    300

tttttttgt ccttttatga tattgttttc catttttgc acttgtcgaa gtaaaaacta    360

cttgaataaa tggttgaatt aagacaaata ttgattaatc tgaaggtatt aaatcattgc    420

attttaattg tcattgaatt catttaacta tctcctagaa aactactctc tcgattttat    480

tttatgtgaa tctatttgat aaaagatgaa aacttaagaa agaacggctt tgaaacttat    540

gagttacatt tcaacatatt tgtgcagtaa aattaaaaaa aaattaaagt aatattattt    600

tttaaatata aaaaagatca tgtcattctt tttaaaacaa gattaaaaag taaattgctc    660

ttttaagtac aactcaattc taccaatggt tttaagttct aactttggtt tggatatcct    720

tttaatttct tcttctttg tcttcaagaa ctactcaact aaagaaattg gttttagtct    780

ttttaaacaa agaggtatga cattttttc gatagcttaa aacggaaagt atgacatata    840

aattggaata tatatatgaa ttaagtacta ttataaatta aatcatattt tttaaggattt    900

tgtcttttat gttacacgac ttgatgagat cattttaata tctctatata tagaaaaaca    960

aggcaaagta gctgaatatt acgagaagca agaaaggttg cttgaagggt tcaatgagat   1020

ggacactgtt catgaatctg gctttttacc cggaagtcta accgaggttt gtctcttttc   1080

ctcacactat taagttactt aaaaaattat taccattatt tatttataat aaataaaatt   1140

agtaacctga aatataagac aaacaatatc ttatacgata tgtatactaa tagtgtaagt   1200
```

```
tttcttgtta cgtcaatatt tcacagatag gtgacatgat gtcggggccg gtgttcccnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn attttccggt gaagggatgc   1860
caattgagtc cccttgccaa tgagtggctc cgccactgct ttcggcataa gtttacttgt   1920
gggaggtcta ctttcctact tttcaagttc cttacttcac ttaggaaatt tttcaaggaa   1980
tttagggtgt tcaaacttga aagaaatgaa aaaatctcca ataaattaaa gagtgttcaa   2040
tatatatata tatatatata tataaagatt aatattttac ctatataatc agtgtaattt   2100
tttgatgaag ggtgatcaat taaccatcat tgattgttac ttaaatttta ttgtatcgta   2160
tcgttaaatc cgtcgttacg taacgacgaa aagtactact ttgtgtaacg accaatttgg   2220
tgtggtctca tcgttacctt gtcttttctc tcatttcgcc cttcattata attaaattat   2280
tttattttat cttttaccct gcttctttat atagtaataa ttttattccg tgtcataatt   2340
tttctttatg atattgcaaa tgtattcttc atattgctgg tacttgatat catgaaacga   2400
cgacaaacga tacaatctat tcaaacattg tatttatcaa acaatacagt acaatataat   2460
acaatacaat atatatacac tgatatcgca aaaaaaatta tttgctataa ttagtaactt   2520
gaaaagtgga acagacaacc taataaaaca tgtttgctgt ctacacttga tatttgacag   2580
gatgaaatga agcagcttgc taagagtgaa aggatggcaa ttcatgtatc aaacatagca   2640
aatttgattc ttttcattgc aaaaatctat gcttctattg caagcagatc tttggctgtg   2700
attgcatcaa ctttggactc tctcttagac ttattgtctg gatttattct gtggttcact   2760
gtttatgcta tgaaaaaacc aaaccaatac cactatccaa ttggtaaaaa gagaatgcag   2820
cctgtggtga gtttcaaata taatgccaca ttttgatatt tattacatgc attttatact   2880
ttgtgtcagt gtgcagtgtg attttaagat ttatacttgt aagtaggggt ggcagacggt   2940
cgggccgggt cgggtatgag cgagccaaaa cggataattt aaaaaaatgg acaaattatc   3000
cgccccgacc cgtatttgaa atggataaaa acgggtttat ccggcgtata tggatatcca   3060
tattatccct ggcttcttaa atatgatcag tacatatgag agaattcttt gtcttccaaa   3120
ctttgaggaa ctccaatttg aagctttaca atgtataagc taaacatatt agttatccat   3180
ttggttaacc attttctgag tggataatat ggttctttat ccatattcga cccattttta   3240
aatggttcat tatccaaccc atgttttaat ggataatatg gatggataac tgttttttta   3300
aaccattttg ccacctttc tggtaagtaa actggccttt atacacaatt aaaagaagca   3360
aaacatctac cctcctcttc atacttaaag attgacaaaa gattggagtt aacttatata   3420
cattaatttt tatattattt ttgctgtaat aggttgtgta ccatcccta taggttatca   3480
tatcatgtta ccggtatcaa aagttacttt ttttgtcaat taacttcata attaatgtac   3540
taattattta cattgtccgt tagagcagtt aagtatacta tttgtgtatt ttgtcctatt   3600
```

-continued

```
attttatatt tgaagttatc aaattagggt tactatagat agttacctgt aattatatgc   3660
cattattata atttgacagt gtaaaaaatt tctaaccgct cggtgtacac aagctaagct   3720
ctaaatgaaa aggtagccaa aactaacatt ttaattatca tatcaaaatc ctttatttcc   3780
ttgtttcttc ttaattaaag actaccaaca acaacaacag caacaaccca gtgtaattcc   3840
acaagtgggg tctggggagg gtaatatgta cgcagacctt acctctaccc cgagggacag   3900
agaggctgtt tccaggagac cctcgcattc tttaacattt tatcatatca tatttacagg   3960
gtattattgt cttcgcatct gtgatggcaa ctcttggatt acaaatacta tttgagtctg   4020
gtaaggaact catatataag gtatgtgact cagttttctg aaggattcta tactaggaat   4080
agatttaaac ttatagtttt aaacctatca aggcatttct gtaatctata aaaaacttct   4140
ttaaggttaa aatgaaaatt taaggctaaa ttattttcaa ctttggatat gtgtcattat   4200
tttttggaca gacgaataaa taatgagtgt cacataaaat caaataaatt gagtaattgg   4260
taacctggta aacatgataa ttgacttact atcacaagtt aaactacagt tatatcataa   4320
aaaaatattt tgtcagtgta tttatcttaa atttatgcat agttaaacct ctctataaca   4380
atctcgttta tttcgaatat ttttggatgt tatagcgaaa tgttgttata gagaatatat   4440
attataacat aatttaaaaa ttggttccga aaaagtttgg cttttatagt gaggtgttgt   4500
tatataggga tactgttata gagaggtccg accgtaaaag taattgaatt tcactagtaa   4560
aatgcttaat gctccactct ttaacaccag atttattgtt tcttctggtt taatgcttat   4620
gatcatcagt ctcgtcctaa tacggattct gagaaggaaa aatggatgat tgggatcatg   4680
gtctctgtca ctgtggtaaa atttctgctg atgttgtatt gtcgaagatt caagaatgaa   4740
attgtaagag cctatgctca agaccatttc tttgatgtca ttaccaactc tgttggatta   4800
gtgactgcag ttttagcaat tcgattctgc tggtggattg atcccatggg agctatattg   4860
gtgagttcac aatcatcact tatacttctt ttgtttttat ctctactttt ctagatggca   4920
gtccggtgca taaagtattg taagtccacg caagatccga atgagagtcg cacccaaaga   4980
gtatgacgta gacatcttac cctaatgcaa ggattagtgg ttgcttccac ggctcgaacc   5040
tgtaaccttt aggtcacatg gagagaactt gcacatatat agtgatgttt gcatcaactg   5100
gcgcacaact caactatttc acttagtaca tgttatctct cactaaaaaa tttaccggac   5160
accttgttac tcaccaaggc ttaggcgtgt ggaataactc gtattttttg tctctactag   5220
taatggaatc ctaatttcaa cctttatacc aattttattg accactaggt catactcgtg   5280
gatgcatcgt gcacacacat acgacactac atctgtctca atttactagg cactatttcc   5340
tttttttttct tttgtcctac aagattgaca tctttatagc tttagaaact ccaaacattt   5400
atttatattt ttatatcaag attgacacct ttatgtacgt atatatggta ttactgactt   5460
atatattaag catatttaac ttctgtgtca gttatctctt ttatttctta aacttcatgt   5520
ctagtcgtgc taaaccaatt gtggtggacg actatcacta aatgaatgag caaataaaat   5580
gagtagaaaa tttcaaagat atccctccaa attttccatt attattaacg ataacattat   5640
gtatttgcag atagcactat acacaattgg cacatgggca aagacagtaa tcgaaaacat   5700
gcgatcactc atcggaagaa cagctccacc agaatttctg gcgaaattga catatcttat   5760
atggaatcat cacaaagaga taaagcacat tgacacagtg agagcataca catttggtgc   5820
aaattacttt gtggaagttg atatagtttt gccagaggac atgcttctaa gccaagcaca   5880
taatattggt gaaacattgc aagaaaaatt agagcagctt cctgatgttg agagagcttt   5940
```

```
tgtgcatgtt gatttcgagt tcactcatag accagagcac aagactatgg tctaatgaca   6000

taaataaact aggtaattaa taattaataa ttagtttgag ctttaacttt attctttgga   6060

cactgtttcc ttgcacctaa agtagtaact taccaaaaaa aaagttcttt aatgtggaga   6120

acccaacaat gttgaaactt gttgaatttg cattctcaaa atttatgtaa cctaatgttt   6180

atttttaact caagatgcct aatgattcat gaacac                             6216
```

```
<210> SEQ ID NO 11
<211> LENGTH: 1200
<212> TYPE: DNA
<213> ORGANISM: Nicotiana tabacum

<400> SEQUENCE: 11

atggagatcg ttggcagcaa cggcggtgat catggcggcg ccacccatca gccggtgccg     60

ttatcttcct cttcaccgtc ggcgtcgtgg aggctgaata taggggagtt tcgtgtccct    120

gaatatggca ctggtgatca tcgtcaatct ttcagtttac gtcgactctt gcgtcgccct    180

tctaaaaaac aaggcaaagt agctgaatat tacgagaagc aagaaaggtt gcttgaaggg    240

ttcaatgaga tggacactgt tcatgaatct ggctttttac ccggaagtct aaccgaggat    300

gaaatgaagc agcttgctaa gagtgaaagg atggcaattc atgtatcaaa catagcaaat    360

ttgattcttt tcattgcaaa aatctatgct tctattgcaa gcagatcttt ggctgtgatt    420

gcatcaactt tggactctct cttagactta ttgtctggat ttattctgtg gttcactgtt    480

tatgctatga aaaaaccaaa ccaataccac tatccaattg gtaaaaagag aatgcagcct    540

gtgggtatta ttgtcttcgc atctgtgatg gcaactcttg gattacaaat actatttgag    600

tctggtaagg aactcatata taagtctcgt cctaatacgg attctgagaa ggaaaaatgg    660

atgattggga tcatggtctc tgtcactgtg gtaaaatttc tgctgatgtt gtattgtcga    720

agattcaaga atgaaattgt aagagcctat gctcaagacc atttctttga tgtcattacc    780

aactctgttg gattagtgac tgcagtttta gcaattcgat tctgctggtg gattgatccc    840

atgggagcta tattgatagc actatacaca attggcacat gggcaaagac agtaatcgaa    900

aacatgcgat cactcatcgg aagaacagct ccaccagaat ttctggcgaa attgacatat    960

cttatatgga atcatcacaa agagataaag cacattgaca cagtgagagc atacacattt   1020

ggtgcaaatt actttgtgga agttgatata gttttgccag aggacatgct tctaagccaa   1080

gcacataata ttggtgaaac attgcaagaa aaattagagc agcttcctga tgttgagaga   1140

gcttttgtgc atgttgattt cgagttcact catagaccag agcacaagac tatggtctaa   1200
```

```
<210> SEQ ID NO 12
<211> LENGTH: 399
<212> TYPE: PRT
<213> ORGANISM: Nicotiana tabacum

<400> SEQUENCE: 12

Met Glu Ile Val Gly Ser Asn Gly Gly Asp His Gly Gly Ala Thr His
1               5                   10                  15

Gln Pro Val Pro Leu Ser Ser Ser Ser Pro Ser Ala Ser Trp Arg Leu
            20                  25                  30

Asn Ile Gly Glu Phe Arg Val Pro Glu Tyr Gly Thr Gly Asp His Arg
        35                  40                  45

Gln Ser Phe Ser Leu Arg Arg Leu Leu Arg Arg Pro Ser Lys Lys Gln
    50                  55                  60

Gly Lys Val Ala Glu Tyr Tyr Glu Lys Gln Glu Arg Leu Leu Glu Gly
```

```
65                  70                  75                  80

Phe Asn Glu Met Asp Thr Val His Glu Ser Gly Phe Leu Pro Gly Ser
                85                  90                  95

Leu Thr Glu Asp Glu Met Lys Gln Leu Ala Lys Ser Glu Arg Met Ala
            100                 105                 110

Ile His Val Ser Asn Ile Ala Asn Leu Ile Leu Phe Ile Ala Lys Ile
        115                 120                 125

Tyr Ala Ser Ile Ala Ser Arg Ser Leu Ala Val Ile Ala Ser Thr Leu
    130                 135                 140

Asp Ser Leu Leu Asp Leu Leu Ser Gly Phe Ile Leu Trp Phe Thr Val
145                 150                 155                 160

Tyr Ala Met Lys Lys Pro Asn Gln Tyr His Tyr Pro Ile Gly Lys Lys
                165                 170                 175

Arg Met Gln Pro Val Gly Ile Ile Val Phe Ala Ser Val Met Ala Thr
            180                 185                 190

Leu Gly Leu Gln Ile Leu Phe Glu Ser Gly Lys Glu Leu Ile Tyr Lys
        195                 200                 205

Ser Arg Pro Asn Thr Asp Ser Glu Lys Glu Lys Trp Met Ile Gly Ile
    210                 215                 220

Met Val Ser Val Thr Val Val Lys Phe Leu Leu Met Leu Tyr Cys Arg
225                 230                 235                 240

Arg Phe Lys Asn Glu Ile Val Arg Ala Tyr Ala Gln Asp His Phe Phe
                245                 250                 255

Asp Val Ile Thr Asn Ser Val Gly Leu Val Thr Ala Val Leu Ala Ile
            260                 265                 270

Arg Phe Cys Trp Trp Ile Asp Pro Met Gly Ala Ile Leu Ile Ala Leu
        275                 280                 285

Tyr Thr Ile Gly Thr Trp Ala Lys Thr Val Ile Glu Asn Met Arg Ser
    290                 295                 300

Leu Ile Gly Arg Thr Ala Pro Pro Glu Phe Leu Ala Lys Leu Thr Tyr
305                 310                 315                 320

Leu Ile Trp Asn His His Lys Glu Ile Lys His Ile Asp Thr Val Arg
                325                 330                 335

Ala Tyr Thr Phe Gly Ala Asn Tyr Phe Val Glu Val Asp Ile Val Leu
            340                 345                 350

Pro Glu Asp Met Leu Leu Ser Gln Ala His Asn Ile Gly Glu Thr Leu
        355                 360                 365

Gln Glu Lys Leu Glu Gln Leu Pro Asp Val Glu Arg Ala Phe Val His
    370                 375                 380

Val Asp Phe Glu Phe Thr His Arg Pro Glu His Lys Thr Met Val
385                 390                 395
```

<210> SEQ ID NO 13
<211> LENGTH: 6329
<212> TYPE: DNA
<213> ORGANISM: Nicotiana tabacum

<400> SEQUENCE: 13

```
aagtactaac gtaagcgagt gtgcgtggtt tcttgattgg acggacggtg ggtgagtggt      60

acggatcctt tgcattccca ttgtccatat tcatgccgta ttcctaattc ctaataataa     120

ctattccagt ataaacagta ttcaaagttc caacgaagtt cataattaac cagcagctac     180

tcatctaaac atggaaatca gtcgcagtaa tgatagtgtc acactggacg acagttttag     240

gacggagttg ctgtctcccg ctgctcaggc ggtggttgat cattccatga ctttggggcc     300
```

-continued

```
gacgtggaag ctcaacacaa ctgacttcca tcttccccaa cgccgctcct ctgatcatca    360
atctttcagt ttcctccgtc tcctacgagt tttcagtaat tcctcagctc atgccattag    420
catttacttt tcaagtactc ctgtttattt tacatgacat gttggagttt tttttttttt    480
ttaaaaaagg aaaacttttt gcatatatta ttctagtgcc tatattccat gttaatctat    540
tattttttgg ggagtcaaat aatatttttt ttaaccacat tttttacaaa tactttttaa    600
atattttgga aaattaacta tggtaattta tagtagtagt tttgatgtaa tttctaaata    660
tgtaaattta atttcaaaaa gatttaaaat tttatgtgca aattcatact aaatattaat    720
tattttgatc ctaactattt tctccggtcc actttaagtg attttttttgg cctttttttgt    780
ggtctacaat atctgattgt ttcatatatt aagaatgaat taacttcttc tttccaaagt    840
tgtctttgga gtaaagaatc taggagtagt ttgttatatt tctaatgaac aaattaaggt    900
taaaatgatt aattttattg ttaattaatt ctaaaaggtg aatttttttaa tatgtgtgaa    960
aagagtaaaa aaaaaatactt aaagtgaacc ggaggaagta ctattaagaa cttgccatta   1020
attgaaaatt taaagctaaa gagttaccgt atacaaagat gtatcctttt agaccatctc   1080
cgactctaac atcaaatttc acaccaaatt tactccaacc attacaccat tttttacact   1140
aaaaagaata tttcttctct ctcttctata ttatattatt atcttctatt taaattttat   1200
tttttatttc cttcaaacaa attctatctt ttttttttcc atattcatca tatataattc   1260
acattcacca cttatataat tttttttcca tattcaccat atataattct atctttagca   1320
acattagata tcttacattt gcatttttta tttttaaata atggttatgt ttcttttttat   1380
acaattataa taataataaa attaacttat aattttatat aaatataata tatacaaaaa   1440
ttaaaatatc aaaaaaatag ggtataaaat taaaattata aatatcttaa tataaaaatt   1500
aattatatac acaatatatg ataaattaaa agttcaaaaa aataaaaaaa ataaaaaaga   1560
tgaataaaat aataataaat caaatttggt gttgatgaat agtgtcgcac cacactattt   1620
acgcactata atggtgcaag atttggtgtt ccattggagc aaaaaaaaaa ataccaaatt   1680
taaattttgt gcaaaaaata gtgcaccttt gaagataccc ttacacttaa atgtttgtta   1740
tttttcttta ggatatctga agcctttgaa actcgatcag tttccctttg accctttaat   1800
ttgtaacctt agagtattct agtgttatta ttataatatc taacaactct ttctgatcat   1860
gactattacc taacttattg attgttaata ctatcgtctt tcaagtggtt cattagcatt   1920
accaaaacaa aaaaaatggt tctttagttt ctgaatatag aatattggag tttgatattt   1980
tctgggagtt gaaggctgaa gggtgaaatt acaatcttgt ttctaatagt actttactta   2040
aagtttcaat tcttgtctgt agcagaatat tattttgtta attttccttc ttccactcta   2100
gcaattttaa ttggtttaag aggggaaatg gtcaaatatt agcgccttat tatttattta   2160
catcttccaa ctaatggaag aggaaaacgg gtagatggtt ttattcaaat cctttactat   2220
ctttaattat gtgggacaag cacagagtta cgattttgaa tcactgaaaa gagaattgct   2280
tggcaaagaa gaattttgaa aagttgtatc taaaaattta gtaaatacaa aatcataaaa   2340
atttaaatac tccgagtctc caagaacagt tgtgcgggat gcacaggatc atgtaacata   2400
ttctgaagct tgtattgctg atttttcata ctaaggtgtc gtttggtaga gatattaaaa   2460
taaaaataaa aataatgcaa gcattagctt aatttgtgca ttactaatcc ctggtttggt   2520
acatttttttc aacatatgtg tattagttat acctccgatt tggtattatc caatgtataa   2580
ctaaaacata acaaactatg gtattaacaa tgcaagagtt tttaatactt gtataaacat   2640
```

```
ggttaaagac ataactgccc ctcaaatccc tcaaaaccta ttccaaatat ttttcgccat   2700
atttttgtgg agggtatatt tgtaaacaat caatttttta agaaattatg caatgcctta   2760
atataccaaa ctaaacagtg gataagaaat aatctcaata taattaatga tagtataact   2820
agtctcaaca ttattaatac catcgttact gatacacctt attcaacatt atttttaaac   2880
ctcctaccaa gcgaccccta agaatgtttt atttgaagta acttcaaatc atatacttga   2940
cctcattctt gtaaaaaaaa tttgtttgtt gagaaggtaa acttgttaaa gaaattagtc   3000
acatttcttc ccttttgcat ataaaactac ggatatcaaa gagtttttgg tgttttattt   3060
tgttcaaggt tattagtcct gtttgatttt gctctacaac tctacagttt tctttcatat   3120
ttactctctt aaaatttaag aaggcgccgg taatttaact accaggttga ggactaccta   3180
gcagcccgcg gatggatagg gtgggggaag cgcgaagggg atggatgtct gagcggttga   3240
aagagtcagt cttgaaaatc aaagtattta tagaataccg gggttcaaa tccctctcca   3300
tccgcgagat cataagttgg tctcttgagt tatatataga taagaagata ttgggtcgac   3360
tggactgata tgatagatgg aatggtagac tgaagttgtt acttattttc agttaaggaa   3420
caaaaattca cttgatactc tgtaagggtg atatgcaaag caggcaacaa aatccatctt   3480
tgttggacca aaatatgctc ttaattactt gtaaatgttc cctgaccaaa tgctttgatt   3540
gctgaagcta atagtttaaa aacttatctt tcttggactg aaataggctc tcttatttgg   3600
aatggacata ttcaagaata taagttatca tacccttagg aatgatatac taagtaggtg   3660
atttcagata atcagattca ttgtttcaga taattaaact ttccatttcc gtcttcactt   3720
tcttgatcac ttgatggaat cgtgttaatc atgtataggg aatcagagaa aagttgctga   3780
atactacaaa aaacaagaaa ggctgcttga aggattcaat gagatggaca caattaatga   3840
atgtggttac ttacctggaa atctaactga ggttggtcta tgagattggc agattcttat   3900
cagtttaatc atcacaattt tttagtcgtc aaaataactt tcttttcttt gttgcactgt   3960
caaccaatat atacaatcac ctttagtgaa attcgtgtgt ttgtggatca acttgtgttt   4020
atcttctatt gttgttcata aagctataat ttgcaatttc aaatctcaga tgttgttttt   4080
caggatgaat tgaagcaaca tgctaagagc gaaaggatgg ctattcttgt gtcaaacata   4140
gcaaatatgg ctcttttcat tgctaaaatc tatgcttcta ttgacagcag atcactggct   4200
gtaattgcgt ctaccttaga ctccctatta gacctcttag ctggatttat tctgtggttc   4260
acttctcatg caatgaaaac gccaaaccaa tactgttatc caattggaaa gaagagaatg   4320
cagccagtgg tgagtcttct actgttttaa tttcttccaa cgaacaccct tgtttcaggg   4380
tatttctccg aaattaaagt aaaaagaaga aaaaaaacat atcccttcag ctcccaagaa   4440
agaaaaagaa aagatgtctt cgccaatttc tgtttattgt ttgaactgat ctgctgcaat   4500
attttcaggg tatagttgtt tttgcatccg taatggcgac cctgggatta caaatattgt   4560
tcgagtctgg taaagaactc ataactaagg tatgtaactt ggttctcttc aagtgtgttg   4620
tgagatggat gtgtcatgtg tgagctggta caaggttgaa tttccaaata catgtatttt   4680
gtaaaattaa tgtcgaattg ataaagaact tccccagaaa gtgcattttg gcagcaaaat   4740
ataaaatatc ttagaaggtt ctgataccat gttaagcaaa ataaattttg gacctaattc   4800
aacacaacag ttcactcatg agatgaggat ttttcgaggt catataaagc gattagagct   4860
caacctgtgt gggatgctaa aaatattcat aattcttctt cccctaaaag tcagtagcct   4920
ggagttctct ctaggttttt gtacttctac aattgatttt aaattattta cagagttgaa   4980
atggtagtac tttgtcccaa gtaattcatt cttcacattg atggacattt atattgttga   5040
```

aaactagcac tagcttttat gttaaatgag atagatttta tgtacgatgt gagtgcttta 5100
ggaaaagtag ttgatcttaa ggatcaaaag gaaagaccaa aattagaagc tgaattgctg 5160
ctaaaaggaa tttgcagtag catgtacaag ttaggccctc taatctatgt ataatggtaa 5220
actagctgtt tgtgctctaa ttgaaatcga ctagtcttga tacgaggatg caacatagat 5280
taataaggac tattcctaca caatacattt tgtattgaag gactgaactc taatttgccg 5340
gaatttcatt ttgtaatatg cctgacactt aacctcaatt tgtttttctg gttccatgct 5400
taatgatttg tttttctggt tctatgctta atgattagtc tcgtcctgat atggaccctg 5460
agaaggaaaa atggatgatc ggaattatgg tttctgtcac tgtggtcaag tttatgcttc 5520
tgatctactg ccgaagattc aaaaatgaaa ttgtaagggc ctatgctcaa gaccatttct 5580
ttgatgtcat taccaactca atcgggttag cggcagcagt cttagccatc catttctatt 5640
ggtggattga tcctactgga gctataattg tgagtttaga attacaacac acgaactctt 5700
taatctatat accttgtctg ttatcgcaat tgagatattt ttgcattcct atggacaact 5760
gatcatcctt tgttatgtgt ttcagatagc actttacaca atgagcacat gggcaaagac 5820
agtgatggaa aatgtgtggt cacttattgg aagaacagct ccacccgaat ttctagcaaa 5880
gttaacatat cttatatgga atcaccatga aaggatcaaa cacattgata ctgttagagc 5940
atataatttt ggcatacaat attttgtgga ggttgatata gtgctgccgg aggacatgtt 6000
cctgaaccag gcacataata ttggtgaaac gctgcaggaa aaattggagc aacttgttga 6060
agttgagcgt gctttcgtcc atgtagattt tgacataact cataggctgg aacataagtc 6120
tatgatcaaa tgacgtcaaa ttgacatata atttttagaa tgacggccgc ttaattcctg 6180
tttaattata ccattgtatt tcctatttgt tactctctat attggatcag atgagcttta 6240
tcatccgtcc cagctgagag ctttatcgtc ctttggtgtg tccctcacct ctctcttttg 6300
aggcctgttt cctctactgt cacttcttt 6329

<210> SEQ ID NO 14
<211> LENGTH: 1224
<212> TYPE: DNA
<213> ORGANISM: Nicotiana tabacum

<400> SEQUENCE: 14
atggaaatca gtcgcagtaa tgatagtgtc acactggacg acagttttag gacggagttg 60
ctgtctcccg ctgctcaggc ggtggttgat cattccatga ctttggggcc gacgtggaag 120
ctcaacacaa ctgacttcca tcttccccaa cgccgctcct ctgatcatca atctttcagt 180
ttcctccgtc tcctacgagt tttcaggaat cagagaaaag ttgctgaata ctacaaaaaa 240
caagaaaggc tgcttgaagg attcaatgag atggacacaa ttaatgaatg tggttactta 300
cctggaaatc taactgagga tgaattgaag caacatgcta agagcgaaag gatggctatt 360
cttgtgtcaa acatagcaaa tatggctctt ttcattgcta aaatctatgc ttctattgac 420
agcagatcac tggctgtaat tgcgtctacc ttagactccc tattagacct cttagctgga 480
tttattctgt ggttcacttc tcatgcaatg aaaacgccaa accaatactg ttatccaatt 540
ggaaagaaga gaatgcagcc agtgggtata gttgtttttg catccgtaat ggcgaccctg 600
ggattacaaa tattgttcga gtctggtaaa gaactcataa ctaagtctcg tcctgatatg 660
gaccctgaga aggaaaaatg gatgatcgga attatggttt ctgtcactgt ggtcaagttt 720
atgcttctga tctactgccg aagattcaaa aatgaaattg taagggccta tgctcaagac 780

```
catttctttg atgtcattac caactcaatc gggttagcgg cagcagtctt agccatccat    840

ttctattggt ggattgatcc tactggagct ataattatag cactttacac aatgagcaca    900

tgggcaaaga cagtgatgga aaatgtgtgg tcacttattg gaagaacagc tccacccgaa    960

tttctagcaa agttaacata tcttatatgg aatcaccatg aaaggatcaa acacattgat   1020

actgttagag catataattt tggcatacaa tattttgtgg aggttgatat agtgctgccg   1080

gaggacatgt tcctgaacca ggcacataat attggtgaaa cgctgcagga aaaattggag   1140

caacttgttg aagttgagcg tgctttcgtc catgtagatt ttgacataac tcataggctg   1200

gaacataagt ctatgatcaa atga                                          1224


<210> SEQ ID NO 15
<211> LENGTH: 407
<212> TYPE: PRT
<213> ORGANISM: Nicotiana tabacum

<400> SEQUENCE: 15

Met Glu Ile Ser Arg Ser Asn Asp Ser Val Thr Leu Asp Asp Ser Phe
1               5                   10                  15

Arg Thr Glu Leu Leu Ser Pro Ala Ala Gln Ala Val Val Asp His Ser
            20                  25                  30

Met Thr Leu Gly Pro Thr Trp Lys Leu Asn Thr Thr Asp Phe His Leu
        35                  40                  45

Pro Gln Arg Arg Ser Ser Asp His Gln Ser Phe Ser Phe Leu Arg Leu
    50                  55                  60

Leu Arg Val Phe Arg Asn Gln Arg Lys Val Ala Glu Tyr Tyr Lys Lys
65                  70                  75                  80

Gln Glu Arg Leu Leu Glu Gly Phe Asn Glu Met Asp Thr Ile Asn Glu
                85                  90                  95

Cys Gly Tyr Leu Pro Gly Asn Leu Thr Glu Asp Glu Leu Lys Gln His
            100                 105                 110

Ala Lys Ser Glu Arg Met Ala Ile Leu Val Ser Asn Ile Ala Asn Met
        115                 120                 125

Ala Leu Phe Ile Ala Lys Ile Tyr Ala Ser Ile Asp Ser Arg Ser Leu
    130                 135                 140

Ala Val Ile Ala Ser Thr Leu Asp Ser Leu Leu Asp Leu Leu Ala Gly
145                 150                 155                 160

Phe Ile Leu Trp Phe Thr Ser His Ala Met Lys Thr Pro Asn Gln Tyr
                165                 170                 175

Cys Tyr Pro Ile Gly Lys Lys Arg Met Gln Pro Val Gly Ile Val Val
            180                 185                 190

Phe Ala Ser Val Met Ala Thr Leu Gly Leu Gln Ile Leu Phe Glu Ser
        195                 200                 205

Gly Lys Glu Leu Ile Thr Lys Ser Arg Pro Asp Met Asp Pro Glu Lys
    210                 215                 220

Glu Lys Trp Met Ile Gly Ile Met Val Ser Val Thr Val Val Lys Phe
225                 230                 235                 240

Met Leu Leu Ile Tyr Cys Arg Arg Phe Lys Asn Glu Ile Val Arg Ala
                245                 250                 255

Tyr Ala Gln Asp His Phe Phe Asp Val Ile Thr Asn Ser Ile Gly Leu
            260                 265                 270

Ala Ala Ala Val Leu Ala Ile His Phe Tyr Trp Trp Ile Asp Pro Thr
        275                 280                 285

Gly Ala Ile Ile Ile Ala Leu Tyr Thr Met Ser Thr Trp Ala Lys Thr
```

290 295 300

Val Met Glu Asn Val Trp Ser Leu Ile Gly Arg Thr Ala Pro Pro Glu
305 310 315 320

Phe Leu Ala Lys Leu Thr Tyr Leu Ile Trp Asn His His Glu Arg Ile
325 330 335

Lys His Ile Asp Thr Val Arg Ala Tyr Asn Phe Gly Ile Gln Tyr Phe
340 345 350

Val Glu Val Asp Ile Val Leu Pro Glu Asp Met Phe Leu Asn Gln Ala
355 360 365

His Asn Ile Gly Glu Thr Leu Gln Glu Lys Leu Glu Gln Leu Val Glu
370 375 380

Val Glu Arg Ala Phe Val His Val Asp Phe Asp Ile Thr His Arg Leu
385 390 395 400

Glu His Lys Ser Met Ile Lys
405

<210> SEQ ID NO 16
<211> LENGTH: 6780
<212> TYPE: DNA
<213> ORGANISM: Nicotiana tabacum

<400> SEQUENCE: 16
tgcattccca ttgtccatat tcacgccgta ttcctaataa ctattctagt ataaacagta 60
ttcaaagttc caacgaagtt cataattaac cagcagctac tcatctaaac atggaaatca 120
gtcgcagtaa tgagagtgtc acactggacg acagttttag gacggagttg ctgtctcccg 180
ctgctcaggc ggtggttgat cactccatgt ctctggggcc gacatggaag ctcaacacaa 240
ctgacttcca tcttccccaa ctccgctcct ctgatcatca atctttcagt ttcctccgtc 300
tcctacgagc tttcagtaat tcctcagctc atgccattag cctaattttc ttttcaacta 360
ctcctgtaat cacatgttgg atttaaaaat aaaaaaaaaa taaaaaatct tttttgcata 420
tattatacta gtgcctatgt tccatgttaa tctattatta tttggggtgt cacataatat 480
tttctttaac cacatttttt acaaatgttt tctaaatact tattttggaa tattaattat 540
ggtaatttat acagtagtag tttttatgta atttctaaat atgtaaattt aaaattacta 600
gttaatttga tcctaactac aattaagtac ttgccattat ttgaaaattt aaagctaaag 660
agttaccgta tacaaagatg tatcctttta catttatttt agtgtttgtt atttttgttt 720
actatgtctg aagcctttga aactcgttcg gtttcccttt gaccttttag tttgtaacct 780
tagagtattc tagtgttatt attataatat ctaactacta tttctgatca taagtcatga 840
ctattaccta acttattgat agttaatact atcgcctttc aagtggttca ttagcattac 900
caaaaaaagt agttctttag tttctgaata tagaatatcg gagttggata ttttcggcga 960
gttgaagcct gaaaagtgaa attacaatct tgtttctaat agtactttac ttcaagtttc 1020
aattcttgtc tgtagcattg tagtggagca gaatatccta atgtgctcag gagatcttat 1080
taacaaagtt ttgaatcgat tagatatgat gggcacttca aagggatcaa acttgctaaa 1140
taaactggca actttataat tcaaacaccg atatgtaaaa gctcatgggc catgtcgcga 1200
cttcattttg tcctaaaagt tcaaagttcc tggtcagatt tttcttttat tattttgtta 1260
attttccttc ttccgctcta gcaattttaa ttggtttaag aggggaaatg gtcaaatatt 1320
agcgccttat tgtttattta catcttccaa ttaatggaag agaaaaacgg gtagatggtt 1380
gtatatccaa atcctttact ttctttaatt atgtgggaca agcacagagt tacgattttg 1440

```
aatcattgaa aagagaattg cttggcaaag aagaattttg aaaagttgaa tctaaaacat   1500
ttagtaaata gaaaatctca aaaatttaaa tactccgagt ctccaagaac aattgtgtgg   1560
gatgcaattg tgaagcttgt attactgatt tttcatacta agggtcgttt ggtaggggat   1620
attaaaaaaa ataatgcagg cattaacttt gtgcattact aattggaaaa atgacaatgt   1680
ataggcgatg taaaaataat agacgaaaaa atgtataaaa tttgtatatt tttttgtata   1740
tatatacatt ttgtattttg tatatatata cattttgtat gttatataca aaaattatgc   1800
aaattttata cacttccggc taccagatgt aaatagtttc tagcgcgggc taaaagtgat   1860
aataccccttt actaatccct tgtttggtac attttttgta ttagttatac atcccattta   1920
gcattatatt atgtataact aaaacatagc aaactatggt attagcaatg caaaagtttt   1980
taatacttgt ataaacatgg ttaaagacat aactacccct caaatccctc aaaacctatt   2040
ccaaatattt ttcaccatat ttttctagag ggtatatttg taaacaatca attttttaag   2100
aaattatgca atgctttaat ataccaaact aaacagtgga taagaaataa tctcagtata   2160
atgccggcat aactaatcca gcactactga tgcaccttat tcaacactat ttttatacct   2220
cctaccaagc gacccctaag attgttttat ttgaagtaac ttcaatgttt tatttgaagt   2280
aacttcaaat catatacttg atctcattct tgtaaaagtg tttttttttt tggttgagaa   2340
ggtaaactta taaaagaaat tagtcacatt tgcttccctt tggcatataa aactacggtg   2400
ttccagatat taaagagttt tgggtgttct atttagtccg cggttattag tcctgtttga   2460
tttttctcta cagctctaga tttttctttc atatttactc tcttaaaagt taagaaggcg   2520
ccgataattt aactaccagg ttgaggacca cctgtcagcg cgcggatgga tagggtggat   2580
gtctgagtgg ttgaaagagt cggtcttgat aaccgaagta tttatagaat accgggggtt   2640
cgaatccctc tccatccgcg agaacataag ttctctcttg agttatctat agataagaag   2700
ttattgggcc gactcgactg atatgataga tggaatggta gactgaagtt gttacttatt   2760
ttcagctaag gaacaaaagt tcacttgata atctgtaagg gtgatctgca aagcaggcaa   2820
caaaatccat ctttgttgga ccaaaatttg ctcttattta cttgtaaatg ttcccttacc   2880
aaatgctttg attgctgaag ctaatagttc aaaaacttat ctttcttgga ctgaaattgg   2940
ctctcttatt tggaatggac ataattcaag agtaatgtgt tataagctaa tataagctat   3000
catacccttta agaataatgc ttaaagtagg tggtttcaga taaccaaatt cattgtttta   3060
ggcaattaaa gttttcactt tgttttttaa tctaacctga ctgcttcatg gaatctctgt   3120
aatcatatat agggaatcag aaaaaagttg ctgaatacta caaaaagcaa gaaaggctgc   3180
ttgaaggatt caatgagatg gacacaatta atgaatgtgg ttatttacct ggaaatctaa   3240
ctgaggttgg tcttttcctc acttgccaca actaatgaat gtggttattt ctgttctttg   3300
ttgcactatt tccaccttca accgaaacaa tcacctttag tgttcagaaa ttcatgtgtc   3360
tctggatcag ataagactac ttgtgtttat gttctttttc ttcttggaga aggtgatttc   3420
ttgatcaatc tctgcctctt caataactac aatgtttttc catgttaacc cgagtgtata   3480
ttaggacttt cagtcagatt cttaggtttc ttgaatcttg atctctgtta atattcgtaa   3540
taagaatcaa caaataatgt tgtttttcct gtctaccaat gattattaat gccaggatga   3600
aatgaagcaa catgctaaga gcgaacgaat ggctattcat gcgtcaaaca tagcaaatat   3660
ggttcttttc attgctaaag tctacgcttc tattgacagc agatcgctgg ctgtaatttc   3720
atcgacctta gactcgctat tagacctctt atctggattt attctgtggt tcacttctca   3780
tgcaatgaaa acgccaaacc agtaccgcta tccaattgga aagaagagaa tgcagccagt   3840
```

ggtgagtctt ctactgtttt ttcttccaag gaacaccctt gtttcagggt atttctccga 3900
aattagagta aaaagaagaa aaaacatatt cctttagctc cctagaaaga ataagaaaag 3960
atgtctgatc accaatttat gtttatatat ctggataata cctttgtgcc ttctgacagt 4020
ttcctcaaga attaacagct taaagggtag cacgtaaacc agaatatctt gcttgtgtgc 4080
aatatttttt acattaatat ggtttattgt ttgaaatgat ctgctgcaat attttcaggg 4140
tatagttgtt tttgcatccg taatggcgac cctaggatta caaatattgt tcgagtctgg 4200
taaagaactc ataactaagg tatgtaactt ggttctcttc agctgtgtca tgagatggat 4260
gtgtcatgtg tgagctggta caaggttgag tattgtgact tctaaaaata atgtcaaatt 4320
gatgaagaac gtttcctcaa atatactttg agagcacaat atccttactg gtcttttaat 4380
aatccatgtt aggcaaaatg aattttggac ctaactcaac agttttgctc aagtgatttc 4440
gcaatatgtg catgtattac aaaagtttac tcgggtgaga tgaggatctt ctagggccat 4500
ataaagagac tacagcttat gccctcaatc agtgtgggac tcttaacaat attcgtattt 4560
ccttcttccc ctaaatatca gcagcctaga gttctctccg gattttgtac ttctatagtt 4620
gattttaagt tgttttgtag tagagtttac ggtagtcctt tgccctaagt aatccctttc 4680
ttaaaattga tggacaattt atattgttga atattaccac tagcttgtct gataaatgaa 4740
atatgtcgta caatgcgaca aaagacctaa aatagaagct gaattgctac taaaagaaag 4800
ttgcagtaac acaagatatg ccctctaatc catgtataaa gatgaactag tcgtttgtgc 4860
tctaactgaa aacaactagt tttgatacta catatgaagc acagattaat aaagattagt 4920
cccacatgat acatttctta ttgaaggact gaactctaat ttaccgcaat ttcactagtg 4980
aaatattgta atatgcttga cacttaacct caatttgttt ttctggttct atgctttaat 5040
tattagtctc gtcctgatat ggaccctgag aaggaacaat ggatgatagg aataatggtt 5100
tctgtcactg tggtcaagtt tatgcttctg atctactgcc gaagattcaa aaatgaaatt 5160
gtaagggcct atgctcaaga tcatttcttt gatgtcatta ccaactcaat cggattaatg 5220
gcagcagtct tagccatcca tttctactgg tggattgatc ctactggagc tataattgtg 5280
agttcagaat aacaccacat agttctttta tttgtatacc ttgtctgttg ttgcaattga 5340
gatgtttttg catttcctat ggagaactga tcatcctttg ttactgcaac agctttttaa 5400
agtagtagta tttgtttagt ttaagcaatt aattagcatt ttgaagaata aagtagcata 5460
tctttattaa ttaatcttat tagtctctgt tgtgtgtttc agatagcact ttacacaatg 5520
agcacatggg caaagacagt gatggaaaat gtgtggtcac ttattggaag aacagctcca 5580
cccgaatttc tagcaaagtt aacatatctt atatggaatc accatgaaag gatcaaacac 5640
attgatactg ttagagcata taactttaga atactattct accactggac cattggtata 5700
ttttatttta agactgtctt ttatttgatt tatacacttt aattgtattt tcgtatgaaa 5760
ataaccgatc aaagttggtc agtttttaa aattatcaac cgaattaacc gaccaacttt 5820
ggtcggtttt tttaatatta atttttattt attttaattg aaaaaccgac caaagttggt 5880
tggtttcttg aaaaataaat tttgcgggac tcaaaaatcg tttcccgcat ttttgcgcca 5940
aagaaaaacg accaaagttg gtcggttttg taaaacaaaa tttaaaaata aaatattttg 6000
aaaaaccgac caactttggt cggtttttg gccggttttt tgatcgacca aagttggtcg 6060
gtcgaccttg gtcagttttt gccgaaacac aatctatggg agcgagttga atgtttgtca 6120
ctagatgata tttaatgaag aatattgcct agtattaaat aggcagccgt tgcagagaat 6180

```
ttgggcattc atgacctgtc gtttcatgtt catcaatgac tccttttatt gtaatttaag   6240

aggggcttga tcctaggatc ttgtttccta ggtatagcta taaatagtag cttcaacaac   6300

cattgtagac agagaaaata tctcgcaaaa acttatgcta cactttattc tcaagctaaa   6360

caatacaaat ttactttcca tatgatattg ctcttatttc tgtcctcgga agcattgctc   6420

ccggagctag gcctgccatt tcctttggtt ttaacgctaa gtcttatttt taatctaatt   6480

tacttattat tttgggttaa atcagtttgc ttgtctataa accacataac gaatacaact   6540

gtaccgtttt acaggtaaac agtttggcgc cccaccgcgg gtcttagaca actgcataat   6600

taagttgatc cttgcatata ttactaactc gtttgattct ttatttctta gaaaaaatag   6660

cacacaacat tgaggcacac caaaatctac ctcaacatga ggattcaatc agtgataccc   6720

gcaatgagag agatgtggaa actccggtcc atggcagaca atatcgccga cacgtgcggg   6780


<210> SEQ ID NO 17
<211> LENGTH: 1102
<212> TYPE: DNA
<213> ORGANISM: Nicotiana tabacum

<400> SEQUENCE: 17

atggaaatca gtcgcagtaa tgagagtgtc acactggacg acagttttag gacggagttg     60

ctgtctcccg ctgctcaggc ggtggttgat cactccatgt ctctggggcc gacatggaag    120

ctcaacacaa ctgacttcca tcttccccaa ctccgctcct ctgatcatca atctttcagt    180

ttcctccgtc tcctacgagc tttcaggaat cagaaaaaag ttgctgaata ctacaaaaag    240

caagaaaggc tgcttgaagg attcaatgag atggacacaa ttaatgaatg tggttattta    300

cctggaaatc taactgagga tgaaatgaag caacatgcta agagcgaacg aatggctatt    360

catgcgtcaa acatagcaaa tatggttctt ttcattgcta aagtctacgc ttctattgac    420

agcagatcgc tggctgtaat ttcatcgacc ttagactcgc tattagacct cttatctgga    480

tttattctgt ggttcacttc tcatgcaatg aaaacgccaa accagtaccg ctatccaatt    540

ggaaagaaga gaatgcagcc agtgggtata gttgtttttg catccgtaat ggcgacccta    600

ggattacaaa tattgttcga gtctggtaaa gaactcataa ctaagtctcg tcctgatatg    660

gaccctgaga aggaacaatg gatgatagga ataatggttt ctgtcactgt ggtcaagttt    720

atgcttctga tctactgccg aagattcaaa aatgaaattg taagggccta tgctcaagat    780

catttctttg atgtcattac caactcaatc ggattaatgg cagcagtctt agccatccat    840

ttctactggt ggattgatcc tactggagct ataattatag cactttacac aatgagcaca    900

tgggcaaaga cagtgatgga aaatgtgtgg tcacttattg gaagaacagc tccacccgaa    960

tttctagcaa agttaacata tcttatatgg aatcaccatg aaaggatcaa acacattgat   1020

actgttagag catataactt tagaatacta ttctaccact ggaccattgg tatattttat   1080

tttaagactg tcttttattt ga                                            1102


<210> SEQ ID NO 18
<211> LENGTH: 366
<212> TYPE: PRT
<213> ORGANISM: Nicotiana tabacum

<400> SEQUENCE: 18

Met Glu Ile Ser Arg Ser Asn Glu Ser Val Thr Leu Asp Asp Ser Phe
1               5                   10                  15

Arg Thr Glu Leu Leu Ser Pro Ala Ala Gln Ala Val Val Asp His Ser
            20                  25                  30
```

```
Met Ser Leu Gly Pro Thr Trp Lys Leu Asn Thr Thr Asp Phe His Leu
        35                  40                  45

Pro Gln Leu Arg Ser Ser Asp His Gln Ser Phe Ser Phe Leu Arg Leu
    50                  55                  60

Leu Arg Ala Phe Arg Asn Gln Lys Lys Val Ala Glu Tyr Tyr Lys Lys
65                  70                  75                  80

Gln Glu Arg Leu Leu Glu Gly Phe Asn Glu Met Asp Thr Ile Asn Glu
                85                  90                  95

Cys Gly Tyr Leu Pro Gly Asn Leu Thr Glu Asp Glu Met Lys Gln His
            100                 105                 110

Ala Lys Ser Glu Arg Met Ala Ile His Ala Ser Asn Ile Ala Asn Met
        115                 120                 125

Val Leu Phe Ile Ala Lys Val Tyr Ala Ser Ile Asp Ser Arg Ser Leu
    130                 135                 140

Ala Val Ile Ser Ser Thr Leu Asp Ser Leu Leu Asp Leu Leu Ser Gly
145                 150                 155                 160

Phe Ile Leu Trp Phe Thr Ser His Ala Met Lys Thr Pro Asn Gln Tyr
                165                 170                 175

Arg Tyr Pro Ile Gly Lys Lys Arg Met Gln Pro Val Gly Ile Val Val
            180                 185                 190

Phe Ala Ser Val Met Ala Thr Leu Gly Leu Gln Ile Leu Phe Glu Ser
        195                 200                 205

Gly Lys Glu Leu Ile Thr Lys Ser Arg Pro Asp Met Asp Pro Glu Lys
    210                 215                 220

Glu Gln Trp Met Ile Gly Ile Met Val Ser Val Thr Val Val Lys Phe
225                 230                 235                 240

Met Leu Leu Ile Tyr Cys Arg Arg Phe Lys Asn Glu Ile Val Arg Ala
                245                 250                 255

Tyr Ala Gln Asp His Phe Phe Asp Val Ile Thr Asn Ser Ile Gly Leu
            260                 265                 270

Met Ala Ala Val Leu Ala Ile His Phe Tyr Trp Trp Ile Asp Pro Thr
        275                 280                 285

Gly Ala Ile Ile Ile Ala Leu Tyr Thr Met Ser Thr Trp Ala Lys Thr
    290                 295                 300

Val Met Glu Asn Val Trp Ser Leu Ile Gly Arg Thr Ala Pro Pro Glu
305                 310                 315                 320

Phe Leu Ala Lys Leu Thr Tyr Leu Ile Trp Asn His His Glu Arg Ile
                325                 330                 335

Lys His Ile Asp Thr Val Arg Ala Tyr Asn Phe Glu Tyr Tyr Ser Thr
            340                 345                 350

Thr Gly Pro Leu Val Tyr Phe Ile Leu Arg Leu Ser Phe Ile
        355                 360                 365
```

<210> SEQ ID NO 19
<211> LENGTH: 5390
<212> TYPE: DNA
<213> ORGANISM: Nicotiana tabacum

<400> SEQUENCE: 19

```
catttttagt tccactttcc ttgttcaaaa aagttccgcc atataaagcc tctacaacta      60

cccacccaaa gaactccaaa ttacataaag gtccctggag ttcatcaaat ttacgcactt     120

taccactccc ctgcggctcc ttcaagtagg tgcctccagt ttttttacct agtgttttca     180

actgtttttt tccctatttt ccggtgaccg gaaaatgttg gaagtagtac ctcttcacgg     240
```

```
cggcgatcac ggcgccggca ccgaagagga gcttttattg ctggagacaa acaatgccga    300
ccggtcatgg agattaaact tcgacgagtt gcggttgtcg tctgaatcca aagagaagcc    360
tccacgtggc ctccatgatt gccttggagt tttaagtaca ttctccacct ctctatgcga    420
cgtcgttttt tgttattctc tgctaatttc ttaactagtt gcattaggtt gacgtaagag    480
agacaccact tgaatagagc ggaatttata taaaggaatt atacagctga ttcctattaa    540
atacttgact gatattctgt tgtgcgtagg attttactaa ttgcggaaat tttcaaacac    600
taagcttact cctttagttg gttaattagt ggggactctt tttatacttt tcagtttcag    660
aaagtatttt cttgccacgt gggttcaatt ttctgaagaa caaaatgatt cttgtatgga    720
tggtgtaaat ttgctaaaga tgttaagcta tattcacttt ttattgttct ctggacaatt    780
gaacatgctt atgggcagtt cactggtttg gagcaaattg gcatatattt gtatgtagat    840
ggatgattct ttttggataa gttttagatg gataattttt gttataagaa catgagcttt    900
agagctcaaa tttaatgcgt ttcagcactt cagtttactg aaaataagaa gggaacttta    960
gctgagtgcg ctcgccaggt aagtttatgt ggttaggtca gtgtaataaa accagaggca   1020
gacctatgtt aatatgtgag ggtgcactgg caccctgtag tttccgatga aactatatgg   1080
agtatataaa attcttataa cactactatg tattttaggt ggcaattgca atgacaaagt   1140
agcggtagga ggatttgtta aaatatgtgt ttttacctga gttgttgtct tctcatattg   1200
aatacttaca taattgaacc aaattaatgc aataccatca aacgaactta atgcacttta   1260
gatgatatga cttgttcgaa tctttagtgc accggcaacc ttcacttggt gtgtgtgtgt   1320
ttgcatgtga catgagccag tcaaaagatt gttccaagag gctacttttg cattctgttg   1380
aattgttaag ttgtcatatg agaatgtatg tttggaattg ataatggtac tttgacaatt   1440
tataatcggc tttggtatga gtggtggact ctaaatgcag gtcagccttg gttctcatca   1500
actctttggt ttagtactta taggaggcta tagtgctata tagagatgca tgtagaatgg   1560
atttactgaa tgctttcact gtaagacatg gggtgttctt gaagggacgg attatgacgc   1620
tgtgtttttc tttggtgctt acaggtcaag aagacaacat tgctgagtac taccagcaac   1680
aggtagaaat gctcgagggc ttcaatgaaa tggacgcctt gaccgatcgc ggttttgtac   1740
ctgggatgtc aaaggttttg atagcttctt ctttatgtat aagaccaacc atttgtttct   1800
tctctagatg tatcattctt atcttattat ataacttgat gacctgatca tctaattaaa   1860
aaagaatgtt actcaaagct tggactgaca agctcaatta atttgattgc aggaagagag   1920
ggaaaaaacg gctagaaatg aaacatttgc cattaggata tcaaatgttg caaacatggt   1980
tctctttgcc gctaaagtat atgcgtcagt caagagtggt tcattggcca tcatagcatc   2040
cacattggat tcgctgcttg atcttctctc tggtttcata ttatggttta cagctttctc   2100
catgcagaca ccaaacccat atcaatatcc tattggaaaa aaacgtatgc agccgttggt   2160
tagtgctgct gcttttattc ttaagttttt tgcatcttct atgccttcaa tcgggccaat   2220
ttgcattctg cacttgtcac ttgctattgg gctaatactc atgactgcat ataataacaa   2280
tttccttgct ttttcatgcg tttaaaaatt gtctaacaag gtaattgtac tatgcattct   2340
tgtcacattt gattctaaag ggaccttaag ttctgccact gctatttttta tgttgtggtc   2400
atggtaagcc ttaacattcg ttttgtttgt tgatgcagag gcaatttagc cttcttcttg   2460
agttcaatct ctaatcatca catgttgtag tccaaaaata aaggaataat tttcacctaa   2520
aagtatggaa ccacgagaaa ttcaaactta atgcatctaa gacaaattaa atgaattaaa   2580
```

acaacatcat atctgatagt aaccatctat aaaaggttga aataaaagaa aagatgtgca 2640
gaattttaat aatgtcctct agcagacagc ttacatgact gcattaaaac ctacagagat 2700
tcaaatcttc agcatctctt tctccaatag ttgtctttta ggtgtagcct cagtggagaa 2760
ccacacatgt ttctgagata gaaaggtgag agaagatagc tgatggcagg ggaaggggaa 2820
agagagagat gagaccagaa gggaaggcca catagattga agctgatttg gcagagagaa 2880
ttgagtgaga tgatgaaaca ctggctgctg tgagtggcag tatagaatta gagagggtgg 2940
ggttacgggg agattatgaa gtgtctatta gtaattttac aagatttagt tgttttgttt 3000
ttactgtgga gggatgaata tggtccttgt ttatgatctg tgatggatac cggagcttat 3060
aacctcccat atgcaccatt ttctcccaca tcaggttagg ttgatagcca ttgcgttcgc 3120
tctaagtagc gatcctcaaa ttcaattaat taatcgtatt atggtgatgt tgatatagac 3180
atctagactg tcactcctga tgttacctat caaaaaaaaa aactatcatc tcctagatgt 3240
ttctattaat ccaatgtctg tacataacta aggagggatc ctagacttga gttacacaga 3300
gattcttaca tagtctttgt tgctgttcat ctcttcctgt tatctcattt tcattatcaa 3360
aattgacagt aagcacttgc tccgtgaatg taactagtct gggcatgaat ttggtgtagt 3420
actcataaca gttgcattta gtttggaagc ttagagagta gtgctttcta gtgtggtggt 3480
ttgatgatta ttttgcgtaa tatctgtaaa taaatacctc tgtgaagttt tactttggtg 3540
ctaagtactt aaattgcaat cgtggagata ctattatcta ttcagataac tttgacgttc 3600
tggtttaaat cagttgataa ttccttagga tactaggatg atcccactgt aagtattatg 3660
agcttatttt gatatttgag atctttattg accattatac atccataaaa gttcccgtac 3720
tttggcagaa ggagactttt cttctgtttc tagagaacca tttgcagaag actgtcattt 3780
ttcaattaca tgatttaaaa gatatggttt tcttcttcca tcatttgttg ctaacagaaa 3840
aaaagaagtg gaaattttga tttagatctg agactctatg taacttccac tatgttgctg 3900
aatgttgtgt agaaaaagat ctagtctgca aacaagtttt gccctgtatg ctggctgatc 3960
ctatgaagtt gacatgattt tacttatctt ttgatttttc atggaggtag agcaaactgc 4020
aggtctatgg ctatcttcat agtgcatgtt gtgtaattcc cagtgggttc aaaatgaact 4080
gtgttttaac tttcagtttt acttgtattt ctaaatatct ggtgataaca tcgtacaggc 4140
atgaatagaa atattgtatg attgttttct attcttcctt gggagctggt ccaatttaac 4200
ttgaaaaatg atacacaggg aatccttgtt tttgcttctg tcatggcgac tttgggactg 4260
cagataattc tggagtctat gcgtacacta atatctgatg taagttgtgg ctcctaagat 4320
aagtttattg ctttattatg ttgtattgtc tggttgaaaa ttacatgcat ggattcttat 4380
aattattcct tgaccctgta caacggcaaa tgttataaac attgaccttc tcacaggagt 4440
ctgatttcaa cctcaccaag gagcaggaga gatgggttgt tgggattatg gtctttgtga 4500
ctttggtgaa actagtttta atgttgtatt gccggtcttt taccaatgag attgtgaaag 4560
catatgccca ggatcatttc tttgatgtta tcacaaacat cattggtctc attgcagcat 4620
tgcttgctaa ctacattacc gactggatag atcccgttgg agctatgatt gtaagttcta 4680
tctccctgat tctgttccac caatcaggat tggaaagaaa agggaaaagt tttaatgtgg 4740
ctgtcaatcc tctcgcttta accaaggtta gtggctttaa gcaattttcc ctctgctgca 4800
gcttgcattg tataccattc gaacttggtc aatgactgta ttggagaatg tgaactctct 4860
cgtcggcaag tctgctgcac cagaatactt acagaagctg acttacctct gctggaacca 4920
tcacaaggcc ataaggcata tagataccgt gagggcttat acatttggtt cgcactactt 4980

```
tgttgaagtt gatatcgtcc tgcctgcgga catgcctttg caagaggcac atgatattgg   5040

tgagtcgttg caggagaagc ttgaactatt gcctgagatt gagcgtgcct tcgttcatct   5100

tgactatgaa tacagccata aacctgaaca tgctcaggca taccaatagt caaaaggatt   5160

ttgtgacatc ttctctagcc aatgtaccta atacctctgc atagtgaact ctgatatgct   5220

gttcgagatc ggctaatctg gtgattgctc tttaaaagaa aatctgggaa agaaaaggct   5280

gctatgatct ggatgttccc tagaacaagt aatatgaatt attattttgt taaattttac   5340

cttgcctatt catatatata acatgatttc tcagtttgct tgctcctggt              5390
```

<210> SEQ ID NO 20
<211> LENGTH: 1200
<212> TYPE: DNA
<213> ORGANISM: Nicotiana tabacum

<400> SEQUENCE: 20

```
atgttggaag tagtacctct tcacggcggc gatcacggcg ccggcaccga agaggagctt     60

ttattgctgg agacaaacaa tgccgaccgg tcatggagat taaacttcga cgagttgcgg    120

ttgtcgtctg aatccaaaga gaagcctcca cgtggcctcc atgattgcct tggagtttta    180

agtcaagaag acaacattgc tgagtactac cagcaacagg tagaaatgct cgagggcttc    240

aatgaaatgg acgccttgac cgatcgcggt tttgtacctg ggatgtcaaa ggaagagagg    300

gaaaaaacgg ctagaaatga aacatttgcc attaggatat caaatgttgc aaacatggtt    360

ctctttgccg ctaaagtata tgcgtcagtc aagagtggtt cattggccat catagcatcc    420

acattggatt cgctgcttga tcttctctct ggtttcatat tatggtttac agctttctcc    480

atgcagacac caaacccata tcaatatcct attggaaaaa aacgtatgca gccgttggga    540

atccttgttt ttgcttctgt catggcgact ttgggactgc agataattct ggagtctatg    600

cgtacactaa tatctgatga gtctgatttc aacctcacca aggagcagga gagatgggtt    660

gttgggatta tggtctttgt gactttggtg aaactagttt taatgttgta ttgccggtct    720

tttaccaatg agattgtgaa agcatatgcc caggatcatt tctttgatgt tatcacaaac    780

atcattggtc tcattgcagc attgcttgct aactacatta ccgactggat agatcccgtt    840

ggagctatga ttcttgcatt gtataccatt cgaacttggt caatgactgt attggagaat    900

gtgaactctc tcgtcggcaa gtctgctgca ccagaatact tacagaagct gacttacctc    960

tgctggaacc atcacaaggc cataaggcat atagataccg tgagggctta tacatttggt   1020

tcgcactact ttgttgaagt tgatatcgtc ctgcctgcgg acatgccttt gcaagaggca   1080

catgatattg gtgagtcgtt gcaggagaag cttgaactat tgcctgagat tgagcgtgcc   1140

ttcgttcatc ttgactatga atacagccat aaacctgaac atgctcaggc ataccaatag   1200
```

<210> SEQ ID NO 21
<211> LENGTH: 399
<212> TYPE: PRT
<213> ORGANISM: Nicotiana tabacum

<400> SEQUENCE: 21

```
Met Leu Glu Val Val Pro Leu His Gly Gly Asp His Gly Ala Gly Thr
1               5                   10                  15

Glu Glu Glu Leu Leu Leu Leu Glu Thr Asn Asn Ala Asp Arg Ser Trp
            20                  25                  30

Arg Leu Asn Phe Asp Glu Leu Arg Leu Ser Ser Glu Ser Lys Glu Lys
        35                  40                  45
```

```
Pro Pro Arg Gly Leu His Asp Cys Leu Gly Val Leu Ser Gln Glu Asp
    50                  55                  60

Asn Ile Ala Glu Tyr Tyr Gln Gln Gln Val Glu Met Leu Glu Gly Phe
65                  70                  75                  80

Asn Glu Met Asp Ala Leu Thr Asp Arg Gly Phe Val Pro Gly Met Ser
                85                  90                  95

Lys Glu Glu Arg Glu Lys Thr Ala Arg Asn Glu Thr Phe Ala Ile Arg
            100                 105                 110

Ile Ser Asn Val Ala Asn Met Val Leu Phe Ala Ala Lys Val Tyr Ala
        115                 120                 125

Ser Val Lys Ser Gly Ser Leu Ala Ile Ile Ala Ser Thr Leu Asp Ser
    130                 135                 140

Leu Leu Asp Leu Leu Ser Gly Phe Ile Leu Trp Phe Thr Ala Phe Ser
145                 150                 155                 160

Met Gln Thr Pro Asn Pro Tyr Gln Tyr Pro Ile Gly Lys Lys Arg Met
                165                 170                 175

Gln Pro Leu Gly Ile Leu Val Phe Ala Ser Val Met Ala Thr Leu Gly
            180                 185                 190

Leu Gln Ile Ile Leu Glu Ser Met Arg Thr Leu Ile Ser Asp Glu Ser
        195                 200                 205

Asp Phe Asn Leu Thr Lys Glu Gln Glu Arg Trp Val Val Gly Ile Met
    210                 215                 220

Val Phe Val Thr Leu Val Lys Leu Val Leu Met Leu Tyr Cys Arg Ser
225                 230                 235                 240

Phe Thr Asn Glu Ile Val Lys Ala Tyr Ala Gln Asp His Phe Phe Asp
                245                 250                 255

Val Ile Thr Asn Ile Ile Gly Leu Ile Ala Ala Leu Leu Ala Asn Tyr
            260                 265                 270

Ile Thr Asp Trp Ile Asp Pro Val Gly Ala Met Ile Leu Ala Leu Tyr
        275                 280                 285

Thr Ile Arg Thr Trp Ser Met Thr Val Leu Glu Asn Val Asn Ser Leu
    290                 295                 300

Val Gly Lys Ser Ala Ala Pro Glu Tyr Leu Gln Lys Leu Thr Tyr Leu
305                 310                 315                 320

Cys Trp Asn His His Lys Ala Ile Arg His Ile Asp Thr Val Arg Ala
                325                 330                 335

Tyr Thr Phe Gly Ser His Tyr Phe Val Glu Val Asp Ile Val Leu Pro
            340                 345                 350

Ala Asp Met Pro Leu Gln Glu Ala His Asp Ile Gly Glu Ser Leu Gln
        355                 360                 365

Glu Lys Leu Glu Leu Leu Pro Glu Ile Glu Arg Ala Phe Val His Leu
    370                 375                 380

Asp Tyr Glu Tyr Ser His Lys Pro Glu His Ala Gln Ala Tyr Gln
385                 390                 395
```

<210> SEQ ID NO 22
<211> LENGTH: 5468
<212> TYPE: DNA
<213> ORGANISM: Nicotiana tabacum

<400> SEQUENCE: 22

```
catttttagt tccactttcc ttgttcaaaa aagttccgcc atatatagcc tccacaacta      60

cccaccacta agaactccaa attacataaa ggtccctcga gtttcatcaa atttactcac     120
```

```
tttaccactt tctgcggctc cttcaagtag gtgccgccag tttttttacct agtgtattca    180
actggttttt tcctgttttc cggtgaccgg aaaatgttag aagtagtacc tcttcacggc    240
ggcgatcaag gcgtcggcgc cgaagaggag cttttattgc tggagacaaa caatgccgac    300
cgatcatgga gattaaactt cgacgagttg cggttatcgt ctgaaaccaa agagaagcct    360
ccacgtggcc tccatgattg ccttggggtt ttaagtacat tctccacctc tctatgcgac    420
gccgctttga gtgttattct ctgctaattt cttaactagt tgcattagga tagtaaatta    480
gtggagacac cacttgaatg gagtggaatt tatataaagg atttatacag ctgattccta    540
ttaatcagtg atggagaaat acttgactga tattctgttg tgcgtaggaa gtttactaat    600
tgtggaaatt ttctaacact aagcttactt ctttagttga gttattaggg ggctcttttt    660
aatacttttc agtgtcagaa agtattcatg ccacgtggat tcaattttcg gaagaacaaa    720
atgattcttg tatggatggt gtaaatttgc taaagatatt aagctatatt cactttttat    780
tgttctctgg acaattgaac atgcttatgg gcagttcact ggtttggagc aaattggcat    840
atattttgta tgtagatgga tgattctttt tggataagtt ttagatggat aattattgtt    900
ataagagcat gagcgttaaa gcttaaattt aatgcgtttc agcacttcag tttactgaaa    960
ataagaagaa aactttagct gagtgcactc accaggtaag tctatgtggt taggtcagtg   1020
taatagaacc agaggcagat ctatgttaat atgtgagggt gcactggcac ccgagtatat   1080
aaaattctta taaaactact actcatgtat tttaggtggc aacctcaatt acaaagtagc   1140
ggtaggagga tttgttaaaa tatgtgtttt tacctgagtt gttgtcttct catattgaat   1200
acttacaaag ttgaatcaaa ttaatgcaat accatcaaac caactgaatg cactttagac   1260
gacatgactt gttcgaagct ttagtgcacc ggcaaccttc aattccttga tatgcctctg   1320
aatagaacag gttaattggt gcgcgtgtgt gtttgcatgt gacatgagcc agtcaacaga   1380
ttgtttcaag aggctacttt tgcattctgt tgaattgtta aattgtcata tgagaatgta   1440
tgtttcgaat tgataatggt actttaacaa tttataattg gttttggtac gagtggtggc   1500
ctttaaatgc aggtcaccct tggttcccat caactctttg gtttagtact tatagggggc   1560
tatagtgagg gatttactga atgctttcac cgtaagacat ggggtgttct tgaaggcacg   1620
gattatgaca ctgtgttttt ctttggtgct tataggtcaa gaagacaaca ttgctgagta   1680
ctaccagcaa caggtagaaa tgctcgaggg cttcaatgaa atggacacct tgactgatcg   1740
tggttttgta cctgggatgt caaaggtttt gatagttttt atctgcttct tctttatgta   1800
taagaccaag catttgtttc ttctctagat gtaatcattc ttatattatt ataagcttgg   1860
actgacaagg tcaattaatt tggttgcagg aagagaggga aaaaactgct agaaatgaaa   1920
catttgccat taggatatca aatgttgcaa acatggttct ctttgctgct aaagtatatg   1980
catcagtcaa gagtggttca ttggccatca tagcatccac attggattcg ctgcttgatc   2040
ttctctctgg tttcatatta tggtttacag ctttctccat gcagacacca aacccatatc   2100
aatatcctat tggaaagaaa cgtatgcagc cgttggttag tgctgctgct tttgttctct   2160
aagtttttta cattttctat gcctttaatc agggcatttt tgcacttgtc acttgctatt   2220
gggctaatgt tgattactgc atataataac aatgttcatg gatttaaaag ttgtctaaca   2280
aggtaattat actatgcgtt cttgtcatat ttgattttaa agggacctta aactctggcg   2340
ctgctatttt tattttgtgg tcatggtaag ccttaatatt cattttgttt gttgatgcag   2400
aggcaactta gccttcttct tgagatcaat ctctaatcat cacatgacgt agtccaaaaa   2460
acaaaggaat aattttcacc taaagtatgg aaccacgaga aatgcaaact taatgcatct   2520
```

aatagcatgt ttggccaagc cttttttttgg gccaaaagtg ttttttttttc aaaaattaag 2580 gtgttttttt tcaaaaagtg tttggccaag cttttagaag gaaaaaattg tgcttttgag 2640
gagacgcaga agtagttttt gagaagcaaa aaaaagtagc ttatctccaa aagcactttt 2700
ctgagaagca cttttgagaa aaatacacat agatgcagtt tttaaaagct tggccaaacg 2760
ctaattactg ctcaaaagtg cttttcaaat taattagcca aacacaaact gcttatcacc 2820
aaaaacactt ttttgaaaag tacttttgag aaaagtactt ctcaaaataa gctgatttta 2880
gaagcttggc caaacaggct ataagacaaa ttaaatgaat taaaacaaca taatatttga 2940
tagtaaccaa ctataaaagg ttgaaataaa agaaacgacg tgcaaacttt caataatgac 3000
ctctagcaga cagcttacat gactgcaata aaacctacag agatgcaaat cttcagcatc 3060
tctttctcca atagttgtct tctaagtgta gcctcagtgg cgaaccacac tgagaatgtt 3120
tgtgagacag aaagagagag agagcagtgg ctgctgttac tgacagtata gaatgagaga 3180
gggtggggtt acaggaagat tattaagcgt ctattagtaa tttggcaaaa atttaggtgt 3240
tctgttttta ctgtggaggg atgaatatgg tctctgttta tgatctgtca tggatattgg 3300
agcttctagc ctcccatatg gaccattttc tcccacatca ggttaggttg atagccattg 3360
tgctcgcttt aagtagcgat cctcaaattc aattagttaa tcgtgttttg gtgatatgca 3420
tatagacatc tagattatca ctcctgatgt tacctataaa aagaactatt atctcctgat 3480
gtttctacta gtccaatgtc tgaacataac taaggaggta acatagactt gagttacact 3540
tggattcttg catagtcttt cttgccgttc atgtattcct gttatctcat ttggattatc 3600
aaaattgaca acaatcactt actcttttat tgttccatga ataattagtt tgggcatgaa 3660
tttggtgtag tactcataac agttgcattt agttagtaag cttaggatgc acatcttaag 3720
gaggaggagt gttttctagc ttcttggttt gaagataatt tgcctaatat ctgtaaataa 3780
ataactccga gaagttttac tttggtgcta agtacttaaa ttgccatcgt ggagatacta 3840
gttcatttaa tttgtgttat ctattcagat ttttgacctt ctggtttaaa tcagttgata 3900
attccttagg atacagggat gatcccactg taaaaatcta gtctgcaaac aagttttgcc 3960
ctgcatgctg gctgatccta tgaagttgaa tgattttaca tgtttgatat tttcatgtag 4020
ctagagcaaa gtgcaggtct atggctatct tcaaagtgca tgttgtgtaa ttcccaatgg 4080
gttcaaagtg aactgtgttt taactttcag ttttacttgt atttctacat atctggtgat 4140
aacaacttac cggcatgaat agagatattg tatgattgtt ttcttttctt ccttgggagc 4200
tggtccaatt taactttgaa aaatgataca cagggaatcc ttgtttttgc ttctgtcatg 4260
gcgactttgg gactgcagat aattctggag tctatgcgta cactaatatc tgatgtaagt 4320
tgtggcttct atgattgcaa atttctgctc tatttatgct gtattgtctg gttgaaaatt 4380
acatggattg ttataattat tccttgatcc tgcacaacga caaatgttaa cattgacctt 4440
ctcacaggag tctgatttca accttaccaa ggagcaggag agatgggttg ttgggattat 4500
ggtctttgtg actttggtga aactagtttt aatgttgtat tgccggtctt ttaccaatga 4560
gattgtgaaa gcatatgccc aggatcattt ctttgatgtt atcacaaaca taattggtct 4620
cattgcagca ttgcttgcta actacatcac cgactggata gatcccgttg gagctatgat 4680
tgtaagttct atctctagat tctattccac caacaacctc ctcccttaaa agaaatgtgc 4740
aaagaaaaag gaaaagtttt aatggggctg tcaatcctct cactttaaac aaggttagtt 4800
gaacaaagtt agtggcttta aactattttc cctctgctgc agctcgcact gtataccatt 4860
cgaacttggt caatgactgt attggagaat gtgaactctc tcgtcggcaa gtcagctgca 4920
ccagaatatc tacagaagct gacttacctt tgctggaatc atcacaaggc cgtaaggcat 4980
atagataccg tgagggctta tacatttggt tctcactact ttgttgaagt tgatatcgtc 5040
ctgcctgcgg acatgccttt gcaagaggca catgatattg gcgagtcgtt gcaggagaag 5100
cttgaactat tgcctgagat tgagcgggcc ttcgttcatc ttgactacga atacagccac 5160
aaacctgaac atgcacaggc ataccaatag tcaaaaggat attgtgacat cttatctaac 5220
caatgtacct aatacctctg cataagtgaa ctctgatatg ctgttcgaga tcggttgatc 5280
tggtgattgc tccttaaaag aaaatatgga aaagaaaagg ctgctatgat ctggatgttc 5340
cctagaacaa gtaatatgaa ttattattat ttttttaatt tactttgcct attcatatat 5400
ataacatgat tcctcagttt gcttgctcct ggtatattgc taacttatat tagaggaatt 5460
tgggtttc 5468

<210> SEQ ID NO 23
<211> LENGTH: 1200
<212> TYPE: DNA
<213> ORGANISM: Nicotiana tabacum

<400> SEQUENCE: 23
atgttagaag tagtacctct tcacggcggc gatcaaggcg tcggcgccga agaggagctt 60
ttattgctgg agacaaacaa tgccgaccga tcatggagat taaacttcga cgagttgcgg 120
ttatcgtctg aaaccaaaga gaagcctcca cgtggcctcc atgattgcct tggggtttta 180
agtcaagaag acaacattgc tgagtactac cagcaacagg tagaaatgct cgagggcttc 240
aatgaaatgg acaccttgac tgatcgtggt tttgtacctg ggatgtcaaa ggaagagagg 300
gaaaaaactg ctagaaatga aacatttgcc attaggatat caaatgttgc aaacatggtt 360
ctctttgctg ctaaagtata tgcatcagtc aagagtggtt cattggccat catagcatcc 420
acattggatt cgctgcttga tcttctctct ggtttcatat tatggtttac agctttctcc 480
atgcagacac caaacccata tcaatatcct attggaaaga aacgtatgca gccgttggga 540
atccttgttt ttgcttctgt catggcgact ttgggactgc agataattct ggagtctatg 600
cgtacactaa tatctgatga gtctgatttc aaccttacca aggagcagga gagatgggtt 660
gttgggatta tggtctttgt gactttggtg aaactagttt taatgttgta ttgccggtct 720
tttaccaatg agattgtgaa agcatatgcc caggatcatt tctttgatgt tatcacaaac 780
ataattggtc tcattgcagc attgcttgct aactacatca ccgactggat agatcccgtt 840
ggagctatga ttctcgcact gtataccatt cgaacttggt caatgactgt attggagaat 900
gtgaactctc tcgtcggcaa gtcagctgca ccagaatatc tacagaagct gacttacctt 960
tgctggaatc atcacaaggc cgtaaggcat atagataccg tgagggctta tacatttggt 1020
tctcactact ttgttgaagt tgatatcgtc ctgcctgcgg acatgccttt gcaagaggca 1080
catgatattg gcgagtcgtt gcaggagaag cttgaactat tgcctgagat tgagcgggcc 1140
ttcgttcatc ttgactacga atacagccac aaacctgaac atgcacaggc ataccaatag 1200

<210> SEQ ID NO 24
<211> LENGTH: 399
<212> TYPE: PRT
<213> ORGANISM: Nicotiana tabacum

<400> SEQUENCE: 24

Met Leu Glu Val Val Pro Leu His Gly Gly Asp Gln Gly Val Gly Ala

-continued

```
1               5                   10                  15

Glu Glu Glu Leu Leu Leu Leu Glu Thr Asn Asn Ala Asp Arg Ser Trp
            20                  25                  30

Arg Leu Asn Phe Asp Glu Leu Arg Leu Ser Ser Glu Thr Lys Glu Lys
        35                  40                  45

Pro Pro Arg Gly Leu His Asp Cys Leu Gly Val Leu Ser Gln Glu Asp
    50                  55                  60

Asn Ile Ala Glu Tyr Tyr Gln Gln Gln Val Glu Met Leu Glu Gly Phe
65                  70                  75                  80

Asn Glu Met Asp Thr Leu Thr Asp Arg Gly Phe Val Pro Gly Met Ser
                85                  90                  95

Lys Glu Glu Arg Glu Lys Thr Ala Arg Asn Glu Thr Phe Ala Ile Arg
            100                 105                 110

Ile Ser Asn Val Ala Asn Met Val Leu Phe Ala Ala Lys Val Tyr Ala
        115                 120                 125

Ser Val Lys Ser Gly Ser Leu Ala Ile Ile Ala Ser Thr Leu Asp Ser
    130                 135                 140

Leu Leu Asp Leu Leu Ser Gly Phe Ile Leu Trp Phe Thr Ala Phe Ser
145                 150                 155                 160

Met Gln Thr Pro Asn Pro Tyr Gln Tyr Pro Ile Gly Lys Lys Arg Met
                165                 170                 175

Gln Pro Leu Gly Ile Leu Val Phe Ala Ser Val Met Ala Thr Leu Gly
            180                 185                 190

Leu Gln Ile Ile Leu Glu Ser Met Arg Thr Leu Ile Ser Asp Glu Ser
        195                 200                 205

Asp Phe Asn Leu Thr Lys Glu Gln Glu Arg Trp Val Val Gly Ile Met
    210                 215                 220

Val Phe Val Thr Leu Val Lys Leu Val Leu Met Leu Tyr Cys Arg Ser
225                 230                 235                 240

Phe Thr Asn Glu Ile Val Lys Ala Tyr Ala Gln Asp His Phe Phe Asp
                245                 250                 255

Val Ile Thr Asn Ile Ile Gly Leu Ile Ala Ala Leu Leu Ala Asn Tyr
            260                 265                 270

Ile Thr Asp Trp Ile Asp Pro Val Gly Ala Met Ile Leu Ala Leu Tyr
        275                 280                 285

Thr Ile Arg Thr Trp Ser Met Thr Val Leu Glu Asn Val Asn Ser Leu
    290                 295                 300

Val Gly Lys Ser Ala Ala Pro Glu Tyr Leu Gln Lys Leu Thr Tyr Leu
305                 310                 315                 320

Cys Trp Asn His His Lys Ala Val Arg His Ile Asp Thr Val Arg Ala
                325                 330                 335

Tyr Thr Phe Gly Ser His Tyr Phe Val Glu Val Asp Ile Val Leu Pro
            340                 345                 350

Ala Asp Met Pro Leu Gln Glu Ala His Asp Ile Gly Glu Ser Leu Gln
        355                 360                 365

Glu Lys Leu Glu Leu Leu Pro Glu Ile Glu Arg Ala Phe Val His Leu
    370                 375                 380

Asp Tyr Glu Tyr Ser His Lys Pro Glu His Ala Gln Ala Tyr Gln
385                 390                 395
```

<210> SEQ ID NO 25
<211> LENGTH: 3680
<212> TYPE: DNA
<213> ORGANISM: Nicotiana tabacum

<400> SEQUENCE: 25
aggcaagacc aaacaagtca catttctcat gcatgccact atttttgaga gcaaaaacat 60
aatctgaaaa tttggatatc tacgcatttt cacatgtttc aaactccttc actttgtcag 120
cacatcaaca gccaattttt ctctctttga aaataaagga aagggaaaga aaggaaaagg 180
gaagttggga aacatatgcc aaatcccctg tcctttcttt ccctaaataa ttcccatttc 240
tggctgtttc gatttcttga tctgaggatc ggaggaattg aatttttaaa attctgttat 300
attccatcca ttgccacttc ttttcttgat tgatttttgg ataagaaaat aaagggattt 360
ttcaaataaa aatggatgtg gaagaggcat tgctgaggaa tgaagttcca aatgtcatac 420
caaagcgtcg aaactcagtt aattctatga gatgtgattt cttctctaaa ctacctagaa 480
aggttaagac agggcttgat cctgaagaac cttttctttt ggacttgtct aaaaccactg 540
gtttaattga aggtaaagcc tcttttaagc atttctaagt gcatcatctt tttgctcatc 600
tcttgttcta atttctatgt tgattttgtt gcttgattct tagctcatct tctaatgtag 660
ttatttatga tcttatgaat aggggagaaa gaatattatg aaagacagat tgcaacttta 720
aagtcctttg aggaagtaga ctcacttgat tcagctgatg tcattgatga agaacaagac 780
ctactagatc aagcacagca tgaaagagca atgaacattt ccaattttgc aaatgtctta 840
ttacttgcct ttaaggtata acttcttttt cattgtttct attgtgcaaa cttttaatgc 900
ctcaaacctt ctcctgaata caccccagga tccctttttat ttctttgtta tgagtattat 960
ctttttacaa ttaacccttg tggcccgacc ttttctcaga ccccacgcat agcatatgca 1020
ggagcttagt gcacccgact accctttttat cttttatata atggtagtgt ctgagctaac 1080
ttgaacgcac ctcaactatt caacatccca ctaacacaag tatcaggtta catctgctca 1140
ctaaggttta ggcaaatggg aagaaatcac ctatcatttc ttatctctgt tgagatttga 1200
atattgatct ctcatgattt tcacccactt ttggcttcta ggctacatcc ccaagatcct 1260
gtttattatc tcaaagaaaa ggaagacagc cctcaggttc agggcagggt agtttgaagt 1320
ttgcaatagc tagtttagct acttaatttt tttattgctc aaattatacc acatgtaagt 1380
ttgacattaa tgacatattg aatgatcatt gtgagacagt aggtagttgt ctccaataat 1440
gttccttgta gagaaaagaa atgttgtata tttcatctac gagtagttaa atttgcttaa 1500
atcaaactga accctcgtta atttggactg tttgcagatc tatgctactg taaaaagtgg 1560
ttctttagcc attgcagcgt cgacgttgga ttcactactt gatctaatgg ctggtggtat 1620
tctttggttc acacacctgt caatgaagag cataaacatt tacaagtacc ctataggaaa 1680
gttaagagtt caaccagtgg ggattatcat ctttgctgct gttatggcta ctcttggtat 1740
gtcctggttc acctgtcata tctttctctt aattttggca gtctagaatt catgaataac 1800
ccttgatact gaagaagagg ataaataact tctatcataa gaataagttc gaccaaaaag 1860
ttctccattg aagcattgtg aattgcaaaa tgatggcgaa tacctctaac cacttcttag 1920
cagtttatat tttgtggatt taggtggttt agtgtggtgt aaagattaag tatacaaaaa 1980
attgcaaaga gaagtgttta aagagaatta gcaattctag atgattgttt gtatcggtca 2040
tgatttctct ccttgtgaaa aaagaaatgg aaaagaacaa tctaaagaag ttacaatgga 2100
agtctgcatt tttgtctcat tctgatctgc atttagacag cgcatgtatg gtgatcgtgt 2160
cctatcacac taattgagta tctgcgattg cataggcttt caagtcttag tgcaggctgt 2220
ggaacaactg ataaaagata caccctcaga caagatgact ggggagcaac tggcttggct 2280

```
atatgcaatc atgctgacag ccactggagt gaagctcgtc ttatggattt attgcagaag   2340
ttcaggaaac aagatagtta gagcatatgc aaaggtcctt tttccccata tactctcctg   2400
aaaaatctca tttaatgcag tgttatcctt tctttcatcc attgagcaac atttgacaaa   2460
ttgtggaacc atgcatgata tccaggatca ttacttcgat gtggtaacaa atgttgtcgg   2520
tttggttgct gctgttctcg gtgatcgatt ctattggtgg atcgatcctg ttggtgctat   2580
tgtccttgct gtatatacaa ttacaaattg gtcaggaact gtgctggaaa atgcaggttc   2640
ttactttttc ctttgtcagc taacatgcat tcacaaatga tgctaatttg attttggttt   2700
cgaaagtaat caacttacgc gaacaaaaaa taatacaccc aaactctaat gctgcagttt   2760
gcaattcttg gatatacttc ttggatcttt tggctcttat agagtagaat tttccccttt   2820
tgtggggaat ggtcagtgaa tgattttgat gtttatttgc tatttaccta gctaacactt   2880
gaatgtttct ctctcctgca gtttctctag ttggacaatc agcccctcct gaatttctac   2940
agaaactgac atatcttgtt ctaaggcatg atcctcagat aaaaagagtt gataccgttc   3000
gagcctatac ttttggagtt ctttactttg ttgaggtgcg atgtccacca ctctgaagtg   3060
cttttctcct gcacaatttt caatttttaa tagttcataa aattggttga agagagcaag   3120
aaaacaacta cgtctcaatt caagcaagtt ggagccaatt atatgaatac tcactatcca   3180
tgtcacttca attaagctcg tccccgctca acattataaa ttattagctt ctctagtagt   3240
ataattttgg aaaatttaga caacttcctt cataatctga taattggcaa ttgtctgttt   3300
tgtaacaggt tgacatagag ctcccagaag atttgccact gaaagaagcc catgccattg   3360
gagagtcact tcagattaag attgaagaac ttccagaagt tgaacgtgct tttgtccatc   3420
ttgattatga gtgtgatcac aaaccagaac actccatttt gagtagaatt cccaacagcc   3480
caccttaata ttctagtctc tcaactccgt gttatttctt agtactttta caatgtaaaa   3540
ttaagagccc attttgctat gtggaagtat catgaagagt gaggcctgac gttgtgatat   3600
gtatacagaa aagaaggaaa ctaatggttg gagaattcca tttttccctt atgaagcacc   3660
taattagctt cacatttcct                                               3680
```

<210> SEQ ID NO 26
<211> LENGTH: 1197
<212> TYPE: DNA
<213> ORGANISM: Nicotiana tabacum

<400> SEQUENCE: 26

```
atggatgtgg aagaggcatt gctgaggaat gaagttccaa atgtcatacc aaagcgtcga     60
aactcagtta attctatgag atgtgatttc ttctctaaac tacctagaaa ggttaagaca    120
gggcttgatc ctgaagaacc ttttcttttg gacttgtcta aaaccactgg tttaattgaa    180
ggggagaaag aatattatga aagacagatt gcaactttaa agtcctttga ggaagtagac    240
tcacttgatt cagctgatgt cattgatgaa gaacaagacc tactagatca agcacagcat    300
gaaagagcaa tgaacatttc caattttgca aatgtcttat tacttgcctt taagatctat    360
gctactgtaa aaagtggttc tttagccatt gcagcgtcga cgttggattc actacttgat    420
ctaatggctg gtggtattct ttggttcaca cacctgtcaa tgaagagcat aaacatttac    480
aagtacccta taggaaagtt aagagttcaa ccagtgggga ttatcatctt tgctgctgtt    540
atggctactc ttggctttca agtcttagtg caggctgtgg aacaactgat aaaagataca    600
ccctcagaca agatgactgg ggagcaactg gcttggctat atgcaatcat gctgacagcc    660
actggagtga agctcgtctt atggatttat tgcagaagtt caggaaacaa gatagttaga    720
```

gcatatgcaa aggatcatta cttcgatgtg gtaacaaatg ttgtcggttt ggttgctgct 780
gttctcggtg atcgattcta ttggtggatc gatcctgttg gtgctattgt ccttgctgta 840
tatacaatta caaattggtc aggaactgtg ctggaaaatg cagtttctct agttggacaa 900
tcagcccctc ctgaatttct acagaaactg acatatcttg ttctaaggca tgatcctcag 960
ataaaaagag ttgataccgt tcgagcctat acttttggag ttctttactt tgttgaggtt 1020
gacatagagc tcccagaaga tttgccactg aaagaagccc atgccattgg agagtcactt 1080
cagattaaga ttgaagaact tccagaagtt gaacgtgctt ttgtccatct tgattatgag 1140
tgtgatcaca aaccagaaca ctccattttg agtagaattc ccaacagccc accttaa 1197

<210> SEQ ID NO 27
<211> LENGTH: 398
<212> TYPE: PRT
<213> ORGANISM: Nicotiana tabacum

<400> SEQUENCE: 27

Met Asp Val Glu Glu Ala Leu Leu Arg Asn Glu Val Pro Asn Val Ile
1 5 10 15

Pro Lys Arg Arg Asn Ser Val Asn Ser Met Arg Cys Asp Phe Phe Ser
20 25 30

Lys Leu Pro Arg Lys Val Lys Thr Gly Leu Asp Pro Glu Glu Pro Phe
35 40 45

Leu Leu Asp Leu Ser Lys Thr Thr Gly Leu Ile Glu Gly Glu Lys Glu
50 55 60

Tyr Tyr Glu Arg Gln Ile Ala Thr Leu Lys Ser Phe Glu Glu Val Asp
65 70 75 80

Ser Leu Asp Ser Ala Asp Val Ile Asp Glu Glu Gln Asp Leu Leu Asp
85 90 95

Gln Ala Gln His Glu Arg Ala Met Asn Ile Ser Asn Phe Ala Asn Val
100 105 110

Leu Leu Leu Ala Phe Lys Ile Tyr Ala Thr Val Lys Ser Gly Ser Leu
115 120 125

Ala Ile Ala Ala Ser Thr Leu Asp Ser Leu Leu Asp Leu Met Ala Gly
130 135 140

Gly Ile Leu Trp Phe Thr His Leu Ser Met Lys Ser Ile Asn Ile Tyr
145 150 155 160

Lys Tyr Pro Ile Gly Lys Leu Arg Val Gln Pro Val Gly Ile Ile Ile
165 170 175

Phe Ala Ala Val Met Ala Thr Leu Gly Phe Gln Val Leu Val Gln Ala
180 185 190

Val Glu Gln Leu Ile Lys Asp Thr Pro Ser Asp Lys Met Thr Gly Glu
195 200 205

Gln Leu Ala Trp Leu Tyr Ala Ile Met Leu Thr Ala Thr Gly Val Lys
210 215 220

Leu Val Leu Trp Ile Tyr Cys Arg Ser Ser Gly Asn Lys Ile Val Arg
225 230 235 240

Ala Tyr Ala Lys Asp His Tyr Phe Asp Val Val Thr Asn Val Val Gly
245 250 255

Leu Val Ala Ala Val Leu Gly Asp Arg Phe Tyr Trp Trp Ile Asp Pro
260 265 270

Val Gly Ala Ile Val Leu Ala Val Tyr Thr Ile Thr Asn Trp Ser Gly
275 280 285

```
Thr Val Leu Glu Asn Ala Val Ser Leu Val Gly Gln Ser Ala Pro Pro
    290                 295                 300

Glu Phe Leu Gln Lys Leu Thr Tyr Leu Val Leu Arg His Asp Pro Gln
305                 310                 315                 320

Ile Lys Arg Val Asp Thr Val Arg Ala Tyr Thr Phe Gly Val Leu Tyr
                325                 330                 335

Phe Val Glu Val Asp Ile Glu Leu Pro Glu Asp Leu Pro Leu Lys Glu
            340                 345                 350

Ala His Ala Ile Gly Glu Ser Leu Gln Ile Lys Ile Glu Glu Leu Pro
        355                 360                 365

Glu Val Glu Arg Ala Phe Val His Leu Asp Tyr Glu Cys Asp His Lys
    370                 375                 380

Pro Glu His Ser Ile Leu Ser Arg Ile Pro Asn Ser Pro Pro
385                 390                 395


<210> SEQ ID NO 28
<211> LENGTH: 4195
<212> TYPE: DNA
<213> ORGANISM: Nicotiana tabacum
<220> FEATURE:
<221> NAME/KEY: misc_feature
<222> LOCATION: (1013)..(1027)
<223> OTHER INFORMATION: n is a, c, g, or t

<400> SEQUENCE: 28

tagcaaaaag acaaagttag caacttaaaa cagaaagttt gagacccaac gcaaagacag     60

tttttttttaa agaaacaaaa ttatctaatg gtttggtagt acgtactacg ttttaatctt    120

ctttatattt ttaattagta caacatctga ctttgtcttt tttctaatta aaataaaagt    180

tagatcatac tcgaagttat atatatctaa tcaatgcaaa tagtgtgaag cttaattaca    240

tgatttggag tttgcattac tgaaaatata tactcctaca actcttgata atggagggag    300

aattagaggc taacaatatt aatggaacta aaacgccatt gttggagggg tggaagctta    360

gcggaagtgg acggcggagc agccggcgtt tcagccggca taactctttt acgtcgctcc    420

gccgtgattt cttgtctagg cttccagata aggtgatcaa ctcttttgtt attgattctg    480

aagcttcata catcattaat aacctctcca tatcctctga cttaaccaaa ggttcttctc    540

tctctctcag gttgtttggt tccggactaa atatgtggtt aactgattat gatatatata    600

aagattatta tatgttgtat aaaactatag tgcttgtaat taatggatta tgtaaagtta    660

agaattagtt ttatcttgct attgttaata tgcatgttct tatatattcc catgaacatg    720

ttcttggctt gagaaaaagt gaaacttttt cttttctatg ctaaatttgg tgtatagact    780

aggttctgtt tgatattaat tactcctatt aaaggattca aacagaagct gttatacaat    840

cgtttgatca tgttaatcca atcacactgc atattaaact ccttaacatc ttttaaagat    900

tagaaaagga tgacctggga tcgaatcccc ctcaatgcct tttgggttga gtctgtcgca    960

catggcttgc ctagtgcgga ttacctctcc tgtgtggctt gcaggctatt acnnnnnnnn   1020

nnnnnnngcg gctgcggggt tttcccctct taaaccaaaa aaaaaaaaaa aaaaagaaaa   1080

aaggaatatc aattttttttc tttttctttt ttccttttttt tttttttttt attttatttg   1140

caaataaagc aaaattttgc tggaaactac actagggaaa ttcaaatatc taccgctaga   1200

aaaggatatc tttaacaccc tcagtcagtg gcgaagccac atggttataa ggatggtcaa   1260

ttgaccaccc ttcgtcgaaa aattacactg tgtatatagg taaaatatta cgttttagcg   1320

gtatacaaca catattgaac accctttgtc gggaattttt tttacttcat tcaaatttga   1380
```

-continued

```
acacctttgg aaaaaaattt aggttcgcca ctgccctcgg tgctccgttg actaagtttt   1440
atgatgatag gagaaaagga atactatgaa aaacagtttg agactttgaa gtcatttgag   1500
gaagttgatt ctgcagttgc ttctgattgc attgatgaag aggatctcga agaacaagct   1560
caacatgaga gagcaatgag aatctccaat tatgcaaaca ttatactgct tgctctcaag   1620
gtgaccagaa attacttaat tgaactcgtc attaacatga gaatgagaaa tcatctatta   1680
atgtgtatgc atttctttgt cctgcaacat ttttatatat gcagtaaaag tgaaattctg   1740
gtttatgttt gaatgacctg gaaaaatgat aaagatggtg gtttatgcct ttttgtcaca   1800
atagcagtat tgacacatat cgcgccttgc agatctatgc cacagtaaag agtggttctt   1860
tagctattgc tgcatctaca ctggattcat tgcttgacct catggctggt ggcatactat   1920
ggtttactca tctttcaatg aaaaatatta atgtctataa atatcctatt ggaaaattga   1980
gagtgcagcc tgttggaatc atcgtctttg ctgctattat ggctacactt ggtatgttat   2040
ctgctttgac tttgcatttg aaattccatt atcgggttag tgaatacata gcgactttag   2100
cttacagaag acatggccct tgacaggagg atatggaggt cgaagattag ggtagaaggg   2160
taataggtcg tagtgtgttt ttctaatatg ttccaggttt attagcgcga gctgactagt   2220
acattgtctt cgattcttag agtgctagta ttagggttgt tttcagtact atcttccgct   2280
tcggttttct agtactttgt cgtaatactg cttgttgcta ttgctttctt ccatttgttt   2340
gttttctcgg ttcatacatt gatagtatca ttttcctggc cttgttgtta ttaccttatt   2400
cctattcttc ctctcgagcc gggagtcttt cggaaatagc ctctctatcc ctcagggtag   2460
gggtaaggtc tgcgtataca ttactctcct catacccac ttgtgggatt ccattgggtt    2520
gttgttgttg ggttagtgaa tacatgtcag tttggacagg tgagagtgag gcattggaaa   2580
taaaaaaaaa aaaaaacagg atgacggctt tcaaaagacg agtaagagac ggggagatgg   2640
aggctctcga aaccaaatga gattagagag aacaggggaa ttagcaccat tcatatgaga   2700
gctaacctct ttgtatatga aattcttcaa tttgcataat catgtgcatt tctttgtagg   2760
ctttcaggtg ctgatccagg ctgtagaaca actagttgaa aataaagctc ctgaaaagat   2820
gactttgaat cagctcgcat ggttatattc catcatgtta actgccacag tagtaaaact   2880
tgccctttgg ctttactgca gaagctcagg aaacaacatt gttcgtgcgt atgcaaaggt   2940
gtgtgtagtg tccttacctt ctggtttcca catcttctcc tgataatctc ttttcctaat   3000
ttgttgatgt atttgtcagg atcactattt tgatgtggtt actaacgtag tcgggttaat   3060
agcagctgta cttggtgata agttctactg gtggattgat cccgttggtg ctcttatcct   3120
tgctatttat acaatctcaa attggtcagc cactgtgata gagaatgcag gtatatactt   3180
acatgttcct gttgaattta tagttcgtca ataattcatg gaagttaaca gcgacgttca   3240
acaaacacag aactagtaac gcagactaga atctaacctt gtaagaaaaa ttatcccttt   3300
aggatgtctg caagaattat gcttgttgga cacctcaagt ctgagcacat aatatatgtt   3360
gtccaagcca acttgcacgc agctcgacta ttccaccggt tacctgctac ctctcaccag   3420
taaacgtatc gagtaactct gctcatcaag gtttaggcag atggaaagaa attaactagt   3480
gtctttttgc caccgctggg gtttgaactg gagacctcat ggttctcctc tcacttcatt   3540
gaccactaga ccacaccctg ggatgcaaaa ctccgatatt ttcttggtgt tatttatatc   3600
aatacatcaa ataaaacttg aatgaggttc ttgatgcagt gtcactggta ggacaatcag   3660
ctcctcctga agttatgcag aagttaacat atgttgttat aagacatcct caagtgaaac   3720
gtattgatac agttcgagca tacacctttg gtgtcttgta ctttgttgag gtcagtctcc   3780
```

aatagcatga aatcattttc ctaaacatct ttggtctgaa ctaactgaat tattaaggca 3840
tagccttttc cagatctctg ctgatttcaa aatgttgctt cctttctttt aacataggtt 3900
gatattgaac tcccggaaga tttgccattg aaagaagcac atattatcgg agagactcta 3960
caaataaagc tcgagaaact ccctgaagtg gaacgcgcat ttgttcatct tgattttgaa 4020
tgtgaacaca aaccagaaca ctccgtcccc agcaagctgc ccaacaatga atcttaagtg 4080
tagaacacac aaactaggag aaatttcaat ataaagaata ggtctttgat tgggagctca 4140
gctgctcctg aacctctata aatactcttg gtcatgtttg aggaatttgc atgat 4195

<210> SEQ ID NO 29
<211> LENGTH: 1251
<212> TYPE: DNA
<213> ORGANISM: Nicotiana tabacum

<400> SEQUENCE: 29
atggagggag aattagaggc taacaatatt aatggaacta aaacgccatt gttggagggg 60
tggaagctta gcggaagtgg acggcggagc agccggcgtt tcagccggca taactctttt 120
acgtcgctcc gccgtgattt cttgtctagg cttccagata aggtgatcaa ctcttttgtt 180
attgattctg aagcttcata catcattaat aacctctcca tatcctctga cttaaccaaa 240
ggagaaaagg aatactatga aaaacagttt gagactttga agtcatttga ggaagttgat 300
tctgcagttg cttctgattg cattgatgaa gaggatctcg aagaacaagc tcaacatgag 360
agagcaatga gaatctccaa ttatgcaaac attatactgc ttgctctcaa gatctatgcc 420
acagtaaaga gtggttcttt agctattgct gcatctacac tggattcatt gcttgacctc 480
atggctggtg gcatactatg gtttactcat ctttcaatga aaaatattaa tgtctataaa 540
tatcctattg gaaaattgag agtgcagcct gttggaatca tcgtctttgc tgctattatg 600
gctacacttg gctttcaggt gctgatccag gctgtagaac aactagttga aaataaagct 660
cctgaaaaga tgactttgaa tcagctcgca tggttatatt ccatcatgtt aactgccaca 720
gtagtaaaac ttgccctttg gctttactgc agaagctcag gaaacaacat tgttcgtgcg 780
tatgcaaagg atcactattt tgatgtggtt actaacgtag tcgggttaat agcagctgta 840
cttggtgata agttctactg gtggattgat cccgttggtg ctcttatcct tgctatttat 900
acaatctcaa attggtcagc cactgtgata gagaatgcag tgtcactggt aggacaatca 960
gctcctcctg aagttatgca gaagttaaca tatgttgtta taagacatcc tcaagtgaaa 1020
cgtattgata cagttcgagc atacaccttt ggtgtcttgt actttgttga ggttgatatt 1080
gaactcccgg aagatttgcc attgaaagaa gcacatatta tcggagagac tctacaaata 1140
aagctcgaga aactccctga agtggaacgc gcatttgttc atcttgattt tgaatgtgaa 1200
cacaaaccag aacactccgt ccccagcaag ctgcccaaca atgaatctta a 1251

<210> SEQ ID NO 30
<211> LENGTH: 416
<212> TYPE: PRT
<213> ORGANISM: Nicotiana tabacum

<400> SEQUENCE: 30

Met Glu Gly Glu Leu Glu Ala Asn Asn Ile Asn Gly Thr Lys Thr Pro
1               5                   10                  15

Leu Leu Glu Gly Trp Lys Leu Ser Gly Ser Gly Arg Arg Ser Ser Arg
            20                  25                  30

```
Arg Phe Ser Arg His Asn Ser Phe Thr Ser Leu Arg Arg Asp Phe Leu
        35                  40                  45

Ser Arg Leu Pro Asp Lys Val Ile Asn Ser Phe Val Ile Asp Ser Glu
    50                  55                  60

Ala Ser Tyr Ile Ile Asn Asn Leu Ser Ile Ser Ser Asp Leu Thr Lys
65                  70                  75                  80

Gly Glu Lys Glu Tyr Tyr Glu Lys Gln Phe Glu Thr Leu Lys Ser Phe
                85                  90                  95

Glu Glu Val Asp Ser Ala Val Ala Ser Asp Cys Ile Asp Glu Glu Asp
            100                 105                 110

Leu Glu Glu Gln Ala Gln His Glu Arg Ala Met Arg Ile Ser Asn Tyr
        115                 120                 125

Ala Asn Ile Ile Leu Leu Ala Leu Lys Ile Tyr Ala Thr Val Lys Ser
    130                 135                 140

Gly Ser Leu Ala Ile Ala Ala Ser Thr Leu Asp Ser Leu Leu Asp Leu
145                 150                 155                 160

Met Ala Gly Gly Ile Leu Trp Phe Thr His Leu Ser Met Lys Asn Ile
                165                 170                 175

Asn Val Tyr Lys Tyr Pro Ile Gly Lys Leu Arg Val Gln Pro Val Gly
            180                 185                 190

Ile Ile Val Phe Ala Ala Ile Met Ala Thr Leu Gly Phe Gln Val Leu
        195                 200                 205

Ile Gln Ala Val Glu Gln Leu Val Glu Asn Lys Ala Pro Glu Lys Met
    210                 215                 220

Thr Leu Asn Gln Leu Ala Trp Leu Tyr Ser Ile Met Leu Thr Ala Thr
225                 230                 235                 240

Val Val Lys Leu Ala Leu Trp Leu Tyr Cys Arg Ser Ser Gly Asn Asn
                245                 250                 255

Ile Val Arg Ala Tyr Ala Lys Asp His Tyr Phe Asp Val Val Thr Asn
            260                 265                 270

Val Val Gly Leu Ile Ala Ala Val Leu Gly Asp Lys Phe Tyr Trp Trp
        275                 280                 285

Ile Asp Pro Val Gly Ala Leu Ile Leu Ala Ile Tyr Thr Ile Ser Asn
    290                 295                 300

Trp Ser Ala Thr Val Ile Glu Asn Ala Val Ser Leu Val Gly Gln Ser
305                 310                 315                 320

Ala Pro Pro Glu Val Met Gln Lys Leu Thr Tyr Val Val Ile Arg His
                325                 330                 335

Pro Gln Val Lys Arg Ile Asp Thr Val Arg Ala Tyr Thr Phe Gly Val
            340                 345                 350

Leu Tyr Phe Val Glu Val Asp Ile Glu Leu Pro Glu Asp Leu Pro Leu
        355                 360                 365

Lys Glu Ala His Ile Ile Gly Glu Thr Leu Gln Ile Lys Leu Glu Lys
    370                 375                 380

Leu Pro Glu Val Glu Arg Ala Phe Val His Leu Asp Phe Glu Cys Glu
385                 390                 395                 400

His Lys Pro Glu His Ser Val Pro Ser Lys Leu Pro Asn Asn Glu Ser
                405                 410                 415
```

<210> SEQ ID NO 31
<211> LENGTH: 299
<212> TYPE: PRT
<213> ORGANISM: Artificial Sequence
<220> FEATURE:
<223> OTHER INFORMATION: polypeptide sequence of a mutated cation efflux protein

<400> SEQUENCE: 31

Met Glu Ile Ser Arg Ser Asn Val Ser Gly Gly Gly Gly Ser Gly Gly
1 5 10 15

Ala Leu Asp Asp Ser Phe Ser Ser Phe Arg Thr Glu Leu Leu Ser Pro
20 25 30

Ala Ala Gln Ala Val Val Asp Gln Ser Ser Ser Ser Ala Ser Trp Arg
35 40 45

Leu Asn Ile Ser Glu Phe Arg Leu Pro Glu Arg Ser Arg Ser Ser Ser
50 55 60

Asp His His Ser Phe Ser Val Arg Arg Leu Leu Pro Thr Pro Arg Lys
65 70 75 80

Gln Gly Lys Ile Ala Glu Tyr Tyr Lys Lys Gln Glu Arg Leu Leu Glu
85 90 95

Gly Phe Asn Glu Met Asp Thr Ile Asn Glu Ser Gly Cys Leu Pro Gly
100 105 110

Ser Leu Thr Glu Asp Glu Met Lys Gln Leu Ala Arg Ser Glu Arg Met
115 120 125

Ala Ile His Leu Ser Asn Met Ala Asn Val Val Leu Phe Ile Ala Lys
130 135 140

Ile Tyr Ala Ser Ile Glu Ser Arg Ser Leu Ala Val Ile Ala Ser Thr
145 150 155 160

Leu Asp Ser Leu Leu Asp Leu Leu Ser Gly Phe Ile Leu Trp Phe Thr
165 170 175

Ser His Ala Met Lys Asn Pro Asn Gln Tyr His Tyr Pro Ile Gly Lys
180 185 190

Lys Arg Met Gln Pro Leu Gly Ile Ile Val Phe Ala Ser Val Met Ala
195 200 205

Thr Leu Gly Leu Gln Ile Leu Phe Glu Ser Ala Lys Glu Leu Ile Thr
210 215 220

Lys Ser Arg Pro Glu Met Asp His Glu Lys Glu Lys Trp Thr Ile Gly
225 230 235 240

Ile Met Val Ser Val Thr Met Val Lys Phe Leu Leu Met Val Tyr Cys
245 250 255

Arg Arg Phe Lys Asn Glu Ile Val Arg Ala Tyr Ala Gln Asp His Phe
260 265 270

Phe Asp Val Ile Thr Asn Ser Val Gly Leu Val Thr Ala Val Leu Ala
275 280 285

Val Arg Phe Tyr Trp Trp Ile Asp Pro Thr Gly
290 295

<210> SEQ ID NO 32
<211> LENGTH: 903
<212> TYPE: DNA
<213> ORGANISM: Artificial Sequence
<220> FEATURE:
<223> OTHER INFORMATION: cDNA sequence of a mutated cation efflux
protein

<400> SEQUENCE: 32
atggagataa gtcgcagcaa tgttagtggt ggtggcggca gcggcggcgc tctggacgac 60
agttttagca gttttaggac ggaactgctg tctccggctg ctcaggcggt ggtggatcag 120
tcgtcttcgt cggcgtcatg gagacttaac attagcgaat tccgtcttcc cgaacgaagc 180
cgctcctcct ccgatcatca ctcctttagt gtccgtcgtc tacttcccac tcccaggaaa 240

```
caaggtaaaa ttgctgaata ctacaaaaaa caagaaaggc tgcttgaagg gttcaatgag    300

atggacacca ttaatgaatc tggttgttta cctggaagtc taactgagga tgaaatgaag    360

cagcttgcaa gaagtgaaag gatggctatt catttatcaa acatggctaa tgtggttctt    420

ttcattgcaa aaatctacgc ttctattgag agcagatctt tggctgtaat cgcgtcaacg    480

ttggactccc tcttagacct cttatcaggg tttatactgt ggttcacttc tcatgccatg    540

aaaaatccaa accagtatca ctatcctatt ggaaaaaaga ggatgcagcc attgggtatt    600

attgtttttg catctgtaat ggcgacacta ggattacaaa tattgttcga gtcagctaaa    660

gaactcataa ctaagtctcg ccctgagatg gaccatgaga aggaaaaatg gacgattggt    720

attatggtct ctgtcactat ggtcaagttt ctgcttatgg tctactgtcg aaggttcaaa    780

aacgaaatcg taagagccta tgctcaagat catttctttg atgtcatcac caactcagtt    840

ggattagtga ctgctgtctt agcagtccga ttctactggt ggattgatcc tacgggagct    900

taa                                                                  903
```

<210> SEQ ID NO 33
<211> LENGTH: 300
<212> TYPE: PRT
<213> ORGANISM: Artificial Sequence
<220> FEATURE:
<223> OTHER INFORMATION: polypeptide sequence of a mutated cation efflux
      protein

<400> SEQUENCE: 33

```
Met Glu Met Lys Gln Leu Ala Arg Ser Glu Arg Met Ala Ile His Leu
1               5                   10                  15

Ser Asn Met Ala Asn Val Val Leu Phe Ile Ala Lys Ile Tyr Ala Ser
            20                  25                  30

Ile Glu Ser Arg Ser Leu Ala Val Ile Ala Ser Thr Leu Asp Ser Leu
        35                  40                  45

Leu Asp Leu Leu Ser Gly Phe Ile Leu Trp Phe Thr Ser His Ala Met
    50                  55                  60

Lys Asn Pro Asn Gln Tyr His Tyr Pro Ile Gly Lys Lys Arg Met Gln
65                  70                  75                  80

Pro Leu Gly Ile Ile Val Phe Ala Ser Val Met Ala Thr Leu Gly Leu
                85                  90                  95

Gln Ile Leu Phe Glu Ser Ala Lys Glu Leu Ile Thr Lys Ser Arg Pro
            100                 105                 110

Glu Met Asp His Glu Lys Glu Lys Trp Thr Ile Gly Ile Met Val Ser
        115                 120                 125

Val Thr Met Val Lys Phe Leu Leu Met Val Tyr Cys Arg Arg Phe Lys
    130                 135                 140

Asn Glu Ile Val Arg Ala Tyr Ala Gln Asp His Phe Phe Asp Val Ile
145                 150                 155                 160

Thr Asn Ser Val Gly Leu Val Thr Ala Val Leu Ala Val Arg Phe Tyr
                165                 170                 175

Trp Trp Ile Asp Pro Thr Gly Ala Ile Ile Ile Ala Met Tyr Thr Ile
            180                 185                 190

Ser Thr Trp Ala Lys Thr Val Ala Glu Asn Val Trp Ser Leu Ile Gly
        195                 200                 205

Arg Thr Ala Pro Pro Asp Phe Leu Thr Lys Leu Thr Tyr Leu Ile Trp
    210                 215                 220

Asn His His Glu Glu Ile Lys His Ile Asp Thr Val Arg Ala Tyr Thr
```

```
225                 230                 235                 240

Phe Gly Ala His Tyr Phe Val Glu Val Asp Ile Val Leu Pro Glu Asp
                245                 250                 255

Met Leu Leu Asn Lys Ala His Asn Ile Gly Glu Thr Leu Gln Glu Lys
            260                 265                 270

Leu Glu Gln Leu Pro Glu Val Glu Arg Ala Phe Val His Ile Asp Phe
        275                 280                 285

Glu Phe Thr His Arg Pro Glu His Lys Thr Met Val
    290                 295                 300


<210> SEQ ID NO 34
<211> LENGTH: 903
<212> TYPE: DNA
<213> ORGANISM: Artificial Sequence
<220> FEATURE:
<223> OTHER INFORMATION: cDNA sequence of a mutated cation efflux
      protein

<400> SEQUENCE: 34

atggaaatga agcagcttgc aagaagtgaa aggatggcta ttcatttatc aaacatggct     60

aatgtggttc ttttcattgc aaaaatctac gcttctattg agagcagatc tttggctgta    120

atcgcgtcaa cgttggactc cctcttagac ctcttatcag ggtttatact gtggttcact    180

tctcatgcca tgaaaaatcc aaaccagtat cactatccta ttggaaaaaa gaggatgcag    240

ccattgggta ttattgtttt tgcatctgta atggcgacac taggattaca aatattgttc    300

gagtcagcta aagaactcat aactaagtct cgccctgaga tggaccatga gaaggaaaaa    360

tggacgattg gtattatggt ctctgtcact atggtcaagt ttctgcttat ggtctactgt    420

cgaaggttca aaaacgaaat cgtaagagcc tatgctcaag atcatttctt tgatgtcatc    480

accaactcag ttggattagt gactgctgtc ttagcagtcc gattctactg gtggattgat    540

cctacgggag ctataattat agctatgtac acaattagca cgtgggcgaa gacagtggca    600

gaaaatgtct ggtcactcat tggaagaaca gctccaccag attttcttac gaaattaacc    660

tatcttatat ggaatcatca cgaagagatc aagcacattg atactgttcg agcatatact    720

tttggtgctc attattttgt agaggttgat atagtgttgc cagaggacat gctgttgaac    780

aaggcacata atattggtga gacactgcaa gaaaaattgg agcaactccc tgaagttgag    840

cgagcttttg ttcatataga cttcgagttc actcacaggc cagaacacaa aactatggta    900

taa                                                                  903


<210> SEQ ID NO 35

<400> SEQUENCE: 35

000


<210> SEQ ID NO 36
<211> LENGTH: 16
<212> TYPE: DNA
<213> ORGANISM: Artificial Sequence
<220> FEATURE:
<223> OTHER INFORMATION: primer M13.fw

<400> SEQUENCE: 36

gtaaaacgac ggccag                                                     16


<210> SEQ ID NO 37
<211> LENGTH: 17
```

<212> TYPE: DNA
<213> ORGANISM: Artificial Sequence
<220> FEATURE:
<223> OTHER INFORMATION: primer M13.rv

<400> SEQUENCE: 37
gtcatagctg tttcctg 17

<210> SEQ ID NO 38
<211> LENGTH: 15123
<212> TYPE: DNA
<213> ORGANISM: Artificial Sequence
<220> FEATURE:
<223> OTHER INFORMATION: Gateway Destination Binary (GDB) expression vector sequence

<400> SEQUENCE: 38
agcttgcatg cctgcaggtc gagcttttag gattccatag tgataagata tgttcttatc 60
taaacaaaaa agcaagcgtc ggcaaaccat acagctgtcc acaaaaagga aaggctgtaa 120
taacaagcgg acccagcttc tcagtggaag atactttatc agacactgaa taatggatgg 180
accctaccac gattaaagag gagcgtctgt ctaaagtaaa gtagatgcgt ctttaataat 240
tcatctactt tagacgtcat gcatgacgtt taacatgcat tgtatccaga tcctccctgg 300
ctatataaag ggagttaaat ttcattgtta aggcatcgaa aaaaaaattt caagtctatc 360
tctcaagaaa aacttagaaa attactttgt cttaaggatc cgggcccagc tgtcacaagt 420
ttgtacaaaa aagctgaacg agaaacgtaa aatgatataa atatcaatat attaaattag 480
attttgcata aaaaacagac tacataatac tgtaaaacac aacatatcca gtcactatgg 540
cgccgcatta ggcaccccag gctttacact ttatgcttcc ggctcgtata atgtgtggat 600
tttgagttac gatccgtcga gattttcagg agctaaggaa gctaaaatgg agaaaaaaat 660
cactggatat accaccgttg atatatccca atggcatcgt aaagaacatt ttgaggcatt 720
tcagtcagtt gctcaatgta cctataacca gaccgttcaa ctggatatta cggccttttt 780
aaagaccgta aagaaaaata agcacaagtt ttatccggcc tttattcaca ttcttgcccg 840
cctgatgaat gctcatccgg aatttcgtat ggcaatgaaa gacggtgagc tggtgatatg 900
ggatagtgtt cacccttgtt acaccgtttt ccatgagcaa actgaaacgt tttcatcgct 960
ctggagtgaa taccacgacg atttccggca gtttctacac atatattcgc aagatgtggc 1020
gtgttacggt gaaaacctgg cctatttccc taaagggttt attgagaata tgtttttcgt 1080
ctcagccaat ccctgggtga gtttcaccag ttttgattta aacgtggcca atatggacaa 1140
cttcttcgcc cccgttttca cgatgggcaa atattatacg caaggcgaca aggtgctgat 1200
gccgctggcg attcaggttc atcatgccgt ttgtgatggc ttccatgtcg gcagaatgct 1260
taatgaatta caacagtact gcgatgagtg gcagggcggg gcgtaaacgc gacgatccgg 1320
cttactaaaa gccagataac agtatgcgta tttgcgcgct gatttttgcg gtataagaat 1380
atatactgat atgtataccc gaagtatgtc aaaaagaggt atgctatgaa gcagcgtatt 1440
acagtgacag ttgacagcga cagctatcag ttgctcaagg catatatgat gtcaatatct 1500
ccggtctggt aagcacaacc atgcagaatg aagcccgtcg tctgcgtgcc gaacgctgga 1560
aagcggaaaa tcaggaaggg atggctgagg tcgcccggtt tattgaaatg aacggctctt 1620
ttgctgacga gaacaggggc tggtgaaatg cagtttaagg tttacaccta taaaagagag 1680
agccgttatc gtctgtttgt ggatgtacag agtgatatta ttgacacgcc tgggcgacgg 1740
atggtgatcc ccctggccag tgcacgtctg ctgtcagata aagtctcccg tgaactttac 1800
ccggtggtgc atatcgggga tgaaagctgg cgcatgatga ccaccgatat ggccagtgtg 1860
ccggtctccg ttatcgggga agaagtggct gatctcagcc accgcgaaaa tgacatcaaa 1920
aacgccatta acctgatgtt ctggggaata taaatgtcag gctcccttat acacagccag 1980
tctgcacctc gaccatagtg actggatatg ttgtgtttta cagtattatg tagtctgttt 2040
tttatgcaaa atctaattta atatattgat atttatatca ttttacgttt ctcgttcagc 2100
tttcttgtac aaagtggtgc agctgagatc taggcctaag taagtaagat cgttcaaaca 2160
tttggcaata aagtttcttt agattgaatc ctgttgccgg tcttgcgatg attatcatat 2220
aatttctgtt gaattacgtt aagcatgtag taattaacat gtaatggatg acgttattta 2280
tgagatgggt ttttatgatt agagtcccgc aattatacat ttaatacgcg atagaaaaca 2340
aaatatagcg cgcaaactag gataaattat cgcgcgcggt gtcatctatg ttactagatc 2400
gaaggccttg ttctcgagca attcactggc cgtcgtttta caacgtcgtg actgggaaaa 2460
ccctggcgtt acccaactta atcgccttgc agcacatccc cctttcgcca gcaggcgtaa 2520
tagcgaagag gcccgcaccg attgcccttc ccaacagttg cgcagcctga atggcgcccg 2580
ctcctttcgc tttcttccct tcctttctcg ccacgttcgc cggctttccc cgtcaagctc 2640
taaatcgggg gctcccttta gggttccgat ttagtgcttt acggcacctc gaccccaaaa 2700
aacttgattt gggtgatggt tcacaaacta tcagtgtttg acaggatata ttggcgggta 2760
aacctaagag aaaagagcgt ttattagaat aatcggatat ttaaaagggc gtgaaaaggt 2820
ttatccgttc gtccatttgt atgtgcatgc caaccacagg cttaagaaaa cttgatttgg 2880
gtgatggttc acaaactatc agtgtttgac aggatatatt ggcgggtaaa cctaagagaa 2940
aagagcgttt attagaataa tcggatattt aaaagggcgt gaaaaggttt atccgttcgt 3000
ccatttgtat gtgcatgcca accacaggct taaggttcta gactggcgcc ggccagcgag 3060
acgagcaaga ttggccgccg cccgaaacga tccgacagcg cgcccagcac aggtgcgcag 3120
gcaaattgca ccaacgcata cagcgccagc agaatgccat agtgggcggt gacctcgttc 3180
gagtgaacca gatcgcgcag gaggcccggc agcaccggca taatcaggcc gatgccgaca 3240
gcgtcgagcg cgacagtgct cagaattacg atcaggggta tgttgggttt cacgtctggc 3300
ctccggacca gcctccgctg gtccgattga acgcgcggat tctttatcac tgataagttg 3360
gtggacatat tatgtttatc agtgataaag tgtcaagcat gacaaagttg cagccgaata 3420
cagtgatccg tgccgccctg gacctgttga acgaggtcgg cgtagacggt ctgacgacac 3480
gcaaactggc ggaacggttg gggttcagc agccggcgct ttactggcac ttcaggaaca 3540
agcgggcgct gctcgacgca ctggccgaag ccatgctggc ggagaatcat acgcattcgg 3600
tgccgagagc cgacgacgac tggcgctcat ttctgatcgg gaatgcccgc agcttcaggc 3660
aggcgctgct cgcctaccgc gatggcgcgc gcatccatgc cggcacgcga ccgggcgcac 3720
cgcagatgga aacggccgac gcgcagcttc gcttcctctg cgaggcgggt ttttcggccg 3780
gggacgccgt caatgcgctg atgacaatca gctacttcac tgttggggcc gtgcttgagg 3840
agcaggccgg cgacagcgat gccggcgagc gcggcggcac cgttgaacag gctccgctct 3900
cgccgctgtt gcgggccgcg atagacgcct tcgacgaagc cggtccggac gcagcgttcg 3960
agcagggact cgcggtgatt gtcgatggat tggcgaaaag gaggctcgtt gtcaggaacg 4020
ttgaaggacc gagaaagggt gacgattgat gaggaccgct gccggagcgc aacccactca 4080
ctacagcaga gccatgtaga caacatcccc tccccctttc caccgcgtca gacgcccgta 4140

-continued

```
gcagcccgct acgggctttt tcatgccctg ccctagcgtc caagcctcac ggccgcgctc   4200
ggcctctctg gcggccttct ggcgctcgtc gaccgctcac tgactcgctg cgctcggtcg   4260
ttcggctgcg gcgagcggta tcagctcact caaaggcggt aatacggtta tccacagaat   4320
caggggataa cgcaggaaag aacatgtgag caaaaggcca gcaaaaggcc aggaaccgta   4380
aaaaggccgc gttgctggcg tttttccata ggctccgccc ccctgacgag catcacaaaa   4440
atcgacgctc aagtcagagg tggcgaaacc cgacaggact ataaagatac caggcgtttc   4500
cccctggaag ctccctcgtg cgctctcctg ttccgaccct gccgcttacc ggatacctgt   4560
ccgcctttct cccttcggga agcgtggcgc ttttccgctg cataaccctg cttcggggtc   4620
attatagcga tttttcggt atatccatcc tttttcgcac gatatacagg attttgccaa    4680
agggttcgtg tagactttcc ttggtgtatc caacggcgtc agccgggcag gataggtgaa   4740
gtaggcccac ccgcgagcgg gtgttccttc ttcactgtcc cttattcgca cctggcggtg   4800
ctcaacggga atcctgctct gcgaggctgg ccggctaccg ccggcgtaac agatgagggc   4860
aagcggatgg ctgatgaaac caagccaacc aggaagggca gcccacctat caaggtgtac   4920
tgccttccag acgaacgaag agcgattgag gaaaaggcgg cggcggccgg catgagcctg   4980
tcggcctacc tgctggccgt cggccagggc tacaaaatca cgggcgtcgt ggactatgag   5040
cacgtccgcg agctggcccg catcaatggc gacctgggcc gcctgggcgg cctgctgaaa   5100
ctctggctca ccgacgaccc gcgcacggcg cggttcggtg atgccacgat cctcgccctg   5160
ctggcgaaga tcgaagagaa gcaggacgag cttggcaagg tcatgatggg cgtggtccgc   5220
ccgagggcag agccatgact tttttagccg ctaaaacggc cggggggtgc gcgtgattgc   5280
caagcacgtc cccatgcgct ccatcaagaa gagcgacttc gcggagctgg tgaagtacat   5340
caccgacgag caaggcaaga ccgagcgcct ttggtacctc accgggctgg ttgccctcgc   5400
cgctgggctg gcggccgtct atggccctgc aaacgcgcca gaaacgccgt cgaagccgtg   5460
tgcgagacac cgccgccgcc ggcgttgtgg atacctcgcg gaaaacttgg ccctcactga   5520
cagatgaggg gcggacgttg acacttgagg ggccgactca cccggcgcgg cgttgacaga   5580
tgaggggcag gctcgatttc ggccggcgac gtggagctgg ccagcctcgc aaatcggcga   5640
aaacgcctga ttttacgcga gtttcccaca gatgatgtgg acaagcctgg ggataagtgc   5700
cctgcggtat tgacacttga ggggcgcgac tactgacaga tgaggggcgc gatccttgac   5760
acttgagggg cagagtgctg acagatgagg ggcgcaccta ttgacatttg aggggctgtc   5820
cacaggcaga aaatccagca tttgcaaggg tttccgcccg tttttcggcc accgctaacc   5880
tgtcttttaa cctgctttta aaccaatatt tataaacctt gtttttaacc agggctgcgc   5940
cctgtgcgcg tgaccgcgca cgccgaaggg gggtgccccc ccttctcgaa ccctcccggc   6000
ccgctaacgc gggcctccca tccccccagg ggctgcgccc ctcggccgcg aacggcctca   6060
ccccaaaaat ggcagcgctg gcagtccttg ccattgccgg gatcggggca gtaacgggat   6120
gggcgatcag cccgagcgcg acgcccggaa gcattgacgt gccgcaggtg ctggcatcga   6180
cattcagcga ccaggtgccg ggcagtgagg gcggcggcct gggtggcggc ctgcccttca   6240
cttcggccgt cggggcattc acggacttca tggcggggcc ggcaattttt accttgggca   6300
ttcttggcat agtggtcgcg ggtgccgtgc tcgtgttcgg gggtgacgcg tgaaaatttt   6360
cgataaaccc agcgaaccat ttgaggtgat aggtaagatt ataccgaggt atgaaaacga   6420
gaattggacc tttacagaat tactctatga agcgccatat ttaaaaagct accaagacga   6480
agaggatgaa gaggatgagg aggcagattg ccttgaatat attgacaata ctgataagat   6540
```

```
aatatatctt ttatatagaa gatatggccg tatgtaagga tttcaggggg caaggcatag   6600
gcagcgcgct tatcaatata tctatagaat gggcaaagca taaaaacttg catggactaa   6660
tgcttgaaac ccaggacaat aaccttatag cttgtaaatt ctatcataat tgggtaatga   6720
ctccaactta ttgatagtgt tttatgttca gataatgccc gatgactttg tcatgcagct   6780
ccaccgattt tgagaacgac agcgacttcc gtcccagccg tgccaggtgc tgcctcagat   6840
tcaggttatg ccgctcaatt cgctgcgtat atcgcttgct gattacgtgc agctttccct   6900
tcaggcggga ttcatacagc ggccagccat ccgtcatcca tatcaccacg tcaaagggtg   6960
acagcaggct cataagacgc cccagcgtcg ccatagtgcg ttcaccgaat acgtgcgcaa   7020
caaccgtctt ccggagactg tcatacgcct aaaacagcca gcgctggcgc gatttagccc   7080
cgacatagcc ccactgttcg tccatttccg cgcagacgat gacgacactg cccggctgta   7140
tgcgcgaggt tacctgctgc cagtggcgat aagtcgtgtc ttaccgggtt ggactcaaga   7200
cgatagttac cggataaggc gcagcggtcg ggctgaacgg ggggttcgtg cacacagccc   7260
agcttggagc gaacgaccta caccgaactg agatacctac agcgtgagct atgagaaagc   7320
gccacgcttc ccgaagggag aaaggcggac aggtatccgg taagcggcag ggtcggaaca   7380
ggagagcgca cgagggagct tccaggggga aacgcctggt atctttatag tcctgtcggg   7440
tttcgccacc tctgacttga gcgtcgattt ttgtgatgct cgtcaggggg gcggagccta   7500
tggaaaaacg ccagcaacgc ggccttttta cggttcctgg ccttttgctg gccttttgct   7560
cacatgttct ttcctgcgtt atcccctgat tctgtggata accgtattac cgcctttgag   7620
tgagctgata ccgctcgccg cagccgaacg accgagcgca gcgagtcagt gagcgaggaa   7680
gcggaagagc gcctgatgcg gtattttctc cttacgcatc tgtgcggtat ttcacaccgc   7740
atagttaccg actgcggcct gagtttttta agtgacgtaa aatcgtgttg aggccaacgc   7800
ccataatgcg ggctgttgcc cggcatccaa cgccattcat ggccatatca atgattttct   7860
ggtgcgtacc gggttgagaa gcggtgtaag tgaacagcag ttgccatgtt ttacggcagt   7920
gagagcagag atagcgctga tgtccggcgg tgcttttgcc gttacgcacc accccgtcag   7980
tagctgaaca ggagggacac ctgatagaca cagaagccac tggagcacct caaaaacacc   8040
atcatacact aaatcagtaa gttggcagca tcacccgtta acataattgt ggtttcaaaa   8100
tcggctccgt cgatactatg ttatacgcca actttgaaaa caactttgaa aaagctgttt   8160
tctggtattt aaggttttag aatgcaagga acagtgaatt ggagttcgtc ttgttataat   8220
tagcttcttg gggtatcttt aaatactgta gaaaagagga aggaaataat aaatggctaa   8280
aatgagaata tcaccggaat tgaaaaaact gatcgaaaaa taccgctgcg taaaagatac   8340
ggaaggaatg tctcctgcta aggtatataa gctggtggga gaaaatgaaa acctatattt   8400
aaaaatgacg gacagccggt ataaagggac cacctatgat gtggaacggg aaaaggacat   8460
gatgctatgg ctggaaggaa agctgcctgt tccaaaggtc ctgcactttg aacggcatga   8520
tggctggagc aatctgctca tgagtgaggc cgatggcgtc ctttgctcgg aagagtatga   8580
agatgaacaa agccctgaaa agattatcga gctgtatgcg gagtgcatca ggctctttca   8640
ctccatcgac atatcggatt gtccctatac gaatagctta gacagccgct tagccgaatt   8700
ggattactta ctgaataacg atctggccga tgtggattgc gaaaactggg aagaagacac   8760
tccatttaaa gatccgcgcg agctgtatga tttttttaaag acggaaaagc ccgaagagga   8820
acttgtcttt tcccacggcg acctgggaga cagcaacatc tttgtgaaag atggcaaagt   8880
```

```
aagtggcttt attgatcttg ggagaagcgg cagggcggac aagtggtatg acattgcctt   8940
ctgcgtccgg tcgatcaggg aggttatcgg ggaagaacag tatgtcgagc tatttttga    9000
cttactgggg atcaagcctg attgggagaa aataaaatat tatattttac tggatgaatt   9060
gttttagtac ctagagaaaa ttttcctagg tgtggcgcaa cgatgccggc gacaagcagg   9120
agcgcaccga cttcttccgc atcaagtgtt ttggctctca ggccgaggcc cacggcaagt   9180
atttgggcaa ggggtcgctg gtattcgtgc agggcaagat tcggaatacc aagtacgaga   9240
aggacggcca gacggtctac gggaccgact tcattgccga taaggtggat tatctggaca   9300
ccaaggcacc aggcgggtca aatcaggaat aagggcacat tgccccggcg tgagtcgggg   9360
caatcccgca aggagggtga atgaatcgga cgtttgaccg gaaggcatac aggcaagaac   9420
tgatcgacgc ggggttttcc gccgaggatg ccgaaaccat cgcaagccgc accgtcatgc   9480
gtgcgccccg cgaaaccttc cagtccgtcg gctcgatggt ccagcaagct acggccaaga   9540
tcgagcgcga cagcgtgcaa ctggctcccc ctgccctgcc cgcgccatcg gccgccgtgg   9600
agcgttcgcg tcgtctcgaa caggaggcgg caggtttggc gaagtcgatg accatcgaca   9660
cgcgaggaac tatgacgacc aagaagcgaa aaaccgccgg cgaggacctg gcaaaacagg   9720
tcagcgaggc caagcaggcc gcgttgctga aacacacgaa gcagcagatc aaggaaatgc   9780
agctttcctt gttcgatatt gcgccgtggc cggacacgat gcgagcgatg ccaaacgaca   9840
cggcccgctc tgccctgttc accacgcgca acaagaaaat cccgcgcgag gcgctgcaaa   9900
acaaggtcat tttccacgtc aacaaggacg tgaagatcac ctacaccggc gtcgagctgc   9960
gggccgacga tgacgaactg gtgtggcagc aggtgttgga gtacgcgaag cgcacccta   10020
tcggcgagcc gatcaccttc acgttctacg agctttgcca ggacctgggc tggtcgatca  10080
atggccggta ttacacgaag gccgaggaat gcctgtcgcg cctacaggcg acggcgatgg  10140
gcttcacgtc cgaccgcgtt gggcacctgg aatcggtgtc gctgctgcac cgcttccgcg  10200
tcctggaccg tggcaagaaa acgtcccgtt gccaggtcct gatcgacgag gaaatcgtcg  10260
tgctgtttgc tggcgaccac tacacgaaat tcatctggga gaagtaccgc aagctgtcgc  10320
cgacggcccg acggatgttc gactatttca gctcgcaccg ggagccgtac ccgctcaagc  10380
tggaaacctt ccgcctcatg tgcggatcgg attccacccg cgtgaagaag tggcgcgagc  10440
aggtcggcga agcctgcgaa gagttgcgag gcagcggcct ggtggaacac gcctgggtca  10500
atgatgacct ggtgcattgc aaacgctagg gccttgtggg gtcagttccg gctgggggtt  10560
cagcagccag cgtgatcact ttactggcat ttcaggaaca agcgggcact gctcgacgca  10620
cttgcttcgc tcagtatcgc tcgggacgca cggcgcgctc tacgaactgc cgataaacag  10680
aggattaaaa ttgacaattg tgattaaggc tcagattcga cggcttggag cggccgacgt  10740
gcaggatttc cgcgagatcc gattgtcggc cctgaagaaa gctccagaga tgttcgggtc  10800
cgtttacgag cacgaggaga aaaagcccat ggaggcgttc gctgaacggt tgcgagatgc  10860
cgtggcattc ggcgcctaca tcgacggcga gatcattggg ctgtcggtct tcaaacagga  10920
ggacggcccc aaggacgctc acaaggcgca tctgtccggc gttttcgtgg agcccgaaca  10980
gcgaggccga ggggtcgccg gtatgctgct gcgggcgttg ccggcgggtt tattgctcgt  11040
gatgatcgtc cgacagattc caacgggaat ctggtggatg cgcatcttca tcctcggcgc  11100
acttaatatt tcgctattct ggagcttgtt gtttatttcg gtctaccgcc tgccgggcgg  11160
ggtcgcggcg acggtaggcg ctgtgcagcc gctgatggtc gtgttcatct ctgccgctct  11220
gctaggtagc ccgatacgat tgatggcggt cctgggggct atttgcggaa ctgcgggcgt  11280
```

ggcgctgttg gtgttgacac caaacgcagc gctagatcct gtcggcgtcg cagcgggcct 11340
ggcgggggcg gtttccatgg cgttcggaac cgtgctgacc cgcaagtggc aacctcccgt 11400
gcctctgctc acctttaccg cctggcaact ggcggccgga ggacttctgc tcgttccagt 11460
agctttagtg tttgatccgc caatcccgat gcctacagga accaatgttc tcggcctggc 11520
gtggctcggc ctgatcggag cgggtttaac ctacttcctt tggttccggg ggatctcgcg 11580
actcgaacct acagttgttt ccttactggg ctttctcagc cccaggtctg ggtcgatca 11640
gccggggatg catcaggccg acagtcggaa cttcgggtcc ccgacctgta ccattcggtg 11700
agcaatggat aggggagttg aaatcgtcaa cgttcacttc taaagaaata gcgccactca 11760
gcttcctcag cggctttatc cagcgatttc ctattatgtc ggcatagttc tcaagatcga 11820
cagcctgtca cggttaagcg agaaatgaat aagaaggctg ataattcgga tctctgcgag 11880
ggagatgata tttgatgaca ggcagcaacg ctctgtcatc gttacaatca acatgctacc 11940
ctccgcgaga tcatccgtgt ttcaaacccg gcagcttagt tgccgttctt ccgaatagca 12000
tcggtaacat gagcaaagtc tgccgcctta caacggctct cccgctgact agtcgtcccg 12060
gagacgtcct gatgggctgc ctgtatcgag tggtgatttt gtgccgagct gccggtcggg 12120
gagctgttgg ctggctggtg gcaggatata ttgtggtgta aacaaattga cgcttagaca 12180
acttaataac acattgcgga cgtttttaat gtactggacg tcctgatggg ctgcctgtat 12240
cgagtggtga ttttgtgccg agctgccggt cggggagctg ttggctggct ggtggcagga 12300
tatattgtgg tgtaaacaaa ttgacgctta gacaacttaa taacacattg cggacgtttt 12360
taatgtactg gggtggtttt tcttttcacc agtgagacgg gcaacacgtg attgcccttc 12420
accgcctggc cctgagagag ttgcagcaag cggtccacgc tggtttgccc cagcaggcga 12480
aaatcctgtt tgatggtggt tccgaaatcg gcaaaatccc ttataaatca aaagaatagc 12540
ccgagatagg gttgagtgtt gttccagttt ggaacaagag tccactatta aagaacgtgg 12600
actccaacgt caaagggcga aaaaccgtct atcagggcga tggcccacaa actgaaggcg 12660
gccgcaaacg atatcaatct catcatgagc ggagaattaa gggagtcacg ttatgacccc 12720
cgccgatgac gcgggacaag ccgttttacg tttggaactg acagaaccgc aacgttgaag 12780
gagccactca gccgccggtt tctggagttt aatgagctaa gcacatacgt cagaaaccat 12840
tattgcgcgt tcaaaagtcg cctaaggtca ctatcagcta gcaaatattt cttgtcaaaa 12900
atgctccact gacgttccat aaattcccct cggtatccaa ttagagtctc atattcactc 12960
tcaatccaaa taatctgcac cggatctgga tcgtttcgca tgattgaaca agatggattg 13020
cacgcaggtt ctccggccgc ttgggtggag aggctattcg gctatgactg ggcacaacag 13080
acaatcggct gctctgatgc cgccgtgttc cggctgtcag cgcaggggcg cccggttctt 13140
tttgtcaaga ccgacctgtc cggtgccctg aatgaactcc aggacgaggc agcgcggcta 13200
tcgtggctgg ccacgacggg cgttccttgc gctgctgtgc tcgacgttgt cactgaagcg 13260
ggaagggact ggctgctatt gggcgaagtg ccggggcagg atctcctgtc atctcacctt 13320
gctcctgccg agaaagtatc catcatggct gatgcaatgc ggcggctgca tacgcttgat 13380
ccggctacct gcccattcga ccaccaagcg aaacatcgca tcgagcgagc acgtactcgg 13440
atggaagccg gtcttgtcga tcaggatgat ctggacgaag agcatcaggg gctcgcgcca 13500
gccgaactgt tcgccaggct caaggcgcgc atgcccgacg gcgatgatct cgtcgtgacc 13560
catggcgatg cctgcttgcc gaatatcatg gtggaaaatg gccgcttttc tggattcatc 13620
gactgtggcc ggctgggtgt ggcggaccgc tatcaggaca tagcgttggc tacccgtgat 13680
attgctgaag agcttggcgg cgaatgggct gaccgcttcc tcgtgcttta cggtatcgcc 13740
gctcccgatt cgcagcgcat cgccttctat cgccttcttg acgagttctt ctgagcggga 13800
ctctggggtt cgaaatgacc gaccaagcga cgcccaacct gccatcacga gatttcgatt 13860
ccaccgccgc cttctatgaa aggttgggct tcggaatcgt tttccgggac gccggctgga 13920
tgatcctcca gcgcggggat ctcatgctgg agttcttcgc ccacgggatc tctgcggaac 13980
aggcggtcga aggtgccgat attattacga cagcaacggc cgacaagcac aacgccacga 14040
tcctgagcga caatatgatc ggacccggcg tccacatcaa cggcgtcggc ggcgactgcc 14100
caggcaagac cgagatgcac cgcgatatat tgctgcgttc ggatattttc gtggagttcc 14160
cgccacagac ccggatgatc cccgaccgtt caaacatttg gcaataaagt ttctaaagat 14220
tgaatcctgt tgccggtctt gcgatgatta tcatataatt tctgttgaat tacgttaagc 14280
atgtaataat taacatgtaa tgcatgacgt tatttatgag atgggttttt atgattagag 14340
tcccgcaatt atacatttaa tacgcgatag aaaacaaaat atagcgcgca aactaggata 14400
aattatcgcg cgcggtgtca tctatgttac tagatcgggc ctcctgatat caatgctgca 14460
gcggcggctc tggtggtggt tctggtggcg gctctgaggg tggtggctct gagggtggcg 14520
gttctgaggg tggcggctct gagggaggcg gttccggtgg tggctctggt tccggtgatt 14580
ttgattatga aaagatggca aacgctaata agggggctat gaccgaaaat gccgatgaaa 14640
acgcgctaca gtctgacgct aaaggcaaac ttgattctgt cgctactgat tacggtgctg 14700
ctatgatggt ttcattggtg acgtttccgg ccttgctaat ggtaatggtg ctactggtga 14760
ttttgctggc tctaattccc aaatggctca agtcggtgac ggtgataatt cacctttaat 14820
gaatatttcc gtcaatattt accttccctc cctcaatcgg ttgaatgtcg cccttttgtc 14880
tttggcccaa tacgcaaacc gcctctcccc gcgcgttggc cgattcatta tgcactggca 14940
cgacaggttt cccgactgga aagcgggcag tgagcgcaac gcaattatgt gagttagctc 15000
actcattagg caccccaggc tttacacttt atgcttccgg ctcgtatgtt gtgtggaatt 15060
gtgagcggat aacaatttca cacaggaaac agctatgacc atgattacgc caagctggcg 15120
cca 15123

<210> SEQ ID NO 39
<211> LENGTH: 1200
<212> TYPE: DNA
<213> ORGANISM: Artificial Sequence
<220> FEATURE:
<223> OTHER INFORMATION: cation efflux antisense (AS) sequence

<400> SEQUENCE: 39
tcaaaaagct cgctcaactt cagggagttg ctccaatttt tcttgcagtg tctcaccaat 60
attatgtgcc ttgttcaaca gcatgtcctc tggcaacact atatcaacct ctacaaaata 120
atgagcacca aaagtatatg ctcgaacagt atcaatgtgc ttgatctctt cgtgatgatt 180
ccatataaga taggttaatt tcgtaagaaa atctggtgga gctgttcttc caatgagtga 240
ccagacattt tctgccactg tcttcgccca cgtgctaatt gtgtacatag ctataattat 300
agctcccgta ggatcaatcc accagtagaa tcggactgct aagacagcag tcactaatcc 360
aactgagttg gtgatgacat caaagaaatg atcttgagca taggctctta cgatttcgtt 420
tttgaacctt cgacagtaga ccataagcag aaacttgacc atagtgacag agaccataat 480
accaatcgtc catttttcct tctcatggtc catctcaggg cgagacttag ttatgagttc 540
tttagctgac tcgaacaata tttgtaatcc tagtgtcgcc attacagatg caaaaacaat 600
aatacccaat ggctgcatcc tcttttttcc aataggatag tgatactggt ttggattttt 660
catggcatga gaagtgaacc acagtataaa ccctgataag aggtctaaga gggagtccaa 720
cgttgacgcg attacagcca aagatctgct ctcaatagaa gcgtagattt ttgcaatgaa 780
aagaaccaca ttagccatgt ttgataaatg aatagccatc ctttcacttc ttgcaagctg 840
cttcatttca tcctcagtta gacttccagg taaacaacca gattcattaa tggtgtccat 900
ctcattgaac ccttcaagca gcctttcttg ttttttgtag tattcagcaa ttttaccttg 960
tttcctggga gtgggaagta gacgacggac actaaaggag tgatgatcgg aggaggagcg 1020
gcttcgttcg ggaagacgga attcgctaat gttaagtctc catgacgccg acgaagacga 1080
ctgatccacc accgcctgag cagccggaga cagcagttcc gtcctaaaac tgctaaaact 1140
gtcgtccaga gcgccgccgc tgccgccacc accactaaca ttgctgcgac ttatctccat 1200

<210> SEQ ID NO 40
<211> LENGTH: 41
<212> TYPE: DNA
<213> ORGANISM: Artificial Sequence
<220> FEATURE:
<223> OTHER INFORMATION: primer AS.fw

<400> SEQUENCE: 40
tgtacaaaaa agcaggctca tcaaaaagct cgctcaactt c 41

<210> SEQ ID NO 41
<211> LENGTH: 39
<212> TYPE: DNA
<213> ORGANISM: Artificial Sequence
<220> FEATURE:
<223> OTHER INFORMATION: primer AS.rv

<400> SEQUENCE: 41
tgtacaagaa agctgggtat ggagataagt cgcagcaat 39

<210> SEQ ID NO 42
<211> LENGTH: 29
<212> TYPE: DNA
<213> ORGANISM: Artificial Sequence
<220> FEATURE:
<223> OTHER INFORMATION: primer attB1

<400> SEQUENCE: 42
ggggacaagt ttgtacaaaa aagcaggct 29

<210> SEQ ID NO 43
<211> LENGTH: 29
<212> TYPE: DNA
<213> ORGANISM: Artificial Sequence
<220> FEATURE:
<223> OTHER INFORMATION: primer attB2

<400> SEQUENCE: 43
ggggaccact ttgtacaaga aagctgggt 29

<210> SEQ ID NO 44
<211> LENGTH: 1653
<212> TYPE: DNA
<213> ORGANISM: Artificial Sequence
<220> FEATURE:
<223> OTHER INFORMATION: luciferase control sequence

<400> SEQUENCE: 44

```
atggaagacg ccaaaaacat aaagaaaggc ccggcgccat tctatccgct ggaagatgga     60
accgctggag agcaactgca taaggctatg aagagatacg ccctggttcc tggaacaatt    120
gcttttacag atgcacatat cgaggtggac attacgtacg ctgagtactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgggcatt    360
tcgcagccta ccgtggtgtt cgtttccaaa aaggggttgc aaaaaatttt gaacgtgcaa    420
aaaaagctcc caatcatcca aaaaattatt atcatggatt ctaaaacgga ttaccaggga    480
tttcagtcga tgtacacgtt cgtcacatct catctacctc ccggttttaa tgaatacgat    540
tttgtgccag agtccttcga tagggacaag acaattgcac tgatcatgaa ctcctctgga    600
tctactggtc tgcctaaagg tgtcgctctg cctcatagaa ctgcctgcgt gagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc caggtatcag gcaaggatat   1020
gggctcactg agactacatc agctattctg attacacccg agggggatga taaaccgggc   1080
gcggtcggta aagttgttcc atttttgaa gcgaaggttg tggatctgga taccgggaaa    1140
acgctgggcg ttaatcaaag aggcgaactg tgtgtgagag gtcctatgat tatgtccggt   1200
tatgtaaaca atccggaagc gaccaacgcc ttgattgaca aggatggatg gctacattct   1260
ggagacatag cttactggga cgaagacgaa cacttcttca tcgttgaccg cctgaagtct   1320
ctgattaagt acaaaggcta tcaggtggct cccgctgaat tggaatccat cttgctccaa   1380
caccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gatcgccgtg taa                                1653
```

<210> SEQ ID NO 45
<211> LENGTH: 41
<212> TYPE: DNA
<213> ORGANISM: Artificial Sequence
<220> FEATURE:
<223> OTHER INFORMATION: primer delta 117C fw

<400> SEQUENCE: 45

```
tgtacaaaaa agcaggctca atggagataa gtcgcagcaa t                         41
```

<210> SEQ ID NO 46
<211> LENGTH: 40
<212> TYPE: DNA
<213> ORGANISM: Artificial Sequence
<220> FEATURE:
<223> OTHER INFORMATION: primer delta 117C rv

<400> SEQUENCE: 46
tgtacaagaa agctgggttt taagctcccg taggatcaat 40

<210> SEQ ID NO 47
<211> LENGTH: 41
<212> TYPE: DNA
<213> ORGANISM: Artificial Sequence
<220> FEATURE:
<223> OTHER INFORMATION: primer delta 117N fw

<400> SEQUENCE: 47
tgtacaaaaa agcaggctca atggaaatga agcagcttgc a 41

<210> SEQ ID NO 48
<211> LENGTH: 42
<212> TYPE: DNA
<213> ORGANISM: Artificial Sequence
<220> FEATURE:
<223> OTHER INFORMATION: primer delta 117N rv

<400> SEQUENCE: 48
tgtacaagaa agctgggttt tataccatag ttttgtgttc tg 42

<210> SEQ ID NO 49
<211> LENGTH: 20173
<212> TYPE: DNA
<213> ORGANISM: Tobacco rattle virus

<400> SEQUENCE: 49
tactccaaaa atgtcaaaga tacagtctca gaagaccaaa gggctattga gacttttcaa 60
caaagggtaa tttcgggaaa cctcctcgga ttccattgcc cagctatctg tcacttcatc 120
gaaaggacag tagaaaagga aggtggctcc tacaaatgcc atcattgcga taaaggaaag 180
gctatcattc aagatgcctc tgccgacagt ggtcccaaag atggaccccc acccacgagg 240
agcatcgtgg aaaaagaaga cgtcccaacc acgtcttcaa agcaagtgga ttgatgtgac 300
atctccactg acgtaaggga tgacgcacaa tcccactatc cttcgcaaga cccttcttct 360
atataaggaa gttcatttca tttggagagg acagcccaag ctttctagag gatccataaa 420
acatttcaat cctttgaacg cggtagaacg tgctaattgg attttggtga gaacgcggta 480
gaacgtactt atcacctaca gttttatttt gtttttcttt ttggtttaat ctatccagct 540
tagtaccgag tgggggaaag tgactggtgt gcctaaaacc ttttctttga tactttgtaa 600
aaatacatac agatacaatg gcgaacggta acttcaagtt gtctcaattg ctcaatgtgg 660
acgagatgtc tgctgagcag aggagtcatt tctttgactt gatgctgact aaacctgatt 720
gtgagatcgg gcaaatgatg caaagagttg ttgttgataa agtcgatgac atgattagag 780
aaagaaagac taaagatcca gtgattgttc atgaagttct ttctcagaag gaacagaaca 840
agttgatgga aatttatcct gaattcaata tcgtgtttaa agacgacaaa aacatggttc 900
atgggtttgc ggctgctgag cgaaaactac aagctttatt gcttttagat agagttcctg 960
ctctgcaaga ggtggatgac atcggtggtc aatggtcgtt ttgggtaact agaggtgaga 1020
aaaggattca ttcctgttgt ccaaatctag atattcggga tgatcagaga gaaatttctc 1080
gacagatatt tcttactgct attggtgatc aagctagaag tggtaagaga cagatgtcgg 1140
agaatgagct gtggatgtat gaccaatttc gtgaaaatat tgctgcgcct aacgcggtta 1200
ggtgcaataa tacatatcag ggttgtacat gtaggggttt ttctgatggt aagaagaaag 1260
gcgcgcagta tgcgatagct cttcacagcc tgtatgactt caagttgaaa gacttgatgg 1320

-continued

```
ctactatggt tgagaagaaa actaaagtgg ttcatgctgc tatgcttttt gctcctgaaa   1380
gtatgttagt ggacgaaggt ccattacctt ctgttgacgg ttactacatg aagaagaacg   1440
ggaagatcta tttcggtttt gagaaagatc cttccttttc ttacattcat gactgggaag   1500
agtacaagaa gtatctactg gggaagccag tgagttacca agggaatgtg ttctacttcg   1560
aaccgtggca ggtgagagga gacacaatgc ttttttcgat ctacaggata gctggagttc   1620
cgaggaggtc tctatcatcg caagagtact accgaagaat atatatcagt agatgggaaa   1680
gcatggttgt tgtcccaatt ttcgatctgg tcgaatcaac gcgagagttg gtcaagaaag   1740
acctgtttgt aagaaacaat tcatggacaa gtgtttggat tacatagcta ggttatctga   1800
ccagcagctg accataagca atgttaaatc atacttgagt tcaaataatt gggtcttatt   1860
cataaacggg gcggccgtga agaacaagca aagtgtagat tctcgagatt tacagttgtt   1920
ggctcaaact ttgctagtga aggaacaagt ggcgagacct gtcatgaggg agttgcgtga   1980
agcaattctg actgagacga aacctatcac gtcattgact gatgtgctgg gtttaatatc   2040
aagaaaactg tggaagcagt ttgctaacaa gatcgcagtc ggcggattcg ttggcatggt   2100
tggtactcta attggattct atccaaagaa ggtactaacc tgggcgaagg acacaccaaa   2160
tggtccagaa ctatgttacg agaactcgca caaaaccaag gtgatagtat ttctgagtgt   2220
tgtgtatgcc attggaggaa tcacgcttat gcgtcgagac atccgagatg gactggtgaa   2280
aaaactatgt gatatgtttg atatcaaacg gggggcccat gtcttagacg ttgagaatcc   2340
gtgccgctat tatgaaatca acgatttctt tagcagtctg tattcggcat ctgagtccgg   2400
tgagaccgtt ttaccagatt tatccgaggt aaaagccaag tctgataagc tattgcagca   2460
gaagaaagaa atcgctgacg agtttctaag tgcaaaattc tctaactatt ctggcagttc   2520
ggtgagaact tctccaccat cggtggtcgg ttcatctcga agcggactgg gtctgttgtt   2580
ggaagacagt aacgtgctga cccaagctag agttggagtt tcaagaaagg tagacgatga   2640
ggagatcatg gagcagtttc tgagtggtct tattgacact gaagcagaaa ttgacgaggt   2700
tgtttcagcc ttttcagctg aatgtgaaag aggggaaaca agcggtacaa aggtgttgtg   2760
taaaccttta acgccaccag gatttgagaa cgtgttgcca gctgtcaaac ctttggtcag   2820
caaaggaaaa acggtcaaac gtgtcgatta cttccaagtg atgggaggtg agagattacc   2880
aaaaaggccg gttgtcagtg gagacgattc tgtggacgct agaagagagt ttctgtacta   2940
cttagatgcg gagagagtcg ctcaaaatga tgaaattatg tctctgtatc gtgactattc   3000
gagaggagtt attcgaactg gaggtcagaa ttacccgcac ggactgggag tgtgggatgt   3060
ggagatgaag aactggtgca tacgtccagt ggtcactgaa catgcttatg tgttccaacc   3120
agacaaacgt atggatgatt ggtcgggata cttagaagtg gctgtttggg aacgaggtat   3180
gttggtcaac gacttcgcgg tcgaaaggat gagtgattat gtcatagttt gcgatcagac   3240
gtatctttgc aataacaggt aataatcctc tctcttgata tttttaaatt atagaattaa   3300
ttagtttact ttattcttta ctatatgatt taaatagttt aatcttgttt ttgagtaaac   3360
tattcgattt tgatatttgt attcgtccta caaagttgga aatactgatg atattttctt   3420
ttgaacgtga tacctaccaa tactaatctt acggaatctt ttaatagagc actaatcaac   3480
atggaactaa agaccaattc ttaagtgtct ctgttgtaca gttcatttta gtagtgcgtt   3540
taagtattat tatctccctt catgcggggc aattatgtag attaaaatcg aaattatata   3600
aaatttacat aagtctaagt ctagggtctc cagctaattg ttattttttt aacgatgttg   3660
actaaagcaa taacgacgtt gacttgtgtt aaacaggttg atcttggaca atttaagtgc   3720
```

cctggatcta ggaccagtta actgttcttt tgaattagtt gacggtgtac ctggttgtgg 3780
taagtcgaca atgattgtca actcagctaa tccttgtgtc gatgtggttc tctctactgg 3840
gagagcagca accgacgact tgatcgagag attcgcgagc aaaggttttc catgcaaatt 3900
gaaaaggaga gtgaagacgg ttgattcttt tttgatgcat tgtgtcgatg gttctttaac 3960
cggagacgtg ttgcatttcg acgaagctct catggcccat gctggtatgg tgtacttttg 4020
cgctcagata gctggtgcta aacgatgtat ctgtcaagga gatcagaatc aaatttcttt 4080
caagcctagg gtatctcaag ttgatttgag gttttctagt ctggtcggaa agtttgacat 4140
tgttacagaa aaaagagaaa cttacagaag tccagcagat gtggctgccg tattgaacaa 4200
gtactatact ggagatgtca gaacacataa cgcgactgct aattcgatga cggtgaggaa 4260
gattgtgtct aaagaacagg tttctttgaa gcctggtgct cagtacataa ctttccttca 4320
gtctgagaag aaggagttgg taaatttgtt ggcattgagg aaagtggcag ctaaagtgag 4380
tacagtacac gagtcgcaag gagagacatt caaagatgta gtcctagtca ggacgaaacc 4440
tacggatgac tcaatcgcta gaggtcggga gtacttaatc gtggcattgt cgcgtcacac 4500
acaatcactt gtgtatgaaa ctgtgaaaga ggacgatgta agcaaagaga tcagggaaag 4560
tgccgcgctt acgaaggcgg ctttggcaag atttttttgtt actgagaccg tcttatgacg 4620
gtttcggtct aggtttgatg tctttagaca tcatgaaggg ccttgcgccg ttccagattc 4680
aggtacgatt acggacttgg agatgtggta cgacgctttg tttccgggaa attcgttaag 4740
agactcaagc ctagacgggt atttggtggc aacgactgat tgcaatttgc gattagacaa 4800
tgttacgatc aaaagtggaa actggaaaga caagtttgct gaaaaagaaa cgtttctgaa 4860
accggttatt cgtactgcta tgcctgacaa aaggaagact actcagttgg agagtttgtt 4920
agcattgcag aaaaggaacc aagcggcacc cgatctacaa gaaaatgtgc acgcgacagt 4980
tctaatcgaa gagacgatga agaagctgaa atctgttgtc tacgatgtgg gaaaaattcg 5040
ggctgatcct attgtcaata gagctcaaat ggagagatgg tggagaaatc aaagcacagc 5100
ggtacaggct aaggtagtag cagatgtgag agagttacat gaaatagact attcgtctta 5160
catgtatatg atcaaatctg acgtgaaacc taagactgat ttaacaccgc aatttgaata 5220
ctcagctcta cagactgttg tgtatcacga gaagttgatc aactcgttgt tcggtccaat 5280
tttcaaagaa attaatgaac gcaagttgga tgctatgcaa ccacattttg tgttcaacac 5340
gagaatgaca tcgagtgatt taaacgatcg agtgaagttc ttaaatacgg aagcggctta 5400
cgactttgtt gagatagaca tgtctaaatt cgacaagtcg gcaaatcgct tccatttaca 5460
actgcagctg gagatttaca ggttatttgg gctggatgag tgggcggcct tcctttggga 5520
ggtgtcgcac actcaaacta ctgtgagaga tattcaaaat ggtatgatgg cgcatatttg 5580
gtaccaacaa aagagtggag atgctgatac ttataatgca aattcagata gaacactgtg 5640
tgcactcttg tctgaattac cattggagaa agcagtcatg gttacatatg gaggagatga 5700
ctcactgatt gcgtttccta gaggaacgca gtttgttgat ccgtgtccaa agttggctac 5760
taagtggaat ttcgagtgca agatttttaa gtacgatgtc ccaatgtttt gtgggaagtt 5820
cttgcttaag acgtcatcgt gttacgagtt cgtgccagat ccggtaaaag ttctgacgaa 5880
gttggggaaa aagagtataa aggatgtgca acatttagcc gagatctaca tctcgctgaa 5940
tgattccaat agagctcttg ggaactacat ggtggtatcc aaactgtccg agtctgtttc 6000
agaccggtat ttgtacaaag gtgattctgt tcatgcgctt tgtgcgctat ggaagcatat 6060

-continued

```
taagagtttt acagctctgt gtacattatt ccgagacgaa aacgataagg aattgaaccc   6120
ggctaaggtt gattggaaga aggcacagag agctgtgtca aacttttacg actggtaata   6180
tggaagacaa gtcattggtc accttgaaga agaagacttt cgaagtctca aaattctcaa   6240
atctaggggc cattgaattg tttgtggacg gtaggaggaa gagaccgaag tattttcaca   6300
gaagaagaga aactgtccta aatcatgttg gtgggaagaa gagtgaacac aagttagacg   6360
tttttgacca aagggattac aaaatgatta aatcttacgc gtttctaaag gtagtaggtg   6420
tacaactagt tgtaacatca catctacctg cagatacgcc tgggttcatt caaatcgatc   6480
tgttggattc gagacttact gagaaaagaa agagaggaaa gactattcag agattcaaag   6540
ctcgagcttg cgataactgt tcagttgcgc agtacaaggt tgaatacagt atttccacac   6600
aggagaacgt acttgatgtc tggaaggtgg gttgtatttc tgagggcgtt ccggtctgtg   6660
acggtacata ccctttcagt atcgaagtgt cgctaatatg ggttgctact gattcgacta   6720
ggcgcctcaa tgtggaagaa ctgaacagtt cggattacat tgaaggcgat tttaccgatc   6780
aagaggtttt cggtgagttc atgtctttga aacaagtgga gatgaagacg attgaggcga   6840
agtacgatgg tccttacaga ccagctacta ctagacctaa gtcattattg tcaagtgaag   6900
atgttaagag agcgtctaat aagaaaaact cgtcttaatg cataaagaaa tttattgtca   6960
atatgacgtg tgtactcaag ggttgtgtga atgaagtcac tgttcttggt cacgagacgt   7020
gtagtatcgg tcatgctaac aaattgcgaa agcaagttgc tgacatggtt ggtgtcacac   7080
gtaggtgtgc ggaaaataat tgtggatggt ttgtctgtgt tgttatcaat gatttttactt   7140
ttgatgtgta taattgttgt ggccgtagtc accttgaaaa gtgtcgtaaa cgtgttgaaa   7200
caagaaatcg agaaatttgg aaacaaattc gacgaaatca agctgaaaac atgtctgcga   7260
cagctaaaaa gtctcataat tcgaagacct ctaagaagaa attcaaagag gacagagaat   7320
ttgggacacc aaaaagattt ttaagagatg atgttccttt cgggattgat cgtttgtttg   7380
ctttttgatt ttattttata ttgttatctg tttctgtgta tagactgttt gagattggcg   7440
cttggccgac tcattgtctt accatagggg aacggacttt gtttgtgttg ttattttatt   7500
tgtattttat taaaattctc aatgatctga aaaggcctcg aggctaagag attattgggg   7560
ggtgagtaag tacttttaaa gtgatgatgg ttacaaaggc aaaaggggta aaacccctcg   7620
cctacgtaag cgttattacg cccggatccc ccggggagct cgaattcgct gaaatcacca   7680
gtctctctct acaaatctat ctctctctat tttttccata aataatgtgt gagtagtttc   7740
ccgataaggg aaattagggt tcttataggg tttcgctcat gtgttgagca tataagaaac   7800
ccttagtatg tatttgtatt tgtaaaatac ttctattatc aataaaattt ctaattccta   7860
aaaccaaaat ccagtactaa aatccagatc tcctaaagtc cctatagatc tttgtcgtga   7920
atataaacca gacacgagac gactaaacct ggagcccaga cgccgttcga agctagaagt   7980
accgcttagg caggaggccg ttagggaaaa gatgctaagg cagggttggt tacgttgact   8040
cccccgtagg tttggtttaa atatgatgaa gtggacggaa ggaaggagga agacaaggaa   8100
ggataaggtt gcaggccctg tgcaaggtaa gaagatggaa atttgataga ggtacgctac   8160
tatacttata ctatacgcta agggaatgct tgtatttata ccctataccc cctaataacc   8220
ccttatcaat ttaagaaata atccgcataa gccccccgctt aaaaattggt atcagagcca   8280
tgaataggtc tatgaccaaa actcaagagg ataaaacctc accaaaatac gaaagagttc   8340
ttaactctaa agataaaaga tctttcaaga tcaaaactag ttccctcaca ccggagcatg   8400
cgatatcctc gacctgcagg catgcaagct tggcgtaatc atggtcatag ctgtttcctg   8460
```

```
tgtgaaattg ttatccgctc acaattccac acaacatacg agccggaagc ataaagtgta   8520
aagcctgggg tgcctaatga gtgagctaac tcacattaat tgcgttgcgc tcactgcccg   8580
ctttccagtc gggaaacctg tcgtgccagc tgcattaatg aatcggccaa cgcgcgggga   8640
gaggcggttt gcgtattggg ccaaagacaa aagggcgaca ttcaaccgat tgagggaggg   8700
aaggtaaata ttgacggaaa ttattcatta aaggtgaatt atcaccgtca ccgacttgag   8760
ccatttggga attagagcca gcaaaatcac cagtagcacc attaccatta gcaaggccgg   8820
aaacgtcacc aatgaaacca tcgatagcag caccgtaatc agtagcgaca gaatcaagtt   8880
tgcctttagc gtcagactgt agcgcgtttt catcggcatt ttcggtcata gccccctat    8940
tagcgtttgc catcttttca taatcaaaat caccggaacc agagccacca ccggaaccgc   9000
ctccctcaga gccgccaccc tcagaaccgc caccctcaga gccaccaccc tcagagccgc   9060
caccagaacc accaccagag ccgccgccag cattgacagg aggcccgatc tagtaacata   9120
gatgacaccg cgcgcgataa tttatcctag tttgcgcgct atattttgtt ttctatcgcg   9180
tattaaatgt ataattgcgg gactctaatc ataaaaaccc atctcataaa taacgtcatg   9240
cattacatgt taattattac atgcttaacg taattcaaca gaaattatat gataatcatc   9300
gcaagaccgg caacaggatt caatcttaag aaactttatt gccaaatgtt tgaacgatcg   9360
gggatcatcc gggtctgtgg cgggaactcc acgaaaatat ccgaacgcag caagatatcg   9420
cggtgcatct cggtcttgcc tgggcagtcg ccgccgacgc cgttgatgtg gacgccgggc   9480
ccgatcatat tgtcgctcag gatcgtggcg ttgtgcttgt cggccgttgc tgtcgtaatg   9540
atatcggcac cttcgaccgc ctgttccgca gagatcccgt gggcgaagaa ctccagcatg   9600
agatccccgc gctggaggat catccagccg gcgtcccgga aaacgattcc gaagcccaac   9660
ctttcataga aggcggcggt ggaatcgaaa tctcgtgatg gcaggttggg cgtcgcttgg   9720
tcggtcattt cgaaccccag agtcccgctc agaagaactc gtcaagaagg cgatagaagg   9780
cgatgcgctg cgaatcggga gcggcgatac cgtaaagcac gaggaagcgg tcagcccatt   9840
cgccgccaag ctcttcagca atatcacggg tagccaacgc tatgtcctga tagcggtccg   9900
ccacacccag ccggccacag tcgatgaatc cagaaaagcg gccattttcc accatgatat   9960
tcggcaagca ggcatcgcca tgggtcacga cgagatcatc gccgtcgggc atgcgcgcct  10020
tgagcctggc gaacagttcg gctggcgcga gcccctgatg ctcttcgtcc agatcatcct  10080
gatcgacaag accggcttcc atccgagtac gtgctcgctc gatgcgatgt ttcgcttggt  10140
ggtcgaatgg gcaggtagcc ggatcaagcg tatgcagccg ccgcattgca tcagccatga  10200
tggatacttt ctcggcagga gcaaggtgag atgacaggag atcctgcccc ggcacttcgc  10260
ccaatagcag ccagtccctt cccgcttcag tgacaacgtc gagcacagct gcgcaaggaa  10320
cgcccgtcgt ggccagccac gatagccgcg ctgcctcgtc ctgcagttca ttcagggcac  10380
cggacaggtc ggtcttgaca aaaagaaccg ggcgcccctg cgctgacagc cggaacacgg  10440
cggcatcaga gcagccgatt gtctgttgtg cccagtcata gccgaatagc ctctccaccc  10500
aagcggccgg agaacctgcg tgcaatccat cttgttcaat catgcgaaac gatccagatc  10560
cggtgcagat tatttggatt gagagtgaat atgagactct aattggatac cgaggggaat  10620
ttatggaacg tcagtggagc atttttgaca agaaatattt gctagctgat agtgacctta  10680
ggcgactttt gaacgcgcaa taatggtttc tgacgtatgt gcttagctca ttaaactcca  10740
gaaacccgcg gctgagtggc tccttcaacg ttgcggttct gtcagttcca aacgtaaaac  10800
```

```
ggcttgtccc gcgtcatcgg cgggggtcat aacgtgactc ccttaattct ccgctcatga  10860
tcagattgtc gtttcccgcc ttcagtttaa actatcagtg tttgacagga tatattggcg  10920
ggtaaaccta agagaaaaga gcgtttatta gaataatcgg atatttaaaa gggcgtgaaa  10980
aggtttatcc gttcgtccat ttgtatgtgc atgccaacca cagggttccc cagatctggc  11040
gccggccagc gagacgagca agattggccg ccgcccgaaa cgatccgaca gcgcgcccag  11100
cacaggtgcg caggcaaatt gcaccaacgc atacagcgcc agcagaatgc catagtgggc  11160
ggtgacgtcg ttcgagtgaa ccagatcgcg caggaggccc ggcagcaccg gcataatcag  11220
gccgatgccg acagcgtcga gcgcgacagt gctcagaatt acgatcaggg gtatgttggg  11280
tttcacgtct ggcctccgga ccagcctccg ctggtccgat tgaacgcgcg gattctttat  11340
cactgataag ttggtggaca tattatgttt atcagtgata aagtgtcaag catgacaaag  11400
ttgcagccga atacagtgat ccgtgccgcc ctggacctgt tgaacgaggt cggcgtagac  11460
ggtctgacga cacgcaaact ggcggaacgg ttgggggttc agcagccggc gctttactgg  11520
cacttcagga acaagcgggc gctgctcgac gcactggccg aagccatgct ggcggagaat  11580
catacgcatt cggtgccgag agccgacgac gactggcgct catttctgat cgggaatgcc  11640
cgcagcttca ggcaggcgct gctcgcctac cgcgatggcg cgcgcatcca tgccggcacg  11700
cgaccgggcg caccgcagat ggaaacggcc gacgcgcagc ttcgcttcct ctgcgaggcg  11760
ggtttttcgg ccggggacgc cgtcaatgcg ctgatgacaa tcagctactt cactgttggg  11820
gccgtgcttg aggagcaggc cggcgacagc gatgccggcg agcgcggcgg caccgttgaa  11880
caggctccgc tctcgccgct gttgcgggcc gcgatagacg ccttcgacga agccggtccg  11940
gacgcagcgt tcgagcaggg actcgcggtg attgtcgatg gattggcgaa aaggaggctc  12000
gttgtcagga acgttgaagg accgagaaag ggtgacgatt gatcaggacc gctgccggag  12060
cgcaacccac tcactacagc agagccatgt agacaacatc ccctccccct ttccaccgcg  12120
tcagacgccc gtagcagccc gctacgggct ttttcatgcc ctgccctagc gtccaagcct  12180
cacggccgcg ctcggcctct ctggcggcct tctggcgctc ttccgcttcc tcgctcactg  12240
actcgctgcg ctcggtcgtt cggctgcggc gagcggtatc agctcactca aaggcggtaa  12300
tacggttatc cacagaatca ggggataacg caggaaagaa catgtgagca aaaggccagc  12360
aaaaggccag gaaccgtaaa aaggccgcgt tgctggcgtt tttccatagg ctccgccccc  12420
ctgacgagca tcacaaaaat cgacgctcaa gtcagaggtg gcgaaacccg acaggactat  12480
aaagatacca ggcgtttccc cctggaagct ccctcgtgcg ctctcctgtt ccgaccctgc  12540
cgcttaccgg atacctgtcc gcctttctcc cttcgggaag cgtggcgctt ttccgctgca  12600
taaccctgct tcggggtcat tatagcgatt ttttcggtat atccatcctt tttcgcacga  12660
tatacaggat tttgccaaag ggttcgtgta gactttcctt ggtgtatcca acggcgtcag  12720
ccgggcagga taggtgaagt aggcccaccc gcgagcgggt gttccttctt cactgtccct  12780
tattcgcacc tggcggtgct caacgggaat cctgctctgc gaggctggcc ggctaccgcc  12840
ggcgtaacag atgagggcaa gcggatggct gatgaaacca agccaaccag gaagggcagc  12900
ccacctatca aggtgtactg ccttccagac gaacgaagag cgattgagga aaaggcggcg  12960
gcggccggca tgagcctgtc ggcctacctg ctggccgtcg gccagggcta caaaatcacg  13020
ggcgtcgtgg actatgagca cgtccgcgag ctggcccgca tcaatggcga cctgggccgc  13080
ctgggcggcc tgctgaaact ctggctcacc gacgacccgc gcacggcgcg gttcggtgat  13140
gccacgatcc tcgccctgct ggcgaagatc gaagagaagc aggacgagct tggcaaggtc  13200
```

atgatgggcg tggtccgccc gagggcagag ccatgacttt tttagccgct aaaacggccg 13260
gggggtgcgc gtgattgcca agcacgtccc catgcgctcc atcaagaaga gcgacttcgc 13320
ggagctggtg aagtacatca ccgacgagca aggcaagacc gagcgccttt gcgacgctca 13380
ccgggctggt tgccctcgcc gctgggctgg cggccgtcta tggccctgca aacgcgccag 13440
aaacgccgtc gaagccgtgt gcgagacacc gcggccgccg gcgttgtgga tacctcgcgg 13500
aaaacttggc cctcactgac agatgagggg cggacgttga cacttgaggg gccgactcac 13560
ccggcgcggc gttgacagat gaggggcagg ctcgatttcg gccggcgacg tggagctggc 13620
cagcctcgca aatcggcgaa aacgcctgat tttacgcgag tttcccacag atgatgtgga 13680
caagcctggg gataagtgcc ctgcggtatt gacacttgag ggcgcgact actgacagat 13740 gaggggcgcg atccttgaca cttgaggggc agagtgctga cagatgaggg gcgcacctat 13800
tgacatttga ggggctgtcc acaggcagaa aatccagcat ttgcaagggt ttccgcccgt 13860
ttttcggcca ccgctaacct gtcttttaac ctgcttttaa accaatattt ataaaccttg 13920
tttttaacca gggctgcgcc ctgtgcgcgt gaccgcgcac gccgaagggg ggtgcccccc 13980
cttctcgaac cctcccggcc cgctaacgcg ggcctcccat ccccccaggg gctgcgcccc 14040
tcggccgcga acggcctcac cccaaaaatg gcagcgctgg cagtccttgc cattgccggg 14100
atcggggcag taacgggatg ggcgatcagc ccgagcgcga cgcccggaag cattgacgtg 14160
ccgcaggtgc tggcatcgac attcagcgac caggtgccgg gcagtgaggg cggcggcctg 14220
ggtggcggcc tgcccttcac ttcggccgtc ggggcattca cggacttcat ggcggggccg 14280
gcaattttta ccttgggcat tcttggcata gtggtcgcgg gtgccgtgct cgtgttcggg 14340
ggtgcgataa acccagcgaa ccatttgagg tgataggtaa gattataccg aggtatgaaa 14400
acgagaattg gacctttaca gaattactct atgaagcgcc atatttaaaa agctaccaag 14460
acgaagagga tgaagaggat gaggaggcag attgccttga atatattgac aatactgata 14520
agataatata tcttttatat agaagatatc gccgtatgta aggatttcag ggggcaaggc 14580
ataggcagcg cgcttatcaa tatatctata gaatgggcaa agcataaaaa cttgcatgga 14640
ctaatgcttg aaacccagga caataacctt atagcttgta aattctatca taattgggta 14700
atgactccaa cttattgata gtgttttatg ttcagataat gcccgatgac tttgtcatgc 14760
agctccaccg attttgagaa cgacagcgac ttccgtccca gccgtgccag gtgctgcctc 14820
agattcaggt tatgccgctc aattcgctgc gtatatcgct tgctgattac gtgcagcttt 14880
cccttcaggc gggattcata cagcggccag ccatccgtca tccatatcac cacgtcaaag 14940
ggtgacagca ggctcataag acgccccagc gtcgccatag tgcgttcacc gaatacgtgc 15000
gcaacaaccg tcttccggag actgtcatac gcgtaaaaca gccagcgctg gcgcgattta 15060
gccccgacat agccccactg ttcgtccatt tccgcgcaga cgatgacgtc actgcccggc 15120
tgtatgcgcg aggttaccga ctgcggcctg agttttttaa gtgacgtaaa atcgtgttga 15180
ggccaacgcc cataatgcgg gctgttgccc ggcatccaac gccattcatg gccatatcaa 15240
tgattttctg gtgcgtaccg ggttgagaag cggtgtaagt gaactgcagt tgccatgttt 15300
tacggcagtg agagcagaga tagcgctgat gtccggcggt gcttttgccg ttacgcacca 15360
ccccgtcagt agctgaacag gagggacagc tgatagacac agaagccact ggagcacctc 15420
aaaaacacca tcatacacta aatcagtaag ttggcagcat cacccataat tgtggtttca 15480
aaatcggctc cgtcgatact atgttatacg ccaactttga aaacaacttt gaaaaagctg 15540

```
ttttctggta tttaaggttt tagaatgcaa ggaacagtga attggagttc gtcttgttat  15600
aattagcttc ttggggtatc tttaaatact gtagaaaaga ggaaggaaat aataaatggc  15660
taaaatgaga atatcaccgg aattgaaaaa actgatcgaa aaataccgct gcgtaaaaga  15720
tacggaagga atgtctcctg ctaaggtata taagctggtg ggagaaaatg aaaacctata  15780
tttaaaaatg acggacagcc ggtataaagg gaccacctat gatgtggaac gggaaaagga  15840
catgatgcta tggctggaag gaaagctgcc tgttccaaag gtcctgcact ttgaacggca  15900
tgatggctgg agcaatctgc tcatgagtga ggccgatggc gtcctttgct cggaagagta  15960
tgaagatgaa caaagccctg aaaagattat cgagctgtat gcggagtgca tcaggctctt  16020
tcactccatc gacatatcgg attgtcccta tacgaatagc ttagacagcc gcttagccga  16080
attggattac ttactgaata acgatctggc cgatgtggat tgcgaaaact gggaagaaga  16140
cactccattt aaagatccgc gcgagctgta tgattttttta aagacggaaa agcccgaaga  16200
ggaacttgtc ttttcccacg gcgacctggg agacagcaac atctttgtga aagatggcaa  16260
agtaagtggc tttattgatc ttgggagaag cggcagggcg gacaagtggt atgacattgc  16320
cttctgcgtc cggtcgatca gggaggatat cggggaagaa cagtatgtcg agctattttt  16380
tgacttactg gggatcaagc ctgattggga gaaaataaaa tattatattt tactggatga  16440
attgttttag tacctagatg tggcgcaacg atgccggcga caagcaggag cgcaccgact  16500
tcttccgcat caagtgtttt ggctctcagg ccgaggccca cggcaagtat ttgggcaagg  16560
ggtcgctggt attcgtgcag ggcaagattc ggaataccaa gtacgagaag gacggccaga  16620
cggtctacgg gaccgacttc attgccgata aggtggatta tctggacacc aaggcaccag  16680
gcgggtcaaa tcaggaataa gggcacattg ccccggcgtg agtcggggca atcccgcaag  16740
gagggtgaat gaatcggacg tttgaccgga aggcatacag gcaagaactg atcgacgcgg  16800
ggttttccgc cgaggatgcc gaaaccatcg caagccgcac cgtcatgcgt gcgccccgcg  16860
aaaccttcca gtccgtcggc tcgatggtcc agcaagctac ggccaagatc gagcgcgaca  16920
gcgtgcaact ggctcccccct gccctgcccg cgccatcggc cgccgtggag cgttcgcgtc  16980
gtctcgaaca ggaggcggca ggtttggcga agtcgatgac catcgacacg cgaggaacta  17040
tgacgaccaa gaagcgaaaa accgccggcg aggacctggc aaaacaggtc agcgaggcca  17100
agcaggccgc gttgctgaaa cacacgaagc agcagatcaa ggaaatgcag ctttccttgt  17160
tcgatattgc gccgtggccg gacacgatgc gagcgatgcc aaacgacacg gcccgctctg  17220
ccctgttcac cacgcgcaac aagaaaatcc cgcgcgaggc gctgcaaaac aaggtcattt  17280
tccacgtcaa caaggacgtg aagatcacct acaccggcgt cgagctgcgg gccgacgatg  17340
acgaactggt gtggcagcag gtgttggagt acgcgaagcg caccccctatc ggcgagccga  17400
tcaccttcac gttctacgag ctttgccagg acctgggctg gtcgatcaat ggccggtatt  17460
acacgaaggc cgaggaatgc ctgtcgcgcc tacaggcgac ggcgatgggc ttcacgtccg  17520
accgcgttgg gcacctggaa tcggtgtcgc tgctgcaccg cttccgcgtc ctggaccgtg  17580
gcaagaaaac gtcccgttgc caggtcctga tcgacgagga aatcgtcgtg ctgtttgctg  17640
gcgaccacta cacgaaattc atatgggaga agtaccgcaa gctgtcgccg acggcccgac  17700
ggatgttcga ctatttcagc tcgcaccggg agccgtaccc gctcaagctg gaaaccttcc  17760
gcctcatgtg cggatcggat tccacccgcg tgaagaagtg gcgcgagcag gtcggcgaag  17820
cctgcgaaga gttgcgaggc agcggcctgg tggaacacgc ctgggtcaat gatgacctgg  17880
tgcattgcaa acgctagggc cttgtggggt cagttccggc tgggggttca gcagccagcg  17940
```

```
ctttactggc atttcaggaa caagcgggca ctgctcgacg cacttgcttc gctcagtatc  18000
gctcgggacg cacggcgcgc tctacgaact gccgataaac agaggattaa aattgacaat  18060
tgtgattaag gctcagattc gacggcttgg agcggccgac gtgcaggatt tccgcgagat  18120
ccgattgtcg gccctgaaga aagctccaga gatgttcggg tccgtttacg agcacgagga  18180
gaaaaagccc atggaggcgt tcgctgaacg gttgcgagat gccgtggcat tcggcgccta  18240
catcgacggc gagatcattg ggctgtcggt cttcaaacag gaggacggcc ccaaggacgc  18300
tcacaaggcg catctgtccg gcgttttcgt ggagcccgaa cagcgaggcc gaggggtcgc  18360
cggtatgctg ctgcgggcgt tgccggcggg tttattgctc gtgatgatcg tccgacagat  18420
tccaacggga atctggtgga tgcgcatctt catcctcggc gcacttaata tttcgctatt  18480
ctggagcttg ttgtttattt cggtctaccg cctgccgggc ggggtcgcgg cgacggtagg  18540
cgctgtgcag ccgctgatgg tcgtgttcat ctctgccgct ctgctaggta gcccgatacg  18600
attgatggcg gtcctggggg ctatttgcgg aactgcgggc gtggcgctgt tggtgttgac  18660
accaaacgca gcgctagatc ctgtcggcgt cgcagcgggc ctggcggggg cggtttccat  18720
ggcgttcgga accgtgctga cccgcaagtg gcaacctccc gtgcctctgc tcacctttac  18780
cgcctggcaa ctggcggccg gaggacttct gctcgttcca gtagctttag tgtttgatcc  18840
gccaatcccg atgcctacag gaaccaatgt tctcggcctg gcgtggctcg gcctgatcgg  18900
agcgggttta acctacttcc tttggttccg ggggatctcg cgactcgaac ctacagttgt  18960
ttccttactg ggctttctca gccccagatc tggggtcgat cagccgggga tgcatcaggc  19020
cgacagtcgg aacttcgggt ccccgacctg taccattcgg tgagcaatgg atagggggagt  19080
tgatatcgtc aacgttcact tctaaagaaa tagcgccact cagcttcctc agcggcttta  19140
tccagcgatt tcctattatg tcggcatagt tctcaagatc gacagcctgt cacggttaag  19200
cgagaaatga ataagaaggc tgataattcg gatctctgcg agggagatga tatttgatca  19260
caggcagcaa cgctctgtca tcgttacaat caacatgcta ccctccgcga gatcatccgt  19320
gtttcaaacc cggcagctta gttgccgttc ttccgaatag catcggtaac atgagcaaag  19380
tctgccgcct tacaacggct ctcccgctga cgccgtcccg gactgatggg ctgcctgtat  19440
cgagtggtga ttttgtgccg agctgccggt cggggagctg ttggctggct ggtggcagga  19500
tatattgtgg tgtaaacaaa ttgacgctta gacaacttaa taacacattg cggacgtttt  19560
taatgtactg gggtggtttt tcttttcacc agtgagacgg gcaacagctg attgcccttc  19620
accgcctggc cctgagagag ttgcagcaag cggtccacgc tggtttgccc cagcaggcga  19680
aaatcctgtt tgatggtggt tccgaaatcg gcaaaatccc ttataaatca aaagaatagc  19740
ccgagatagg gttgagtgtt gttccagttt ggaacaagag tccactatta aagaacgtgg  19800
actccaacgt caaagggcga aaaaccgtct atcagggcga tggcccacta cgtgaaccat  19860
cacccaaatc aagttttttg gggtcgaggt gccgtaaagc actaaatcgg aaccctaaag  19920
ggagcccccg atttagagct tgacggggaa agccggcgaa cgtggcgaga aaggaaggga  19980
agaaagcgaa aggagcgggc gccattcagg ctgcgcaact gttgggaagg gcgatcggtg  20040
cgggcctctt cgctattacg ccagctggcg aaagggggat gtgctgcaag gcgattaagt  20100
tgggtaacgc cagggttttc ccagtcacga cgttgtaaaa cgacggccag tgaattcgag  20160
ctcggtaccc ccc                                                     20173
```

<210> SEQ ID NO 50

<211> LENGTH: 9663
<212> TYPE: DNA
<213> ORGANISM: Tobacco rattle virus

<400> SEQUENCE: 50
ataaaacatt gcacctatgg tgttgccctg gctggggtat gtcagtgatc gcagtagaat 60
gtactaattg acaagttgga gaatacggta gaacgtcctt atccaacaca gcctttatcc 120
ctctccctga cgaggttttt gtcagtgtaa tatttctttt tgaactatcc agcttagtac 180
cgtacgggaa agtgactggt gtgcttatct ttgaaatgtt actttgggtt tcggttcttt 240
aggttagtaa gaaagcactt gtcttctcat acaaaggaaa acctgagacg tatcgcttac 300
gaaagtagca atgaaagaaa ggtggtggtt ttaatcgcta ccgcaaaaac gatggggtcg 360
ttttaattaa cttctcctac gcaagcgtct aaacggacgt tggggttttg ctagtttctt 420
tagagaaaac tagctaagtc tttaatgtta tcattagaga tggcataaat ataatacttg 480
tgtctgctga taagatcatt ttaatttgga cgattagact tgttgaacta caggttactg 540
aatcacttgc gctaatcaac atgggagata tgtacgatga atcatttgac aagtcgggcg 600
gtcctgctga cttgatggac gattcttggg tggaatcagt ttcgtggaaa gatctgttga 660
agaagttaca cagcataaaa tttgcactac agtctggtag agatgagatc actgggttac 720
tagcggcact gaatagacag tgtccttatt caccatatga gcagtttcca gataagaagg 780
tgtatttcct tttagactca cgggctaaca gtgctcttgg tgtgattcag aacgcttcag 840
cgttcaagag acgagctgat gagaagaatg cagtggcggg tgttacaaat attcctgcga 900
atccaaacac aacggttacg acgaaccaag ggagtactac tactaccaag gcgaacactg 960
gctcgacttt ggaagaagac ttgtacactt attacaaatt cgatgatgcc tctacagctt 1020
tccacaaatc tctaacttcg ttagagaaca tggagttgaa gagttattac cgaaggaact 1080
ttgagaaagt attcgggatt aagtttggtg gagcagctgc tagttcatct gcaccgcctc 1140
cagcgagtgg aggtccgata cgtcctaatc cctagggatt taaggacgtg aactctgttg 1200
agatctctgt gaaattcaga gggtgggtga taccatattc actgatgcca ttagcgacat 1260
ctaaataggg ctaattgtga ctaatttgag ggaatttcct ttaccattga cgtcagtgtc 1320
gttggtagca tttgagtttc gcaatgcacg aattacttag gaagtggctt gacgacacta 1380
atgtgttatt gttagataat ggtttggtgg tcaaggtacg tagtagagtc ccacatattc 1440
gcacgtatga agtaattgga aagttgtcag tttttgataa ttcactggga gatgatacgc 1500
tgtttgaggg aaaagtagag aacgtatttg tttttatgtt caggcggttc ttgtgtgtca 1560
acaaagatgg acattgttac tcaaggaagc acgatgagct ttattattac ggacgagtgg 1620
acttagattc tgtgagtaag gttaccgaat tctctagaag gcctccatgg ggatccggta 1680
ccgagctcac gcgtctcgag gcccgggcat gtcccgaaga cattaaacta cggttcttta 1740
agtagatccg tgtctgaagt tttaggttca atttaaacct acgagattga cattctcgac 1800
tgatcttgat tgatcggtaa gtcttttgta atttaatttt ctttttgatt ttattttaaa 1860
ttgttatctg tttctgtgta tagactgttt gagatcggcg tttggccgac tcattgtctt 1920
accatagggg aacggacttt gtttgtgttg ttattttatt tgtattttat taaaattctc 1980
aacgatctga aaaagcctcg cggctaagag attgttgggg ggtgagtaag tacttttaaa 2040
gtgatgatgg ttacaaaggc aaaaggggta aaacccctcg cctacgtaag cgttattacg 2100
cccgtctgta cttatatcag tacactgacg agtccctaaa ggacgaaacg ggagaacgct 2160
agccaccacc accaccacca cgtgtgaatt acaggtgacc agctcgaatt tccccgatcg 2220

```
ttcaaacatt tggcaataaa gtttcttaag attgaatcct gttgccggtc ttgcgatgat   2280
tatcatataa tttctgttga attacgttaa gcatgtaata attaacatgt aatgcatgac   2340
gttatttatg agatgggttt ttatgattag agtcccgcaa ttatacattt aatacgcgat   2400
agaaaacaaa atatagcgcg caaactagga taaattatcg cgcgcggtgt catctatgtt   2460
actagatcgg gaattaaact atcagtgttt gacaggatat attggcgggt aaacctaaga   2520
gaaaagagcg tttattagaa taacggatat ttaaaagggc gtgaaaaggt ttatccgttc   2580
gtccatttgt atgtgcatgc caaccacagg gttcccctcg ggatcaaagt actttgatcc   2640
aacccctccg ctgctatagt gcagtcggct tctgacgttc agtgcagccg tcttctgaaa   2700
acgacatgtc gcacaagtcc taagttacgc gacaggctgc cgccctgccc ttttcctggc   2760
gttttcttgt cgcgtgtttt agtcgcataa agtagaatac ttgcgactag aaccggagac   2820
attacgccat gaacaagagc gccgccgctg gcctgctggg ctatgcccgc gtcagcaccg   2880
acgaccagga cttgaccaac caacgggccg aactgcacgc ggccggctgc accaagctgt   2940
tttccgagaa gatcaccggc accaggcgcg accgcccgga gctggccagg atgcttgacc   3000
acctacgccc tggcgacgtt gtgacagtga ccaggctaga ccgcctggcc cgcagcaccc   3060
gcgacctact ggacattgcc gagcgcatcc aggaggccgg cgcgggcctg cgtagcctgg   3120
cagagccgtg ggccgacacc accacgccgg ccggccgcat ggtgttgacc gtgttcgccg   3180
gcattgccga gttcgagcgt tccctaatca tcgaccgcac ccggagcggg cgcgaggccg   3240
ccaaggcccg aggcgtgaag tttggccccc gccctaccct caccccggca cagatcgcgc   3300
acgcccgcga gctgatcgac caggaaggcc gcaccgtgaa agaggcggct gcactgcttg   3360
gcgtgcatcg ctcgaccctg taccgcgcac ttgagcgcag cgaggaagtg acgcccaccg   3420
aggccaggcg gcgcggtgcc ttccgtgagg acgcattgac cgaggccgac gccctggcgg   3480
ccgccgagaa tgaacgccaa gaggaacaag catgaaaccg caccaggacg gccaggacga   3540
accgtttttc attaccgaag agatcgaggc ggagatgatc gcggccgggt acgtgttcga   3600
gccgcccgcg cacgtctcaa ccgtgcggct gcatgaaatc ctggccggtt tgtctgatgc   3660
caagctggcg gcctggccgg ccagcttggc cgctgaagaa accgagcgcc gccgtctaaa   3720
aaggtgatgt gtatttgagt aaaacagctt gcgtcatgcg gtcgctgcgt atatgatgcg   3780
atgagtaaat aaacaaatac gcaaggggaa cgcatgaagg ttatcgctgt acttaaccag   3840
aaaggcgggt caggcaagac gaccatcgca acccatctag cccgcgccct gcaactcgcc   3900
ggggccgatg ttctgttagt cgattccgat ccccagggca gtgcccgcga ttgggcggcc   3960
gtgcgggaag atcaaccgct aaccgttgtc ggcatcgacc gcccgacgat tgaccgcgac   4020
gtgaaggcca tcggccggcg cgacttcgta gtgatcgacg gagcgcccca ggcggcggac   4080
ttggctgtgt ccgcgatcaa ggcagccgac ttcgtgctga ttccggtgca gccaagccct   4140
tacgacatat gggccaccgc cgacctggtg gagctggtta agcagcgcat tgaggtcacg   4200
gatggaaggc tacaagcggc ctttgtcgtg tcgcgggcga tcaaaggcac gcgcatcggc   4260
ggtgaggttg ccgaggcgct ggccgggtac gagctgccca ttcttgagtc ccgtatcacg   4320
cagcgcgtga gctacccagg cactgccgcc gccggcacaa ccgttcttga atcagaaccc   4380
gagggcgacg ctgcccgcga ggtccaggcg ctggccgctg aaattaaatc aaaactcatt   4440
tgagttaatg aggtaaagag aaaatgagca aaagcacaaa cacgctaagt gccggccgtc   4500
cgagcgcacg cagcagcaag gctgcaacgt tggccagcct ggcagacacg ccagccatga   4560
```

-continued

```
agcgggtcaa ctttcagttg ccggcggagg atcacaccaa gctgaagatg tacgcggtac   4620
gccaaggcaa gaccattacc gagctgctat ctgaatacat cgcgcagcta ccagagtaaa   4680
tgagcaaatg aataaatgag tagatgaatt ttagcggcta aaggaggcgg catggaaaat   4740
caagaacaac caggcaccga cgccgtggaa tgccccatgt gtggaggaac gggcggttgg   4800
ccaggcgtaa gcggctgggt tgtctgccgg ccctgcaatg gcactggaac ccccaagccc   4860
gaggaatcgg cgtgacggtc gcaaaccatc cggcccggta caaatcggcg cggcgctggg   4920
tgatgacctg gtggagaagt tgaaggccgc gcaggccgcc cagcggcaac gcatcgaggc   4980
agaagcacgc cccggtgaat cgtggcaagc ggccgctgat cgaatccgca aagaatcccg   5040
gcaaccgccg gcagccggtg cgccgtcgat taggaagccg cccaagggcg acgagcaacc   5100
agattttttc gttccgatgc tctatgacgt gggcacccgc gatagtcgca gcatcatgga   5160
cgtggccgtt ttccgtctgt cgaagcgtga ccgacgagct ggcgaggtga tccgctacga   5220
gcttccagac gggcacgtag aggtttccgc agggccggcc ggcatggcca gtgtgtggga   5280
ttacgacctg gtactgatgg cggtttccca tctaaccgaa tccatgaacc gataccggga   5340
agggaaggga gacaagcccg gccgcgtgtt ccgtccacac gttgcggacg tactcaagtt   5400
ctgccggcga gccgatggcg gaaagcagaa agacgacctg gtagaaacct gcattcggtt   5460
aaacaccacg cacgttgcca tgcagcgtac gaagaaggcc aagaacggcc gcctggtgac   5520
ggtatccgag ggtgaagcct tgattagccg ctacaagatc gtaaagagcg aaaccgggcg   5580
gccggagtac atcgagatcg agctagctga ttggatgtac cgcgagatca cagaaggcaa   5640
gaacccggac gtgctgacgg ttcaccccga ttactttttg atcgatcccg gcatcggccg   5700
ttttctctac cgcctggcac gccgcgccgc aggcaaggca gaagccagat ggttgttcaa   5760
gacgatctac gaacgcagtg gcagcgccgg agagttcaag aagttctgtt tcaccgtgcg   5820
caagctgatc gggtcaaatg acctgccgga gtacgatttg aaggaggagg cggggcaggc   5880
tggcccgatc ctagtcatgc gctaccgcaa cctgatcgag ggcgaagcat ccgccggttc   5940
ctaatgtacg gagcagatgc tagggcaaat tgccctagca ggggaaaaag gtcgaaaagg   6000
tctctttcct gtggatagca cgtacattgg gaacccaaag ccgtacattg ggaaccggaa   6060
cccgtacatt gggaacccaa agccgtacat tgggaaccgg tcacacatgt aagtgactga   6120
tataaaagag aaaaaaggcg atttttccgc ctaaaactct ttaaaactta ttaaaactct   6180
taaaacccgc ctggcctgtg cataactgtc tggccagcgc acagccgaag agctgcaaaa   6240
agcgcctacc cttcggtcgc tgcgctccct acgccccgcc gcttcgcgtc ggcctatcgc   6300
ggccgctggc cgctcaaaaa tggctggcct acggccaggc aatctaccag ggcgcggaca   6360
agccgcgccg tcgccactcg accgccggcg cccacatcaa ggcaccctgc ctcgcgcgtt   6420
tcggtgatga cggtgaaaac ctctgacaca tgcagctccc ggagacggtc acagcttgtc   6480
tgtaagcgga tgccgggagc agacaagccc gtcagggcgc gtcagcgggt gttggcgggt   6540
gtcggggcgc agccatgacc cagtcacgta gcgatagcgg agtgtatact ggcttaacta   6600
tgcggcatca gagcagattg tactgagagt gcaccatatg cggtgtgaaa taccgcacag   6660
atgcgtaagg agaaaatacc gcatcaggcg ctcttccgct tcctcgctca ctgactcgct   6720
gcgctcggtc gttcggctgc ggcgagcggt atcagctcac tcaaaggcgg taatacggtt   6780
atccacagaa tcaggggata acgcaggaaa gaacatgtga gcaaaaggcc agcaaaaggc   6840
caggaaccgt aaaaaggccg cgttgctggc gtttttccat aggctccgcc cccctgacga   6900
gcatcacaaa aatcgacgct caagtcagag gtggcgaaac ccgacaggac tataaagata   6960
```

ccaggcgttt cccccctggaa gctccctcgt gcgctctcct gttccgaccc tgccgcttac 7020
cggatacctg tccgcctttc tcccttcggg aagcgtggcg ctttctcata gctcacgctg 7080
taggtatctc agttcggtgt aggtcgttcg ctccaagctg ggctgtgtgc acgaaccccc 7140
cgttcagccc gaccgctgcg ccttatccgg taactatcgt cttgagtcca acccggtaag 7200
acacgactta tcgccactgg cagcagccac tggtaacagg attagcagag cgaggtatgt 7260
aggcggtgct acagagttct tgaagtggtg gcctaactac ggctacacta gaaggacagt 7320
atttggtatc tgcgctctgc tgaagccagt taccttcgga aaaagagttg gtagctcttg 7380
atccggcaaa caaaccaccg ctggtagcgg tggttttttt gtttgcaagc agcagattac 7440
gcgcagaaaa aaaggatctc aagaagatcc tttgatcttt tctacggggt ctgacgctca 7500
gtggaacgaa aactcacgtt aagggatttt ggtcatgcat tctaggtact aaaacaattc 7560
atccagtaaa atataatatt ttattttctc ccaatcaggc ttgatcccca gtaagtcaaa 7620
aaatagctcg acatactgtt cttccccgat atcctccctg atcgaccgga cgcagaaggc 7680
aatgtcatac cacttgtccg ccctgccgct tctcccaaga tcaataaagc cacttacttt 7740
gccatctttc acaaagatgt tgctgtctcc caggtcgccg tgggaaaaga caagttcctc 7800
ttcgggcttt tccgtcttta aaaaatcata cagctcgcgc ggatctttaa atggagtgtc 7860
ttcttcccag ttttcgcaat ccacatcggc cagatcgtta ttcagtaagt aatccaattc 7920
ggctaagcgg ctgtctaagc tattcgtata gggacaatcc gatatgtcga tggagtgaaa 7980
gagcctgatg cactccgcat acagctcgat aatcttttca gggctttgtt catcttcata 8040
ctcttccgag caaaggacgc catcggcctc actcatgagc agattgctcc agccatcatg 8100
ccgttcaaag tgcaggacct ttggaacagg cagctttcct tccagccata gcatcatgtc 8160
ccttttcccgt tccacatcat aggtggtccc tttataccgg ctgtccgtca tttttaaata 8220
taggttttca ttttctccca ccagcttata taccttagca ggagacattc cttccgtatc 8280
ttttacgcag cggtattttt cgatcagttt tttcaattcc ggtgatattc tcattttagc 8340
catttattat ttccttcctc ttttctacag tatttaaaga taccccaaga agctaattat 8400
aacaagacga actccaattc actgttcctt gcattctaaa accttaaata ccagaaaaca 8460
gctttttcaa agttgttttc aaagttggcg tataacatag tatcgacgga gccgattttg 8520
aaaccgcggt gatcacaggc agcaacgctc tgtcatcgtt acaatcaaca tgctaccctc 8580
cgcgagatca tccgtgtttc aaacccggca gcttagttgc cgttcttccg aatagcatcg 8640
gtaacatgag caaagtctgc cgccttacaa cggctctccc gctgacgccg tcccggactg 8700
atgggctgcc tgtatcgagt ggtgattttg tgccgagctg ccggtcgggg agctgttggc 8760
tggctggtgg caggatatat tgtggtgtaa acaaattgac gcttagacaa cttaataaca 8820
cattgcggac gtttttaatg tactgaatta acgccgaatt aattcctagg ccaccatgtt 8880
gggcccggcg cgccaagctt gcatgcctgc aggtcaacat ggtggagcac gacactctcg 8940
tctactccaa gaatatcaaa gatacagtct cagaagacca gagggctatt gagacttttc 9000
aacaaagggt aatatcggga aacctcctcg gattccattg cccagctatc tgtcacttca 9060
tcgaaaggac agtagaaaag gaagatggct tctacaaatg ccatcattgc gataaaggaa 9120
aggctatcgt tcaagatgcc tctaccgaca gtggtcccaa agatggaccc ccacccacga 9180
ggaacatcgt ggaaaaagaa gacgttccaa ccacgtcttc aaagcaagtg gattgatgtg 9240
atggtcaaca tggtggagca cgacactctc gtctactcca agaatatcaa agatacagtc 9300
tcagaagacc agagggctat tgagactttt caacaaaggg taatatcggg aaacctcctc 9360
ggattccatt gcccagctat ctgtcacttc atcgaaagga cagtagaaaa ggaagatggc 9420
ttctacaaat gccatcattg cgataaagga aaggctatcg ttcaagatgc ctctaccgac 9480
agtggtccca aagatggacc cccacccacg aggaacatcg tggaaaaaga agacgttcca 9540
accacgtctt caaagcaagt ggattgatgt gatatctcca ctgacgtaag ggatgacgca 9600
caatcccact atccttcgca agacccttcc tctatataag gaagttcatt tcatttggag 9660
agg 9663

<210> SEQ ID NO 51
<211> LENGTH: 300
<212> TYPE: DNA
<213> ORGANISM: Artificial Sequence
<220> FEATURE:
<223> OTHER INFORMATION: virus-induced gene silencing (VIGS) target sequence

<400> SEQUENCE: 51
attatagcta tgtacacaat tagcacgtgg gcgaagacag tggcagaaaa tgtctggtca 60
ctcattggaa gaacagctcc accagatttt cttacgaaat taacctatct tatatggaat 120
catcacgaag agatcaagca cattgatact gttcgagcat atacttttgg tgctcattat 180
tttgtagagg ttgatatagt gttgccagag gacatgctgt tgaacaaggc acataatatt 240
ggtgagacac tgcaagaaaa attggagcaa ctccctgaag ttgagcgagc ttttgttcat 300

<210> SEQ ID NO 52
<211> LENGTH: 300
<212> TYPE: DNA
<213> ORGANISM: Artificial Sequence
<220> FEATURE:
<223> OTHER INFORMATION: VIGS control sequence

<400> SEQUENCE: 52
cgtcgtccaa cattatcatg gcctcgtgaa atcccgttag taaaaggtgg taaacctgac 60
gttgtacaaa ttgttaggaa ttataatgct tatctacgtg caagtgatga tttaccaaaa 120
atgtttattg aatcggaccc aggattcttt tccaatgcta ttgttgaagg tgccaagaag 180
tttcctaata ctgaatttgt caaagtaaaa ggtcttcatt tttcgcaaga agatgcacct 240
gatgaaatgg gaaaatatat caaatcgttc gttgagcgag ttctcaaaaa tgaacaataa 300

<210> SEQ ID NO 53
<211> LENGTH: 39
<212> TYPE: DNA
<213> ORGANISM: Artificial Sequence
<220> FEATURE:
<223> OTHER INFORMATION: yeast Fw primer

<400> SEQUENCE: 53
agggaatatt aagcttatgg agataagtcg cagcaatgt 39

<210> SEQ ID NO 54
<211> LENGTH: 38
<212> TYPE: DNA
<213> ORGANISM: Artificial Sequence
<220> FEATURE:
<223> OTHER INFORMATION: yeast Rv primer

<400> SEQUENCE: 54
gttactagtg gatccttata ccatagtttt gtgttctg 38

<210> SEQ ID NO 55
<211> LENGTH: 14971
<212> TYPE: DNA
<213> ORGANISM: Artificial Sequence
<220> FEATURE:
<223> OTHER INFORMATION: modified pTES3 vector pYES3/UT.1

<400> SEQUENCE: 55
agcttgcatg cctgcaggtc gagcttttag gattccatag tgataagata tgttcttatc 60
taaacaaaaa agcaagcgtc ggcaaaccat acagctgtcc acaaaaagga aaggctgtaa 120
taacaagcgg acccagcttc tcagtggaag atactttatc agacactgaa taatggatgg 180
accctaccac gattaaagag gagcgtctgt ctaaagtaaa gtagatgcgt ctttaataat 240
tcatctactt tagacgtcat gcatgacgtt taacatgcat tgtatccaga tcctccctgg 300
ctatataaag ggagttaaat ttcattgtta aggcatcgaa aaaaaaattt caagtctatc 360
tctcaagaaa aacttagaaa attactttgt cttaaggatc cgggcccagc tgtcacaagt 420
ttgtacaaaa aagcaggcta ctaaaagctc gctcaacttc agggagttgc tccaattttt 480
cttgcagtgt ctcaccaata ttatgtgcct tgttcaacag catgtcctct ggcaacacta 540
tatcaacctc tacaaaataa tgagcaccaa aagtatatgc tcgaacagta tcaatgtgct 600
tgatctcttc gtgatgattc catataagat aggttaattt cgtaagaaaa tctggtggag 660
ctgttcttcc aatgagtgac cagacatttt ctgccactgt cttcgcccac gtgctaattg 720
tgtacatagc tatgatttcg tttttgaacc ttcgacagta gaccataagc agaaacttga 780
ccatagtgac agagaccata ataccaatcg tccatttttc cttctcatgg tccatctcag 840
ggcgagactg atcgtaagca tagaaccacc gaaacaacaa acgtagatta agatgtcaag 900
ggtaatgcaa ttgttagtga aattgcagta agttacaagt ctatatccta caattgaagt 960
agcactatgc gagttaatct tcacttagct atgcaacatc agtagaaata tcaaaaccag 1020 tccctttta ttaggtagta tacagtagcc taatttatct tatgtaaaca tctttggcct 1080
aactggtttg gctacaactt catttcagta gtaactcaac ccgtttttcg tcttcttgtt 1140
tcctataaat tgcatgtttt tttttgtctt gatgtaaaag attttagaaa ctcaaaactc 1200
tactaaccat aggaacctgc tgctctgaaa attctcagga tagttgaagt gaagcaattc 1260
acatacctta gttatgagtt ctttagctga ctcgaacaat atttgtaatc ctagtgtcgc 1320
cattacagat gcaaaaacaa taatacccaa tggctgcatc ctcttttttc caataggata 1380
gtgatactgg tttggatttt tcatggcatg agaagtgaac cacagtataa accctgataa 1440
gaggtctaag agggagtcca acgttgacgc gattacagcc aaagatctgc tctcaataga 1500
agcgtagatt tttgcaatga aaagaaccac attagccatg tttgataaat gaatagccat 1560
cctttcactt cttgcaagct gcttcatttc atcctcagtt agacttccag gtaaacaacc 1620
agattcatta atggtgtcca tctcattgaa cccttcaagc agcctttctt gtttttgta 1680 gtattcagca attttacctt gtttcctggg agtgggaagt agacgacgga cactaaagga 1740
gtgatgatcg gaggaggagc ggcttcgttc gggaagacgg aattcgctaa tgttaagtct 1800
ccatgacgcc gacgaagacg actgatccac caccgcctga gcagccggag acagcagttc 1860
cgtcctaaaa ctgctaaaac tgtcgtccag agcgccgccg ctgccgccac caccactaac 1920
attgctgcga cttatctcca tacccagctt tcttgtacaa agtggtgcag ctgagatcta 1980
ggcctaagta agtaagatcg ttcaaacatt tggcaataaa gtttctttag attgaatcct 2040
gttgccggtc ttgcgatgat tatcatataa tttctgttga attacgttaa gcatgtagta 2100

-continued

```
attaacatgt aatggatgac gttatttatg agatgggttt ttatgattag agtcccgcaa   2160
ttatacattt aatacgcgat agaaaacaaa atatagcgcg caaactagga taaattatcg   2220
cgcgcggtgt catctatgtt actagatcga aggccttgtt ctcgagcaat tcactggccg   2280
tcgttttaca acgtcgtgac tgggaaaacc ctggcgttac ccaacttaat cgccttgcag   2340
cacatccccc tttcgccagc aggcgtaata gcgaagaggc ccgcaccgat tgcccttccc   2400
aacagttgcg cagcctgaat ggcgcccgct cctttcgctt tcttcccttc ctttctcgcc   2460
acgttcgccg gctttccccg tcaagctcta aatcgggggc tccctttagg gttccgattt   2520
agtgctttac ggcacctcga ccccaaaaaa cttgatttgg gtgatggttc acaaactatc   2580
agtgtttgac aggatatatt ggcgggtaaa cctaagagaa aagagcgttt attagaataa   2640
tcggatattt aaaagggcgt gaaaaggttt atccgttcgt ccatttgtat gtgcatgcca   2700
accacaggct taagaaaact tgatttgggt gatggttcac aaactatcag tgtttgacag   2760
gatatattgg cgggtaaacc taagagaaaa gagcgtttat tagaataatc ggatatttaa   2820
aagggcgtga aaaggtttat ccgttcgtcc atttgtatgt gcatgccaac cacaggctta   2880
aggttctaga ctggcgccgg ccagcgagac gagcaagatt ggccgccgcc cgaaacgatc   2940
cgacagcgcg cccagcacag gtgcgcaggc aaattgcacc aacgcataca gcgccagcag   3000
aatgccatag tgggcggtga cctcgttcga gtgaaccaga tcgcgcagga ggcccggcag   3060
caccggcata atcaggccga tgccgacagc gtcgagcgcg acagtgctca gaattacgat   3120
caggggtatg ttgggtttca cgtctggcct ccggaccagc ctccgctggt ccgattgaac   3180
gcgcggattc tttatcactg ataagttggt ggacatatta tgtttatcag tgataaagtg   3240
tcaagcatga caaagttgca gccgaataca gtgatccgtg ccgccctgga cctgttgaac   3300
gaggtcggcg tagacggtct gacgacacgc aaactggcgg aacggttggg ggttcagcag   3360
ccggcgcttt actggcactt caggaacaag cgggcgctgc tcgacgcact ggccgaagcc   3420
atgctggcgg agaatcatac gcattcggtg ccgagagccg acgacgactg gcgctcattt   3480
ctgatcggga atgcccgcag cttcaggcag gcgctgctcg cctaccgcga tggcgcgcgc   3540
atccatgccg gcacgcgacc gggcgcaccg cagatggaaa cggccgacgc gcagcttcgc   3600
ttcctctgcg aggcgggttt ttcggccggg gacgccgtca atgcgctgat gacaatcagc   3660
tacttcactg ttggggccgt gcttgaggag caggccggcg acagcgatgc cggcgagcgc   3720
ggcggcaccg ttgaacaggc tccgctctcg ccgctgttgc gggccgcgat agacgccttc   3780
gacgaagccg gtccggacgc agcgttcgag cagggactcg cggtgattgt cgatggattg   3840
gcgaaaagga ggctcgttgt caggaacgtt gaaggaccga gaaagggtga cgattgatga   3900
ggaccgctgc cggagcgcaa cccactcact acagcagagc catgtagaca acatcccctc   3960
cccctttcca ccgcgtcaga cgcccgtagc agcccgctac gggctttttc atgccctgcc   4020
ctagcgtcca agcctcacgg ccgcgctcgg cctctctggc ggccttctgg cgctcgtcga   4080
ccgctcactg actcgctgcg ctcggtcgtt cggctgcggc gagcggtatc agctcactca   4140
aaggcggtaa tacggttatc cacagaatca ggggataacg caggaaagaa catgtgagca   4200
aaaggccagc aaaaggccag gaaccgtaaa aaggccgcgt tgctggcgtt tttccatagg   4260
ctccgccccc ctgacgagca tcacaaaaat cgacgctcaa gtcagaggtg gcgaaacccg   4320
acaggactat aaagatacca ggcgtttccc cctggaagct ccctcgtgcg ctctcctgtt   4380
ccgaccctgc cgcttaccgg atacctgtcc gcctttctcc cttcgggaag cgtggcgctt   4440
```

-continued ttccgctgca taaccctgct tcggggtcat tatagcgatt ttttcggtat atccatcctt 4500
tttcgcacga tatacaggat tttgccaaag ggttcgtgta gactttcctt ggtgtatcca 4560
acggcgtcag ccgggcagga taggtgaagt aggcccaccc gcgagcgggt gttccttctt 4620
cactgtccct tattcgcacc tggcggtgct caacgggaat cctgctctgc gaggctggcc 4680
ggctaccgcc ggcgtaacag atgagggcaa gcggatggct gatgaaacca agccaaccag 4740
gaagggcagc ccacctatca aggtgtactg ccttccagac gaacgaagag cgattgagga 4800
aaaggcggcg gcggccggca tgagcctgtc ggcctacctg ctggccgtcg gccagggcta 4860
caaaatcacg ggcgtcgtgg actatgagca cgtccgcgag ctggcccgca tcaatggcga 4920
cctgggccgc ctgggcggcc tgctgaaact ctggctcacc gacgacccgc gcacggcgcg 4980
gttcggtgat gccacgatcc tcgccctgct ggcgaagatc gaagagaagc aggacgagct 5040
tggcaaggtc atgatgggcg tggtccgccc gagggcagag ccatgacttt tttagccgct 5100
aaaacggccg gggggtgcgc gtgattgcca agcacgtccc catgcgctcc atcaagaaga 5160
gcgacttcgc ggagctggtg aagtacatca ccgacgagca aggcaagacc gagcgccttt 5220
ggtacctcac cgggctggtt gccctcgccg ctgggctggc ggccgtctat ggccctgcaa 5280
acgcgccaga aacgccgtcg aagccgtgtg cgagacaccg ccgccgccgg cgttgtggat 5340
acctcgcgga aaacttggcc ctcactgaca gatgaggggc ggacgttgac acttgagggg 5400
ccgactcacc cggcgcggcg ttgacagatg aggggcaggc tcgatttcgg ccggcgacgt 5460
ggagctggcc agcctcgcaa atcggcgaaa acgcctgatt ttacgcgagt ttcccacaga 5520
tgatgtggac aagcctgggg ataagtgccc tgcggtattg acacttgagg ggcgcgacta 5580
ctgacagatg aggggcgcga tccttgacac ttgaggggca gagtgctgac agatgagggg 5640
cgcacctatt gacatttgag gggctgtcca caggcagaaa atccagcatt tgcaagggtt 5700
tccgcccgtt tttcggccac cgctaacctg tcttttaacc tgcttttaaa ccaatattta 5760
taaaccttgt ttttaaccag ggctgcgccc tgtgcgcgtg accgcgcacg ccgaaggggg 5820
gtgccccccc ttctcgaacc ctcccggccc gctaacgcgg gcctcccatc cccccagggg 5880
ctgcgcccct cggccgcgaa cggcctcacc ccaaaaatgg cagcgctggc agtccttgcc 5940
attgccggga tcggggcagt aacgggatgg gcgatcagcc cgagcgcgac gcccggaagc 6000
attgacgtgc cgcaggtgct ggcatcgaca ttcagcgacc aggtgccggg cagtgagggc 6060
ggcggcctgg gtggcggcct gcccttcact tcggccgtcg gggcattcac ggacttcatg 6120
gcggggccgg caatttttac cttgggcatt cttggcatag tggtcgcggg tgccgtgctc 6180
gtgttcgggg gtgacgcgtg aaaattttcg ataaacccag cgaaccattt gaggtgatag 6240
gtaagattat accgaggtat gaaaacgaga attggacctt tacagaatta ctctatgaag 6300
cgccatattt aaaaagctac caagacgaag aggatgaaga ggatgaggag gcagattgcc 6360
ttgaatatat tgacaatact gataagataa tatatctttt atatagaaga tatggccgta 6420
tgtaaggatt tcagggggca aggcataggc agcgcgctta tcaatatatc tatagaatgg 6480
gcaaagcata aaaacttgca tggactaatg cttgaaaccc aggacaataa ccttatagct 6540
tgtaaattct atcataattg ggtaatgact ccaacttatt gatagtgttt tatgttcaga 6600
taatgcccga tgactttgtc atgcagctcc accgattttg agaacgacag cgacttccgt 6660
cccagccgtg ccaggtgctg cctcagattc aggttatgcc gctcaattcg ctgcgtatat 6720
cgcttgctga ttacgtgcag ctttcccttc aggcgggatt catacagcgg ccagccatcc 6780
gtcatccata tcaccacgtc aaagggtgac agcaggctca taagacgccc cagcgtcgcc 6840

```
atagtgcgtt caccgaatac gtgcgcaaca accgtcttcc ggagactgtc atacgcctaa   6900
aacagccagc gctggcgcga tttagccccg acatagcccc actgttcgtc catttccgcg   6960
cagacgatga cgacactgcc cggctgtatg cgcgaggtta cctgctgcca gtggcgataa   7020
gtcgtgtctt accgggttgg actcaagacg atagttaccg gataaggcgc agcggtcggg   7080
ctgaacgggg ggttcgtgca cacagcccag cttggagcga acgacctaca ccgaactgag   7140
atacctacag cgtgagctat gagaaagcgc cacgcttccc gaagggagaa aggcggacag   7200
gtatccggta agcggcaggg tcggaacagg agagcgcacg agggagcttc caggggggaaa  7260
cgcctggtat ctttatagtc ctgtcgggtt tcgccacctc tgacttgagc gtcgattttt   7320
gtgatgctcg tcaggggggc ggagcctatg gaaaaacgcc agcaacgcgg cctttttacg   7380
gttcctggcc ttttgctggc cttttgctca catgttcttt cctgcgttat cccctgattc   7440
tgtggataac cgtattaccg cctttgagtg agctgatacc gctcgccgca gccgaacgac   7500
cgagcgcagc gagtcagtga gcgaggaagc ggaagagcgc ctgatgcggt attttctcct   7560
tacgcatctg tgcggtattt cacaccgcat agttaccgac tgcggcctga gtttttaag    7620
tgacgtaaaa tcgtgttgag gccaacgccc ataatgcggg ctgttgcccg gcatccaacg   7680
ccattcatgg ccatatcaat gattttctgg tgcgtaccgg gttgagaagc ggtgtaagtg   7740
aacagcagtt gccatgtttt acggcagtga gagcagagat agcgctgatg tccggcggtg   7800
cttttgccgt tacgcaccac cccgtcagta gctgaacagg agggacacct gatagacaca   7860
gaagccactg gagcacctca aaaacaccat catacactaa atcagtaagt tggcagcatc   7920
acccgttaac ataattgtgg tttcaaaatc ggctccgtcg atactatgtt atacgccaac   7980
tttgaaaaca actttgaaaa agctgttttc tggtatttaa ggttttagaa tgcaaggaac   8040
agtgaattgg agttcgtctt gttataatta gcttcttggg gtatctttaa atactgtaga   8100
aaagaggaag gaaataataa atggctaaaa tgagaatatc accggaattg aaaaaactga   8160
tcgaaaaata ccgctgcgta aaagatacgg aaggaatgtc tcctgctaag gtatataagc   8220
tggtgggaga aaatgaaaac ctatatttaa aaatgacgga cagccggtat aaagggacca   8280
cctatgatgt ggaacgggaa aaggacatga tgctatggct ggaaggaaag ctgcctgttc   8340
caaaggtcct gcactttgaa cggcatgatg gctggagcaa tctgctcatg agtgaggccg   8400
atggcgtcct ttgctcggaa gagtatgaag atgaacaaag ccctgaaaag attatcgagc   8460
tgtatgcgga gtgcatcagg ctctttcact ccatcgacat atcggattgt ccctatacga   8520
atagcttaga cagccgctta gccgaattgg attacttact gaataacgat ctggccgatg   8580
tggattgcga aaactgggaa gaagacactc catttaaaga tccgcgcgag ctgtatgatt   8640
ttttaaagac ggaaaagccc gaagaggaac ttgtcttttc ccacggcgac ctgggagaca   8700
gcaacatctt tgtgaaagat ggcaaagtaa gtggctttat tgatcttggg agaagcggca   8760
gggcggacaa gtggtatgac attgccttct gcgtccggtc gatcagggag gttatcgggg   8820
aagaacagta tgtcgagcta ttttttgact tactggggat caagcctgat tgggagaaaa   8880
taaaatatta tattttactg gatgaattgt tttagtacct agagaaaatt ttcctaggtg   8940
tggcgcaacg atgccggcga caagcaggag cgcaccgact tcttccgcat caagtgtttt   9000
ggctctcagg ccgaggccca cggcaagtat ttgggcaagg ggtcgctggt attcgtgcag   9060
ggcaagattc ggaataccaa gtacgagaag gacggccaga cggtctacgg gaccgacttc   9120
attgccgata aggtggatta tctggacacc aaggcaccag gcgggtcaaa tcaggaataa   9180
```

-continued

```
gggcacattg ccccggcgtg agtcggggca atcccgcaag gagggtgaat gaatcggacg   9240
tttgaccgga aggcatacag gcaagaactg atcgacgcgg ggttttccgc cgaggatgcc   9300
gaaaccatcg caagccgcac cgtcatgcgt gcgccccgcg aaaccttcca gtccgtcggc   9360
tcgatggtcc agcaagctac ggccaagatc gagcgcgaca gcgtgcaact ggctccccct   9420
gccctgcccg cgccatcggc cgccgtggag cgttcgcgtc gtctcgaaca ggaggcggca   9480
ggtttggcga agtcgatgac catcgacacg cgaggaacta tgacgaccaa gaagcgaaaa   9540
accgccggcg aggacctggc aaaacaggtc agcgaggcca agcaggccgc gttgctgaaa   9600
cacacgaagc agcagatcaa ggaaatgcag ctttccttgt tcgatattgc gccgtggccg   9660
gacacgatgc gagcgatgcc aaacgacacg gcccgctctg ccctgttcac cacgcgcaac   9720
aagaaaatcc cgcgcgaggc gctgcaaaac aaggtcattt tccacgtcaa caaggacgtg   9780
aagatcacct acaccggcgt cgagctgcgg gccgacgatg acgaactggt gtggcagcag   9840
gtgttggagt acgcgaagcg cacccctatc ggcgagccga tcaccttcac gttctacgag   9900
ctttgccagg acctgggctg gtcgatcaat ggccggtatt acacgaaggc cgaggaatgc   9960
ctgtcgcgcc tacaggcgac ggcgatgggc ttcacgtccg accgcgttgg gcacctggaa  10020
tcggtgtcgc tgctgcaccg cttccgcgtc ctggaccgtg gcaagaaaac gtcccgttgc  10080
caggtcctga tcgacgagga aatcgtcgtg ctgtttgctg gcgaccacta cacgaaattc  10140
atctgggaga agtaccgcaa gctgtcgccg acggcccgac ggatgttcga ctatttcagc  10200
tcgcaccggg agccgtaccc gctcaagctg gaaaccttcc gcctcatgtg cggatcggat  10260
tccacccgcg tgaagaagtg gcgcgagcag gtcggcgaag cctgcgaaga gttgcgaggc  10320
agcggcctgg tggaacacgc ctgggtcaat gatgacctgg tgcattgcaa acgctagggc  10380
cttgtggggt cagttccggc tgggggttca gcagccagcg tgatcacttt actggcattt  10440
caggaacaag cgggcactgc tcgacgcact tgcttcgctc agtatcgctc gggacgcacg  10500
gcgcgctcta cgaactgccg ataaacagag gattaaaatt gacaattgtg attaaggctc  10560
agattcgacg gcttggagcg gccgacgtgc aggatttccg cgagatccga ttgtcggccc  10620
tgaagaaagc tccagagatg ttcgggtccg tttacgagca cgaggagaaa aagcccatgg  10680
aggcgttcgc tgaacggttg cgagatgccg tggcattcgg cgcctacatc gacggcgaga  10740
tcattgggct gtcggtcttc aaacaggagg acggccccaa ggacgctcac aaggcgcatc  10800
tgtccggcgt tttcgtggag cccgaacagc gaggccgagg ggtcgccggt atgctgctgc  10860
gggcgttgcc ggcgggttta ttgctcgtga tgatcgtccg acagattcca acgggaatct  10920
ggtggatgcg catcttcatc ctcggcgcac ttaatatttc gctattctgg agcttgttgt  10980
ttatttcggt ctaccgcctg ccgggcgggg tcgcggcgac ggtaggcgct gtgcagccgc  11040
tgatggtcgt gttcatctct gccgctctgc taggtagccc gatacgattg atggcggtcc  11100
tgggggctat ttgcggaact gcgggcgtgg cgctgttggt gttgacacca aacgcagcgc  11160
tagatcctgt cggcgtcgca gcgggcctgg cgggggcggt ttccatggcg ttcggaaccg  11220
tgctgacccg caagtggcaa cctcccgtgc ctctgctcac ctttaccgcc tggcaactgg  11280
cggccggagg acttctgctc gttccagtag ctttagtgtt tgatccgcca atcccgatgc  11340
ctacaggaac caatgttctc ggcctggcgt ggctcggcct gatcggagcg ggtttaacct  11400
acttcctttg gttccggggg atctcgcgac tcgaacctac agttgtttcc ttactgggct  11460
ttctcagccc caggtctggg gtcgatcagc cggggatgca tcaggccgac agtcggaact  11520
tcgggtcccc gacctgtacc attcggtgag caatggatag gggagttgaa atcgtcaacg  11580
```

ttcacttcta aagaaatagc gccactcagc ttcctcagcg gctttatcca gcgatttcct 11640
attatgtcgg catagttctc aagatcgaca gcctgtcacg gttaagcgag aaatgaataa 11700
gaaggctgat aattcggatc tctgcgaggg agatgatatt tgatgacagg cagcaacgct 11760
ctgtcatcgt tacaatcaac atgctaccct ccgcgagatc atccgtgttt caaacccggc 11820
agcttagttg ccgttcttcc gaatagcatc ggtaacatga gcaaagtctg ccgccttaca 11880
acggctctcc cgctgactag tcgtcccgga gacgtcctga tgggctgcct gtatcgagtg 11940
gtgattttgt gccgagctgc cggtcgggga gctgttggct ggctggtggc aggatatatt 12000
gtggtgtaaa caaattgacg cttagacaac ttaataacac attgcggacg tttttaatgt 12060
actggacgtc ctgatgggct gcctgtatcg agtggtgatt ttgtgccgag ctgccggtcg 12120
gggagctgtt ggctggctgg tggcaggata tattgtggtg taaacaaatt gacgcttaga 12180
caacttaata acacattgcg gacgttttta atgtactggg gtggtttttc ttttcaccag 12240
tgagacgggc aacacgtgat tgcccttcac cgcctggccc tgagagagtt gcagcaagcg 12300
gtccacgctg gtttgcccca gcaggcgaaa atcctgtttg atggtggttc cgaaatcggc 12360
aaaatccctt ataaatcaaa agaatagccc gagatagggt tgagtgttgt tccagtttgg 12420
aacaagagtc cactattaaa gaacgtggac tccaacgtca aagggcgaaa aaccgtctat 12480
cagggcgatg gcccacaaac tgaaggcggc cgcaaacgat atcaatctca tcatgagcgg 12540
agaattaagg gagtcacgtt atgacccccg ccgatgacgc gggacaagcc gttttacgtt 12600
tggaactgac agaaccgcaa cgttgaagga gccactcagc cgccggtttc tggagtttaa 12660
tgagctaagc acatacgtca gaaaccatta ttgcgcgttc aaaagtcgcc taaggtcact 12720
atcagctagc aaatatttct tgtcaaaaat gctccactga cgttccataa attcccctcg 12780
gtatccaatt agagtctcat attcactctc aatccaaata atctgcaccg gatctggatc 12840
gtttcgcatg attgaacaag atggattgca cgcaggttct ccggccgctt gggtggagag 12900
gctattcggc tatgactggg cacaacagac aatcggctgc tctgatgccg ccgtgttccg 12960
gctgtcagcg caggggcgcc cggttctttt tgtcaagacc gacctgtccg gtgccctgaa 13020
tgaactccag gacgaggcag cgcggctatc gtggctggcc acgacgggcg ttccttgcgc 13080
tgctgtgctc gacgttgtca ctgaagcggg aagggactgg ctgctattgg gcgaagtgcc 13140
ggggcaggat ctcctgtcat ctcaccttgc tcctgccgag aaagtatcca tcatggctga 13200
tgcaatgcgg cggctgcata cgcttgatcc ggctacctgc ccattcgacc accaagcgaa 13260
acatcgcatc gagcgagcac gtactcggat ggaagccggt cttgtcgatc aggatgatct 13320
ggacgaagag catcaggggc tcgcgccagc cgaactgttc gccaggctca aggcgcgcat 13380
gcccgacggc gatgatctcg tcgtgaccca tggcgatgcc tgcttgccga atatcatggt 13440
ggaaaatggc cgcttttctg gattcatcga ctgtggccgg ctgggtgtgg cggaccgcta 13500
tcaggacata gcgttggcta cccgtgatat tgctgaagag cttggcggcg aatgggctga 13560
ccgcttcctc gtgctttacg gtatcgccgc tcccgattcg cagcgcatcg ccttctatcg 13620
ccttcttgac gagttcttct gagcgggact ctggggttcg aaatgaccga ccaagcgacg 13680
cccaacctgc catcacgaga tttcgattcc accgccgcct tctatgaaag gttgggcttc 13740
ggaatcgttt tccgggacgc cggctggatg atcctccagc gcggggatct catgctggag 13800
ttcttcgccc acgggatctc tgcggaacag gcggtcgaag gtgccgatat tattacgaca 13860
gcaacggccg acaagcacaa cgccacgatc ctgagcgaca atatgatcgg acccggcgtc 13920

```
cacatcaacg gcgtcggcgg cgactgccca ggcaagaccg agatgcaccg cgatatattg  13980

ctgcgttcgg atattttcgt ggagttcccg ccacagaccc ggatgatccc cgaccgttca  14040

aacatttggc aataaagttt ctaaagattg aatcctgttg ccggtcttgc gatgattatc  14100

atataatttc tgttgaatta cgttaagcat gtaataatta acatgtaatg catgacgtta  14160

tttatgagat gggtttttat gattagagtc ccgcaattat acatttaata cgcgatagaa  14220

aacaaaatat agcgcgcaaa ctaggataaa ttatcgcgcg cggtgtcatc tatgttacta  14280

gatcgggcct cctgatatca atgctgcagc ggcggctctg gtggtggttc tggtggcggc  14340

tctgagggtg gtggctctga gggtggcggt tctgagggtg gcggctctga gggaggcggt  14400

tccggtggtg gctctggttc cggtgatttt gattatgaaa agatggcaaa cgctaataag  14460

ggggctatga ccgaaaatgc cgatgaaaac gcgctacagt ctgacgctaa aggcaaactt  14520

gattctgtcg ctactgatta cggtgctgct atgatggttt cattggtgac gtttccggcc  14580

ttgctaatgg taatggtgct actggtgatt ttgctggctc taattcccaa atggctcaag  14640

tcggtgacgg tgataattca cctttaatga atatttccgt caatatttac cttccctccc  14700

tcaatcggtt gaatgtcgcc cttttgtctt tggcccaata cgcaaaccgc ctctccccgc  14760

gcgttggccg attcattatg cactggcacg acaggtttcc cgactggaaa gcgggcagtg  14820

agcgcaacgc aattatgtga gttagctcac tcattaggca ccccaggctt tacactttat  14880

gcttccggct cgtatgttgt gtggaattgt gagcggataa caatttcaca caggaaacag  14940

ctatgaccat gattacgcca agctggcgcc a                                 14971
```

```
<210> SEQ ID NO 56
<211> LENGTH: 37
<212> TYPE: DNA
<213> ORGANISM: Artificial Sequence
<220> FEATURE:
<223> OTHER INFORMATION: delta117C Fw primer

<400> SEQUENCE: 56

agggaatatt aagcttatgg agataagtcg cagcaat                              37


<210> SEQ ID NO 57
<211> LENGTH: 36
<212> TYPE: DNA
<213> ORGANISM: Artificial Sequence
<220> FEATURE:
<223> OTHER INFORMATION: delta117C Rv primer

<400> SEQUENCE: 57

gttactagtg gatccttaag ctcccgtagg atcaat                               36


<210> SEQ ID NO 58
<211> LENGTH: 5775
<212> TYPE: DNA
<213> ORGANISM: Artificial Sequence
<220> FEATURE:
<223> OTHER INFORMATION: pTES3 vector pYES3/UT.2

<400> SEQUENCE: 58

acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300
```

```
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagcttggta ccgagctcgg atccactagt aacggccgcc    540
agtgtgctgg aattctgcag atatccagca cagtggcggc cgctcgaaaa cccgctgatc    600
ctagagggcc gcatcatgta attagttatg tcacgcttac attcacgccc tccccccaca    660
tccgctctaa ccgaaaagga aggagttaga caacctgaag tctaggtccc tatttatttt    720
tttatagtta tgttagtatt aagaacgtta tttatatttc aaatttttct ttttttttctg    780
tacagacgcg tgtacgcatg taacattata ctgaaaacct tgcttgagaa ggttttggga    840
cgctcgaagg ctttaatttg caagctgcgg ccctgcatta atgaatcggc caacgcgcgg    900
ggagaggcgg tttgcgtatt gggcgctctt ccgcttcctc gctcactgac tcgctgcgct    960
cggtcgttcg gctgcggcga gcggtatcag ctcactcaaa ggcggtaata cggttatcca   1020
cagaatcagg ggataacgca ggaaagaaca tgtgagcaaa aggccagcaa aagcccagga   1080
accgtaaaaa ggccgcgttg ctggcgtttt tccataggct ccgcccccct gacgagcatc   1140
acaaaaatcg acgctcaagt cagaggtggc gaaacccgac aggactataa agataccagg   1200
cgtttccccc tggaagctcc ctcgtgcgct ctcctgttcc gaccctgccg cttaccggat   1260
acctgtccgc ctttctccct tcgggaagcg tggcgctttc tcatagctca cgctgtaggt   1320
atctcagttc ggtgtaggtc gttcgctcca agctgggctg tgtgcacgaa ccccccgttc   1380
agcccgaccg ctgcgcctta tccggtaact atcgtcttga gtccaacccg gtaagacacg   1440
acttatcgcc actggcagca gccactggta acaggattag cagagcgagg tatgtaggcg   1500
gtgctacaga gttcttgaag tggtggccta actacggcta cactagaagg acagtatttg   1560
gtatctgcgc tctgctgaag ccagttacct tcggaaaaag agttggtagc tcttgatccg   1620
gcaaacaaac caccgctggt agcggtggtt tttttgtttg caagcagcag attacgcgca   1680
gaaaaaaagg atctcaagaa gatcctttga tcttttctac ggggtctgac gctcagtgga   1740
acgaaaactc acgttaaggg attttggtca tgagattatc aaaaaggatc ttcacctaga   1800
tccttttaaa ttaaaaatga agttttaaat caatctaaag tatatatgag taaacttggt   1860
ctgacagtta ccaatgctta atcagtgagg cacctatctc agcgatctgt ctatttcgtt   1920
catccatagt tgcctgactc cccgtcgtgt agataactac gatacgggag cgcttaccat   1980
ctggccccag tgctgcaatg ataccgcgag acccacgctc accggctcca gatttatcag   2040
caataaacca gccagccgga agggccgagc gcagaagtgg tcctgcaact ttatccgcct   2100
ccatccagtc tattaattgt tgccgggaag ctagagtaag tagttcgcca gttaatagtt   2160
tgcgcaacgt tgttgccatt gctacaggca tcgtggtgtc acgctcgtcg tttggtatgg   2220
cttcattcag ctccggttcc caacgatcaa ggcgagttac atgatccccc atgttgtgca   2280
aaaaagcggt tagctccttc ggtcctccga tcgttgtcag aagtaagttg gccgcagtgt   2340
tatcactcat ggttatggca gcactgcata attctcttac tgtcatgcca tccgtaagat   2400
gcttttctgt gactggtgag tactcaacca agtcattctg agaatagtgt atgcggcgac   2460
cgagttgctc ttgcccggcg tcaacacggg ataataccgc gccacatagc agaactttaa   2520
aagtgctcat cattggaaaa cgttcttcgg ggcgaaaact ctcaaggatc ttaccgctgt   2580
tgagatccag ttcgatgtaa cccactcgtg cacccaactg atcttcagca tcttttactt   2640
```

tcaccagcgt ttctgggtga gcaaaaacag gaaggcaaaa tgccgcaaaa aagggaataa 2700
gggcgacacg gaaatgttga atactcatac tcttcctttt tcaatattat tgaagcattt 2760
atcagggtta ttgtctcatg agcggataca tatttgaatg tatttagaaa aataaacaaa 2820
taggggttcc gcgcacattt ccccgaaaag tgccacctga cgtctaagaa accattatta 2880
tcatgacatt aacctataaa aataggcgta tcacgaggcc ctttcgtctt caagaaattc 2940
ggtcgaaaaa agaaaaggag agggccaaga gggagggcat tggtgactat tgagcacgtg 3000
agtatacgtg attaagcaca caaaggcagc ttggagtatg tctgttatta atttcacagg 3060
tagttctggt ccattggtga aagtttgcgg cttgcagagc acagaggccg cagaatgtgc 3120
tctagattcc gatgctgact tgctgggtat tatatgtgtg cccaatagaa agagaacaat 3180
tgacccggtt attgcaagga aaatttcaag tcttgtaaaa gcatataaaa atagttcagg 3240
cactccgaaa tacttggttg gcgtgtttcg taatcaacct aaggaggatg ttttggctct 3300
ggtcaatgat tacggcattg atatcgtcca actgcacgga gatgagtcgt ggcaagaata 3360
ccaagagttc ctcggtttgc cagttattaa aagactcgta tttccaaaag actgcaacat 3420
actactcagt gcagcttcac agaaacctca ttcgtttatt cccttgtttg attcagaagc 3480
aggtgggaca ggtgaacttt tggattggaa ctcgatttct gactgggttg gaaggcaaga 3540
gagccccgag agcttacatt ttatgttagc tggtggactg acgccagaaa atgttggtga 3600
tgcgcttaga ttaaatggcg ttattggtgt tgatgtaagc ggaggtgtgg agacaaatgg 3660
tgtaaaagac tctaacaaaa tagcaaattt cgtcaaaaat gctaagaaat aggttattac 3720
tgagtagtat ttatttaagt attgtttgtg cacttgccct agcttatcga tgataagctg 3780
tcaaagatga gaattaattc cacggactat agactatact agatactccg tctactgtac 3840
gatacacttc cgctcaggtc cttgtccttt aacgaggcct taccactctt ttgttactct 3900
attgatccag ctcagcaaag gcagtgtgat ctaagattct atcttcgcga tgtagtaaaa 3960
ctagctagac cgagaaagag actagaaatg caaaaggcac ttctacaatg gctgccatca 4020
ttattatccg atgtgacgct gcagcttctc aatgatattc gaatacgctt tgaggagata 4080
cagcctaata tccgacaaac tgttttacag atttacgatc gtacttgtta cccatcattg 4140
aattttgaac atccgaacct gggagttttc cctgaaacag atagtatatt tgaacctgta 4200
taataatata tagtctagcg ctttacggaa gacaatgtat gtatttcggt tcctggagaa 4260
actattgcat ctattgcata ggtaatcttg cacgtcgcat ccccggttca ttttctgcgt 4320
ttccatcttg cacttcaata gcatatcttt gttaacgaag catctgtgct tcattttgta 4380
gaacaaaaat gcaacgcgag agcgctaatt tttcaaacaa agaatctgag ctgcattttt 4440
acagaacaga aatgcaacgc gaaagcgcta ttttaccaac gaagaatctg tgcttcattt 4500
ttgtaaaaca aaaatgcaac gcgacgagag cgctaatttt tcaaacaaag aatctgagct 4560
gcatttttac agaacagaaa tgcaacgcga gagcgctatt ttaccaacaa agaatctata 4620
cttctttttt gttctacaaa aatgcatccc gagagcgcta tttttctaac aaagcatctt 4680
agattacttt ttttctcctt tgtgcgctct ataatgcagt ctcttgataa ctttttgcac 4740
tgtaggtccg ttaaggttag aagaaggcta ctttggtgtc tattttctct tccataaaaa 4800
aagcctgact ccacttcccg cgtttactga ttactagcga agctgcgggt gcattttttc 4860
aagataaagg catccccgat tatattctat accgatgtgg attgcgcata ctttgtgaac 4920
agaaagtgat agcgttgatg attcttcatt ggtcagaaaa ttatgaacgg tttcttctat 4980
tttgtctcta tatactacgt ataggaaatg tttacatttt cgtattgttt tcgattcact 5040

```
ctatgaatag ttcttactac aattttttttg tctaaagagt aatactagag ataaacataa   5100

aaaatgtaga ggtcgagttt agatgcaagt tcaaggagcg aaaggtggat gggtaggtta   5160

tatagggata tagcacagag atatatagca aagagatact tttgagcaat gtttgtggaa   5220

gcggtattcg caatgggaag ctccaccccg gttgataatc agaaaagccc caaaaacagg   5280

aagattgtat aagcaaatat ttaaattgta aacgttaata ttttgttaaa attcgcgtta   5340

aatttttgtt aaatcagctc atttttttaac gaatagcccg aaatcggcaa aatcccttat   5400

aaatcaaaag aatagaccga gatagggttg agtgttgttc cagtttccaa caagagtcca   5460

ctattaaaga acgtggactc caacgtcaaa gggcgaaaaa gggtctatca gggcgatggc   5520

ccactacgtg aaccatcacc ctaatcaagt tttttggggt cgaggtgccg taaagcagta   5580

aatcggaagg gtaaacggat gcccccattt agagcttgac ggggaaagcc ggcgaacgtg   5640

gcgagaaagg aagggaagaa agcgaaagga gcgggggcta gggcggtggg aagtgtaggg   5700

gtcacgctgg gcgtaaccac cacacccgcc gcgcttaatg ggcgctaca gggcgcgtgg   5760

ggatgatcca ctagt                                                     5775


<210> SEQ ID NO 59
<211> LENGTH: 37
<212> TYPE: DNA
<213> ORGANISM: Artificial Sequence
<220> FEATURE:
<223> OTHER INFORMATION: delta117N Fw primer

<400> SEQUENCE: 59

agggaatatt aagcttatgg aaatgaagca gcttgca                               37


<210> SEQ ID NO 60
<211> LENGTH: 38
<212> TYPE: DNA
<213> ORGANISM: Artificial Sequence
<220> FEATURE:
<223> OTHER INFORMATION: delta117N Rv primer

<400> SEQUENCE: 60

gttactagtg gatccttata ccatagtttt gtgttctg                              38
```